(12) United States Patent
Rajagopalan et al.

(10) Patent No.: US 11,185,367 B2
(45) Date of Patent: *Nov. 30, 2021

(54) METHODS AND SYSTEMS FOR TREATING DIABETES AND RELATED DISEASES AND DISORDERS

(71) Applicant: Fractyl Laboratories, Inc., Lexington, MA (US)

(72) Inventors: Harith Rajagopalan, Wellesley Hills, MA (US); Jay Caplan, Belmont, MA (US); Craig M. Gardner, Belmont, MA (US); J. Christopher Flaherty, Auburndale, FL (US)

(73) Assignee: Fractyl Health, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/189,772

(22) Filed: Mar. 2, 2021

(65) Prior Publication Data

US 2021/0220045 A1 Jul. 22, 2021

Related U.S. Application Data

(63) Continuation of application No. 17/096,855, filed on Nov. 12, 2020, which is a continuation of application
(Continued)

(51) Int. Cl.
*A61B 18/14* (2006.01)
*A61M 29/02* (2006.01)
(Continued)

(52) U.S. Cl.
CPC ......... *A61B 18/1492* (2013.01); *A61M 29/02* (2013.01); *A61B 2018/0022* (2013.01);
(Continued)

(58) Field of Classification Search
CPC ...... A61B 18/1492; A61B 2018/00029; A61B 2018/00196; A61B 2018/0022;
(Continued)

(56) References Cited

U.S. PATENT DOCUMENTS 5,084,044 A 1/1992 Quint
5,190,540 A 3/1993 Lee
(Continued)

FOREIGN PATENT DOCUMENTS

CA 2666661 C 1/2015
CN 1771888 A 5/2006
(Continued)

OTHER PUBLICATIONS

S Colagiuri, CA Cull, RR Holman. Are Lower Fasting Plasma Glucose Levels at Diagnosis of Type 2 Diabetes Associated With Improved Outcomes? Diabetes Care, vol. 25, No. 9, Aug. 2002 pp. 1410-1417 (Year: 2002).*

(Continued)

*Primary Examiner* — Michael F Peffley
*Assistant Examiner* — Bo Ouyang
(74) *Attorney, Agent, or Firm* — Wilson Sonsini Goodrich & Rosati

(57) ABSTRACT

Systems, devices and methods treat target tissue to provide a therapeutic benefit to the patient. A tissue treatment device comprises a tissue treatment element constructed and arranged to treat target tissue, such as duodenal mucosa and/or submucosal tissue. Patients treated can safely eliminate or reduce their daily insulin intake.

27 Claims, 58 Drawing Sheets

Related U.S. Application Data

No. 15/406,572, filed on Jan. 13, 2017, now Pat. No. 10,869,718, which is a continuation of application No. PCT/US2015/040775, filed on Jul. 16, 2015.

(60) Provisional application No. 63/085,375, filed on Sep. 30, 2020, provisional application No. 63/076,737, filed on Sep. 10, 2020, provisional application No. 62/991,219, filed on Mar. 18, 2020, provisional application No. 62/025,307, filed on Jul. 16, 2014.

(51) Int. Cl.
   *A61B 18/00* (2006.01)
   *A61M 25/00* (2006.01)

(52) U.S. Cl.
   CPC ........... *A61B 2018/00029* (2013.01); *A61B 2018/0041* (2013.01); *A61B 2018/00196* (2013.01); *A61B 2018/00404* (2013.01); *A61B 2018/00577* (2013.01); *A61B 2018/00779* (2013.01); *A61B 2018/00797* (2013.01); *A61B 2018/00839* (2013.01); *A61B 2018/00875* (2013.01); *A61B 2018/00994* (2013.01); *A61B 2018/1467* (2013.01); *A61M 2025/0087* (2013.01)

(58) Field of Classification Search
   CPC .. A61B 2018/00404; A61B 2018/0041; A61B 2018/00875; A61M 2025/0087; A61M 29/02
   See application file for complete search history.

(56) References Cited

U.S. PATENT DOCUMENTS

| | | |
|---|---|---|
| 5,423,754 A | 6/1995 | Cornelius et al. |
| 5,471,982 A | 12/1995 | Edwards et al. |
| 5,496,311 A | 3/1996 | Abele et al. |
| 5,515,100 A | 5/1996 | Nogo |
| 5,542,928 A | 8/1996 | Evans et al. |
| 5,549,559 A | 8/1996 | Eshel |
| 5,575,772 A | 11/1996 | Lennox |
| 5,704,934 A | 1/1998 | Neuwirth et al. |
| 5,730,719 A | 3/1998 | Edwards |
| 5,800,484 A | 9/1998 | Gough et al. |
| 5,827,269 A | 10/1998 | Saadat |
| 5,859,037 A | 1/1999 | Whitcomb et al. |
| 5,869,037 A | 2/1999 | Crystal et al. |
| 5,871,525 A | 2/1999 | Edwards et al. |
| 5,879,347 A | 3/1999 | Saadat et al. |
| 5,957,962 A | 9/1999 | Wallsten et al. |
| 5,964,753 A | 10/1999 | Edwards |
| 6,009,877 A | 1/2000 | Edwards |
| 6,053,937 A | 4/2000 | Edwards et al. |
| 6,056,744 A | 5/2000 | Edwards et al. |
| 6,066,132 A | 5/2000 | Chen et al. |
| 6,077,257 A | 6/2000 | Edwards et al. |
| 6,112,123 A | 8/2000 | Kelleher et al. |
| 6,293,909 B1 | 9/2001 | Chu et al. |
| 6,325,777 B1 | 12/2001 | Zadno-Azizi et al. |
| 6,325,798 B1 | 12/2001 | Edwards et al. |
| 6,338,726 B1 | 1/2002 | Edwards et al. |
| 6,358,245 B1 | 3/2002 | Edwards et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,425,887 B1 | 7/2002 | McGuckin et al. |
| 6,443,947 B1 | 9/2002 | Marko et al. |
| 6,544,226 B1 | 4/2003 | Gaiser et al. |
| 6,673,070 B2 | 1/2004 | Edwards et al. |
| 6,712,814 B2 | 3/2004 | Edwards et al. |
| 6,802,841 B2 | 10/2004 | Utley et al. |
| 6,905,496 B1 | 6/2005 | Ellman et al. |
| 6,962,587 B2 | 11/2005 | Johnson et al. |
| 6,974,456 B2 | 12/2005 | Edwards et al. |
| 7,077,841 B2 | 7/2006 | Gaiser et al. |
| 7,111,627 B2 | 9/2006 | Stack et al. |
| 7,122,031 B2 | 10/2006 | Edwards et al. |
| 7,125,407 B2 | 10/2006 | Edwards et al. |
| 7,156,860 B2 | 1/2007 | Wallsten |
| 7,165,551 B2 | 1/2007 | Edwards et al. |
| 7,241,295 B2 | 7/2007 | Maguire |
| 7,326,207 B2 | 2/2008 | Edwards |
| 7,371,215 B2 | 5/2008 | Colliou et al. |
| 7,387,626 B2 | 6/2008 | Edwards et al. |
| 7,422,587 B2 | 9/2008 | Bek et al. |
| 7,507,234 B2 | 3/2009 | Utley et al. |
| 7,507,238 B2 | 3/2009 | Utley et al. |
| 7,530,979 B2 | 5/2009 | Ganz et al. |
| 7,556,628 B2 | 7/2009 | Utley et al. |
| 7,585,296 B2 | 9/2009 | Edward et al. |
| 7,632,268 B2 | 12/2009 | Utley et al. |
| 7,632,291 B2 | 12/2009 | Stephens et al. |
| 7,648,500 B2 | 1/2010 | Edwards et al. |
| 7,758,623 B2 | 7/2010 | Dzeng et al. |
| 7,762,977 B2 | 7/2010 | Porter et al. |
| 7,947,038 B2 | 5/2011 | Edwards |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,066,689 B2 | 11/2011 | Mitelberg et al. |
| 8,152,803 B2 | 4/2012 | Edwards et al. |
| 8,177,853 B2 | 5/2012 | Stack et al. |
| 8,192,426 B2 | 6/2012 | Stern et al. |
| 8,251,992 B2 | 8/2012 | Utley et al. |
| 8,273,012 B2 | 9/2012 | Wallace et al. |
| 8,323,229 B2 | 12/2012 | Shin et al. |
| 8,364,237 B2 | 1/2013 | Stone et al. |
| 8,377,055 B2 | 2/2013 | Jackson et al. |
| 8,486,005 B2 | 7/2013 | Yodfat et al. |
| 8,641,711 B2 | 2/2014 | Kelly et al. |
| 8,740,894 B2 | 6/2014 | Edwards |
| 8,790,705 B2 | 7/2014 | Geigle et al. |
| 9,364,283 B2 | 6/2016 | Utley et al. |
| 9,555,020 B2 | 1/2017 | Pasricha et al. |
| 9,615,880 B2 | 4/2017 | Gittard et al. |
| 9,757,535 B2 | 9/2017 | Rajagopalan et al. |
| 9,844,641 B2 | 12/2017 | Rajagopalan et al. |
| 10,232,143 B2 | 3/2019 | Rajagopalan et al. |
| 10,299,857 B2 | 5/2019 | Rajagopalan et al. |
| 10,349,998 B2 | 7/2019 | Levin et al. |
| 10,610,663 B2 | 4/2020 | Rajagopalan et al. |
| 10,765,474 B2 | 9/2020 | Kadamus et al. |
| 10,864,352 B2 | 12/2020 | Rajagopalan et al. |
| 10,869,718 B2 | 12/2020 | Rajagopalan et al. |
| 2002/0013581 A1 | 1/2002 | Edwards et al. |
| 2002/0077594 A1 | 6/2002 | Chien et al. |
| 2002/0115992 A1 | 8/2002 | Utley et al. |
| 2002/0192162 A1 | 12/2002 | Green |
| 2003/0040804 A1 | 2/2003 | Stack et al. |
| 2003/0093072 A1 | 5/2003 | Friedman |
| 2003/0153905 A1 | 8/2003 | Edwards et al. |
| 2003/0233065 A1 | 12/2003 | Steward et al. |
| 2004/0082859 A1 | 4/2004 | Schaer |
| 2004/0087936 A1 | 5/2004 | Stern et al. |
| 2004/0133256 A1 | 7/2004 | Callister |
| 2004/0148034 A1 | 7/2004 | Kagan et al. |
| 2004/0204768 A1 | 10/2004 | Geitz |
| 2004/0215180 A1 | 10/2004 | Starkebaum et al. |
| 2004/0215296 A1 | 10/2004 | Ganz et al. |
| 2004/0220559 A1 | 11/2004 | Kramer et al. |
| 2005/0096638 A1 | 5/2005 | Starkebaum et al. |
| 2005/0154386 A1 | 7/2005 | West et al. |
| 2005/0165437 A1 | 7/2005 | Takimoto |
| 2005/0171524 A1 | 8/2005 | Stern et al. |
| 2005/0192652 A1 | 9/2005 | Cioanta et al. |
| 2005/0203489 A1 | 9/2005 | Saadat et al. |
| 2005/0222558 A1 | 10/2005 | Baxter et al. |
| 2005/0245943 A1 | 11/2005 | Zvuloni et al. |
| 2005/0251116 A1 | 11/2005 | Steinke et al. |
| 2005/0273090 A1 | 12/2005 | Nieman et al. |
| 2006/0070631 A1 | 4/2006 | Scopton et al. |

(56) References Cited

U.S. PATENT DOCUMENTS

| | | |
|---|---|---|
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1 | 9/2006 | Lubock et al. |
| 2006/0247683 A1 | 11/2006 | Danek et al. |
| 2006/0259030 A1 | 11/2006 | Utley et al. |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van Der Weide et al. |
| 2008/0207994 A1 | 8/2008 | Gonon |
| 2008/0243112 A1 | 10/2008 | De |
| 2008/0275445 A1* | 11/2008 | Kelly .............. A61B 18/18 606/45 |
| 2008/0319504 A1 | 12/2008 | Loushin et al. |
| 2009/0012469 A1 | 1/2009 | Nita |
| 2009/0012512 A1 | 1/2009 | Utley et al. |
| 2009/0012518 A1 | 1/2009 | Utley et al. |
| 2009/0018533 A1 | 1/2009 | Perkins et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0234840 A1 | 9/2010 | Jackson et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0184401 A1 | 7/2011 | Iwata et al. |
| 2011/0208175 A1* | 8/2011 | Sobotka ........... A61B 18/1492 606/21 |
| 2011/0319809 A1 | 12/2011 | Smith |
| 2012/0004654 A1 | 1/2012 | Jackson et al. |
| 2012/0016364 A1 | 1/2012 | Mayse et al. |
| 2012/0059364 A1 | 3/2012 | Baust et al. |
| 2012/0197245 A1 | 8/2012 | Burnett et al. |
| 2012/0238554 A1* | 9/2012 | Cowen ............... A61P 1/16 514/223.5 |
| 2012/0271277 A1 | 10/2012 | Fischell et al. |
| 2012/0271301 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2013/0190675 A1* | 7/2013 | Sandoski ........... A61F 5/0076 604/8 |
| 2013/0345670 A1 | 12/2013 | Rajagopalan et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1* | 7/2014 | Pasricha ............. A61B 18/02 514/450 |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan et al. |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0310200 A1 | 10/2016 | Wang |
| 2016/0354144 A1 | 12/2016 | Caplan et al. |
| 2017/0007324 A1 | 1/2017 | Kadamus et al. |
| 2017/0014596 A1 | 1/2017 | Rajagopalan et al. |
| 2017/0191035 A1 | 7/2017 | Sia et al. |
| 2018/0193078 A1 | 7/2018 | Rajagopalan et al. |
| 2018/0193590 A1 | 7/2018 | Rajagopalan et al. |
| 2018/0221622 A1 | 8/2018 | Rajagopalan et al. |
| 2020/0060758 A1 | 2/2020 | Rajagopalan et al. |
| 2020/0060942 A1 | 2/2020 | Rajagopalan et al. |
| 2020/0138505 A1 | 5/2020 | Levin et al. |
| 2020/0155217 A1 | 5/2020 | Morneau et al. |
| 2020/0261144 A1 | 8/2020 | Caplan et al. |
| 2020/0305972 A1 | 10/2020 | Kadamus et al. |
| 2020/0405388 A1 | 12/2020 | Rajagopalan et al. |
| 2021/0008336 A1 | 1/2021 | Rajagopalan et al. |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2004180934 A | 7/2004 |
| JP | 2006509536 A | 3/2006 |
| JP | 2006136726 A | 6/2006 |
| JP | 2007502690 A | 2/2007 |
| JP | 2008515464 A | 5/2008 |
| JP | 2010142661 A | 7/2010 |
| JP | 2010533036 A | 10/2010 |
| JP | 2011517599 A | 6/2011 |
| JP | 2013543423 A | 12/2013 |
| JP | 2014503256 A | 2/2014 |
| KR | 20080013945 A | 2/2008 |
| WO | WO-9418896 A1 | 9/1994 |
| WO | WO-9912489 A2 | 3/1999 |
| WO | WO-0207628 A2 | 1/2002 |
| WO | WO-02058577 A1 | 8/2002 |
| WO | WO-02096327 A2 | 12/2002 |
| WO | WO-02102453 A2 | 12/2002 |
| WO | WO-03033045 A2 | 4/2003 |
| WO | WO-03092609 A2 | 11/2003 |
| WO | WO-2004064600 A2 | 8/2004 |
| WO | WO-2006020370 A2 | 2/2006 |
| WO | WO-2007044244 A2 | 4/2007 |
| WO | WO-2007067919 A2 | 6/2007 |
| WO | WO-2008002654 A2 | 1/2008 |
| WO | WO-2010042461 A1 | 4/2010 |
| WO | WO-2010125570 A1 | 11/2010 |
| WO | WO-2011060301 A1 | 5/2011 |
| WO | WO-2012009486 A2 | 1/2012 |
| WO | WO-2012099974 A2 | 7/2012 |
| WO | WO-2013130655 A1 | 9/2013 |
| WO | WO-2013134541 A2 | 9/2013 |
| WO | WO-2013159066 A1 | 10/2013 |
| WO | WO-2014022436 A1 | 2/2014 |
| WO | WO-2014026055 A1 | 2/2014 |
| WO | WO-2014055997 A1 | 4/2014 |
| WO | WO-2014070136 A1 | 5/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2017004432 A1 | 1/2017 |
| WO | WO-2018089773 A1 | 5/2018 |
| WO | WO-2019018362 A1 | 1/2019 |
| WO | WO-2019136240 A1 | 7/2019 |

OTHER PUBLICATIONS

(56) References Cited

OTHER PUBLICATIONS

RD White. Insulin Dosing: How High Can You Go? https://www.patientcareonline.com/view/insulin-dosing-how-high-can-you-go Feb. 10, 2010. Accessed May 19, 2021 (Year: 2010).*

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.

Araki, et al. Oral glucose-stimulated serum C-peptide predicts successful switching from insulin therapy to liraglutide monotherapy in Japanese patients with type 2 diabetes and renal impairment. Journal of diabetes investigation 5.4 (2014): 435-441.

Bruinstroop, et al. Retrospective Analysis of an Insulin-to-Liraglutide Switch in Patients with Type 2 Diabetes Mellitus. Diabetes Therapy 9.3 (2018): 1369-1375.

Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.

Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.

Co-pending U.S. Appl. No. 16/905,274, inventors Rajagopalan; Harith et al., filed Jun. 18, 2020.
Co-pending U.S. Appl. No. 17/095,108, inventors Rajagopalan; Harith et al., filed Nov. 11, 2020.
Co-pending U.S. Appl. No. 17/096,855, inventors Rajagopalan; Harith et al., filed Nov. 12, 2020.
Co-pending U.S. Appl. No. 17/110,720, inventors J.; Kadamus Christopher J. et al., filed Dec. 3, 2020.
Co-pending U.S. Appl. No. 17/181,969, inventors Rajagopalan; Harith et al., filed Feb. 22, 2021.

Davis, et al. Exploring the substitution of exenatide for insulin in patients with type 2 diabetes treated with insulin in combination with oral antidiabetes agents.Diabetes care 30.11 (2007): 2767-2772.

EP12736438.8 The Extended European Search Report dated Nov. 22, 2016.
EP14844285.8 The Extended European Search Report dated Apr. 25, 2017.
EP20150391.9 The Extended European Search Report dated Aug. 20, 2020.
EP20159816.6 The Extended European Search Report dated Aug. 17, 2020.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report and search opinion dated Nov. 25, 2015 for EP Application No. 13777572.2.
European search report with written opinion dated Feb. 1, 2018 for EP Application No. 15822378.
European search report with written opinion dated Dec. 2, 2016 for EP Application No. 14807116.
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 2019 for U.S. Appl. No. 14/609,332.
Final Office action dated Jul. 10, 2019 for U.S. Appl. No. 15/274,948.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.

Grikscheit, et al. Tissue-engineered small intestine improves recovery after massive small bowel resection. Ann Surg., 2004, 240:748-754.

International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
International search report and written opinion dated Oct. 23, 2015 for PCT/US2015/040775.
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
International search report with written opinion dated Jan. 9, 2018 for PCT/US2017/061074.

Kawata, et al. Is a switch from insulin therapy to liraglutide possible in Japanese type 2 diabetes mellitus patients?Journal of clinical medicine research 6.2 (2014): 138-144.

Kozawa, et al. Liraglutide is effective in type 2 diabetic patients with sustained endogenous insulin-secreting capacity.Journal of diabetes investigation 3.3 (2012): 294-297.

Miyawaki, et al. Inhibition of gastric inhibitory polypeptide signaling prevents obesity. Nat Med. Jul. 2002;8(7):738-42. Epub Jun. 17, 2002.

Nambu, et al. Liraglutide administration in type 2 diabetic patients who either received no previous treatment or were treated with an oral hypoglycemic agent showed greater efficacy than that in patients switching from insulin.Journal of diabetes investigation 4.1 (2013): 69-77.

Notice of Allowance dated Jul. 7, 2017 for U.S. Appl. No. 15/274,764.
Notice of Allowance dated Sep. 14, 2017 for U.S. Appl. No. 15/274,809.
Office Action date Jul. 11, 2018 for U.S. Appl. No. 14/917,243.
Office Action date Aug. 9, 2018 for U.S. Appl. No. 14/673,565.
Office action dated Jan. 8, 2018 for U.S. Appl. No. 14/609,334.
Office Action dated Jan. 13, 2017 for U.S. Appl. No. 14/609,332.
Office action dated Feb. 29, 2016 for U.S. Appl. No. 14/609,334.
Office action dated Mar. 7, 2019 for U.S. Appl. No. 13/945,138.
Office Action dated Mar. 7, 2017 for U.S. Appl. No. 15/274,764.
Office Action dated Mar. 7, 2017 for U.S. Appl. No. 15/274,809.
Office action dated Mar. 7, 2019 for U.S. Appl. No. 14/673,565.
Office action dated Mar. 12, 2015 for U.S. Appl. No. 13/945,138.
Office action dated Mar. 19, 2018 for U.S. Appl. No. 14/470,503.
Office Action dated Mar. 23, 2017 for U.S. Appl. No. 13/945,138.
Office action dated Mar. 28, 2016 for U.S. Appl. No. 14/673,565.
Office action dated Apr. 4, 2018 for U.S. Appl. No. 15/156,585.
Office action dated May 16, 2019 for U.S. Appl. No. 14/515,324.
Office action dated May 18, 2018 for U.S. Appl. No. 14/956,710.
Office Action dated May 31, 2017 for U.S. Appl. No. 15/274,764.
Office action dated Jun. 6, 2019 for U.S. Appl. No. 15/683,713.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
Office action dated Sep. 7, 2018 for U.S. Appl. No. 14/609,332.
Office Action dated Sep. 23, 2016 for U.S. Appl. No. 14/515,324.
Office action dated Oct. 4, 2018 for U.S. Appl. No. 14/515,324.
Office Action dated Oct. 7, 2016 for U.S. Appl. No. 13/945,138.

(56) References Cited

OTHER PUBLICATIONS

Office Action dated Nov. 2, 2017 for U.S. Appl. No. 15/156,585.
Office action dated Nov. 2, 2018 for U.S. Appl. No. 14/609,334.
Office Action dated Nov. 15, 2016 for U.S. Appl. No. 14/609,334.
Office action dated Nov. 16, 2017 for U.S. Appl. No. 14/609,332.
Office action dated Nov. 30, 2015 for U.S. Appl. No. 13/945,138.
Office action dated Nov. 30, 2017 for U.S. Appl. No. 14/673,565.
Office action dated Dec. 17, 2015 for U.S. Appl. No. 14/515,324.
Office action dated Dec. 18, 2017 for U.S. Appl. No. 14/515,324.
Office action dated Dec. 18, 2018 for U.S. Appl. No. 14/470,503.
Office action dated Dec. 19, 2017 for U.S. Appl. No. 13/945,138.
PCT/US14/66829 International Search Report dated Feb. 20, 2015.
PCT/US2018/042438 International Search Report dated Sep. 14, 2018.
PCT/US2019/012338 International Search Report dated Apr. 15, 2019.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.
Tolman, et al. Spectrum of liver disease in type 2 diabetes and management of patients with diabetes and liver disease. Diabetes care 30.3 (2007): 734-743.
Tomizawa, et al. Clinical Outcome of Endoscopic Mucosal Resection (EMR) of Sporadic, Non-Ampullary Duodenal Adenoma (SNADA) : Predictor Analysis of Safety and Efficacy From a High vol. U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
U.S. Appl. No. 14/917,243 Office Action dated Jun. 5, 2020.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 14/673,565 Office Action dated Dec. 24, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/274,948 Office Action dated Nov. 20, 2018.
U.S. Appl. No. 15/406,572 Notice of Allowance dated Oct. 28, 2020.
U.S. Appl. No. 15/406,572 Office Action dated Apr. 14, 2020.
U.S. Appl. No. 15/406,572 Office Action dated Feb. 7, 2019.
U.S. Appl. No. 15/406,572 Office Action dated Nov. 15, 2019.
U.S. Appl. No. 15/917,480 Notice of Allowance dated Dec. 17, 2020.
U.S. Appl. No. 15/917,480 Office Action dated Nov. 20, 2020.
U.S. Appl. No. 16/267,771 Notice of Allowance dated Aug. 10, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 17/110,720 Office Action dated Feb. 2, 2021.
U.S. Appl. No. 13/945,138 Office Action dated Dec. 10, 2019.
U.S. Appl. No. 14/470,503 Notice of Allowance dated Feb. 27, 2019.
U.S. Appl. No. 14/515,324 Office Action dated Mar. 31, 2020.
U.S. Appl. No. 14/609,334 Office Action dated Jan. 8, 2020.
U.S. Appl. No. 14/956,710 Notice of Allowance dated Jan. 9, 2019.
U.S. Appl. No. 15/683,713 Notice of Allowance dated Mar. 10, 2020.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 16/267,771 Office Action dated Feb. 6, 2020.
Usui, et al. Retrospective analysis of safety and efficacy of insulin-to-liraglutide switch in Japanese type 2 diabetes: a caution against inappropriate use in patients with reduced β-cell function.Journal of diabetes investigation 4.6 (2013): 585-594.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.

* cited by examiner

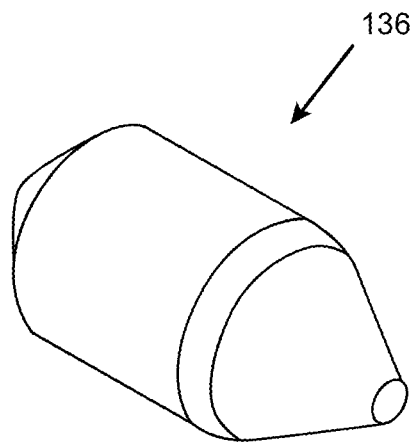
FIG 4A
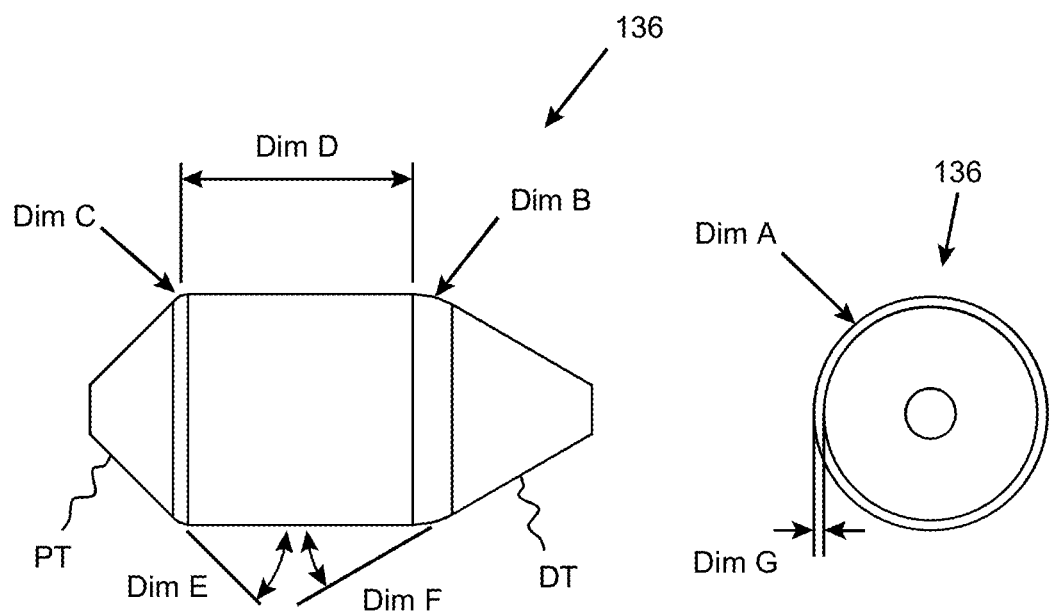
FIG 4B
FIG 4C

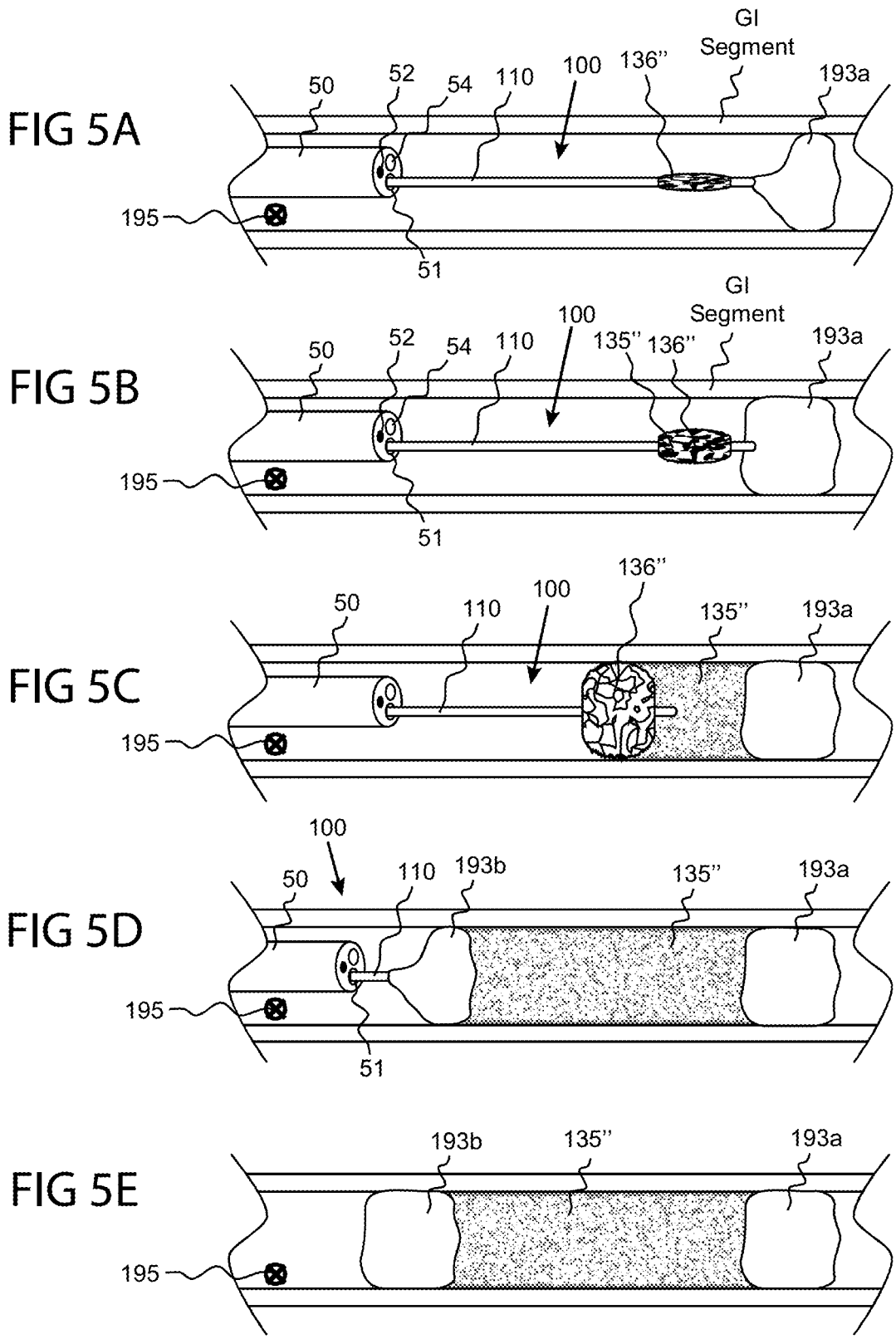

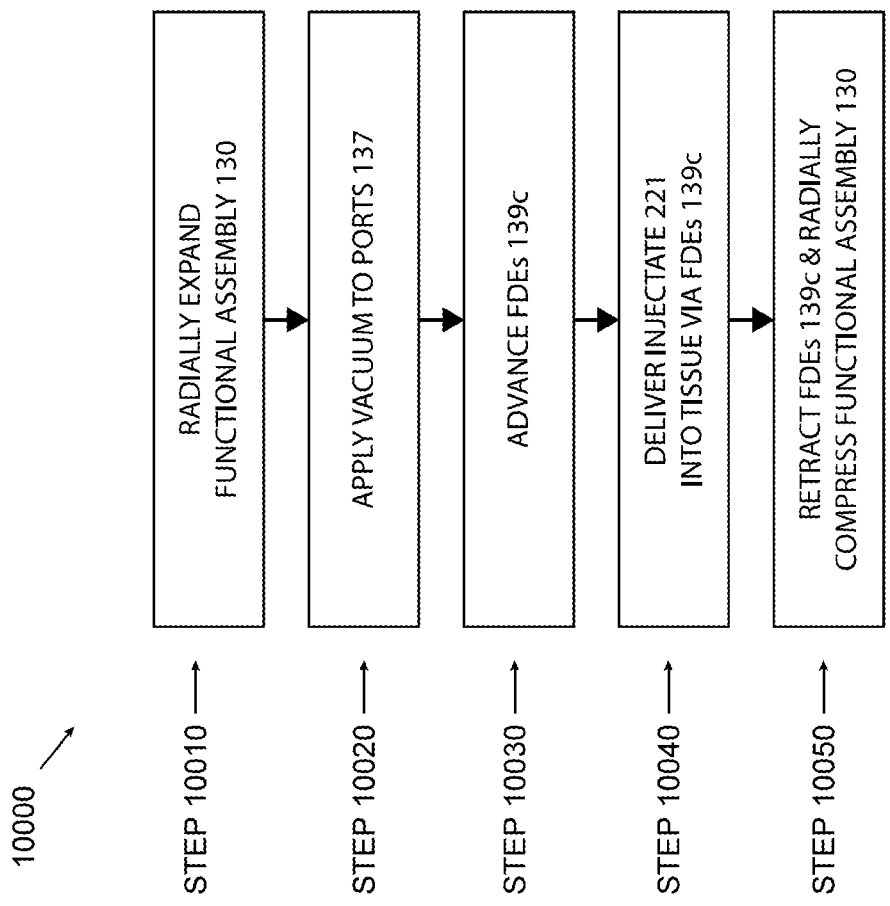

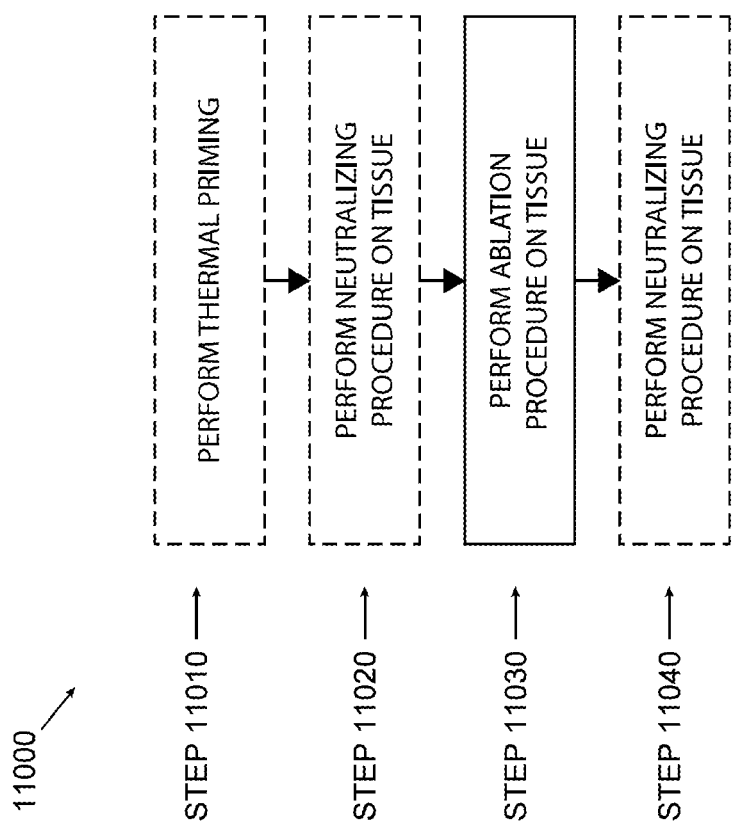

| Table 1. Baseline Characteristics and Demographics (EU mITT Population[a]) | | |
|---|---|---|
| Parameter | DMR N = 39 | Sham N = 36 |
| Age, years | 59·0 (13·0) | 56·5 (14·0) |
| Sex, n (%) | | |
|   Female | 9 (23·1) | 8 (22·2) |
|   Male | 30 (76·9) | 28 (77·8) |
| Race, n (%) | | |
|   White | 25 (64·1) | 21 (58·3) |
|   Black or African American | 0 | 0 |
|   Asian | 0 | 1 (2·8) |
|   Other | 1 (2·6) | 2 (5·6) |
|   Undisclosed | 13 (33·3) | 12 (33·3) |
| Weight, kg | 93·1 (16·5) | 94·4 (24·6) |
| BMI, kg/m² | 31·4 (4·5) | 30·4 (6·1) |
| HbA1c, % | 65·0 (7·0) | 66·0 (10·0) |
| Fasting insulin, mU/L | n = 39<br>68·1 (5·6) | 58·0 (28·5) |
| HOMA-IR | 4·8 (3·9) | 3·9 (2·3) |
| Fasting glucose, mg/dL | 10·6 (4·3) | 10·3 (3·2) |
| C-peptide, ng/mL | 0·8 (0·4) | 0·8 (0·3) |
| MRI-PDFF, %[b] | 16·5 (10·2) | 16·1 (13·6) |
|   >5% at baseline, n (%) | 33 (85·0) | 27 (75·0) |
| ALT, U/L | 31·0 (18·0) | 29·0 (21·5) |
| AST, U/L | 21·0 (12·0) | 19·5 (10·5) |
| Duration of T2D, years | 10·3 (8·7) | 10·2 (8·1) |
| Antidiabetic medications, n (%) | | |
|   1 | 10 (25·6) | 10 (27·8) |
|   2 | 16 (41·0) | 13 (36·1) |
|   3 | 12 (30·8) | 13 (36·1) |
|   >3 | 1 (2·6) | 0 (0) |
| Diabetes medication use at screening, years | 8·2 (7·1) | 6·9 (8·4) | mITT population data for continuous variables are presented as median (Q1, Q3), unless otherwise noted.
[a] EU (Italy, United Kingdom, Belgium, Netherlands) mITT population defined as all randomized patients in whom the study procedure (DMR or sham) is attempted and who have a baseline measurement for at least one primary endpoint.
[b] MRI-PDFF in patients with MRI-PDFF >5% at baseline.
ALT = alanine aminotransferase; AST = aspartate transaminase; BMI = body mass index; DMR = duodenal mucosal resurfacing; DPP-4 = dipeptidyl peptidase-4; EU = European Union; HbA1c = glycated hemoglobin A1c; HOMA-IR = homeostatic model assessment of insulin resistance; Q1 = lower quartile; Q3 = upper quartile; SD = standard deviation; SGLT-2 = sodium-glucose co-transporter-2; T2D = type 2 diabetes mellitus.

FIG 17

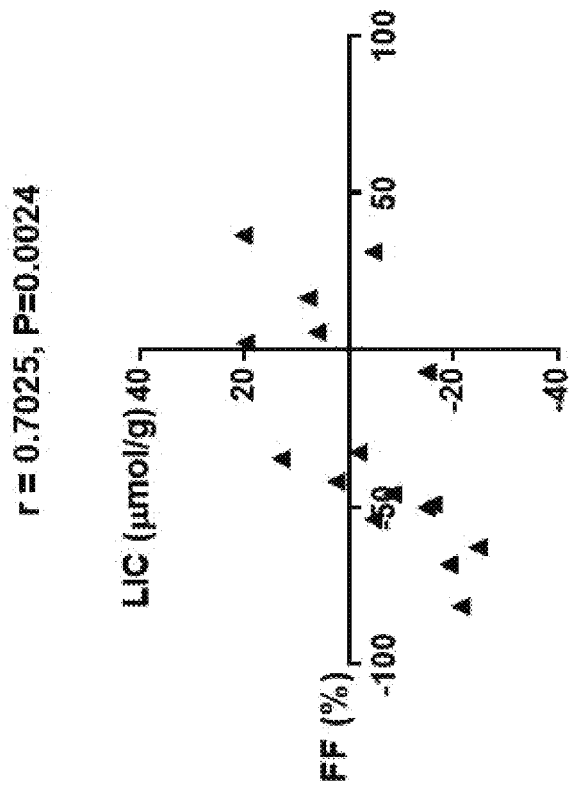
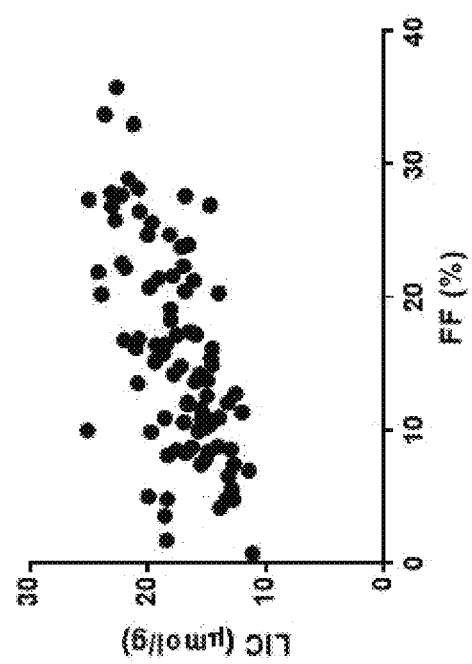
FIG 20B
FIG 20A

| Characteristic | Value (N=32) | N in calc |
|---|---|---|
| Duration diabetes - yr | 5.1 +/- 2.9 | 27 |
| Age - yr | 52.9 +/- 7.6 | 26 |
| Female sex - N (%) | 12 (46.2) | 26 |
| Weight - kg | 86.7 +/- 13.2 | 26 |
| Height - cm | 165.7 +/- 10.2 | 26 |
| BMI - kg/m^2 | 31.6 +/- 4.0 | 26 |
| BP Systolic - mmHg | 122.5 +/- 16.2 | 26 |
| BP Diastolic - mmHg | 77.2 +/- 8.0 | 26 |
| Medications - N | 1.7 +/- 0.6 | 19 |

FIG 22

|       |              | Baseline | | 1 month | | | 3 months | | |
|-------|--------------|---|-------|---|-------|-------|---|-------|-------|
|       |              | N | Value | N | Value | Delta | N | Value | Delta |
| HbA1c | All subjects | 26 | 9.22 | 23 | 8.25 | -0.97 | 14 | 7.99 | -1.23 |
|       | >=3 ablations | 16 | 9.42 | 15 | 7.91 | -1.51 | 8 | 7.08 | -2.34 |
|       | <3 ablations | 10 | 8.91 | 8 | 8.90 | -0.01 | 6 | 9.22 | 0.31 |
| FPG   | All subjects | 26 | 187.6 | 23 | 141.7 | -45.8 | 14 | 160.1 | -27.4 |
|       | >=3 ablations | 16 | 186.7 | 15 | 123.1 | -63.6 | 8 | 129.8 | -56.9 |
|       | <3 ablations | 10 | 189.0 | 8 | 176.6 | -12.4 | 6 | 200.7 | 11.7 |
| 2hPG  | All subjects | 26 | 263.1 | 20 | 199.3 | -63.9 | 14 | 207.1 | -56.0 |
|       | >=3 ablations | 16 | 268.9 | 13 | 183.6 | -85.3 | 8 | 163.8 | 105.1 |
|       | <3 ablations | 10 | 253.9 | 7 | 228.3 | -25.6 | 6 | 264.8 | 10.9 |

FIG 23

1 MONTH

| Characteristic | 3 or more | less than 3 | p-value |
|---|---|---|---|
| Number subjects | 15 | 8 | |
| Baseline HbA1c - % | 9.39 +/- 1.42 | 9.08 +/- 1.03 | 0.58 |
| HbA1c Change - % | -1.49 +/- 0.92 | -0.18 +/- 1.00 | 0.0047 |
| Baseline FPG - mg/dL | 187 +/- 68 | 202 +/- 45 | 0.61 |
| FPG Change - mg/dL | -64 +/- 74 | -25 +/- 44 | 0.19 |

3 MONTHS

| Characteristic | 3 or more | less than 3 | p-value |
|---|---|---|---|
| Number subjects | 8 | 6 | |
| Baseline HbA1c - % | 9.36 +/- 1.48 | 9.30 +/- 1.11 | 0.93 |
| HbA1c Change - % | -2.29 +/- 1.24 | -0.08 +/- 1.61 | 0.013 |
| Baseline FPG - mg/dL | 187 +/- 55 | 218 +/- 33 | 0.25 |
| FPG Change - mg/dL | -57 +/- 46 | -18 +/- 64 | 0.20 |

FIG 37

| Characteristic | Value (N=39) |
|---|---|
| Duration diabetes - yr | 5.9 +/- 2.2 |
| Age - yr | 53.7 +/- 7.3 |
| Female sex - N (%) | 14 (35.9) |
| Weight - kg | 85.1 +/- 12.0 |
| Height - cm | 165.5 +/- 8.8 |
| BMI - kg/m$^2$ | 31.0 +/- 3.4 |

FIG 38

| Treatment Received | Patients with reduction in glycemic meds | Patients with no med changes | Patients with increases in glycemic meds |
|---|---|---|---|
| LS-DMR | 13 | 12 | 1 |
| SS-DMR | 4 | 3 | 3 |

FIG 41

| Parameter | Min - Max | Average Values are expressed as medians (IQRs) unless stated otherwise |
|---|---|---|
| Age | 55-67 | 61 |
| Weight [kg] | 80.2–100.4 kg | 87.5 kg |
| HbA1c | ITT: 7.1–7.9 % <br> ITT: 54-63 mmol/mol <br> PP: 7.1–7.6 % <br> PP: 54–60 mmol/mol | ITT:7.5 % <br> ITT:58 mmol/mol <br> PP: 7.4% <br> PP: 57 mmol/mol |
| C-peptide Level [nmol/l] | ITT: 0.55–0.91 <br> PP: 0.59–0.97 | ITT:0.63 <br> PP: 0.65 |
| FPG Level | 160.2–216 | 181.8 |
| HOMA-IR | 4.3–11.8 | 8.1 |
| Fasting Insulin | ITT: 49–185 <br> PP: 58–195 | ITT: 114 <br> PP: 129 |
| BMI | 26.5–32.0 | 29.3 |
| Antidiabetic medication | | |
| Insulin Therapy Dosage - Mean number of daily units of insulin | 16–47 units | 31 units |
| Insulin monotherapy, n (%) | | 2 (12.5%) |
| Oral antidiabetic medications, n (%) | | 14 (87.5%) |
| Metformin, n (%) | | 13 (93%) |

FIG 45

| Parameter | Min - Max | Average<br>Values are expressed as medians (IQRs) unless stated otherwise |
|---|---|---|
| Cumulative Tissue Length Treated | 12 - 18 cm | 15 cm |
| Procedure Time | 46 - 56 minutes | 51 minutes |

FIG 46

| | HbA1c (mmol/mol) | Δ HbA1c | C-pep (nmol/L) | FPG (mmol/L) | HOMA-IR | Weight (kg) | Δ Weight | BMI |
|---|---|---|---|---|---|---|---|---|
| average | 55.2 | (2.8) | 0.9 | 8.5 | 3.3 | 88.5 | (6.3) | 28.1 |
| median | 52.0 | (4.0) | 0.9 | 8.5 | 3.6 | 80.8 | (6.5) | 27.9 |
| Min | 42 | -16 | 0.85 | 8.5 | 1.0 | 72.9 | (15.0) | 20.2 |
| Max | 73 | 15 | 0.85 | 8.5 | 7.4 | 136.0 | (0.9) | 39.7 |

FIG 47

| Δ C-pep (nmol/L) | Δ FPG (mmol/L) | Δ HOMA-IR | Δ BMI |
|---|---|---|---|
| 0.1 | (1.7) | (6.3) | (2.0) |
| 0.1 | (2.6) | (5.4) | (2.1) |
| -0.56 | -4.1 | (15.0) | (4.4) |

FIG 48

| Parameter | Shown as: PT GROUP: MEDIAN (Min-Max) |
|---|---|
| HbA1c [%, mmol/mol] Median (95% CI) | ITT: 7.0 (6.2-7.9) - % ITT: 53 (50-63) - mmol/mol PP: 6.7 (6.6-7.3) % PP: 50 (49-56) mmol/mol |
| Δ HbA1c [%, mmol/mol] Median (95% CI) | ITT: -0.3 (-0.6-0.3) % - p.value 0.178 ITT: -2.8 (-6.5-3.0) mmol/mol p.value = 0.178 PP: -0.6 (-0.9 - -0.2) % - p.value 0.009 PP: -5. (-8 - -2) mmol/mol - p.value = 0.009 |
| C-peptide Level | ITT: 0.55 (0.48-0.70) PP 0.58 (0.51-0.81) |
| Δ C-peptide Median (95% CI) | ITT: -0.07 (-0.16-0.02) p.value = 0.124 PP: -0.080 (-0.19-0.01) p.value = 0.183 |
| FPG Level | ITT: 8.0 (6.6-9.3) PP: 7.6 (6.3-8.8) |
| Δ FPG Level Median (95% CI) | ITT: -2.0 (-3.1 - -0.9) p.value = 0.011 PP: -2.9 (-4.2- -2.0) p.value = 0.003 |
| ALT Level in pts with elevated baseline | ITT: 21 (18-26) PP: 21 (16-21) |
| Δ ALT Level in pts with elevated baseline Median (95% CI) | ITT: -4 (-9 - -2) p.value = 0.004 PP: -4 (-8 - -2) p.value = 0.018 |
| Fasting Insulin | ITT: 43 (29-64) PP: 43 (26-83) |
| Δ Fasting Insulin Median (95% CI) | ITT: -60 (-98 - -23) p.value = 0.003 PP: -61 (-115- -27) p.value = 0.006 |
| BMI | ITT: 25.8 (24.3-29.8) kg/m² PP: 27.2 (24.3-31.9) |
| Δ BMI Median (95% CI) | ITT: -2.4 (-2.9 - -1.9) kg/m² - p.value = 0.000 PP: -2.3 (-3.0 - -1.9) kg/m² - p.value = 0.002 |
| Total body fat | ITT: 28.3 (24.9-38.3) % PP: 31.1 (24.5-38.3) % |
| Δ Total body fat Median (95% CI) | ITT: -2.8 (-3.8 - -1.8) % - p.value = 0.000 PP: -2.2 (-3.3 - -1.3) % - p.value = 0.002 |
| PDFF | ITT: 5.3 (3.9-11.9) % PP: 4.6 (2.4-11.9) % |
| Δ PDFF Median (95% CI) | ITT: -3.3 (-6.3-0.2) % - p.value = 0.053 PP: -3.6 (-6.6 - -0.5) % - p.value = 0.036 |
| FFM | ITT: 55896 (51649-65224) g PP: 58670 (59633-72817) g |
| Δ FFM Median (95% CI) | ITT: -2250 (-3337 - -1219) g - p.value = 0.002 PP: -2376 (-3502 - -1205) g - p.value = 0.003 |
| Postprandial glucose peak | ITT: 12.5 (10.4-14.6) mmol/L PP: 11.6 (10.2-13.3) mmol/L |
| Δ Postprandial glucose peak Median (95% CI) | ITT: -3.5 (-5.6 - -0.5) mmol/L - p.value = 0.030 PP: -4.6 (-6.0 - -3.0) mmol/L - p.value = 0.002 |
| Postprandial glucose AUC | ITT: 2398 (2053-2977) mmol/L*min PP: 2232 (2028-2541) mmol/L*min |
| Δ Postprandial glucose AUC Median (95% CI) | ITT: -798 (-1218 - -364) mmol/L*min - p.value = 0.005 PP: -835 (-1232- -792) mmol/L*min - p.value = 0.002 |
| Postprandial glucose iAUC | ITT: 532 (460-688) mmol/L*min PP: 482 (408-594) mmol/L*min |
| Δ Postprandial glucose iAUC Median (95% CI) | ITT: -222 (-329 - -157) mmol/L*min - p.value = 0.000 PP: -234 (-329- -157) mmol/L*min - p.value = 0.002 |

FIG 49

| Cold Reservoir Temp (°C) | Ablation Time (seconds) |
| --- | --- |
| 9.0 – 10.9 | 10.0 |
| 11.0-12.9 | 9.8 |
| 13.0-14.9 | 9.6 |
| 15.0-16.9 | 9.4 |
| 17.0-18.9 | 9.2 |
| 19.0-20.9 | 9.0 |
| 21.0-22.9 | 8.8 |
| 23.0-25.0 | 8.6 |

FIG 50

METHODS AND SYSTEMS FOR TREATING DIABETES AND RELATED DISEASES AND DISORDERS

CROSS-REFERENCE TO RELATED APPLICATIONS

This application is a continuation-in-part of U.S. patent application Ser. No. 17/096,855, filed Nov. 12, 2020, which is a continuation of U.S. patent application Ser. No. 15/406,572, filed Jan. 13, 2017, now U.S. Pat. No. 10,869,718, which is a continuation of International PCT Patent Application No. PCT/US2015/040775, filed Jul. 16, 2015, which claims the benefit of U.S. Provisional Patent Application No. 62/025,307, filed Jul. 16, 2014; this application also claims the benefit of U.S. Provisional Patent Application No. 62/273,015, filed Dec. 30, 2015; U.S. Provisional Patent Application No. 62/991,219, filed Mar. 18, 2020; U.S. Provisional Patent Application No. 63/076,737, filed Sep. 10, 2020; and U.S. Provisional Patent Application No. 63/085,375, filed Sep. 30, 2020; the contents of each of which is incorporated herein by reference in its entirety for all purposes.

This application is related to: U.S. patent application Ser. No. 13/945,138, entitled "Devices and Methods for the Treatment of Tissue", filed Jul. 18, 2013; U.S. patent application Ser. No. 15/917,480, entitled "Devices and Methods for the Treatment of Tissue", filed Mar. 9, 2018; U.S. patent application Ser. No. 16/438,362, entitled "Heat Ablation Systems, Devices and Methods for the Treatment of Tissue", filed Jun. 11, 2019; U.S. patent application Ser. No. 14/515,324, entitled "Tissue Expansion Devices, Systems and Methods", filed Oct. 15, 2014; U.S. patent application Ser. No. 16/711,236, entitled "Electrical Energy Ablation Systems, Devices and Methods for the Treatment of Tissue", filed Dec. 11, 2019; U.S. patent application Ser. No. 14/609,334, entitled "Ablation Systems, Devices, and Methods for the Treatment of Tissue", filed Jan. 29, 2015; U.S. patent application Ser. No. 14/673,565, entitled "Methods, Systems and Devices for Performing Multiple Treatments on a Patient", filed Mar. 30, 2015; U.S. patent application Ser. No. 16/379,554, entitled "Methods, Systems and Devices for Reducing the Luminal Surface Area of the Gastrointestinal Tract", filed Apr. 9, 2019; U.S. patent application Ser. No. 14/917,243, entitled "Systems, Methods and Devices for Treatment of Target Tissue", filed Mar. 7, 2016; U.S. patent application Ser. No. 16/742,645, entitled "Intestinal Catheter Device and System", filed Jan. 14, 2020; U.S. patent application Ser. No. 16/900,563, entitled "Injectate Delivery Devices, Systems and Methods", filed Jun. 12, 2020; U.S. patent application Ser. No. 16/798,117, entitled "Systems, Devices and Methods for Performing Medical Procedures in the Intestine", filed Feb. 21, 2020; U.S. patent application Ser. No. 15/812,969, entitled "Systems, Devices and Methods for Performing Medical Procedures in the Intestine", filed Nov. 14, 2017; U.S. patent application Ser. No. 16/400,491, entitled "Systems, Devices and Methods for Performing Medical Procedures in the Intestine", filed May 1, 2019; U.S. patent application Ser. No. 16/905,274, entitled "Material Depositing System for Treating a Patient", filed Jun. 18, 2020; International PCT Patent Application Serial Number PCT/US2019/54088, entitled "Systems and Methods for Deposition Material in a Patient", filed Oct. 1, 2019; International PCT Patent Application Serial Number PCT/US2020/025925, entitled "Systems, Devices and Methods for Treating Metabolic Medical Conditions", filed Mar. 31, 2020; International PCT Patent Application Serial Number PCT/US2020/056627, entitled "Systems, Devices, and Methods for Performing Medical Procedures in the Intestine", filed Oct. 21, 2020; U.S. patent application Ser. No. 17/095,108, entitled "Systems, Devices and Methods for the Creation of a Therapeutic Restriction in the Gastrointestinal Tract", filed Nov. 11, 2020; U.S. patent application Ser. No. 17/096,855, entitled "Methods and Systems for Treating Diabetes and Related Diseases and Disorders", filed Nov. 12, 2020; U.S. patent application Ser. No. 17/110,720, entitled "Injectate Delivery Devices, Systems and Methods", filed Dec. 3, 2020; International PCT Patent Application Serial Number PCT/US2021/013072, entitled "Tissue Treatment Devices, Systems, and Methods", filed Jan. 12, 2021; and International PCT Patent Application Serial Number PCT/US2021/013600, entitled "Automated Tissue Treatment Devices, Systems, and Methods", filed Jan. 15, 2021; the contents of each of which is incorporated herein by reference in its entirety for all purposes.

TECHNICAL FIELD

The embodiments disclosed herein relate generally to methods, systems, and devices for treating a patient, particularly for treating tissue of the gastrointestinal tract to provide a therapy.

BACKGROUND OF THE INVENTION

The current paradigm for medical therapy for type 2 diabetes begins with improvements in diet and exercise. The vast majority of patients do not achieve sustained good glycemic control with lifestyle changes alone. Several classes of pharmacologic therapy are available, including drugs that increase insulin secretion from the pancreas, drugs that enhance the body's sensitivity to insulin, and a variety of other drug classes. Despite these oral therapies, diabetes control will usually deteriorate over time and treatment with insulin will become necessary. All told, however, a large proportion of patients remain poorly controlled despite all of these measures.

There are many reasons for the limited effectiveness of current pharmacologic interventions in the general population. First, today's medicines may lower blood sugar but they do not address the fundamental pathogenesis of Type 2 Diabetes. Second, poor compliance to complicated pharmacologic regimens is well documented and a structural barrier to better glycemic control. Third, clinical inertia on the part of physicians prevents drug regimen escalation even in patients with access to excellent medical care. Fourth, psychological resistance to insulin prevents the use of this class of agents. Fifth, hypoglycemia (and the risk thereof) limits the degree of pharmacologic intervention with which physicians and patients feel comfort. Taken together, nearly 50% of patients remain poorly controlled throughout Europe and the United States.

Interestingly, certain forms of bariatric surgery have a profound anti-diabetic effect in ways that clinicians have only begun to appreciate and characterize. Though the mechanisms underlying this improvement in glucose homeostasis are not completely understood, certain compelling observations have been made. In particular, surgeries that divert the passage of nutrients around the duodenum (or first portion of the small intestine) appear to lead to nearly immediate, extremely durable, and weight-independent anti-diabetic effects. Because the GI tract is the largest endocrine organ in the body, the bypass of the proximal small bowel leads to hormonal changes that improve glucose homeostasis. This effect appears to occur without substantial changes in absorption from the intestine. Rather, these hormonal changes restore the ability of the liver and muscle to suppress endogenous glucose production in response to insulin, a physiologic process that is otherwise impaired in patients with diabetes.

There are two main theories as to why bypass of the proximal small bowel exert such a strong anti-diabetic effect, both of which are likely at least partial contributors. First, some believe that the delivery of excess nutrients to the distal small bowel leads to enhanced secretion of GLP-1 (and perhaps additional related insulin secreting hormones) from the GLP-1-rich entero-endocrine cells of the terminal ileum and colon. Enhanced GLP-1 release into the blood stream after an ingested meal has a number of beneficial effects on glucose homeostasis. A second theory is that patients with diabetes acquire mucosal alterations in their proximal small bowel that contribute to insulin resistance and glucose intolerance. Data from rats and humans suggest that prolonged exposure to a Western diet leads to an increase in enteroendocrine cell numbers and subsequent gastric inhibitory peptide (GIP) after a meal. Other studies have demonstrated hypertrophy of the mucosa of the small bowel in patients with diabetes. In this way, the body's insulin resistance arises from hormones produced by the proximal small bowel as a consequence of these mucosal alterations. Bypass of nutrients around the duodenum prevents the release of these hormones and therefore immediately leads to an improvement in glucose tolerance after surgery.

Unfortunately, as effective as these bariatric surgeries are, one cannot imagine that surgery can be offered to enough patients to adequately address the diabetes pandemic. There are several reasons for this limitation. The primary indication for bariatric surgery remains morbid obesity, yet most diabetics are not morbidly obese. Also, the risks (of major morbidity, mortality, and need for re-operation) from bypass surgeries are quite real and pose a significant barrier to its wholesale adoption as a treatment for type 2 diabetes. Finally, surgery is invasive, psychologically difficult, and physically demanding. For all these reasons, only a minority of patients with diabetes currently undergoes surgery as a treatment for their diabetes.

For these and other reasons, there is a need for improved systems, devices and method for the treatment of diabetes and similar patient diseases and disorders.

SUMMARY

According to an aspect of the present inventive concepts, a method of treating a medical condition of a patient comprises: selecting a patient diagnosed with type 2 diabetes that is being treated with daily insulin at a first dosage level and having a first HbA1c level of at least 7.5% and performing a tissue treatment procedure comprising treating one or more segments of the selected patient's intestinal tissue, such that the tissue segments comprise duodenal mucosal tissue and/or duodenal submucosal tissue. After the tissue treatment procedure is performed, the selected patient receives daily insulin at a second dosage level less than the first dosage level and maintains a second HbA1c level that is no greater than the first HbA1c level.

In some embodiments, the selected patient has a c-peptide level of at least 0.5 ng/mL prior to the performing of the tissue treatment procedure.

In some embodiments, the second HbA1c level comprises an HbA1c level of the selected patient measured 24 weeks after the performance of the tissue treatment procedure.

In some embodiments, the second HbA1c level is less than the first HbA1c level. The second HbA1c level can comprise a level of at least 0.5% less than the first HbA1c level.

In some embodiments, the second HbA1c level comprises an HbA1c level less than or equal to 7.5%. The second HbA1c level can comprise an HbA1c level less than or equal to 7.0% The second dosage level can be zero units of insulin per day.

In some embodiments, the tissue treatment procedure comprises ablating the duodenal mucosal tissue and/or duodenal submucosal tissue.

In some embodiments, the tissue treatment procedure comprises ablating neuronal cells of the duodenal mucosa and/or duodenal submucosa.

In some embodiments, the tissue treatment procedure comprises a tissue treatment selected from the group consisting of: thermal coagulation; desiccation; non-desiccating tissue ablation; heat ablation; cryoablation; radiofrequency ablation; electroporation; ultrasound and/or other sound-based ablation; sonoporation; laser and/or other light-based ablation; mechanical abrasion; chemical abrasion and/or chemical ablation; and combinations thereof.

In some embodiments, the method results in a therapeutic benefit to the selected patient comprising a decrease in total body weight.

In some embodiments, the method results in a therapeutic benefit to the selected patient comprising a weight loss of at least 5% of the patient's weight prior to the performing of the tissue treatment procedure.

In some embodiments, the method results in a therapeutic benefit to the selected patient comprising a reduced risk of hypoglycemia. The risk of hypoglycemia can be reduced to a level of no more than 0.1% occurrence rate of serious hypoglycemic events per year.

In some embodiments, the second dosage level is zero units of insulin per day.

In some embodiments, the second dosage level is no more than 50% of the first dosage level.

In some embodiments, the first dosage level comprises a level of at least 10 units of insulin per day. The first dosage level can comprise a level of at least 20 units of insulin per day. The first dosage level can comprise a level of at least 50 units of insulin per day. The first dosage level can comprise a level of at least 60 units of insulin per day.

In some embodiments, the first dosage level comprises a level of at least 0.5 units of insulin per kilogram of patient body weight per day.

In some embodiments, at the time of selection, the selected patient is further taking a non-insulin anti-diabetic medication.

In some embodiments, at the time of selection, the selected patient has a c-peptide level of at least 0.6 ng/mL. At the time of selection, the selected patient can have a c-peptide level of at least 1.0 ng/mL.

In some embodiments, at the time of selection, the selected patient further comprises a patient with a fasting plasma glucose level of at least 140 mg/dL. At the time of selection, the selected patient can further comprise a patient with a fasting plasma glucose level of at least 160 mg/dL. At the time of selection, the selected patient can further comprise a patient with a fasting plasma glucose level of at least 180 mg/dL.

In some embodiments, the method further comprises the selected patient taking at least one non-insulin anti-diabetic medication after the performance of the tissue treatment procedure.

According to another aspect of the present inventive concepts, a system for treating target tissue comprises a tissue treatment device comprising a tissue treatment element constructed and arranged to treat target tissue, the target tissue comprising duodenal mucosa. The system is constructed and arranged to provide a therapeutic benefit to the patient, such as to treat diabetes or another patient disease or disorder.

In some embodiments, the system is configured to counteract duodenal mucosal changes that cause an intestinal hormonal impairment leading to insulin resistance in patients.

In some embodiments, the system is configured to improve the body's ability to process sugar and/or to improve glycemic control in patients with insulin resistance and/or Type 2 diabetes.

In some embodiments, the system is configured to treat diabetes.

In some embodiments, the system is configured to treat hypercholesterolemia.

In some embodiments, the system is configured to treat at least one of a disease or disorder selected from the group consisting of: diabetes; pre-diabetes; impaired glucose tolerance; insulin resistance; obesity or otherwise being overweight; a metabolic disorder and/or disease; and combinations thereof.

In some embodiments, the system is configured to treat at least one of a disease or disorder selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease; stroke; TIA; cognitive decline; dementia; diabetic nephropathy; neuropathy; retinopathy; diabetic heart disease; diabetic heart failure; and combinations thereof.

In some embodiments, the system is configured to treat two or more of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease; stroke; TIA; cognitive decline; dementia; diabetic nephropathy; neuropathy; retinopathy; diabetic heart disease; and diabetic heart failure.

In some embodiments, the system is configured to avoid treatment of non-target tissue. The non-target tissue can comprise the ampulla of Vater. The non-target tissue can comprise tissue selected from the group consisting of: gastrointestinal adventitia; duodenal adventitia; the tunica serosa; the tunica muscularis; the outermost partial layer of the submucosa; ampulla of Vater; pancreas; bile duct; pylorus; and combinations thereof.

In some embodiments, the target tissue comprises at least two axial segments of duodenal mucosa, and the therapeutic benefit results from the treatment of the at least two axial segments by the tissue treatment element. Each axial segment can comprise a length between approximately 1.9 cm and 3.3 cm. Each axial segment can comprise a length of approximately 3 cm. The target tissue can comprise an approximately full circumferential portion of each axial segment (i.e. approximately 360° of the mucosal layer of each axial segment) or a partial circumferential portion of each axial segment (i.e. less than 3600 of the mucosal layer of each axial segment).

In some embodiments, the target tissue comprises at least four (full or partial circumferential) axial segments of duodenal mucosa, and the therapeutic benefit results from the treatment of the at least four axial segments by the tissue treatment element. The target tissue can comprise at least six axial segments of duodenal mucosa, and the therapeutic benefit results from the treatment of the at least six axial segments by the tissue treatment element. Each axial segment can comprise a length between approximately 0.7 cm and 2.0 cm.

In some embodiments, the system is configured to cause a therapeutic benefit selected from the group consisting of: improvement in HbA1c, fasting glucose and/or post-prandial glucose; at least a 1% improvement in HbA1c; a resultant HbA1c of less than 7.5%, less than 7.0%, less than 6.5%, or less than 6.0%; improvement in one or more triglyceride levels; improvement in AST, ALT, liver fibrosis panel, liver fibrosis score, NAFLD assessment and/or or NASH assessment; improvement in risk of myocardial infarction, stroke, TIA and/or peripheral vascular disease or diabetic cardiomyopathy; improvement in microvascular disease risk such as nephropathy, retinopathy and/or neuropathy; reduced development of end-stage renal disease, blindness and/or amputation; reduced insulin requirement (e.g. in patients with insulin-dependent diabetes) or other injectable therapy requirement; reduced medication requirement (e.g. in patients with diabetes) either in number of medicines or dosage of medicines; improved fetal birth outcomes (e.g. in patients with gestational diabetes); improved fertility in patients with polycystic ovarian syndrome and/or reduced hirsutism; weight loss of at least 5% of excess body weight, or at least 10%, 20%, 30% or 40% of excess body weight; reduced blood pressure; reduced cardiovascular risk; improved diabetes control and/or reduced diabetic complications; reduced obesity and/or reduced weight; reduced cognitive decline or prevention of dementia; and combinations thereof. The therapeutic benefit can have a clinically significant durability of at least 3 months. The therapeutic benefit can have a clinically significant durability of at least 6 months, or at least 1 year.

In some embodiments, the system is configured to reduce the HbA1c level of the patient. The system can be configured to cause an HbA1c reduction of approximately 2.18%. The system can be configured to cause an HbA1c reduction of at least 0.7%. The system can be configured to cause an HbA1c reduction of at least 1.0%. The system can be configured to cause an HbA1c reduction of at least 1.5%. The system can be configured to cause an HbA1c reduction of at least 2.0%. The system can be configured to cause an HbA1c reduction of at least 2.5%. The system can be configured to reduce HbA1c to a target level less than or equal to 7.5%. The system can be configured to reduce HbA1c to a target level less than or equal to 7.0%. The system can be configured to reduce HbA1c to a target level less than or equal to 5.5%. The system can be configured to cause an HbA1c level below 7.5% at least 150 days after performance of the target tissue treatment.

In some embodiments, the system is configured to reduce FPG. The system can be configured to cause an FPG reduction of approximately 63.5 mg/dl. The system can be configured to reduce FPG to a target level less than or equal to 150 mg/dl. The system can be configured to reduce FPG to a target level less than or equal to 126 mg/dl. The system can be configured to reduce FPG to a target level less than or equal to 100 mg/dl.

In some embodiments, the system is configured to improve fasting glucose and/or HbA1c without causing a significant decline in fasting insulin and/or post-prandial insulin.

In some embodiments, the system is configured to improve beta cell insulin secretory capacity for at least 3 months. The system can be configured to improve beta cell insulin secretory capacity for at least 6 months, or at least 1 year.

In some embodiments, the system is configured to prevent the decline of beta cell insulin secretory capacity for at least 3 months.

In some embodiments, the system is configured to reduce 2hPG. The system can be configured to cause a 2hPH reduction of approximately 103.7 mg/dl. The system can be configured to reduce 2hPG to a target level less than or equal to 250 mg/dl. The system can be configured to reduce 2hPG to a target level less than or equal to 200 mg/dl. The system can be configured to reduce 2hPG to a target level less than or equal to 175 mg/dl.

In some embodiments, the system is configured to provide an improvement in a patient condition as measured by the SF-36 Health Survey. The improvement can comprise an improvement in the Mental Change score of the SF-36 Health Survey. The improvement can comprise a score change of at least 3 points, or at least 5 points. The improvement can comprise a score change of at least 10 points.

In some embodiments, the system is configured to provide a reduction in excess body weight of the patient. The reduction can comprise a reduction of at least 5% of excess body weight. The reduction can comprise a reduction of at least 10% of excess body weight. The reduction can comprise a reduction of at least 20% of excess body weight. The reduction can comprise a reduction of at least 30% of excess body weight. The reduction can comprise a reduction of at least 40% of excess body weight.

In some embodiments, the system is configured to treat a patient with a duration of diabetes less than 10 years.

In some embodiments, the system is configured to treat a patient with an age between 18 years and 75 years.

In some embodiments, the system is configured to treat a patient with an age between 5 years and 18 years.

In some embodiments, the system is configured to treat a patient with a BMI between 22 and 60.

In some embodiments, the system is configured to treat a patient with an HbA1c between 6.0% and 12.0%. The system can be configured to treat a patient with an HbA1c between 7.5% and 12.0%. The system can be configured to treat a patient with an HbA1c between 7.5% and 10.0%, such as between 7.5% and 9.0%.

In some embodiments, the target tissue further comprises non-duodenal mucosa tissue.

In some embodiments, the target tissue comprises duodenal mucosa located distal to the ampulla of Vater.

In some embodiments, the target tissue comprises at least 10% of the duodenal mucosa located distal to the ampulla of Vater.

In some embodiments, the target tissue comprises at least 15% of the duodenal mucosa located distal to the ampulla of Vater.

In some embodiments, the target tissue comprises at least 25% of the duodenal mucosa located distal to the ampulla of Vater.

In some embodiments, the target tissue comprises at least 15% of the duodenal mucosa located distal to the ampulla of Vater.

In some embodiments, the target tissue comprises at least 50% of the duodenal mucosa located distal to the ampulla of Vater.

In some embodiments, the target tissue comprises an axial length (e.g. a cumulative axial length) of duodenal mucosa of at least 6 cm, such as at least 7 cm, at least 8 cm, at least 9 cm or approximately 9.3 cm of duodenal mucosa. The cumulative axial length can be treated by treating (e.g. ablating) one or more (e.g. three) full or partial circumferential axial segments of the duodenum.

In some embodiments, the target tissue does not comprise any duodenal mucosa located proximal to the ampulla of Vater.

In some embodiments, the target tissue comprises no more than 70% of the duodenal mucosa located distal to the ampulla of Vater and the target tissue does not comprise any duodenal mucosa tissue located proximal to the ampulla of Vater.

In some embodiments, the target tissue comprises no more than 90% of the duodenal mucosa located distal to the ampulla of Vater and the target tissue does not comprise any duodenal mucosa tissue located proximal to the ampulla of Vater.

In some embodiments, the target tissue comprises tissue located at least 1cm distal to the ampulla of Vater, such as when the target tissue does not include tissue within 1 cm of the ampulla of Vater.

In some embodiments, the system further comprises at least one deployable marker, and the target tissue comprises tissue selected based on the deployment location of the at least one marker.

In some embodiments, the system is configured to alter the intestinal mucosal hormone production from the region of treated target tissue.

In some embodiments, the system is configured to alter a hormonal secretion pattern that affects blood glucose levels in the fasting and post-prandial states.

In some embodiments, the system is configured to change the blood levels of GIP and/or GLP-1 to change glucose homeostasis in the fasting and/or post-prandial states.

In some embodiments, the system is configured to change insulin and/or glucagon secretion from the pancreas and/or insulin and/or glucagon levels in the bloodstream.

In some embodiments, the system is configured to change pancreatic beta cell function and/or health through direct hormonal consequences of the treated duodenal tissue and/or indirectly through improved blood glucose levels.

In some embodiments, the system is configured to cause a change in a patient secretion parameter. The system can be configured to cause the change in a patient secretion parameter by causing an effect selected from the group consisting of: modifying the target tissue; ablating, removing and/or causing the necrosis of the target tissue resulting in replacement of the target tissue with new tissue; reducing the surface area of the target tissue; and combinations thereof. The system can be configured to modify the target tissue to cause the change in a patient secretion parameter. The modified target tissue can comprise tissue with different secretion parameters than the pre-treated tissue. The modified target tissue can comprise tissue with reduced surface area than the pre-treated tissue. The system can be configured to ablate, cause the necrosis of and/or remove the target tissue, resulting in replacement of the target tissue with new tissue, to cause the change in a patient secretion parameter. The new tissue can comprise tissue with different secretion parameters than the pre-treated tissue. The new tissue can comprise tissue with reduced surface area than the pre-treated tissue. The patient secretion parameter can comprise a secretion parameter selected from the group consisting of: quantity of a patient secretion during a time period; average rate of a patient secretion during a time period; peak excursion of a patient secretion parameter; and combinations thereof. The system can be configured to cause a change in multiple patient secretion parameters. The change in a patient secretion parameter can be exhibited when the patient is in a state selected from the group consisting of: fasting state; post-prandial state; and combinations thereof. The change in a patient secretion parameter can comprise at least a 10% reduction in GIP secretions. The at least a 10% reduction in GIP secretions can comprise at least a 10% reduction in the amount of GIP secreted in a time period. The at least a 10% reduction in GIP secretions can comprise at least a 10% reduction in the average rate of GIP secretions during a time period. The at least a 10% reduction in GIP secretions can comprise at least a 25% reduction in GIP secretions. The at least a 10% reduction in GIP secretions can comprise at least a 50% reduction in GIP secretions. The change in a patient secretion parameter can result in a reduction in GIP serum concentration selected from the group consisting of: reduced 10%; reduced 25%; and/or reduced 50%. The change in a patient secretion parameter can comprise at least a 10% increase in GLP-1 secretions. The at least a 10% increase in GLP-1 secretions can comprise at least a 10% increase in the amount of GLP-1 secreted in a time period. The at least a 10% increase in GLP-1 secretions can comprise at least a 10% increase in the average rate of GLP-1 secretions during a time period. The at least a 10% increase in GLP-1 secretions can comprise at least a 25% increase in GLP-1 secretions. The at least a 10% increase in GLP-1 secretions can comprise at least a 50% increase in GLP-1 secretions. The change in a patient secretion parameter can result in an increase in GLP-1 serum concentration selected from the group consisting of: increased 10%; increased 25%; and/or increased 50%. The change in a patient secretion parameter can comprise at least a 10% reduction in glucagon secretions. The at least a 10% reduction in glucagon secretions can comprise at least a 10% reduction in the amount of glucagon secreted in a time period. The at least a 10% reduction in glucagon secretions can comprise at least a 10% reduction in the average rate of glucagon secretions during a time period. The at least a 10% reduction in glucagon secretions can comprise at least a 25% reduction in glucagon secretions. The at least a 10% reduction in glucagon secretions can comprise at least a 50% reduction in glucagon secretions. The change in a patient secretion parameter can result in a reduction in glucagon serum concentration selected from the group consisting of: reduced 10%; reduced 25%; and reduced 50%.

In some embodiments, the system is configured to cause a change in a patient absorption parameter. The system can be configured to cause the change in a patient absorption parameter by causing an effect selected from the group consisting of: modifying the target tissue; ablating, removing and/or causing the necrosis of target tissue resulting in replacement of the target tissue with new tissue; reducing the surface area of the target tissue; and combinations thereof. The system can be configured to modify the target tissue to cause the change in a patient absorption parameter. The modified target tissue can comprise tissue with different absorption parameters than the pre-treated tissue. The modified target tissue can comprise tissue with reduced surface area than the pre-treated tissue. The system can be configured to ablate, cause the necrosis of and/or remove the target tissue, resulting in replacement of the target tissue with new tissue, to cause the change in a patient absorption parameter. The new tissue can comprise tissue with different absorption parameters than the pre-treated tissue. The new tissue can comprise tissue with reduced surface area than the pre-treated tissue. The patient absorption parameter can comprise an absorption parameter selected from the group consisting of: quantity of a substance absorbed during a time period; average rate of a substance absorbed during a time period; and combinations thereof. The system can be configured to cause a change in multiple patient absorption parameters. The change in a patient absorption parameter can be exhibited when the patient is in a state selected from the group consisting of: fasting state; post-prandial state; and combinations thereof. The change in a patient absorption parameter can comprise at least a 10% decrease in glucose absorption. The at least a 10% decrease in glucose absorption can comprise at least a 10% decrease in the amount of glucose absorbed in a time period. The at least a 10% decrease in glucose absorption can comprise at least a 10% decrease in the average rate of glucose absorption during a time period. The at least a 10% decrease in glucose absorption can comprise at least a 25% decrease in glucose absorption. The at least a 10% decrease in glucose absorption can comprise at least a 50% decrease in glucose absorption.

In some embodiments, the system is configured to cause a decrease in GIP and an increase in GLP-1.

In some embodiments, a pre-treatment GIP/GLP-1 ratio comprises the ratio of GIP secretion levels prior to the treatment of the target tissue compared to the GLP-1 secretion levels prior to the treatment of the target tissue, and a post-treatment GIP/GLP-1 ratio comprises the ratio of GIP secretion levels after the treatment of the target tissue compared to the GLP-1 secretion levels after the treatment of the target tissue. A treatment effect comprises the ratio of the post-treatment GIP/GLP-1 ratio compared to the pre-treatment GIP/GLP-1 ratio and the system can be configured to cause a treatment effect of less than 1.0. The system can be configured to cause a treatment effect of less than 0.90. The system can be configured to cause a treatment effect of less than 0.75. The system can be configured to cause a treatment effect of less than 0.50.

In some embodiments, the tissue treatment device further comprises a tissue expanding element.

In some embodiments, the tissue treatment element comprises an element selected from the group consisting of: an ablative fluid delivered to a balloon or other expandable fluid reservoir; a tissue treatment element comprising an energy delivery element mounted to an expandable assembly such as an electrode or other energy delivery element configured to deliver radiofrequency (RF) energy and/or microwave energy; a light delivery element configured to deliver laser or other light energy; a fluid delivery element configured to deliver ablative fluid directly onto tissue; a sound delivery element such as a ultrasonic and/or subsonic sound delivery element; and combinations thereof.

In some embodiments, the tissue treatment element comprises a first tissue treatment element and a second tissue treatment element. The first tissue treatment element can be dissimilar to the second tissue treatment element.

In some embodiments, the tissue treatment device further comprises an expandable balloon, and the tissue treatment element comprises ablative fluid delivered to the expandable balloon. The ablative fluid can comprise fluid at sufficiently high temperature to cause tissue necrosis. The expandable balloon can comprise a material selected from the group consisting of: polyethylene terephthalate (PET); nylon; latex; polyurethane; Pebax; and combinations thereof. The expandable balloon can comprise a wall comprising a thickness between approximately 0.0002" and 0.0020". The expandable balloon can comprise a wall comprising a thickness of approximately 0.0005". The expandable balloon can comprise a wall comprising a thickness of approximately 0.0010". The expandable balloon can comprise a tissue contacting portion. The tissue contacting portion can comprise a diameter of between approximately 19.0 mm and 32.0 mm. The tissue contacting portion can comprise a length of between approximately 16.0 mm and 35.0 mm. The tissue contacting portion can comprise a length of between approximately 19.5 mm and 32.9 mm. The tissue contacting portion can comprise a surface area of between approximately 1750 mm$^2$ and 2150 mm$^2$. The tissue contacting portion can comprise a surface area of approximately 1950 mm$^2$. The expandable balloon can comprise a tapered distal end. The expandable balloon tapered distal end can comprise a taper between approximately 27° and 33°. The expandable balloon can comprise a tapered proximal end. The expandable balloon tapered proximal end can comprise a taper between approximately 420 and 48°. The expandable balloon can be constructed and arranged to be filled with approximately 10 ml to 35 ml of ablative fluid. The tissue treatment device can comprise a first tissue treatment device, and the system can further comprise a second tissue treatment device comprising a second tissue treatment element and a second expandable balloon. The first tissue treatment device expandable balloon can comprise a first tissue contacting surface area and the second expandable balloon can comprise a second tissue contacting surface area similar to the first tissue contacting surface area. The first tissue treatment device expandable balloon can comprise a different length and/or diameter than the second expandable balloon of the second tissue treatment device.

In some embodiments, the system is configured to both cool and heat the target tissue. The system can be configured to: in a first step, cool the target tissue with the tissue treatment element by supplying a first fluid to the treatment element for a first time period, and the first fluid is supplied within a first temperature range; in a second step, heat the target tissue with the tissue treatment element by supplying a second fluid to the treatment element for a second time period, and the second fluid is supplied within a second temperature range; and in a third step, cool the target tissue with the tissue treatment element by supplying a third fluid to the treatment element for a third time period, and the third fluid is supplied within a third temperature range. The heating of the target tissue in the second step can be configured to ablate the target tissue. The first time period can comprise a duration (e.g. a time duration) of between approximately 15 seconds and 30 seconds. The first temperature range can comprise one or more temperatures between approximately 5° C. and 25° C., such as between 15° C. and 25° C. The second time period can comprise a duration of between approximately 8 seconds and 15 seconds. The first temperature range can comprise one or more temperatures between approximately 85° C. and 95° C. The second time period can comprise a duration of between approximately 15 seconds and 30 seconds. The first temperature range can comprise one or more temperatures between approximately 5° C. and 25° C., such as between 15° C. and 25° C. The second time period can comprise a duration less than the first time period duration. The second time period can comprise a duration less than the third time period duration. The second time period can comprise a duration less than both the first time period duration and the third time period duration. The second temperature can comprise a temperature at least 180 above the first temperature and/or the third temperature. The second temperature can comprise a temperature at least 600 above the first temperature and/or the third temperature. The first temperature and the third temperature can comprise similar temperatures.

In some embodiments, the tissue treatment device comprises an expandable assembly comprising the tissue treatment element, and the system is configured to monitor the pressure and/or volume of the expandable assembly. The system can be configured to use the monitored pressure and/or volume to compensate for peristalsis and/or muscle contractions of the GI tract. The system can be configured to use the monitored pressure and/or volume to compensate for changes in GI tract lumen diameter.

In some embodiments, the system is configured expand tissue, and the system is further configured to only ablate target tissue comprising: the expanded tissue and/or tissue proximate the expanded tissue.

In some embodiments, the tissue treatment element comprises ablative fluid and the tissue treatment device comprises an expandable balloon constructed and arranged to receive the ablative fluid. The expandable balloon comprises a tissue contacting portion including a length, and the system is configured to translate the expandable balloon approximately the length of the tissue contacting portion after a first portion of target tissue is treated. The translation can comprise a manual translation (e.g. performed by a clinician). The system can further comprise a motion transfer assembly and the translation comprises at least a semi-automated translation.

In some embodiments, the system is configured to treat a first, second and third portion of target tissue and to perform an assessment of the distance between the most proximal tissue treated and non-target tissue. The second target tissue portion can be distal to the third target tissue portion, and the first target tissue portion can be distal to the second target tissue portion, and the system can be configured to treat the first target tissue portion, the second target tissue portion, and then the third target tissue portion sequentially. The non-target tissue can comprise the ampulla of Vater, and non-target tissue can include tissue within 1 cm of the ampulla of Vater (e.g. on either side). The system can be configured to treat a fourth portion of target tissue proximal to the most proximal tissue treated, if the distance between the most proximal tissue treated and the non-target tissue is above a threshold.

In some embodiments, the system is configured to prevent two ablations within a pre-determined time period. The pre-determined time period can be configured to prevent repetitive ablations in similar portions of the GI tract.

In some embodiments, the system is configured to prevent a tissue ablation and/or tissue treatment until a submucosal expansion step has been performed.

In some embodiments, the system is configured to expand tissue, and the treatment of the target tissue is completed within 120 minutes of initiating tissue expansion. The treatment of the target tissue can be completed within 60 minutes of initiating tissue expansion. The treatment of the target tissue can be completed within 45 minutes of initiating tissue expansion.

In some embodiments, the system is configured to select target tissue based on a patient condition. The amount of target tissue can be proportional to the severity of the patient condition. The amount of target tissue can be proportional to the disease burden of the patient condition. An elevated disease burden can comprise one or more of relatively long duration since diagnosis; higher HbA1c level than a standard diabetic patient; and more mucosal hypertrophy than a standard diabetic patient. The amount of target tissue can be proportional to the HbA1c level of the patient.

In some embodiments, the system is configured to provide post-procedure management of the patient after the treatment of the target tissue. The post-procedure management can comprise a liquid diet for at least one day. The post-procedure management can comprise a low sugar diet and/or a low fat diet for at least one week. The post-procedure management can comprise a standardized diabetic diet for at least 1 week. The post-procedure management can comprise nutritional counseling for at least 1 week.

In some embodiments, the system further comprises a console configured to interface with at least the tissue treatment device. The console can comprise a controller. The console can comprise an energy delivery unit. The tissue treatment element can comprise ablative fluid and the energy delivery unit can be constructed and arranged to provide the ablative fluid to the tissue treatment device. The console can comprise a user interface. The console can comprise a safety-switch. The safety-switch can be configured to be activated without articulation of an operator digit of a hand. The tissue treatment device can comprise an expandable assembly, and the system can be configured to automatically contract the expandable assembly if the safety-switch is not activated. The tissue treatment device can comprise a balloon, the tissue treatment element can comprise ablative fluid, the system can comprise neutralizing fluid, and the system can be configured to automatically replace ablative fluid in the balloon with the neutralizing fluid if the safety switch is not activated. The tissue treatment device can comprise a balloon, the tissue treatment element can comprise ablative fluid, the system can comprise cooling fluid, and the system can be configured to deliver the ablative fluid to the balloon upon activation of the safety-switch, such as at a time after which cooling fluid has been delivered to the balloon and an operator has confirmed proper position of the balloon for treatment of target tissue. The safety-switch can be configured to allow hands-free activation and/or maintenance of a treatment step such that one or more operators can maintain their hands on one or more of: the tissue treatment device; an endoscope; a tissue expansion device; and a lumen diameter sizing device. The safety-switch can comprise a foot activated switch. The safety-switch can comprise a hand-detection sensor. The tissue treatment device can comprise a handle, and the safety switch can be constructed and arranged to detect the position of an operator hand on at least the tissue treatment device handle. The system can comprise an endoscope including a handle, and the safety switch can be constructed and arranged to detect the position of an operator hand on at least the endoscope handle. The console can comprise a pressure assembly. The console can comprise a fluid source. The console can comprise a functional element.

In some embodiments, the system further comprises a functional element. The tissue treatment device can comprise the functional element. The system can further comprise a console and the console can comprise the functional element. The system can further comprise a tissue expansion device, and the tissue expansion device can comprise the functional element. The system can further comprise a gastrointestinal lumen sizing device and the sizing device can comprise the function element. The functional element can comprise a sensor selected from the group consisting of: temperature sensor such as a thermocouple, thermistor, resistance temperature detector and optical temperature sensor; strain gauge; impedance sensor such as a tissue impedance sensor; pressure sensor; blood sensor; optical sensor such as a light sensor; sound sensor such as an ultrasound sensor; electromagnetic sensor such as an electromagnetic field sensor; visual sensor; and combinations thereof. The functional element can comprise a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; a motor; a vibrational transducer; a fluid agitating element; and combinations thereof.

In some embodiments, the system further comprises a tissue expansion device including at least one fluid delivery element constructed and arranged to deliver injectate to expand one or more tissue layers. The system can further comprise an injectate, and the injectate is selected from the group consisting of water; saline; a fluid with a dye such as a visible dye such as indigo carmine; methylene blue; India ink; SPOT™ dye; a gel; a hydrogel; a protein hydrogel; a fluid containing a visualizable media such as a media visualizable under X-ray, ultrasound imaging and/or magnetic resonance imaging; ethylene vinyl alcohol (EVOH); and combinations thereof. The tissue expansion device can comprise an expandable balloon and the at least one fluid delivery element can be attached to the balloon. The tissue expansion device can further comprise a tissue capture port surround the at least one fluid delivery element. The system can be configured to deliver a first fluid volume to the expandable balloon and measure a first pressure and to deliver a second fluid volume to the expandable balloon and measure a second pressure, such as when the second fluid of volume is less than the first fluid volume. The system can be further configured to apply a first vacuum while the expandable balloon is filled with the second volume of fluid, to cause tissue to enter the tissue capture port. The system can be configured to confirm the first pressure is less than the second pressure. The tissue expansion device can further comprise an expandable assembly comprising the at least one fluid delivery element. The expandable assembly can comprise an expandable balloon. The system can be configured to measure the pressure and/or volume and to determine if a proper volume of the injectate has been delivered to achieve adequate tissue expansion based on the measured pressure and/or volume. The system can be configured to expand tissue located at least 0.5 cm distal to the ampulla of Vater, such as when tissue within 0.5 cm distal to the ampulla of Vater is not expanded and/or is not subsequently ablated. The system can be configured to expand tissue located at least 1 cm distal to the ampulla of Vater, such as when tissue within 1 cm of the ampulla of Vater is not expanded and/or is not subsequently ablated. The system can be configured to expand tissue located at least 2 cm distal to the ampulla of Vater, such as when tissue within 2 cm of the ampulla of Vater is not expanded and/or is not subsequently ablated. The system can be configured to expand tissue located at least 3 cm distal to the ampulla of Vater, such as when tissue within 3 cm of the ampulla of Vater is not expanded and/or is not subsequently ablated. The system can be configured to expand tissue located within 5 cm distal to the ampulla of Vater. The system can be configured to expand tissue located within 10 cm distal to the ampulla of Vater. The at least one fluid delivery element can comprise at least three fluid delivery elements. The tissue expansion device can further comprise an expandable assembly, and the at least three fluid delivery elements can comprise three fluid delivery elements positioned with approximately 1200 separation on the expandable assembly. The at least three fluid delivery elements can be constructed and arranged to create full circumferential expansion of a segment of submucosal tissue of the duodenum. The tissue expansion device can be constructed and arranged to deliver at least 1 ml of injectate per injection from the at least one fluid delivery element. The tissue expansion device can be constructed and arranged to deliver at least 2 ml of injectate per injection from the at least one fluid delivery element. The tissue expansion device can be constructed and arranged to deliver at least 5 ml of injectate per injection from the at least one fluid delivery element. The tissue expansion device can be constructed and arranged to deliver at least 8 ml of injectate per injection from the at least one fluid delivery element. The tissue expansion device can be configured to deliver multiple injections of injectate along a length of the GI tract, and the injections can be axially separated by at least 0.5 cm. The tissue expansion device can be configured to deliver the multiple injections of injectate with an axial separation of at least 1.0 cm. The tissue expansion device can be configured to deliver the multiple injections of injectate with an axial separation of at least 2.0 cm. The tissue expansion device can be configured to deliver the multiple injections of injectate with an axial separation of at least 3.0 cm. The tissue expansion device can be configured to deliver the multiple injections of injectate with an axial separation of at least 4.0 cm. The tissue expansion device can be configured to deliver the multiple injections of injectate with an axial separation of at least 6.0 cm. The at least one fluid delivery element can comprise at least two fluid delivery elements (e.g. multiple fluid delivery elements configured to simultaneously or sequentially deliver sets of injections), and the tissue expansion device can be configured to deliver at least 5 sets of injections at different axial locations along the length of the duodenum. The tissue expansion device can be configured to deliver at least 8 sets of injections at different axial locations along the length of the duodenum. The tissue expansion device can be configured to deliver between 8 and 12 sets of injections at different axial locations along the length of the duodenum. Each set of injections can comprise a first injection from a first fluid delivery element and a second injection from a second fluid delivery element, each set of injections delivered along a circumference of a GI tract axial location. Each set of injections can comprise a first injection from a first fluid delivery element, a second injection from a second fluid delivery element, and a third injection from a third fluid delivery element, each set of injections delivered along a circumference of a GI tract axial location. The sets of injections can be positioned with an axial separation of at least 0.5 cm. The sets of injections can be positioned with an axial separation of between 1.0 cm and 5.0 cm. The sets of injections can be positioned with an axial separation of between 1.0 cm and 2.0 cm. The tissue expansion device can comprise a balloon with a balloon length and the at least two fluid delivery element are mounted to the balloon, and the sets of injections can be positioned with an axial separation of approximately one-half the balloon length. The sets of injections can be delivered proximally to distally along the GI tract. The sets of injections can be delivered distally to proximally along the GI tract.

In some embodiments, the system further comprises a lumen diameter sizing device constructed and arranged to provide GI lumen diameter information. The lumen diameter sizing device can comprise an expandable balloon. The system can be configured to determine the volume delivered to the lumen diameter sizing device expandable balloon. The system can be configured to deliver fluid to the lumen diameter sizing device expandable balloon until a threshold pressure is achieved. The threshold pressure can comprise a threshold of at least 0.7 psi. The lumen diameter sizing device can be configured to determine the luminal diameter of at least two GI tract axial locations. The system can be configured to determine the size of the tissue treatment device to be used based on the GI lumen diameter information provided by the lumen diameter sizing device. The system can further comprise a tissue expansion device and the system can be configured to determine the size of the tissue expansion device to be used based on the GI lumen diameter information provided by the lumen diameter sizing device.

In some embodiments, the system further comprises an agent. The agent can be configured to be delivered to the GI tract. The agent can be configured to be delivered systemically to the patient. The agent can comprise an anti-peristaltic agent. The agent can comprise L-menthol. The agent can comprise an agent selected from the group consisting of: glucagon; buscopan; and combinations thereof.

In some embodiments, the system further comprises a marker constructed and arranged to be deployed within the patient. The marker can be constructed and arranged to identify a location relative to non-target tissue. The non-target tissue can comprise the ampulla of Vater, and it can include tissue proximate the ampulla of Vater, such as tissue within 1 cm, 2 cm or 3 cm of the ampulla of Vater. The marker can comprise an element selected from the group consisting of: a visible marker; a radiographic marker; an ultrasonically reflectable marker; ink; dye; and combinations thereof. The marker can comprise multiple markers. The system can further comprise an endoscope and the marker can be constructed and arranged to be deployed by the endoscope. The marker can be constructed and arranged to be deployed by the tissue treatment device.

In some embodiments, the system further comprises an endoscope and a scope attached sheath attachable to the endoscope. The tissue treatment device can be constructed and arranged to be inserted through the scope attached sheath.

According to another aspect of the present inventive concepts, a tissue treatment device for treating target tissue comprises a tissue treatment element constructed and arranged to apply a tissue modifying agent to target tissue and the system is constructed and arranged to provide a therapeutic benefit to the patient.

In some embodiments, the target tissue comprises duodenal mucosa.

In some embodiments, the tissue treatment element comprises an expandable element. The tissue treatment element can expand when contacted with fluid. The tissue treatment element can expand when contacted with the tissue modifying agent.

In some embodiments, the tissue treatment element comprises a sponge material. The sponge material can be selected from the group consisting of a sponge material such as a natural sponge material or a synthetic sponge material; a foamed polyurethane; a polyvinyl alcohol (PVA) sponge; a hydrogel; a super-absorbent polymer; and combinations thereof.

In some embodiments, the tissue treatment element comprises a balloon. The balloon can comprise a permeable balloon.

In some embodiments, the tissue treatment device further comprises the tissue modifying agent.

In some embodiments, the tissue modifying agent is configured to cause necrosis of the target tissue. The tissue modifying agent can be selected from the group consisting of a chemical peeling agent; a mild acid such as glycolic acid; trichloroacetic acid; a mild base; phenol; retinoic acid; and combinations thereof.

In some embodiments, the tissue treatment device further comprises a shaft with a proximal end and a distal portion, and the tissue treatment element is positioned on the distal portion of the shaft. The shaft can comprise a length sufficient to position the tissue treatment element proximate the distal end of the duodenum of the patient. The shaft can comprise a lumen constructed and arranged for over-the-wire insertion of the tissue treatment device. The tissue treatment device can further comprise a handle positioned on the proximal end of the shaft.

In some embodiments, the tissue treatment device further comprises at least one occluding element constructed and arranged to at least partially occlude a lumen of the GI tract. The at least one occluding element can be further configured to prevent migration of the tissue modifying agent to non-target tissue. The at least one occluding element can comprise a radially expandable element. The at least one occluding element can comprise an expandable balloon. The at least one occluding element can comprise an expandable sponge. The at least one occluding element can comprise multiple occluding elements. The at least one occluding element can be constructed and arranged to be evacuated from the patient by the patient's digestive system. The tissue treatment device can further comprise a grasping device, and the at least one occluding element can be constructed and arranged to be removed from the patient by the grasping device. The tissue treatment device can further comprise a shaft with a lumen, and the at least one occluding element can be constructed and arranged to be deployed into the patient via the shaft lumen. The tissue treatment device can further comprise a push rod translatable through the lumen and constructed and arranged to expel the occluding element from the shaft.

According to another aspect of the present inventive concepts, a tissue modifying agent delivery system comprises a tissue treatment device as described herein. The system further comprises a tissue modifying agent delivery unit configured to deliver a tissue modifying agent to the tissue treatment element.

In some embodiments, the tissue modifying agent delivery system comprises a system as described herein.

In some embodiments, the target tissue comprises duodenal mucosa located distal to the ampulla of Vater. The target tissue can comprise tissue at least 0.5 cm distal to the ampulla of Vater, such as when tissue within 0.5 cm of the ampulla of Vater is not ablated or otherwise treated. The target tissue can comprise tissue at least 1 cm distal to the ampulla of Vater, such as when tissue within 1 cm of the ampulla of Vater is not ablated or otherwise treated. The target tissue comprises tissue at least 2 cm distal to the ampulla of Vater, such as when tissue within 2 cm of the ampulla of Vater is not ablated or otherwise treated. The target tissue comprises tissue at least 3 cm distal to the ampulla of Vater, such as when tissue within 3 cm of the ampulla of Vater is not ablated or otherwise treated.

In some embodiments, the target tissue comprises at least 25% of the duodenal mucosa located distal to the ampulla of Vater.

In some embodiments, the target tissue comprises at least 50% of the duodenal mucosa located distal to the ampulla of Vater.

In some embodiments, the target tissue does not comprise any duodenal mucosa located proximal to the ampulla of Vater.

In some embodiments, the target tissue comprises no more than 75% of the duodenal mucosa located distal to the ampulla of Vater and the target tissue does not comprise any duodenal mucosa tissue located proximal to the ampulla of Vater.

In some embodiments, the target tissue comprises no more than 90% of the duodenal mucosa located distal to the ampulla of Vater and the target tissue does not comprise any duodenal mucosa tissue located proximal to the ampulla of Vater.

In some embodiments, the target tissue comprises tissue located at least 1cm distal to the ampulla of Vater.

In some embodiments, the system further comprises at least one deployable marker, and the target tissue comprises tissue selected based on the deployment location of the at least one marker.

In some embodiments, the target tissue comprises an axial length of at least 6 cm. The target tissue can comprise an axial length of at least 9 cm.

In some embodiments, the target tissue comprises a single contiguous segment of duodenal mucosa.

In some embodiments, the target tissue comprises multiple discontiguous segments of duodenal mucosa.

In some embodiments, the target tissue comprises tissue at least 1 cm distal to the ampulla of Vater, such as when tissue within 1 cm of the ampulla of Vater is not ablated or otherwise treated. The target tissue can comprise tissue at least 2 cm distal to the ampulla of Vater, such as when tissue within 2 cm of the ampulla of Vater is not ablated or otherwise treated. The target tissue can comprise tissue at least 3 cm distal to the ampulla of Vater, such as when tissue within 3 cm of the ampulla of Vater is not ablated or otherwise treated.

In some embodiments, the system of the present inventive concepts comprises a first tissue treatment device and a second tissue treatment device, each tissue treatment device comprising a tissue treatment element constructed and arranged to treat (e.g. ablate, remove or otherwise modify) target tissue. The first tissue treatment device is constructed and arranged to treat duodenal mucosa in a first procedure, and the second tissue treatment device is constructed and arranged to treat duodenal mucosa in a second procedure, such as a second procedure performed at least one week after the first procedure. The target tissue can comprise at least duodenal mucosa tissue, such as to treat diabetes of a patient.

According to another aspect of the present inventive concepts, a method of treating tissue is performed using any of the systems and/or devices described herein.

According to another aspect of the present inventive concepts, a method of treating a medical condition of a patient comprises: selecting a patient; selecting a tissue treatment device; performing a first treatment; and performing a second treatment. The patient selected for treatment comprises a type 2 diabetes patient currently taking insulin at a first dosage level. The first treatment comprises treating the intestine of the patient with the treatment device. The second treatment comprises delivering insulin to the patient at a second dosage level, wherein the second dosage level is less than the first dosage level. The method results in a therapeutic benefit to the patient, such as a benefit with an efficacy period of at least 3 months in which glycemic control is maintained.

In some embodiments, the second dosage level comprises 0 units/day of insulin.

In some embodiments, the second dosage level comprises at least 15 units/day of insulin less than the first dosage level.

In some embodiments, the first dosage level comprises at least 10 units/day and/or at least 20 units/day of insulin.

In some embodiments, the first dosage level comprises no more than 50 units/day, no more than 60 units/day, and/or no more than 0.5 units/kg/day of insulin.

In some embodiments, prior to performing the first treatment the selected patient is further taking a non-insulin anti-diabetic medication. The non-insulin anti-diabetic medication can comprise a medication selected from the group consisting of: an insulin sensitizing medication such as a biguanide and/or a thiazolidinedione; an insulin secretagogue such as a sulfonylurea or a meglitinide; an alpha-glucosidase inhibitor; a DPP-4 inhibitor; a peptide analog such as an incretin mimetic (e.g. a GLP-1 analog, GIP analog, and/or GIP antagonists); an amylin analogue; a glycosuric medication (e.g. an SGLT2 inhibitor); and combinations thereof.

In some embodiments, the patient is selected based on having a c-peptide level of at least 0.5, 0.6, and/or 1.0 at the time of the selection.

In some embodiments, the patient is selected based on having a fasting plasma glucose level of at least 140 mg/dL, 160 mg/dL and/or 180 mg/dL at the time of the selection. The fasting plasma glucose level can be measured after the patient has been withdrawn from insulin therapy for at least 12 hours and/or at least 24 hours prior to the measurement.

In some embodiments, the patient is selected based on having an HbA1C level of no more than 9.5% and/or 10.0% at the time of the selection.

In some embodiments, the patient is selected based on having an HbA1C level of at least 6.5%, 7.0%, 7.5%, 8.0%, 9.5% and/or 10.0%.

In some embodiments, the therapeutic benefit comprises at least 6 months of glycemic control. The glycemic control can comprise the patient maintaining an HbA1C level that can be no more than 0.2% and/or 0.3% and/or no more than 0.4% greater than the patient's HbA1C level prior to the performing of the first treatment. The second dosage can comprise 0 units/day of insulin. The second treatment can further comprise the patient taking at least one anti-diabetic medication. The at least one diabetic medication can comprise a medication selected from the group consisting of: an insulin sensitizing medication such as a biguanide and/or a thiazolidinedione; an insulin secretagogue such as a sulfonylurea or a meglitinide; an alpha-glucosidase inhibitor; a DPP-4 inhibitor; a peptide analog such as an incretin mimetic; an amylin analogue; a glycosuric medication (e.g. an SGLT2 inhibitor); and combinations thereof. The at least one diabetic medication can comprise a medication selected from the group consisting of: an agonist of GLP-1; an agonist of a GLP-1 analog; an antagonist of SGLT2; an antagonist of an SGLT2 analog; and combinations thereof.

In some embodiments, the therapeutic benefit comprises at least 12 months of glycemic control. The glycemic control can comprise the patient maintaining an HbA1C level that can be no more than 0.2% and/or 0.3% and/or no more than 0.4% greater than the patient's HbA1C level prior to the performing of the first treatment. The second dosage can comprise 0 units/day of insulin. The second treatment can further comprise the patient taking at least one anti-diabetic medication. The at least one diabetic medication can comprise a medication selected from the group consisting of: an agonist of GLP-1; an agonist of a GLP-1 analog; an antagonist of SGLT2; an antagonist of an SGLT2 analog; and combinations thereof.

In some embodiments, the glycemic control comprises the patient maintaining an HbA1C level of no more than 8.5%, 8.0%, 7.5%, and/or 7.0%.

In some embodiments, the glycemic control comprises the patient maintaining an HbA1C level that is no more than 0.2% and/or 0.3% and/or no more than 0.4% greater than the patient's HbA1C level prior to the performing of the first treatment.

In some embodiments, the therapeutic benefit further comprises a weight loss of at least 5% of the patient's weight prior to the performing of the first treatment.

In some embodiments, the therapeutic benefit further comprises a reduced risk of hypoglycemia. The risk of hypoglycemia can be reduced to a level of no more than 0.1% occurrence rate of serious hypoglycemic events per year. The patient can achieve an HbA1C of no more than 7.5% during that year.

In some embodiments, the therapeutic benefit further comprises increased patient satisfaction. The patient satisfaction can be demonstrated through use of a diabetes treatment and/or patient-reported safety questionnaire.

In some embodiments, the first treatment comprises treating one or more tissue segments of the duodenum that are located distal to the papilla and/or distal to the ampulla of Vater. The one or more tissue segments can be located at least 0.1 cm from the ampulla of Vater. The one or more tissue segments can be located at least 0.5 cm, and/or at least 1.0 cm from the ampulla of Vater. The one or more tissue segments comprise tissue located within 3 cm of the ampulla of Vater. The one or more tissue segments comprise tissue located within 2 cm and/or within 1 cm of the ampulla of Vater.

In some embodiments, the first treatment comprises treating one or more tissue segments of the duodenum with a cumulative axial length of at least 3.0 cm, 5.0 cm, 7.5 cm, and/or 10.0 cm. At least 50%, 60%, and/or 70% of the surface area of the cumulative axial length can be caused to necrose. At least 30%, 40%, 50%, and/or 60% of the crypts of the cumulative axial length can be caused to necrose. No more than 20%, 10%, and/or 5% of the muscularis propria of the cumulative axial length can be adversely affected.

In some embodiments, the first treatment comprises ablating a minimum tissue surface area, and the minimum tissue surface area ablated comprises at least 10 cm2, 15 cm2, 20 cm2, 30 cm2, 40 cm2, and/or 50 cm2 of a duodenal mucosal tissue surface. The minimum duodenal mucosal tissue surface ablated can comprise multiple tissue surface segments. The minimum duodenal mucosal tissue surface ablated can comprise a continuous segment of tissue surface. The first treatment can comprise delivering energy and/or a tissue-modifying agent to a first quantity of a tissue surface area. The first quantity of tissue surface area can be less than or equal to the minimum tissue surface area ablated. The first treatment can comprise delivering energy selected from the group consisting of thermal energy; electromagnetic energy; light energy; sound energy; and combinations thereof. The first treatment can comprise delivering a tissue modifying agent comprising a necrotic agent.

In some embodiments, the first treatment is configured to damage, remove, and/or cause replacement of cells.

In some embodiments, the first treatment comprises a tissue treatment selected from the group consisting of: thermal coagulation; desiccation; non-desiccating tissue ablation; heat ablation; cryoablation; radiofrequency (RF) ablation; electroporation; ultrasound and/or other sound-based ablation; sonoporation; laser and/or other light-based ablation; mechanical abrasion; chemical abrasion and/or chemical ablation; and combinations thereof.

In some embodiments, the treatment device comprises a device configured to modify tissue. The treatment device can be configured to modify tissue by delivering energy. The delivered energy can comprise tissue ablating energy. The treatment device can be configured to deliver to tissue one or more forms of energy selected from the group consisting of: thermal coagulation energy; desiccation energy; non-desiccating tissue ablating energy; heat energy; cryogenic energy; radiofrequency energy; microwave energy; electroporation energy; ultrasound and/or other sound-based energy; sonoporation energy; laser and/or other light-based energy; mechanical energy; chemical energy; and combinations thereof. The treatment device can be further configured to deliver an agent and/or to deliver an implanted device. The treatment device can be configured to modify tissue by delivering an agent. The delivered agent can comprise a tissue-modifying agent. The tissue-modifying agent can comprise a tissue-ablating and/or a tissue-sclerosing agent. The tissue-modifying agent can comprise a tissue cell-function-modifying agent. The treatment device can be configured to modify tissue by delivering a tissue-coating agent. The treatment device can comprise one or more delivery elements configured to deliver the tissue-coating agent. The treatment device can comprise an ingestible carrier which carries the tissue-coating agent and can be configured to be swallowed by the patient. The treatment device can be further configured to modify tissue and/or to deliver an implantable device. The treatment device can comprise a device configured to deliver an implantable device. The treatment device can be configured to deliver an implantable tissue barrier device. The tissue barrier device can comprise an implantable sleeve and/or an implantable coating. The tissue barrier device can comprise a tissue-modifying agent. The treatment device can be further configured to modify tissue and/or to deliver an agent.

In some embodiments, the treatment device comprises a tissue barrier device. The tissue barrier device can comprise a sleeve. The tissue barrier device can comprise a coating.

In some embodiments, the second treatment further comprises the patient taking at least one medication selected from the group consisting of: an insulin sensitizing medication such as a biguanide and/or a thiazolidinedione; an insulin secretagogue such as a sulfonylurea or a meglitinide; an alpha-glucosidase inhibitor; a DPP-4 inhibitor; a peptide analog such as an incretin mimetic; an amylin analogue; a glycosuric medication (e.g. an SGLT2 inhibitor); and combinations thereof.

In some embodiments, the second treatment further comprises the patient undergoing a particular diet plan. The patient can undergo the particular diet plan for a period of at least one week, and/or at least two weeks.

In some embodiments, the method can further comprise performing a patient diagnostic procedure. The patient diagnostic procedure can comprise continuous glucose monitoring. The patient diagnostic procedure can comprise a procedure selected from the group consisting of: blood glucose test; blood pressure test; weight assessment; blood test; urine test; and combinations thereof.

According to another aspect of the present inventive concepts, a method of treating a medical condition of a patient, the method comprises: selecting a patient, and the patient comprises a type 2 diabetes patient currently taking at least one oral glucose lowering medication, and having: an HbA1c greater than or equal to 7.5% and a fasting c-peptide greater than or equal to 0.6 ng/mL; selecting a tissue treatment device; and performing a treatment comprising: treating the intestine of the patient with the treatment device; and the method results in a therapeutic benefit to the patient, and the therapeutic benefit comprises a reduction in patient fasting plasma glucose at 24 weeks after the treatment is performed. The reduction in fasting plasma glucose can be at least 26.5 mg/dL. The therapeutic benefit can further comprise a reduction in patient weight at 24 weeks after the treatment. The therapeutic benefit can further comprise a reduction in patient hepatic insulin resistance. The therapeutic benefit can further comprise an improvement in patient beta cell function. The treatment can be performed in the post-papillary duodenum. Selecting the patient can further include the patient having an MRI-PDFF greater than or equal to 5%. The therapeutic benefit can be achieved without the patient changing the at least one oral glucose lowering medication.

According to another aspect of the present inventive concepts, a method of treating a medical condition of a patient, the method comprising: selecting a patient, and the patient comprises a type 2 diabetes patient currently taking at least one oral glucose lowering medication, and having: a fasting plasma glucose greater than or equal to 140 mg/dL and a fasting c-peptide greater than or equal to 0.6 ng/mL; selecting a tissue treatment device; and performing a treatment comprising: treating the intestine of the patient with the treatment device; and the method results in a therapeutic benefit to the patient, and the therapeutic benefit comprises a reduction in patient fasting plasma glucose at 24 weeks after the treatment is performed. The reduction in fasting plasma glucose can be at least 26.5 mg/dL. The therapeutic benefit can further comprise a reduction in patient weight at 24 weeks after the treatment. The therapeutic benefit can further comprise a reduction in patient hepatic insulin resistance. The therapeutic benefit can further comprise an improvement in patient beta cell function. The treatment can be performed in the post-papillary duodenum. Selecting the patient can further include the patient having an MRI-PDFF greater than or equal to 5%. The therapeutic benefit can be achieved without the patient changing the at least one oral glucose lowering medication.

According to another aspect of the present inventive concepts, a method of treating a medical condition of a patient, the method comprising: selecting a patient, and the patient comprises a type 2 diabetes patient currently taking at least one oral glucose lowering medication, and having: an MRI-PDFF greater than or equal to 5% and a fasting c-peptide greater than or equal to 0.6 ng/mL; selecting a tissue treatment device; and performing a treatment comprising: treating the intestine of the patient with the treatment device; and the method results in a therapeutic benefit to the patient, and the therapeutic benefit comprises a reduction in patient MRI-PDFF at 12 weeks after the treatment is performed. The relative reduction in patient MRI-PDFF can be at least 30%. The therapeutic benefit can further comprise a reduction in patient weight at 24 weeks after the treatment. The therapeutic benefit can further comprise a reduction in patient hepatic insulin resistance.

The therapeutic benefit can further comprise an improvement in patient beta cell function. The treatment can be performed in the post-papillary duodenum. Selecting the patient can further include the patient having a fasting plasma glucose greater than or equal to 140 mg/dL. The therapeutic benefit can be achieved without the patient changing the at least one oral glucose lowering medication.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIGS. 4A, 4B and 4C illustrate perspective, side and end views, respectively, of an expandable element comprising a balloon, consistent with the present inventive concepts.

FIGS. 5A-5E illustrate side sectional views of a series of steps for treating a surface of gastrointestinal tissue using the tissue treatment device of FIG. 5, consistent with the present inventive concepts.

FIG. 15 illustrates a flow chart of a method of expanding tissue with a treatment device, consistent with the present inventive concepts.

FIG. 16 illustrates a flow chart of a method of ablating or otherwise treating tissue with a treatment device, consistent with the present inventive concepts.

FIGS. 17-20D illustrate results from studies conducted by applicant to investigate the safety and efficacy of duodenal mucosal resurfacing (DMR) on glycemic and hepatic parameters in patients with type 2 diabetes (T2D), consistent with the present inventive concepts.

FIG. 22 is a table of cumulative demographic information, consistent with the present inventive concepts.

FIG. 23 illustrates a table showing results of applicant's studies, consistent with the present inventive concepts.

FIG. 37 illustrates a table presenting the large effect size of high dose cohort, consistent with the present inventive concepts.

FIG. 38 illustrates a table presenting the patient demographics of the 39 patients from which the data were collected, consistent with the present inventive concepts.

FIG. 41 illustrates a table presenting the number of patients in each treatment arm with medication changes preceding the six month post-procedure follow up visit, consistent with the present inventive concepts.

FIG. 45 illustrates a table presenting patient data prior to performance of a tissue treatment, consistent with the present inventive concepts.

FIG. 46 illustrates a table presenting data of the tissue treatment procedures performed by the applicant, consistent with the present inventive concepts.

FIG. 47 illustrates a table presenting data collected at a follow-up procedure performed on 13 patients, approximately 3 months after the duodenal treatment procedure, consistent with the present inventive concepts.

FIG. 48 illustrates a table presenting data collected at a follow-up procedure performed on 13 patients, approximately 3 months after the duodenal treatment procedure, consistent with the present inventive concepts.

FIG. 49 illustrates a table presenting data collected at a follow-up procedure performed approximately 6 months after the duodenal treatment procedure, consistent with the present inventive concepts.

FIG. 50 illustrates a table presenting the fluid temperatures and respective ablation times of a tissue treatment procedure, consistent with the present inventive concepts.

DETAILED DESCRIPTION OF THE DRAWINGS

Figure 1:
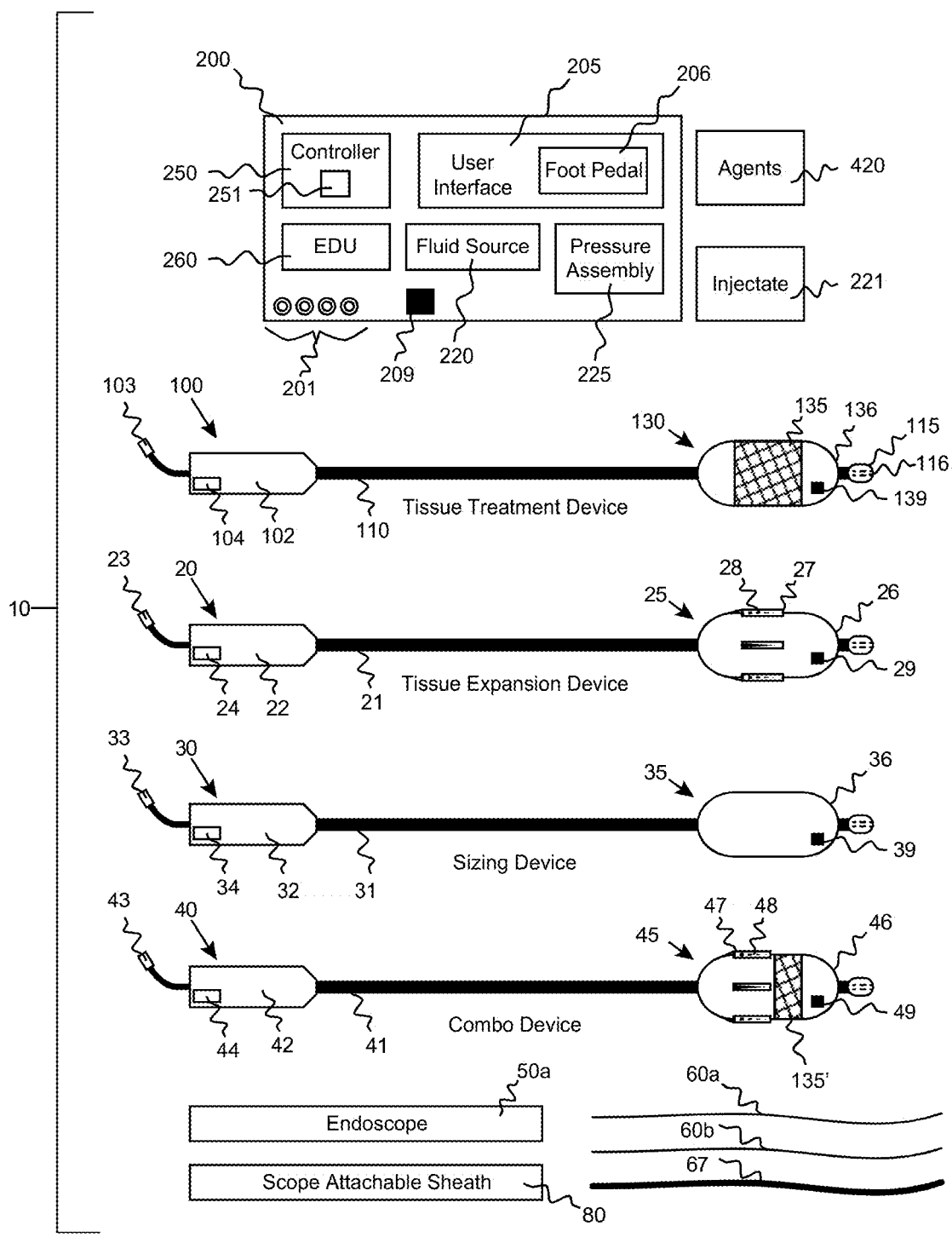
FIG. 1 illustrates a schematic view of a system for treating target tissue of a patient, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way. It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of two or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g. efficacious therapy) and/or to prevent or otherwise reduce (hereinafter "prevent") an undesired event (e.g. a device and/or clinical adverse event). In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "fluid" can refer to a liquid, gas, gel, or any flowable material, such as a material which can be propelled through a lumen and/or opening.

As used herein, the term "material" can refer to a single material, or a combination of two, three, four, or more materials.

As used herein, the term "transducer" is to be taken to include any component or combination of components that receives energy or any input and produces an output. For example, a transducer can include an electrode that receives electrical energy and distributes the electrical energy to tissue (e.g. based on the size of the electrode). In some configurations, a transducer converts an electrical signal into any output, such as: light (e.g. a transducer comprising a light emitting diode or light bulb), sound (e.g. a transducer comprising a piezo crystal configured to deliver ultrasound energy); pressure (e.g. an applied pressure or force); heat energy; cryogenic energy; chemical energy; mechanical energy (e.g. a transducer comprising a motor or a solenoid); magnetic energy; and/or a different electrical signal (e.g. different than the input signal to the transducer). Alternatively or additionally, a transducer can convert a physical quantity (e.g. variations in a physical quantity) into an electrical signal. A transducer can include any component that delivers energy and/or an agent to tissue, such as a transducer configured to deliver one or more of: heat energy to tissue; cryogenic energy to tissue; electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of two or more of these. A transducer can include a component configured to neutralize an ablative process, such as a transducer configured to cool tissue prior to and/or after a heat ablation of tissue, and/or a transducer configured to warm tissue prior to and/or after a cryogenic ablation of tissue. Alternatively or additionally, a transducer can comprise a mechanism, such as: a valve; a grasping element; an anchoring mechanism; an electrically-activated mechanism; a mechanically-activated mechanism; and/or a thermally activated mechanism.

As used herein, the term "functional element" is to be taken to include one or more elements constructed and arranged to perform a function. A functional element can comprise one or more sensors and/or one or more transducers. In some embodiments, a functional element is configured to deliver energy and/or otherwise treat tissue (e.g. a functional element configured as a treatment element). Alternatively or additionally, a functional element (e.g. comprising one or more sensors) can be configured to record one or more parameters, such as a patient physiologic parameter; a patient anatomical parameter (e.g. a tissue parameter); a patient environment parameter; and/or a system parameter (e.g. temperature and/or pressure within the system). In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a patient anatomical parameter; and combinations of two or more of these. A functional element can comprise a fluid, such as an ablative fluid (as described herein) comprising a liquid, gel, and/or gas configured to ablate or otherwise treat tissue. A functional element can comprise a reservoir, such as an expandable balloon configured to receive an ablative fluid. A "functional assembly" can comprise an assembly constructed and arranged to perform a function, such as is described herein, such as a therapeutic function or a diagnostic function. In some embodiments, a functional assembly is configured to deliver energy and/or otherwise treat tissue (e.g. a functional assembly configured as a treatment assembly). Alternatively or additionally, a functional assembly can be configured to record one or more parameters, such as a patient physiologic parameter; a patient anatomical parameter; a patient environment parameter; and/or a system parameter. A functional assembly can comprise an expandable assembly. A functional assembly can comprise one or more functional elements.

As used herein, the term "ablative temperature" refers to a temperature at which tissue necrosis or other desired tissue treatment occurs (e.g. a temperature sufficiently hot or sufficiently cold to cause tissue necrosis). As used herein, the term "ablative fluid" refers to one or more liquids, gases, gels or other fluids whose thermal properties cause tissue necrosis and/or another desired tissue treatment (e.g. one or more fluids at an ablative temperature). Alternatively or additionally, "ablative fluid" refers to one or more fluids whose chemical properties (at room temperature, body temperature or otherwise) cause tissue necrosis or another desired tissue treatment. A tissue treatment element (e.g. a functional element) of the present inventive concepts can comprise one or more ablative fluids.

As used herein, the term "tissue contacting surface" refers to a surface of a system or device component that makes physical contact with tissue, such as a portion of an external surface of an expandable component (e.g. a portion of a balloon's surface) which contacts tissue once expanded. In some embodiments, tissue contacting a tissue contacting surface directly receives energy from the tissue contacting surface of the expandable components, however tissue in proximity (e.g. below or alongside) also receives energy (e.g. via conduction of the delivered energy and/or a resultant heat energy).

It is an object of the present inventive concepts to provide systems, methods and devices for safely and effectively treating and/or diagnosing a volume of tissue (the "target tissue"), such as to treat and/or diagnose a patient disease or disorder. Target tissue can comprise one or more target tissue segments or other target tissue portions, such as target tissue located in the intestine of a patient. Clinical procedures in the duodenum and other locations of the small intestine are challenging for a number of reasons, such as those caused by the long distance between the mouth and the intestine and the complexities of the gastrointestinal passageway encountered (including passage through the stomach) during device (e.g. catheter) insertion and operation. Intestinal diameter varies along its length, and effective devices must accommodate this variation. The intestine is quite distensible in the longitudinal and radial directions, further complicating device (e.g. catheter) manipulation and operation (e.g. delivery of energy to tissue). Mobility of intestinal mucosa relative to muscularis is present, as well as mobility of the full wall, but can result in undesired stretching, compression and intussusception. The duodenum is normally closed, and it can require insufflation to open (e.g. for visualization). The insufflation medium (e.g. gas) moves through the intestine, so more must be delivered, while excess gas causes discomfort or other adverse effect for the patient. Duodenal and other intestinal tissue tends to stretch or compress as a device is advanced or retracted, respectively, such as to cause retrograde expulsion of devices if a stabilization force is not maintained. It is difficult to manipulate and control devices that include treatment and other elements positioned in the small intestine. The small intestine wraps around the pancreas, and the curvature is quite variable from patient to patient. The length of the intestine along an outer curve is longer than that along an inner curve. In many procedures, there is a desire to avoid damage to the ampulla of Vater (e.g. to avoid restricting bile and/or pancreatic fluid), tissue which can be difficult to visualize or otherwise identify. There are relatively few endoscopically visualizable landmarks in the intestine, making it difficult to know where in the intestine a portion (e.g. a distal portion) of a device is positioned. Access to the intestine through the stomach via an over-the wire catheter loses one-to-one motion between a proximal handle and a distal portion of the device, as slack can accumulate in the stomach during advancement and slack can be relieved from the stomach during withdrawal. Accessing the intestine can include entering the intestine through the pylorus, a small sphincter, from the stomach, and in obese patients, large stretchable stomachs make it difficult to direct a device to the pylorus. The intestinal mucosa has a very irregular surface due to plicae circulares and mucosal villi, and performing a treatment (e.g. an ablation treatment) of the intestinal mucosa is quite different from a treatment procedure performed in the stomach or esophagus, because of this irregularity. Peristalsis present in the small intestine is dynamic and unpredictable and can alter functional element, functional assembly and/or other device component position and/or contact level with tissue. The intestine is not only thin-walled, but the thickness of the wall is highly variable, even within small axial segments of the small intestine, thus complicating preferential ablation of inner layers versus outer layers of the small intestine. The muscularis is innervated and scars and/or stenoses easily, and as such, even minimal trauma to the muscularis should be avoided.

Target tissue can comprise one or more layers of a portion of tubular or non-tubular tissue, such as tissue of an organ or tissue of the gastrointestinal (GI) tract of a patient, such as tissue of the small intestine or large intestine. The systems and devices of the present inventive concepts can include one or more functional assemblies and/or functional elements configured to treat target tissue, such as a treatment element comprising fluid at an ablative temperature delivered to a balloon (ablative temperature fluid and/or balloon filled with ablative fluid each referred to singly or collectively as a "functional element" or a "treatment element" of the present inventive concepts). One or more functional elements can be provided in, on and/or within an expandable functional assembly or other radially deployable mechanism. Functional assemblies and/or functional elements can be configured to treat target tissue (e.g. deliver energy to target tissue), such as to modify target tissue (e.g. to modify the secretions from the target tissue and/or absorption of the target tissue), ablate target tissue (e.g. to cause the replacement of the target tissue with "new tissue") and/or to cause a reduction in the surface area of target tissue (e.g. the luminal surface area of an inner wall of tubular tissue) at and/or proximate to one or more locations where the treatment was performed (e.g. at and/or proximate the location where energy was delivered). The luminal or other tissue treatment can occur acutely and/or it can take place over time, such as days, weeks or months. A tissue surface area reduction can correspond to a reduction in mucosal surface area available to function in an absorptive, neuronal signaling, and/or a hormonal secretory capacity. A target tissue treatment can result in the replacement of target tissue with new tissue with different absorptive and/or secretory capacity and/or other desirable effect related to replacement and/or modification of target tissue. The treatment of target tissue with the systems, devices and methods of the present inventive concepts can provide a therapeutic benefit to the patient, such as to treat one or more diseases or disorders of the patient, as described in detail herein.

Each functional assembly (e.g. treatment assembly) can comprise at least one functional element (e.g. tissue treatment element) such as a tissue treatment element selected from the group consisting of: ablative fluid delivered to a balloon or other expandable fluid reservoir; energy delivery element mounted to an expandable functional assembly such as an electrode or other energy delivery element configured to deliver radiofrequency (RF) energy and/or microwave energy; light delivery element configured to deliver laser or other light energy; fluid delivery element (e.g. needle or nozzle) configured to deliver ablative fluid directly onto and/or into tissue; sound delivery element such as an ultrasonic and/or subsonic sound delivery element; and combinations of two or more of these. Numerous forms of functional assemblies and/or functional elements can be included. In some embodiments, the functional assemblies and/or the one or more functional elements contained therein are configured as described in: applicant's co-pending U.S. patent application Ser. No. 13/945,138, entitled "Devices and Methods for the Treatment of Tissue", filed Jul. 18, 2013; applicant's co-pending U.S. patent application Ser. No. 16/438,362, entitled "Heat Ablation Systems, Devices and Methods for the Treatment of Tissue", filed Jun. 11, 2019; applicant's co-pending U.S. patent application Ser. No. 16/711,236, entitled "Electrical Energy Ablation Systems, Devices and Methods for the Treatment of Tissue", filed Dec. 11, 2019; and/or applicant's co-pending U.S. patent application Ser. No. 14/609,334, entitled "Ablation Systems, Devices and Methods for the Treatment of Tissue", filed Jan. 29, 2015.

The treatment assemblies and/or treatment elements of the present inventive concepts can be constructed and arranged to deliver one or more treatments (e.g. deliver energy, deliver a chemically ablative fluid, mechanically abrade and/or otherwise treat tissue) directly to a particular area of tissue, the "delivery zone". The area of tissue treated can comprise a segment of the small intestine, or other body lumen, where the delivery zone comprises a length representing the axial length of the segment treated, and a width such as a width representing a full or partial circumferential portion of the segment. A treatment element can be configured to ablate or otherwise treat an energy delivery zone with a "treatment length" and a "treatment width". During a single delivery of treatment, a treatment element can be constructed and arranged to deliver treatment to a relatively continuous surface of tissue (e.g. a continuous surface of tissue in contact with a balloon filled with ablative fluid or a surface of tissue onto which a chemically ablative fluid is sprayed, coated or otherwise delivered). In these continuous-surface treatment delivery embodiments, the delivery zone comprises the continuous surface of tissue receiving the treatment directly. Alternatively, a treatment element can be constructed and arranged to deliver treatment to multiple discrete portions of a tissue surface, with one or more tissue surface portions in-between other surface portions that do not directly receive energy or other treatment from the treatment element. In these segmented-surface treatment delivery embodiments, the delivery zone is defined by a periphery of the multiple tissue surface area portions receiving treatment, similar to a "convex hull" or "convex envelope" used in mathematics to define an area including a number of discrete locations that define a periphery. A delivery zone can comprise two or more contiguous or non-contiguous delivery zones, and multiple delivery zones can be treated sequentially and/or simultaneously.

For example, in embodiments where the treatment element is hot fluid (e.g. ablative fluid at a sufficiently high temperature to cause tissue necrosis) positioned within a balloon, the delivery zone comprises all tissue surfaces contacted by the balloon that directly receive ablative thermal energy from the ablative fluid through the balloon. In embodiments where the treatment element is a balloon filled with cold fluid (e.g. ablative fluid at a sufficiently low temperature to cause tissue necrosis), the delivery zone can comprise all tissue surfaces contacted by the balloon that have heat directly extracted from them by the cold fluid (e.g. at a sufficient cold temperature to treat the tissue). In embodiments where the treatment element is an array of electrodes configured to deliver electrical energy (e.g. radiofrequency and/or other electromagnetic energy) to tissue, the delivery zone can comprise an area defined by the electrodes on the periphery of the array (e.g. a convex hull as described above), such as when the electrodes are positioned and energy is delivered to treat relatively the entire surface of tissue within the periphery. In embodiments where the treatment element comprises one or more fluid delivery elements delivering ablative fluid directly onto tissue (e.g. an ablative fluid whose chemical nature modifies tissue, at body temperature or otherwise), the delivery zone can comprise a surface defined by the periphery of tissue locations receiving the ablative fluid, such as when the ablative fluid is delivered (e.g. sprayed or otherwise applied, such as via a sponge) to relatively the entire surface within the periphery. In embodiments where the treatment element comprises one or more light delivery elements such as those that deliver laser energy to tissue, the delivery zone can comprise a surface area defined by the periphery of tissue locations receiving the light energy, such as when light is delivered at a set of locations and with a magnitude of energy configured to treat relatively the entire surface of tissue within the periphery. In these embodiments, light can be delivered to relatively the entire energy delivery zone, or to a large number (e.g. greater than 100) of tissue locations within the periphery of the delivery zone (e.g. making up less than 50%, less than 20% or less than 10% of the total surface area of the delivery zone). In embodiments where the treatment element comprises one or more sound delivery elements such as those that deliver sub-sonic and/or ultrasonic sound energy to tissue, the delivery zone can comprise a surface area defined by the periphery of tissue locations receiving the sound energy, such as when ablative sound energy is delivered at a set of locations and with a magnitude of energy configured to treat relatively the entire surface of tissue within the periphery. In embodiments in which the treatment element comprises a mechanical cutter or other abrasion element, the delivery zone can comprise a surface defined by all tissue dissected, cut, mechanically disrupted and/or otherwise modified during a single abrading step of the mechanical abrader.

A delivery zone can comprise a cumulative set of delivery zones that receive treatment simultaneously and/or sequentially, by one or more tissue treatment elements, such as those described herein. A delivery zone can comprise a first delivery zone defined when a treatment element treats target tissue in a first treatment delivery, plus a second delivery zone defined when the treatment element treats target tissue in a second treatment delivery, and so on. In these embodiments, the treatment element can be translated, rotated and/or otherwise repositioned between treatments (e.g. energy delivery), where each delivery zone is associated with the position of the treatment element during each treatment. Multiple delivery zones can receive treatment in a single procedure, such as within a period of less than twenty-four hours. A delivery zone can comprise a set of multiple delivery zones treated by two or more treatment elements.

Target tissue treated by each energy delivery and/or other treatment delivery comprises the tissue directly receiving treatment (i.e. the tissue defined by the delivery zone) plus "neighboring tissue" which is also modified by the associated treatment delivery. The neighboring tissue can comprise tissue alongside, below (e.g. in a deeper tissue layer) and/or otherwise proximate the delivery zone tissue. The neighboring tissue treatment can be due to one or more of conduction and/or convection of heat or cold from the delivery zone; flow of ablative fluid from the delivery zone; flow of toxins or other agents that occur during cell degradation and/or cell death; radiation; luminescence, light dissipation; and other energy and/or chemical propagation mechanisms. In some embodiments, an area (i.e. the delivery zone) comprising an inner surface of mucosal tissue directly receives treatment from one or more treatment elements (e.g. an ablative fluid contained within a balloon), and the total volume of target tissue treated by that single treatment delivery includes: the delivery zone tissue (i.e. surface mucosal tissue directly receiving energy and/or other treatment from the treatment element); surface mucosal tissue in close proximity (e.g. adjacent) to the delivery zone tissue; and mucosal and potentially submucosal tissue layers beneath (deeper than) the delivery zone tissue and the treated adjacent surface mucosal tissue.

In some embodiments, a "treatment neutralizing" procedure is performed after one or more treatments (e.g. energy deliveries), such as a treatment neutralizing cooling procedure performed after one or more treatment elements deliver heat to treat target tissue, or a treatment neutralizing warming procedure performed after one or more treatment elements deliver cryogenic energy to treat target tissue. In these embodiments, the treatment neutralizing cooling or warming fluid can be delivered to the same functional assembly (e.g. an expandable functional assembly comprising a balloon) delivering the heat or cryogenic treatment, respectively, and/or the neutralizing fluid can be delivered directly to tissue by the same or different functional assembly or functional element. In some embodiments, a functional element delivers an ablating agent to target tissue (e.g. a chemical or other agent configured to cause target tissue necrosis or otherwise treat target tissue), and a treatment neutralizing procedure comprises delivery of a neutralizing agent (by the same or different functional element) to target and/or non-target tissue to reduce continued ablation due to the delivered caustic ablative fluid (e.g. a base to neutralize a delivered acid or an acid to neutralize a delivered base).

Each functional assembly and/or functional element of the present inventive concepts can be configured to be positioned in one or more intestinal and/or other locations of the patient, such as to perform a function (e.g. perform a treatment, deliver fluid and/or record data) at one or more contiguous or discontiguous tissue locations. Target tissue to be treated (e.g. ablated) comprises a three dimensional volume of tissue, and can include a first portion, a treatment portion, whose treatment has a therapeutic benefit to a patient; as well as a second portion, a "safety-margin" portion, whose treatment has minimal or no adverse effects to the patient. "Non-target tissue" can be identified (e.g. prior to and/or during the medical procedure), wherein the non-target tissue comprises tissue whose treatment by the treatment assembly and/or treatment element should be reduced or avoided such as to reduce or prevent an undesired effect to the patient.

The target tissue treatment can cause one or more modifications of the target tissue such as a modification selected from the group consisting of modification of cellular function; cell death; apoptosis; instant cell death; cell necrosis; denaturing of cells; removal of cells; and combinations of two or more of these. In some embodiments, the target tissue treatment is configured to create scar tissue. Target tissue can be selected such that after treatment the treated target tissue and/or the tissue that replaces the target tissue functions differently than the pre-treated target tissue, such as to have a therapeutic benefit for the patient. The modified and/or replacement tissue (singly or collectively "treated tissue") can exhibit different properties than the pre-treated target tissue, such as different properties that are used to treat a patient disease or disorder. The treated tissue can have different secretions and/or quantities of secretions than the pre-treated target tissue, such as to treat diabetes, hypercholesterolemia and/or another patient disease or disorder. The treated tissue can have different absorptive properties than the target tissue, such as to treat diabetes, hypercholesterolemia and/or another patient disease or disorder. The treated tissue can have a different surface topography than the target tissue, such as a modification of the topography of the inner wall of the GI tract that includes a smoothing or flattening of its inner surface, such as a modification in which the luminal surface area of one or more segments of the GI tract is reduced after treatment. The effect of the treatment (e.g. the effect on the target tissue) can occur acutely, such as within twenty-four hours, or after longer periods of time, such as greater than twenty-four hours or greater than one week.

Target tissue to be treated can comprise two or more discrete tissue segments, such as two or more axial segments of the GI tract. Each tissue segment can comprise a full (e.g. approximately 360°) or partial circumferential segment of the tissue segment. Multiple tissue segments can be treated with the same or different functional elements (e.g. treatment elements), and they can be treated simultaneously or in sequential steps (e.g. sequential energy delivery steps that deliver energy to multiple delivery zones). Multiple tissue segments can be treated in the same or different clinical procedures (e.g. procedures performed on different days). In some embodiments, a series of tissue segments comprising a series of axial segments of the GI tract are treated in a single clinical procedure. The first and second tissue segments can be directly adjacent, they can contain overlapping portions of tissue, and/or there can be gaps between the segments. Dissimilarities in treatment elements can include type and/or amount of energy to be delivered by an energy delivery-based treatment element. Dissimilarities in target tissue treatments can include: target tissue area treated; target tissue volume treated; target tissue length treated; target tissue depth treated; target tissue circumferential portion treated; ablative fluid type, volume and/or temperature delivered to a reservoir such as a balloon; ablative fluid type, volume and/or temperature delivered directly to tissue; energy delivery type; energy delivery rate and/or amount; peak energy delivered; average temperature of target tissue achieved during target tissue treatment; maximum temperature achieved during target tissue treatment; temperature profile of target tissue treatment; duration of target tissue treatment; surface area reduction achieved by target tissue treatment; and combinations of two or more of these.

Target tissue can include tissue of the duodenum, such as tissue including substantially all or a portion of the mucosal layer of one or more axial segments of the duodenum (e.g. including all or a portion of the plicae circulares), such as to treat diabetes, hypercholesterolemia and/or another patient disease or disorder, such as while leaving the duodenum anatomically connected after treatment. Target tissue can include one or more portions of a tissue layer selected from the group consisting of mucosa; mucosa through superficial submucosa; mucosa through mid-submucosa; mucosa through deep-submucosa; and combinations of two or more of these. Replacement tissue can comprise cells that have migrated from one or more of gastric mucosa; jejunal mucosa; an untreated portion of the duodenum whose mucosal tissue functions differently than the treated mucosal tissue functions prior to treatment; and combinations of two or more of these. Replacement tissue can include one or more tissue types selected from the group consisting of: scar tissue; normal intestinal mucosa; gastric mucosa; and combinations of two or more of these. In some embodiments, replacement tissue comprises tissue that has been delivered onto and/or into tissue by a catheter of the present inventive concepts. In some embodiments, target tissue includes a treatment portion comprising the mucosal layer of the duodenum, and a safety-margin portion comprising a near-full or partial layer of the submucosal layer of the duodenum. In some embodiments, the target tissue comprises nearly the entire mucosal layer of the duodenum, and this tissue can include a portion of the pylorus contiguous with the duodenal mucosa and/or a portion of the jejunum contiguous with the duodenal mucosa. In some embodiments, the target tissue comprises all or a portion of the duodenal mucosa distal to the ampulla of Vater (e.g. avoiding tissue within at least 0.5 cm, 1.0 cm or 1.5 cm from the ampulla of Vater while including tissue within 5 cm, 10 cm or 15 cm distal to the ampulla of Vater). In these embodiments, the target tissue can comprise at least 10%, at least 15%, at least 25%, at least 30% or at least 50% of the duodenal mucosa distal to the ampulla of Vater. Alternatively or additionally, the target tissue can comprise no more than 70% or no more than 90% of the duodenal mucosa distal to the ampulla of Vater. In these embodiments, tissue proximal to and/or proximate the ampulla of Vater can comprise non-target tissue (i.e. tissue whose treatment is avoided or at least reduced).

In some embodiments, the target tissue comprises neuronal cells of duodenal mucosal tissue. In some embodiments, the target tissue comprises neuronal cells of duodenal submucosa tissue.

In some embodiments, the target tissue comprises at least a portion of duodenal mucosal tissue, and the systems, methods and devices of the present inventive concepts are configured to counteract duodenal mucosal changes that cause an intestinal hormonal impairment leading to insulin resistance in patients. In these embodiments, the therapy provided can improve the body's ability to process sugar and dramatically improve glycemic control for patients with insulin resistance and/or Type 2 diabetes. In some embodiments, target tissue is treated to prevent and/or reduce cognitive decline (e.g. Alzheimer's Disease), such as by improving sugar metabolism in the brain, overcoming insulin resistance in the brain, reducing toxicity of beta amyloid, reducing oxidative stress, and/or reducing inflammation in the brain associated with neuronal death. In some embodiments, target tissue is treated to: prevent liver fibrosis and/or cirrhosis (e.g. non-alcoholic fatty liver disease NAFLD or non-alcoholic steatohepatitis NASH); reduce liver fat; reduce oxidative stress; and/or reduce inflammation in the liver associated with liver fibrosis and toxicity. The systems and methods of the present inventive concepts can be configured to lower insulin requirements by improving insulin resistance (e.g. as opposed to improving insulin secretion), and/or by direct glucose lowering (e.g. by causing an increase in glucose excretion in the urine). Alternatively or additionally, the systems and methods of the present inventive concepts can be configured to lower insulin requirements by improving hepatic insulin resistance and/or by improving muscle insulin resistance.

Hormones released from the intestinal mucosa play an important role in modulating glucose homeostasis, and different axial segments of the intestinal mucosa release different hormones in the fasting and post-prandial state, in order to modulate blood glucose in the fasting and post-prandial states, respectively. After a meal, the proximal intestinal mucosa senses the intestine for ingested glucose and releases a collection of hormones in response to this signal. These hormones initiate the process of insulin release into the bloodstream after a meal, but they also induce some insulin resistance to prevent the released insulin from causing hypoglycemia before the body has a chance to absorb the ingested glucose. One such hormone that plays a role in this is GIP. Distal gut hormones (produced in the jejunum or a more distal location), on the contrary, allow the release of more insulin but also play a role in helping the body now become sensitive to its circulating insulin. Teleologically, the explanation for this difference in the type of gut hormones produced by different segments of the intestine is that enough glucose will have been absorbed by the time nutrients reach the distal intestine to allow the insulin to begin to function to reduce blood glucose levels. Releasing different hormones at different times (e.g. from different segments of the intestine) enables the body to absorb and process glucose in such a way as to avoid hypoglycemia (blood sugars that are too low) and hyperglycemia (blood sugars that are too high). In this way, intestinal hormonal signaling is important for whole body glucose homeostasis in the fasting and post-prandial states. The treatment can also lead to weight loss through decreased absorption of nutrients, increased sensation of satiety, altered food preferences, increased energy expenditure, and combinations of two or more of these.

In patients with Type 2 diabetes, a lifetime of exposure to fat and sugar can lead to intestinal changes that occur in regions with the highest exposure to these nutrients, predominantly in the proximal intestine. These changes are characterized by an excess proximal intestinal mucosa's hormonal contribution to the fasting and post-prandial glucose homeostasis. The net result of these intestinal changes is to create a condition of insulin resistance and impaired glucose tolerance. Treatment of duodenal mucosal tissue with the systems, devices and methods of the present inventive concepts can be performed to alter the intestinal mucosal hormone production from the region of treated tissue. The treated tissue can then have an altered hormonal secretion pattern that affects blood glucose levels in the fasting and post-prandial states. The tissue treatment of the present inventive concepts can be performed to effect duodenal mucosal tissue secretion of GIP and/or GLP-1. The tissue treatment can lead to changes in the blood levels of GIP and/or GLP-1 (and other gut hormones) that can lead to changes in glucose homeostasis in the fasting and/or post-prandial states. The treatment can lead to changes in insulin and/or glucagon secretion from the pancreas and/or insulin and/or glucagon levels in the bloodstream. The treatment can lead to changes in pancreatic beta cell function and/or health through direct hormonal consequences of the treated duodenal tissue and/or indirectly through improved blood glucose levels. In some embodiments, the treatment of the present inventive concepts is configured to at least one of reduce a blood glucose level and/or reduce a lipoprotein level.

Treatment of intestinal tissue (e.g. duodenal mucosal tissue) using the systems, devices, and methods of the present inventive concepts can be performed to treat a medical condition (e.g. a disease and/or disorder) selected from the group consisting of: diabetes; pre-diabetes; impaired glucose tolerance; insulin resistance; a condition caused by or otherwise related to insulin resistance; obesity or otherwise being overweight; a metabolic disorder and/or disease; a condition caused by or otherwise related to a metabolic disorder and/or disease; and combinations of two or more of these. In some embodiments, treatment of intestinal tissue (e.g. at least duodenal mucosal tissue) using the systems, devices and/or methods of the present inventive concepts can be performed to treat one or more medical conditions selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome (PCOS); hypertriglyceridemia; hypercholesterolemia; psoriasis; GERD; coronary artery disease (e.g. as a secondary prevention); stroke; TIA; cognitive decline; dementia; Alzheimer's disease; neuropathy; diabetic nephropathy; retinopathy; heart disease; diabetic heart disease; heart failure; diabetic heart failure; hirsutism; hyperandrogenism; fertility issues; menstrual dysfunction; cancer such as liver cancer, ovarian cancer, breast cancer, endometrial cancer, cholangiocarcinoma, adenocarcinoma, glandular tissue tumor(s), stomach cancer, large bowel cancer, and/or prostate cancer; diastolic dysfunction; hypertension; myocardial infarction; microvascular disease related to diabetes; sleep apnea; arthritis; rheumatoid arthritis; hypogonadism; insufficient total testosterone levels; insufficient free testosterone levels; and combinations of two or more of these. In some embodiments, two, three, or more of the above medical conditions listed immediately hereabove are treated using the systems, devices, and methods of the present inventive concepts. A near full circumferential portion (e.g. approximately 360°) of the mucosal layer of one or more axial segments of GI tissue can be treated. In some embodiments, less than 360° of one or more axial segments of tubular tissue is treated, such as one or more circumferential portions less than 350°, or between 300° and 350°, such as to prevent a full circumferential scar from being created at the one or more axial segment locations. In order to achieve a desired therapeutic benefit, a minimum amount of mucosal tissue can be treated, such as is described herein.

In some embodiments, the systems, devices, and methods of the present inventive concepts are used to treat arthritis, such as rheumatoid arthritis. In these embodiments, arthritis and another disease or disorder of the patient can be treated, such as when one, two, or more of the following are treated in addition to arthritis: insulin resistance, diabetes, non-alcoholic fatty liver disease (NAFLD); non-alcoholic steatohepatitis (NASH); polycystic ovarian syndrome (PCOS); and combinations of these. For example, patients with arthritis may exhibit abnormal and/or dysfunctional glucose metabolism. In some embodiments, a patient exhibiting insulin resistance as well as arthritis (e.g. rheumatoid arthritis) has their small intestinal mucosa (e.g. their duodenal mucosa) treated with the systems of the present inventive concepts.

Target tissue can be selected to treat two or more patient diseases or disorders, such as two or more patient diseases or disorders as described herein.

Target tissue can comprise tissue of the terminal ileum, such as to treat hypercholesterolemia and/or diabetes. In these embodiments, the target tissue can extend into the proximal ileum and/or the colon.

Target tissue can comprise gastric mucosal tissue, such as tissue regions that produce ghrelin and/or other appetite regulating hormones, such as to treat obesity and/or an appetite disorder.

Target tissue can comprise tissue selected from the group consisting of: large and/or flat colonic polyps; margin tissue remaining after a polypectomy; and combinations of two or more of these. These tissue locations can be treated to treat residual cancer cells.

Target tissue can comprise at least a portion of the intestinal tract afflicted with inflammatory bowel disease, such that Crohn's disease and/or ulcerative colitis can be treated.

Target tissue can comprise GI tissue selected to treat Celiac disease and/or to improve intestinal barrier function.

The functional assemblies, functional elements, systems, devices and methods of the present inventive concepts can be configured to avoid ablating or otherwise adversely affecting certain tissue, termed "non-target tissue" herein. Depending on the location of tissue intended for treatment (i.e. target tissue), different non-target tissue can be applicable. In certain embodiments, non-target tissue can comprise tissue selected from the group consisting of: gastrointestinal adventitia; duodenal adventitia; the tunica serosa; the tunica muscularis; the outermost partial layer of the submucosa; ampulla of Vater; papilla; pancreas; bile duct; pylorus; and combinations of two or more of these.

In some embodiments, two or more clinical procedures are performed in which one or more volumes of target tissue are treated in each clinical procedure, such as is described in applicant's co-pending U.S. patent application Ser. No. 14/673,565, entitled "Methods, Systems and Devices for Performing Multiple Treatments on a Patient", filed Mar. 30, 2015. For example, a second clinical procedure can be performed at least twenty-four hours after the first clinical procedure, such as a second clinical procedure performed within six months of a first clinical procedure or a clinical procedure performed after at least six months after the first clinical procedure. The first and second clinical procedures can be performed using similar or dissimilar methods, and they can be performed using similar or dissimilar systems and/or devices (e.g. performed with similar or dissimilar treatment and/or other functional elements). The first and second clinical procedures can treat similar or dissimilar volumes of target tissue (e.g. similar or dissimilar amounts of tissue treated and/or locations of tissue treated), and they can deliver energy to similar or dissimilar sets of multiple delivery zones. In some embodiments, the first and second clinical procedures can include treating and/or delivering energy to contiguous and/or overlapping regions of the GI tract either in the circumferential and/or axial dimensions. In other embodiments, the first and second clinical procedures can include the treatment of disparate regions of the GI tract (such as disparate regions of the duodenum, ileum, and/or stomach). The first and second clinical procedures can be performed using similar or dissimilar devices (e.g. catheters). The first and second clinical procedures can comprise similar or dissimilar deliveries of energy to treat the target tissue. The first and second clinical procedures can be performed at similar or dissimilar temperatures. The second clinical procedure can be performed based on diagnostic results collected after the first clinical procedure has been performed, such as when the diagnostic results are based on a biopsy of mucosal tissue.

The functional assemblies, treatment assemblies, treatment elements and other functional elements of the present inventive concepts can comprise an expandable element or otherwise be configured to automatically and/or manually expand or traverse in at least one radial direction. Typical expandable elements include but are not limited to: an inflatable balloon; a radially expandable cage or stent; one or more radially deployable arms; an expandable helix; an unfurlable compacted coiled structure; an unfurlable sheet; an unfoldable compacted structure; and combinations of two or more of these. In some embodiments, an expandable element can comprise a radially expandable tube, such as a sheet of material resiliently biased in a radially expanded condition that can be compacted through a furling operation, or a sheet of material resiliently biased in a radially compact condition that can be expanded through an unfurling operation. An expandable element can comprise a foldable sheet, such as a sheet configured to be folded to be radially compacted and/or to be unfolded to radially expand. In some embodiments, an expandable element expands to contact tissue, such as to expand to a diameter similar to the diameter of the luminal wall tissue into which the expandable element has been placed. In some embodiments, an expandable element expands to be closer to wall tissue, but the element remains at a distance (e.g. a fixed or predetermined distance) from the tissue surface, such as when the tissue is subsequently brought into contact with all or a portion of an expanded functional assembly or functional element (e.g. using insufflation fluid withdrawal techniques). In some embodiments, an expandable element expands to be larger than the diameter of the luminal wall tissue into which the expandable element has been placed, such as to improve the quality of the apposition of the expandable element against the uneven surface of the tissue. In these embodiments, the fully expanded diameter of an expandable element would be configured to avoid a diameter large enough to cause lasting mechanical damage to the apposed tissue and/or to tissue proximate the apposed tissue. In some embodiments, the expansion of an expandable element (e.g. the expansion of an expandable functional assembly) is monitored and/or varied (e.g. decreased and/or increased), such as to accommodate or otherwise compensate for peristalsis or other muscle contractions that occur in the GI tract (e.g. contractions that occur when a foreign body is present in the GI tract) and/or varied to accommodate changes in GI lumen diameter imposed by aspects of the procedure itself.

Any device (e.g. catheter) of the present inventive concepts can include one or more functional elements comprising one or more treatment elements configured to deliver energy to one or more delivery zones, to treat at least a portion of target tissue. Any device can include one or more functional elements comprising one or more fluid delivery elements, such as one or more nozzles or needles configured to deliver fluid toward and/or into tissue. The fluid delivery elements can be constructed and arranged to deliver fluid to perform a function selected from the group consisting of expanding one or more tissue layers; warming or cooling tissue; removing debris or other substance from a tissue surface; delivering energy to a delivery zone comprising a continuous or segmented surface; treating target tissue; and combinations of two or more of these. Any of the expandable functional assemblies of the present inventive concepts can include one or more other functional elements, such as are described herein. The treatment elements and/or other functional elements (e.g. fluid delivery elements) can be mounted on, within (e.g. within the wall) and/or inside of an expandable element such as a balloon or expandable cage. In some embodiments, one or more functional elements is not mounted to an expandable element, such as those attached to a shaft or other non-expandable catheter component.

In some embodiments, a catheter comprises at least one functional element configured to deliver energy to a delivery zone such as to ablate target tissue. Examples of ablation-based functional elements include but are not limited to: ablative fluids, such as hot or cold ablative fluids delivered to a balloon and/or directly to target tissue; one or more fluid delivery elements configured to deliver ablative fluid directly to target tissue; a radiofrequency (RF) and/or microwave energy delivery element such as one or more electrodes; an ultrasonic and/or subsonic transducer such as one or more piezo crystals configured to ablate tissue with ultrasonic or subsonic energy, respectively, sound waves; a laser energy delivery element such as one or more optical fibers, laser diodes, prisms and/or lenses; a rotating ablation element; a circumferential array of ablation elements; and combinations of two or more of these.

The expandable elements comprising balloons of the present inventive concepts can be divided into two general categories: those that are composed of a substantially elastic material, such as silicone, latex, low-durometer polyurethane, and the like; and those that are composed of a substantially inelastic material, such as polyethylene terephthalate (PET), nylon, high-durometer polyurethane and the like. A third category includes balloons which include both elastic and inelastic portions. Within the category of elastic balloons, two subcategories exist: a first sub-category wherein a combination of material properties and/or wall thickness can be combined to produce a balloon that exhibits a measurable pressure-threshold for inflation (i.e. the balloon becomes inflated only after a minimum fluidic pressure is applied to the interior of the balloon); and a second sub-category, wherein the balloon expands elastically until an elastic limit is reached which effectively restricts the balloon diameter to a maximum value. The individual properties of the balloons in each of these categories can be applied to one or more advantages in the specific embodiments disclosed herein, these properties integrated singly or in combination. By way of example only, one or more of the following configurations can be employed: a highly elastic balloon can be used to achieve a wide range of operating diameters during treatment (e.g. during operation a desired balloon diameter can be achieved by adjustment of a combination of fluid temperature and pressure); a substantially inelastic balloon or a balloon that reaches its elastic limit within a diameter approximating a target tissue diameter (e.g. a duodenal mucosal diameter) can be used to achieve a relatively constant operating diameter that will be substantially independent of operating pressure and temperature; a balloon with a pressure-threshold for inflation can be used to maintain an uninflated diameter during relatively low pressure conditions of fluid flow and then achieve a larger operating diameter at higher pressure conditions of flow. Pressure-thresholded balloons can be configured in numerous ways. In one embodiment, a balloon is configured to have a relatively thick wall in its uninflated state, such as to maximize an electrically and/or thermally insulating effect while the balloon is maintained in this uninflated state. The balloon can be further configured such that its wall thickness decreases during radial expansion (e.g. to decrease an electrically and/or thermally insulating effect). In another embodiment, a balloon is configured to have a relatively small diameter in its uninflated state (e.g. a diameter that is small relative to the inner diameter of tubular target tissue such as the diameter of the mucosal layer of duodenal wall tissue), such as to minimize or completely eliminate apposition between the balloon and the surrounding tissue to minimize heat, RF and/or other energy transfer into the surrounding tissue until the balloon is fully inflated. In another embodiment, a balloon and an ablation system or catheter are configured to circulate a flow of fluid through the balloon (e.g. an elastic balloon or an inelastic balloon) at a sufficiently low enough pressure to prevent apposition of the balloon or other catheter component with target tissue, such as to pre-heat one or more surfaces of the ablation system or ablation device that are in fluid communication with the balloon. In this configuration, when the balloon or other ablation element is positioned to deliver energy to target tissue, the temperature of the balloon or other ablation element will be at a desired level or it will rapidly and efficiently reach the desired level for treatment (i.e. minimal heat loss to the fluid path components due to the pre-heating or pre-cooling). These configurations provide a method of delivering energy to tissue with an ablative fluid filled balloon. A "thermal priming" procedure can be performed prior to one or more target tissue treatments, such as to improve thermal response time of one or more portions of the catheter. Ablative fluid filled balloon catheters as well as thermal priming devices and methods can be configured as is described in applicant's co-pending U.S. patent application Ser. No. 16/438,362, entitled "Heat Ablation Systems, Devices and Methods for the Treatment of Tissue", filed Jun. 11, 2019.

A fluid evacuation procedure can be performed on one or more internal locations of the catheters, functional assemblies and/or functional elements of the present inventive concepts, such as when a negative pressure is applied to purge or otherwise evacuate fluid from one or more locations. A fluid evacuation procedure can be performed prior to a thermal priming procedure and/or prior to delivering ablative fluid to a treatment element.

At times during target tissue treatment when it is desirable to initiate, increase and/or otherwise modify the treatment of tissue by one or more treatment elements (e.g. a fluid delivery element delivering ablative fluid, a mechanically abrasive element, a hot or cold fluid balloon delivering a thermal energy to tissue and/or an electrode delivering RF energy), the diameter of the treatment assembly and/or treatment element (e.g. the diameter of a balloon, deployable cage, expandable tube or other expandable assembly) can be increased in situ to move a treatment element closer to target tissue and/or to change the contact force between the treatment element and the target tissue. At times during treatment when it is desirable to stop or otherwise decrease the amount of tissue treatment, the diameter of the treatment assembly and/or treatment element can be reduced in situ, such as to prevent or otherwise reduce delivery of energy or other treatment to the target tissue by eliminating or reducing tissue contact of one or more treatment elements (e.g. electrodes, abrasive surfaces or ablative fluid-filled balloons). For those cases where the native diameter of the target tissue varies substantially within a delivery zone, then a highly elastic or compliant balloon or other expandable element can be employed, such as a balloon or deployable cage which can be adjusted to achieve a wide range of operating diameters.

Alternatively or additionally, to initiate, increase and/or otherwise modify the treatment of tissue by one or more functional elements (e.g. a fluid delivery element delivering ablative fluid, a mechanically abrasive element, a hot or cold fluid balloon delivering thermal energy to or from tissue and/or an electrode delivering RF energy), the diameter of the target tissue can be decreased in situ to move target tissue closer to a treatment element and/or to change the contact force between the target tissue and the treatment element. To stop or otherwise decrease ablation of tissue, the diameter of tissue neighboring a treatment element can be increased in situ, such as to prevent or otherwise reduce delivery of energy or other treatment to the target tissue by eliminating or reducing tissue contact of one or more treatment elements (e.g. electrodes, abrasive surfaces or ablative fluid filled balloons). The diameter of the tissue proximate a functional assembly can be increased or decreased, independent of the functional assembly diameter, by means of delivering and/or withdrawing a fluid, to and/or from a body lumen (e.g. a lumen of a segment of the intestine) surrounded by target tissue, such as by using standard GI insufflation techniques. Typical insufflation fluids include but are not limited to: gases such as carbon dioxide or air; liquids such as water or saline solution; and combinations of two or more of these. The insufflation fluids can be introduced through a catheter, through an endoscope such as an endoscope through which the catheter is inserted, and/or via another device placed proximate the target tissue. Delivery of insufflation fluids can be performed to move target tissue away from one or more functional elements, such as to stop transfer of energy to target tissue at the end of a treatment of target tissue as described herein. Alternatively or additionally, delivery of insufflation fluids can be performed to manipulate tissue, such as to distend and/or elongate tissue. Extraction of these insufflation fluids and/or the application of a vacuum or other negative pressure can be used to decrease the diameter of the target tissue, such as to bring the target tissue in closer proximity to one or more functional elements and/or to increase the contact force between target tissue and one or more functional elements, also as described herein. In this tissue diameter-controlled approach, a functional assembly including a balloon that can be maintained at a substantially constant diameter can be desirable, such as a substantially inelastic balloon such as a balloon with an elastic-limit.

The systems of the present inventive concepts can include one or more tissue expansion catheters that comprise one or more functional elements configured as fluid delivery elements. In these embodiments, the one or more functional elements can comprise one or more needles, nozzles and/or fluid jets configured to deliver one or more fluids or other injectates to tissue, such as to expand target tissue and/or tissue proximate the target tissue (e.g. safety margin tissue) prior to treatment of target tissue by a tissue treatment element. The expanded tissue layer acts as a safety volume of tissue, reducing the specificity of the treatment (e.g. ablation) required and/or the need to protect the underlying non-target tissue from damage. In some embodiments, a vacuum pressure can be used to manipulate tissue and/or to maintain proximity between a portion of a tissue expansion device and tissue. The vacuum can be provided by one or more vacuum sources, such as via one or more operator adjustable vacuum sources.

Many patients with type 2 diabetes (T2D) are prescribed insulin therapy, "daily insulin", in order to treat high blood sugar. While insulin administration is a mainstay of type 2 diabetes therapy, more than half of patients do not achieve glycemic targets. Typically, insulin-treated patients have a higher prevalence of severe comorbidities, such as cardiovascular, renal, and/or hepatic comorbidities, than non-insulin-treated patients. Further, insulin therapy for type 2 diabetes is associated with weight gain (an increase in visceral adiposity), loss of beta-cell function, worsening of insulin resistance, and/or a high frequency of hypoglycemia, which is associated with poorer health outcomes and increased mortality. Moreover, insulin therapy in T2D is a symptomatic treatment of high blood sugar rather than a pharmacotherapy targeting the underlying insulin resistance that leads to the progressive nature of the disease. As such, insulin therapy quickly becomes insufficient and treatment intensification is needed. These factors taken together lead to tremendous dissatisfaction on the part of patients, poor clinical outcomes, and high cost of care. Therapies that reduce the need for insulin enable improved glycemic control with reduced rates of hypoglycemia and reduced rates of weight gain. The systems and methods (e.g. treatments) of the present inventive concepts provide improved glycemic control with reduced rates of hypoglycemia, weight loss, improvements to hepatic disease (such as improved liver fat content), and other benefits. These systems and methods can be configured to not require significant adherence to a drug protocol by the patient (e.g. including minimization or complete avoidance of taking one or more drugs previously part of the patient's treatment). Similarly, undesirable side-effects of these drugs can be avoided (e.g. nausea with GLP-1, or increased rates of urologic infections with SGLT2 inhibitors). The systems and methods of the present inventive concepts can be configured to allow an operator to perform a tissue treatment procedure (e.g. a tissue ablation procedure) on one or more segments of the patient's duodenum and/or other portions of the patient's gastrointestinal (GI) tract. The systems and methods of the present inventive concepts can reduce insulin intake by the patient without requiring the patient to adhere to a special diet (e.g. differing from diet-based approaches to insulin reduction). The systems and methods of the present inventive concepts can be configured to provide a reduction in therapeutic complications (e.g. as compared to a previous therapy in which the patient was treated) such as a reduction in microvascular complications (e.g. diabetic kidney disease, diabetic retinopathy) and/or macrovascular complications (e.g. myocardial infarction, stroke). The therapeutic benefits provided by the present inventive concepts can also include improvements in blood pressure, microalbuminuria, glomerular filtration rate, and/or other microvascular and macrovascular risk factors. The therapeutic benefits provided by the present inventive concepts can include a reduction in total body weight. The therapeutic benefits provided by the present inventive concepts can include a reduction in the likelihood of liver disease such as cirrhosis or liver carcinoma.

Referring now to FIG. 1, a schematic view of a system and device for performing a medical procedure on the small intestine of a patient is illustrated, consistent with the present inventive concepts. System 10 can be constructed and arranged to perform the method described in FIG. 2 herebelow, such as to treat one or more patient diseases or disorders, also as described herein. System 10 comprises device 100 and console 200. Device 100 is constructed and arranged to treat target tissue, such as via the delivery of energy and/or an ablating agent to target tissue. Device 100 includes connector 103 which operably attaches to connector 203 of console 200. In some embodiments, system 10 further comprises a tissue expansion device, device 20 shown, which is constructed and arranged to expand one or more layers of tissue, such as one or more layers of target tissue and/or one or more layers of tissue proximate target tissue (e.g. one or more layers of safety-margin tissue as described herein). In some embodiments, system 10 further comprises one or more lumen diameter sizing devices, device 30, which is constructed and arranged to collect information correlated to the diameter of a portion of tubular tissue (e.g. one, two or more diameters of a GI lumen within and/or proximate target tissue). In some embodiments, system 10 comprises one or more multi-function devices, device 40, which is constructed and arranged to perform two or more functions selected from the group consisting of: tissue treatment (e.g. tissue ablation); tissue expansion; luminal diameter sizing; and combinations of two or more of these. In some embodiments, system 10 comprises multi-function device 40, and does not include one or more of: device 100, tissue expansion device 20 and/or sizing device 30.

System 10 can further comprise a body introduction device, such as a vascular introducer, laparoscopic port, and/or endoscope, such as endoscope 50a shown. System 10 can further comprise one or more guidewires, such as guidewires 60a and 60b (singly or collectively guidewire 60). In some embodiments, one or more guidewires 60 comprise a guidewire selected from the group consisting of: a Savary-Gilliard® 400 cm guidewire; a Dreamwire™ guidewire; a super stiff Jagwire™ guidewire; and/or a similar guidewire. In some embodiments, system 10 includes scope attached sheath, sheath 80 shown. Sheath 80 can comprise an elongate hollow tube which attaches (e.g. in a side-by-side manner) at one or more points along endoscope 50a. Sheath 80 can attach to endoscope 50a along a majority of its length. In some embodiments, sheath 80 comprises the Reach® overtube manufactured by U.S. Endoscopy, or similar.

Device 100, tissue expansion device 20, lumen diameter sizing device 30 and multi-function device 40 comprise handles 102, 22, 32 and 42, respectively. Handles 102, 22, 32 and 42 each comprise one or more controls, controls 104, 24, 34 and 44, respectively. Controls 104, 24, 34 and 44 are configured to allow an operator to control one or more functions of the associated device, such as a function selected from the group consisting of: inflate or otherwise expand a functional assembly (e.g. functional assembly 130); deliver energy; modify energy delivery; deliver an insufflation fluid; insufflate a portion of the GI tract; desufflate a portion of the GI tract; deliver an injectate (e.g. into tissue and/or onto the surface of tissue); deliver a tissue expanding fluid (e.g. into tissue); steer the distal portion of a shaft; translate a control cable or control rod (hereinafter "control rod"); activate a sensor (e.g. record a signal); activate a transducer; and combinations of two or more of these. In some embodiments, handles 102, 22, 32 and/or 42 comprise a user interface configured to control one or more components of system 10, such as controls 104, 24, 34 and/or 44, respectively, each of which can be constructed and arranged to control operation of one or more of: device 100, device 20, device 30, device 40 and/or console 200. In some embodiments, controls 104, 24, 34 and/or 44 comprise one or more user input and/or user output components, such as a component selected from the group consisting of: screen; touchscreen; light; audible transducer such as a beeper or speaker; tactical transducer such as a vibratory motor assembly; a keyboard; a membrane keypad; a switch; a safety-switch 206 such as a foot-activated switch; a mouse; a microphone; and combinations of two or more of these.

Handles 102, 22, 32 and 42 each attach to the proximal end of shafts 110, 21, 31 and 41, respectively. Shafts 110, 21, 31 and 41 each typically comprise a relatively flexible shaft comprising one or more internal lumens or other passageways. Shafts 110, 21, 31 and/or 41 can comprise a lumen, such as lumen 116 of shaft 110 shown, that is sized and configured to perform a function selected from the group consisting of: provide for the delivery or extraction of one or more fluids such as ablation fluids, cooling fluids, insufflation fluids, pneumatic fluids, hydraulic fluids and/or balloon expanding fluids; allow over the guidewire delivery of the associated device; surround an electrical wire providing electrical energy and/or signals; slidingly receive a control shaft or other control filament such as a control filament used to expand or contract a functional assembly (e.g. functional assembly 130) or otherwise modify the shape of a portion of the device; and combinations of two or more of these. Shafts 110, 21, 31 and/or 41 can comprise a braided or otherwise reinforced shaft or they can include one or more portions which are reinforced. Shafts 110, 21, 31 and/or 41 can comprise a multi-layer construction, such as a construction including a braid, a friction-reduced (e.g. PTFE) liner, a thermally insulating layer and/or an electrically insulating layer. Shafts 110, 21, 31 and/or 41 can include a bulbous distal end, such as tip 115 of shaft 110 shown, a circular or elliptical shaped enlarged end configured to improve traversing the innermost tissue of the duodenum or other luminal tissue of the GI tract (e.g. to smoothly advance within a lumen whose walls include villi and/or one or more folds). As described herein, shafts 110, 21, 31 and/or 41 can include a guidewire lumen, such as lumen 116 of shaft 110.

Positioned on the distal end or on a distal portion of shafts 110, 21, 31 and 41 is an expandable functional assembly, functional assemblies 130, 25, 35 and 45, respectively. Functional assemblies 130, 25, 35 and 45 are each constructed and arranged to be radially expanded and subsequently radially compacted (each shown in their radially expanded state in FIG. 1), one or more times during use. Each of functional assemblies 130, 25, 35 and 45 can include an expandable element selected from the group consisting of an inflatable balloon; a radially expandable cage or stent; one or more radially deployable arms; an expandable helix; an unfurlable compacted coiled structure; an unfurlable sheet; an unfoldable compacted structure; and combinations of two or more of these. Each functional assembly 130, 25, 35, and 45 can comprise a balloon, balloons 136, 26, 36, and 46, respectively, as shown. Functional assemblies 130 and/or 45 can each comprise one or more treatment elements, treatment elements 135 and/or 135' shown, respectively, each an element which can be configured to treat target tissue. Treatment element 135 and/or 135' (singly or collectively treatment element 135) can be similar to one or more functional elements 139 described herein in reference to device 100.

In some embodiments, device 100, tissue expansion device 20, lumen diameter sizing device 30 and/or multi-function device 40, with their functional assemblies 130, 25, 35 and 45 (respectively) in their radially compacted state, are sized and configured to be inserted through a working channel of endoscope 50a and/or sheath 80, after endoscope 50a and/or sheath 80 have been inserted into a patient (e.g. through the mouth and advanced such that their distal end resides in the duodenum or other GI tract location). In some embodiments, device 100, tissue expansion device 20, sizing device 30 and/or multi-function device 40 are sized and configured to be inserted through the mouth and into a patient's GI tract alongside endoscope 50a. In some embodiments, device 100, tissue expansion device 20, lumen diameter sizing device 30 and/or multi-function device 40 are sized and configured to be inserted into a patient over one or more guidewires 60. For insertion over a guidewire, the shafts 110, 21, 31 and/or 41 and the distal portions of the associated device 100, 20, 30 and/or 40 can comprise a distal portion with sufficient length and flexibility to traverse the pylorus and enter the duodenum, while having sufficient column strength, torsional strength, and length to be advanced through the duodenum. In some embodiments, one or more portions of the shafts 110, 21, 31 and/or 41 have variable stiffness (e.g. stiffer in a proximal portion of the shaft) and/or include a lumen configured to accept a stiffening wire or other stiffening mandrel (e.g. a tapered mandrel), such as stiffening wire 67. Alternatively or additionally, stiffening wire 67 can be inserted into endoscope 50*a* and/or sheath 80, such as to facilitate their advancement through the stomach and into the duodenum. In some embodiments, shaft 110, 21, 31, and/or 41 comprises at least a braided portion. In some embodiments, shaft 110, 21, 31, and/or 41 comprises a tapered portion.

Figure 6:
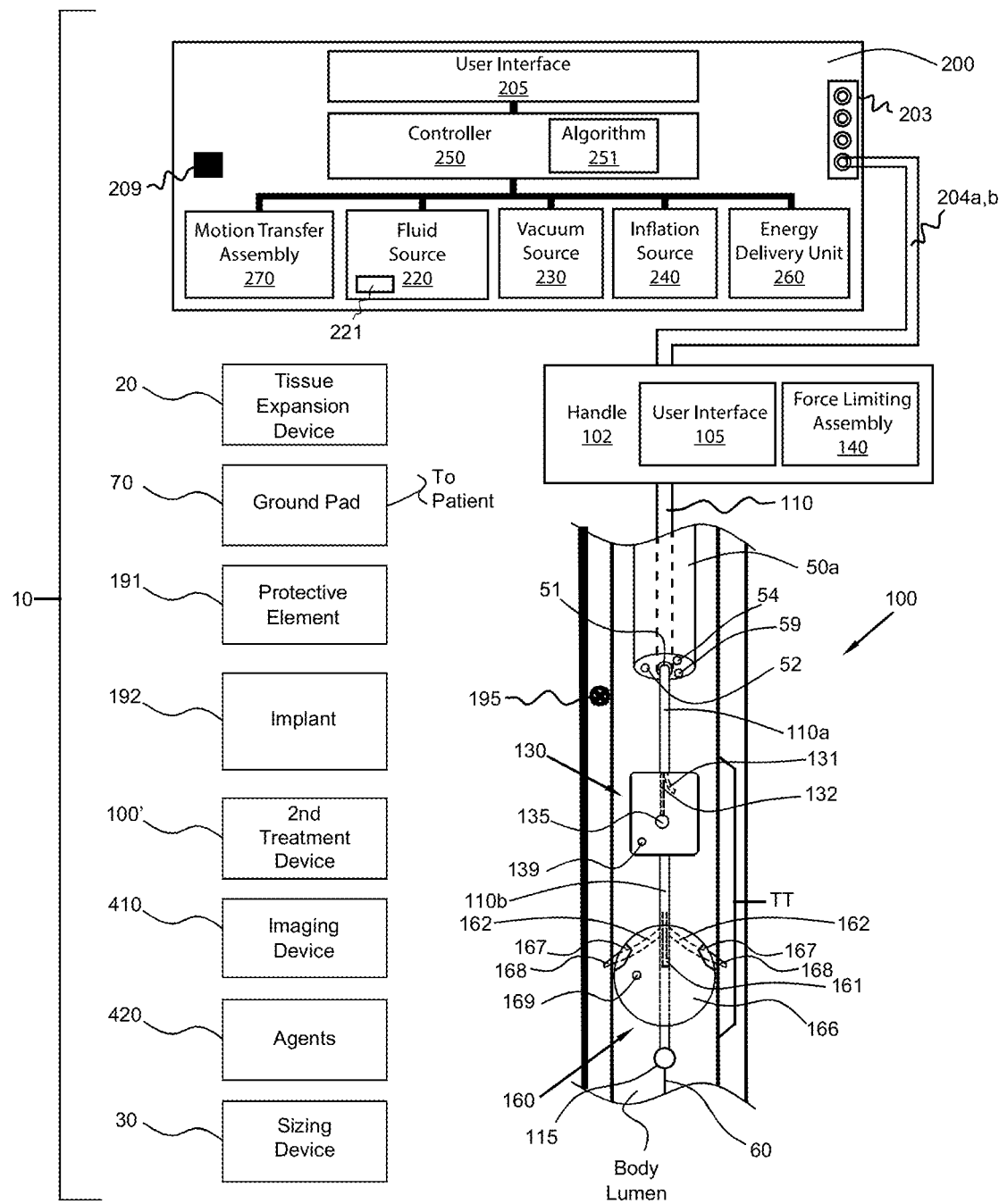
FIG. 6 illustrates a schematic view of a system for treating target tissue of a patient, consistent with the present inventive concepts.

Console 200 can be constructed and arranged in a similar fashion to console 200 of FIGS. 6 and/or 9 described herein. Console 200 can comprise an operator (e.g. clinician) accessible user interface 205. User interface 205 can comprise one or more user output and/or user input components, such as a component selected from the group consisting of: screen; touchscreen; light; audible transducer such as a beeper or speaker; tactical transducer such as a vibratory motor assembly; a keyboard; a membrane keypad; a switch; a safety-switch, such as switch 206 shown (e.g. a foot-activated switch); a mouse; a microphone; and combinations of two or more of these.

Console 200 can comprise a controller, such as controller 250. Controller 250 can comprise one or more components or assemblies selected from the group consisting of: an electronics module; a power supply; memory (e.g. volatile or non-volatile memory circuitry); a microcontroller; a microprocessor; a signal analyzer; an analog to digital converter; a digital to analog converter; a sensor interface; transducer drive circuitry; software; and combinations of two or more of these. Controller 250 can comprise one or more algorithms 251, which can be constructed and arranged to automatically and/or manually control and/or monitor one or more devices, assemblies and/or components of system 10. Algorithm 251 of controller 250 can be configured to determine one or more tissue expansion, tissue ablation, and/or other tissue treatment parameters. In some embodiments, algorithm 251 processes one or more sensor signals (e.g. signals from functional elements 139, 29, 39 and/or 49 described herein) to modify one or more of: volume of tissue expansion fluid delivered; rate of tissue expansion fluid delivery; temperature of tissue expansion fluid delivery; amount of ablative fluid delivered; rate of ablative fluid delivery; energy delivered; power of energy delivered; voltage of energy delivered; current of energy delivered; temperature of ablative fluid or energy delivered; device and/or treatment element location within the GI tract; functional assembly pressure (e.g. balloon pressure); and combinations of two or more of these. Treatment elements 135 and/or 135' can deliver energy to a surface of tissue, such as to a delivery zone as described herein, which comprises a subset of the target tissue treated by that energy delivery (e.g. due to the conduction of heat or other energy to neighboring tissue). Algorithm 251 can comprise an algorithm configured to determine a delivery zone parameter such as a delivery zone parameter selected from the group consisting of: anatomical location of a delivery zone; size of delivery zone; percentage of delivery zone to receive energy; type of energy to be delivered to a delivery zone; amount of energy to be delivered to a delivery zone; and combinations of two or more of these. Information regarding the delivery zone parameter can be provided to an operator of system 10 (e.g. a clinician), such as via user interface 205. This information can be employed to set a delivery zone parameter, assist the operator in determining the completion status of the procedure (e.g. determining when the procedure is sufficiently complete) and/or to advise the operator to continue to complete a pre-specified area or volume of target tissue. The total area of treatment or number of delivery zones or number of treatments during a particular procedure (any of which can be employed in algorithm 251) can be defined by clinical and/or demographic data of the patient.

Console 200 can comprise one or more reservoirs or other sources of fluid, such as reservoir 220. Reservoir 220 can be configured to provide one or more of: fluid at an ablative temperature (e.g. sufficiently hot or cold to ablate tissue); a treatment neutralizing (e.g. cooling or warming) fluid configured to reduce and/or limit ablative effects; an insufflation fluid, injectate 221 (e.g. similar to injectate 221 described herein in reference to FIG. 9); an agent (e.g. agent 420 described herein in reference to FIGS. 7 and/or 9); and/or another fluid. Console 200 can comprise an energy delivery unit, such as EDU 260, configured to deliver energy to treatment element 135, treatment element 135', and/or one or more other components of system 10, such as one or more components of devices 100, 20, 30 and/or 40 (e.g. to functional assemblies 130, 25, 35, and/or 45, respectively). Controller 250, reservoir 220 and/or EDU 260 can be of similar construction and arrangement as controller 250, reservoir 220 and/or EDU 260, respectively, of FIGS. 6 and/or 9 described herein.

Console 200 can comprise a pressure or other fluid pumping assembly, such as pumping assembly 225 constructed and arranged to deliver positive pressure or vacuum pressure (e.g. any pressure below another pressure) to one or more fluid pathways (e.g. lumens), fluid delivery elements, and/or balloons of system 10. Pumping assembly 225 can be constructed and arranged to provide and/or extract fluid to radially expand and/or radially compact, respectively, one or more expandable assemblies, such as functional assemblies 130, 25, 35 and/or 45 comprising a balloon or other fluid expandable structure ("balloon" herein). Pumping assembly 225 can comprise one or more pumps or other fluid delivery mechanisms, and/or other pressure or vacuum generators. In some embodiments, pumping assembly 225 is constructed and arranged to provide a recirculating ablative fluid (e.g. hot or cold) to device 100 and/or device 40 (e.g. to balloon 136 and/or 46, respectively). In these embodiments, pumping assembly 225 can be constructed and arranged to further provide a recirculating "neutralizing fluid" (e.g. a cooling or warming fluid, respectively, to counteract the ablative effects of the previously circulated ablative fluid) to balloon 136 and/or 46, respectively. Pumping assembly 225 can be of similar construction and arrangement as pumping assembly 225 of FIG. 9 described herein. In some embodiments, pumping assembly 225 is constructed and arranged to deliver injectate 221 to a functional assembly 130, 25, 35 and/or 45, such as an injectate configured to expand tissue and/or to create a therapeutic restriction, as described herein, such as an injectate similar to injectate 221 described herein in reference to FIG. 9.

Console 200 includes connector 203, which is operably attached to one or more of: user interface 205 (e.g. safety-switch 206 or another component of user interface 205), controller 250, reservoir 220 and/or pumping assembly 225. Connector 203 is constructed and arranged to operably attach (e.g. fluidly, electrically, optically, acoustically, mechanically and/or otherwise operably attach) to one or more of connectors 103, 23, 33 and 43 of devices 100, 20, 30 and 40, respectively. Console 200 can be constructed and arranged to deliver fluids and/or energy via connector 203 to one or more of devices 100, 20, 30 and 40. In some embodiments, an inflation fluid and/or a fluid at an ablative temperature is provided and/or recovered by console 200, such as a fluid at an ablative temperature delivered to functional assembly 130 of device 100 and/or functional assembly 45 of device 40. In some embodiments, insufflation, pneumatic and/or hydraulic fluids are delivered and/or recovered by console 200 via connector 203. In some embodiments, an injectate 221 is delivered by console 200, such as is described herein in reference to tissue expansion device 20 and multi-function device 40. In some embodiments, one or more control rods (not shown) are translated (e.g. advanced and/or retracted) within one or more lumens or other openings of device 100, 20, 30 and/or 40, such as to expand a cage, deploy a radially deployable arm, change the shape of an assembly, translate an assembly, rotate an assembly and/or otherwise control the position, shape and/or configuration of an assembly of system 10.

Console 200 can provide energy to, send information to and/or record and/or receive a signal from one or more other elements of device 100, such as functional elements 139, 29, 39 and/or 49 described herein.

Device 100 and/or device 40 can be constructed and arranged to treat target tissue of a patient. In some embodiments, device 100 and/or device 40 is of similar construction and arrangement as device 100 of FIGS. 6 and/or 9 described herein. Device 100 comprises handle 102 which attaches to a proximal end of shaft 110 and includes connector 103 for operable attachment to console 200. Positioned on the distal end or on a distal portion of shaft 110 is functional assembly 130. Device 40 comprises handle 42 which attaches to a proximal end of shaft 41 and includes connector 43 for operable attachment to console 200. Positioned on the distal end or on a distal portion of shaft 41 is functional assembly 45. Functional assembly 130 or 45 can comprise an expandable element selected from the group consisting of an inflatable balloon such as balloons 136 and 46 shown; a radially expandable cage or stent; one or more radially deployable arms; an expandable helix; an unfurlable compacted coiled structure; an unfurlable sheet; an unfoldable compacted structure; and combinations of two or more of these. Functional assembly 130 or 45 can comprise an energy delivery element or other tissue treatment element, elements 135 and 135', respectively, such as an energy delivery element configured to deliver thermal, electrical, light, sound and/or ablative chemical energy to target tissue. In some embodiments, treatment element 135 or 135' comprises a mechanical abrader configured to treat tissue through abrasion. In some embodiments, functional assembly 130 or 45 comprises a balloon, balloon 136 and 46, respectively, which can be configured to receive one or more expansion and/or ablative fluids. Balloon 136 or 46 can comprise a compliant balloon, a non-compliant balloon, a pressure-thresholded balloon and/or otherwise be constructed and arranged as described in detail herein. Functional assembly 130 or 45 can be configured to both ablate (e.g. via a hot or cold ablative fluid) and neutralize the ablation (e.g. via a cooling or warming fluid, respectively), prior to and/or after the ablation, as described herein.

Via connectors 103 or 43, console 200 can provide and/or extract one or more fluids to and/or from one or more lumens or other flow pathways of devices 100 or 40, such as fluid provided by reservoir 220 and/or propelled by (i.e. delivered and/or extracted by) pumping assembly 225. Console 200, via EDU 260, can be configured to provide energy to one or more treatment elements 135 or 135' of devices 100 or 40, respectively, such as energy contained in fluid at an ablative temperature (hot and/or cold), electrical energy (e.g. RF or microwave energy), light energy (e.g. laser light energy), or sound energy (e.g. subsonic or ultrasonic sound energy). In some embodiments, console 200 provides a fluid configured to treat target tissue with direct contact, such as an ablating agent (e.g. a sclerosant or other chemically ablative agent) and/or a fluid at an ablative temperature, either or both delivered directly to a target tissue surface.

In some embodiments, treatment elements 135 or 135' comprises a fluid at an ablative temperature provided by console 200. In these embodiments, treatment elements 135 or 135' can comprise a sufficiently hot fluid that is introduced into balloon 136 or 46, respectively, for a first time period to ablate target tissue, after which a cooling fluid is introduced into the balloon for a second time period, to extract heat from tissue (e.g. extract heat from target tissue and/or non-target tissue to reduce the ablation effect). Alternatively or additionally, a cooling fluid can be introduced into balloon 136 or 46 prior to the delivery of the hot fluid (e.g. for a third time period). In some embodiments, treatment element 135 or 135' comprises a sufficiently cold fluid that is introduced into balloon 136 or 46, respectively, for a first time period to ablate target tissue, after which a higher temperature fluid is introduced into the balloon for a second time period, to warm tissue (e.g. warm target tissue and/or non-target tissue to reduce the ablation effect). Alternatively or additionally, a warming fluid can be introduced into balloon 136 or 46 prior to the delivery of the cold fluid (e.g. for a third time period). Both the ablative and ablation-reducing fluids can be provided by console 200. These fluids can be provided in a recirculating manner as described in applicant's co-pending application U.S. patent application Ser. No. 16/438,362, entitled "Heat Ablation Systems, Devices and Methods for the Treatment of Tissue", filed Jun. 11, 2019. Alternatively or additionally, these fluids can be provided in a single bolus manner as described in applicant's co-pending U.S. patent application Ser. No. 14/917,243, entitled "Systems, Method and Devices for Treatment of Target Tissue", filed Mar. 7, 2016. In some embodiments, thermal ablation is performed using system 10 as described herein.

In some embodiments, target tissue and/or tissue proximate the target tissue is cooled, heated and subsequently cooled again, such as via a procedure using device 100. In these embodiments, target tissue and/or tissue proximate the target tissue can be cooled during at least a portion of a first step, such as a first step including supplying a first fluid (e.g. a recirculating fluid) to functional assembly 130 or 45 for a first time period (e.g. a duration of at least 10 seconds or approximately between 15-30 seconds), wherein the first fluid is supplied at a cooling temperature (e.g. continuously supplied by reservoir 220 at a temperature of approximately 10° C.-25° C.). In a subsequent second step, target tissue and/or tissue proximate the target tissue can be heated (e.g. ablated) during at least a portion of the second step, such as a second step including supplying a second fluid (e.g. a recirculating fluid) to functional assembly 130 or 45 for a second time period (e.g. a duration of at least 5 seconds or approximately between 8-15 seconds), wherein the second fluid is supplied at a heat ablating temperature (e.g. continuously supplied by reservoir 220 at a temperature of approximately 85° C.-95° C.). In a subsequent third step, target tissue and/or tissue proximate the target tissue can be cooled during at least a portion of the third step, such as a third step including supplying a third fluid (e.g. a recirculating fluid) to functional assembly 130 or 45 for a third time period (e.g. a duration of at least 10 seconds or approximately between 15-30 seconds), wherein the second fluid is supplied at a cooling temperature (e.g. continuously supplied by reservoir 220 at a temperature of approximately 10° C.-25° C.). In some embodiments, other temperatures and/or durations for each heating or cooling cycle are used. In some embodiments, the second time period in which a hot fluid is supplied to functional assembly 130 or 45 comprises a time less than the first time period and/or the third time period. In some embodiments, the temperature of the fluid supplied to functional assembly 130 or 45 during the first time period and/or the third time period is at least 18° C. less and/or at least 60° C. less than the temperature of the fluid supplied to functional assembly 130 or 45 during the second time period. In some embodiments, the first temperature and the third temperature comprise a similar temperature. In some embodiments, a cooling fluid at approximately 10° C. is delivered to functional assembly 130 or 45 for approximately 30 seconds, after which an ablative fluid at approximately 95° C. is delivered to functional assembly 130 or 45 for approximately 12 seconds, after which a cooling fluid at approximately 10° C. is delivered to functional assembly 130 or 45 for approximately 30 seconds. Alternatively, a warming fluid can be delivered to functional assembly 130 or 45 prior to and/or after the delivery of a cryogenically ablative fluid (e.g. for the similar time periods as described herein in reference to heat ablation). In some embodiments, the volume, temperature and/or duration of fluid delivered to functional assembly 130 or 45 is automatically and/or dynamically adjusted, such as an adjustment performed based on a signal provided by one or more sensors as described herein. For example, a temperature and/or duration can be adjusted during a first ablation of an axial segment of intestine and/or during a subsequent second ablation of the same or different axial segment of intestine. In some embodiments, a pre-cooling and/or post-cooling step is used to avoid the need for a tissue expansion step (e.g. tissue expansion proximate tissue to be ablated in a heat ablation step). In other embodiments, a tissue expansion step is included.

In some embodiments, a first axial segment of tubular tissue is cooled (e.g. non-ablatively cooled), via functional assembly 130 or 45, for a first time period $TP_1$, and subsequently heat ablated for a second time period $TP_2$. A first reservoir $220_A$ includes the cooling fluid at a temperature $T_A$, (e.g. fluid continuously maintained or at least initially provided at temperature $T_A$) and a second reservoir $220_B$ includes the (heat) ablative fluid at a temperature $T_B$ (e.g. fluid continuously maintained or at least initially provided at temperature $T_B$). In some embodiments, after the heat ablation during time period $TP_2$, an additional tissue cooling step is performed via functional assembly 130 or 45, for a third time period $TP_3$. Additionally, axial segments of tubular tissue can subsequently be treated (e.g. additional axial segments treated via tissue cooling and subsequent heat ablation, with or without a subsequent tissue cooling step). $T_A$ can comprise a temperature at or below approximately 25° C., such as a temperature at or below approximately 20° C. and/or 15° C., and $T_B$ can comprise a temperature at or above approximately 65° C., such as a temperature at or above approximately 75° C., 85° C. and/or 95° C. $TP_1$ can comprise a time duration of between 3 seconds and 60 seconds (e.g. between 20 seconds and 40 seconds); $TP_2$ can comprise a time duration of between 1 seconds and 30 seconds (e.g. between 5 seconds and 15 seconds); and $TP_3$ can comprise a time duration of between 3 seconds and 60 seconds (e.g. between 20 seconds and 40 seconds). In these embodiments, $T_A$, $T_B$, $TP_1$, $TP_2$ and/or $TP_3$ can be varied (e.g. automatically by system 10), based on information recorded by a sensor of the present inventive concepts (e.g. a sensor measuring temperature, pressure, flow rate and/or other parameter at one or more locations of device 100 and/or 40, console 200 or other component of system 10). One or more of $T_A$, $T_B$, $TP_1$, $TP_2$ and/or $TP_3$ can be held relatively constant or unchanged, during one or more axial tissue segment ablations. However, one or more of $T_A$, $T_B$, $TP_1$, $TP_2$ and/or $TP_3$ can vary (e.g. be allowed to vary), such as when $T_A$ increases during an extraction of cooling fluid from device 100 (e.g. the recovered fluid warms the cooling fluid in the first reservoir $220_A$). These variations (e.g. as measured by one or more sensors of system 10) can result in an adjustment (e.g. an automatic adjustment) to another parameter (e.g. $T_A$, $T_B$, $TP_1$, $TP_2$ and/or $TP_3$), such as an adjustment made by algorithm 251 (e.g. an algorithm comprising a lookup table including reservoir temperatures and corresponding treatment durations) based on a signal produced by one or more functional elements 109, 119, 139, 209, 229 and/or 309 described herein in reference to FIG. 9, that have been configured as a sensor (e.g. configured to provide a signal used to adjust one or more console settings 201). In some embodiments, $T_A$, $T_B$ $TP_1$, $TP_2$ and/or $TP_3$ are varied based on the value of $T_A$ and/or $T_B$. For example, if the temperature $T_A$ of the cooling fluid were to increase during a multi-ablation procedure, the time period $TP_2$ and/or temperature $T_B$ could be compensatingly adjusted (e.g. decreased). In some embodiments, time period $TP_2$ is decreased by up to 2 seconds (e.g. from an initial time period of approximately 11 to 13 seconds, in one or more decrements), as the temperature $T_A$ increases by up to 16° C. (e.g. from a starting temperature of approximately 9° C.), such as during a clinical procedure comprising ablation of two or more axial segments (e.g. ablation of between two and six axial segments). While the previous embodiments have been described in reference to a cooling of tissue followed by a heat ablation of tissue (which may also include a subsequent tissue cooling step), alternatively, system 10 can be configured to (non-ablatively) warm tissue, followed by cryogenic ablation of tissue (which can also include a subsequent tissue warming step).

In some embodiments, treatment element 135 or 135' comprises one or more energy or other tissue treatment elements positioned in, on and/or within functional assembly 130 or 45, respectively. Treatment element 135 or 135' can comprise one or more energy delivery elements configured to deliver energy to target tissue, such as an energy delivery element selected from the group consisting of a fixed or recirculating volume of fluid at a high enough temperature to ablate tissue; a fixed or recirculating volume of fluid at a low enough temperature to ablate tissue; one or more thermal energy delivery elements such as one or more elements configured to deliver heat energy or cryogenic energy; an array of electrodes such as an array of electrodes configured to deliver radiofrequency (RF) energy; one or more electromagnetic energy delivery elements such as one or more elements configured to deliver microwave energy; one or more optical elements configured to deliver light energy such as laser light energy; one or more sound energy delivery elements such as one or more elements configured to deliver subsonic and/or ultrasonic sound energy; one or more chemical or other agent delivery elements; and combinations of two or more of these. In some embodiments, device 100 or 40 is constructed and arranged to deliver RF energy, such as is described in applicant's co-pending U.S. patent application Ser. No. 16/711,236, entitled "Electrical Energy Ablation Systems, Devices and Methods for the Treatment of Tissue", filed Dec. 11, 2019; and/or to deliver ablative fluid directly to tissue, such as is described in applicant's co-pending U.S. patent application Ser. No. 14/609,334, entitled "Ablation Systems, Devices and Methods for the Treatment of Tissue", filed Jan. 29, 2015.

In some embodiments, device 100 or 40 is further constructed and arranged to provide geometric information (e.g. diameter information) of a luminal structure such as the duodenum. In these embodiments, device 100 or 40, and associated functional assembly 130 or 45, respectively, can be of similar construction and arrangement as lumen diameter sizing device 30 and its functional assembly 35, described herein.

In some embodiments, system 10 comprises one or more devices for expanding target tissue or tissue proximate target tissue, such as tissue expansion device 20 or multi-function device 40. In some embodiments, target tissue to be treated comprises mucosal tissue and the tissue to be expanded comprises submucosal tissue proximate the mucosal tissue to be treated. In some embodiments, tissue expansion device 20 or multi-function device 40 is of similar construction and arrangement as device 100 described herein in reference to FIGS. 6 and/or 9. In some embodiments, tissue expansion device 20 or multi-function device 40 is of similar construction and arrangement as a tissue expansion device described in applicant's co-pending U.S. patent application Ser. No. 16/900,563, entitled "Injectate Delivery Devices, Systems and Methods", filed Jun. 12, 2020. Device 20 or 40 can be configured to expand a full or partial circumferential segment of luminal wall tissue, such as to expand one or more layers of submucosal tissue in one or more axial segments of the duodenum or other portion of the GI tract. Device 20 or 40 can be configured to expand multiple segments of GI tract tissue, such as multiple relatively contiguous segments of submucosal tissue expanded as described in detail herein.

Tissue expansion device 20 comprises handle 22 which attaches to a proximal end of shaft 21 and includes connector 23 for operable attachment to console 200. Positioned on the distal end of shaft 21 or on a distal portion of device 20 is functional assembly 25. Functional assembly 25 can comprise an expandable element selected from the group consisting of: an inflatable balloon such as balloon 26 shown; a radially expandable cage or stent; one or more radially deployable arms; an expandable helix; an unfurlable compacted coiled structure; an unfurlable sheet; an unfoldable compacted structure; and combinations of two or more of these.

Balloon 26 or 46 can comprise a compliant balloon, a non-compliant balloon, a pressure-thresholded balloon and/or otherwise it can be constructed and arranged as described in detail herein. Balloon 26 or 46 can comprise a tissue-contacting length of between 20 mm and 26 mm, such as a tissue-contacting length of approximately 23 mm. Balloon 26 can comprise a wall thickness of between 0.0002" and 0.0010", such as a wall thickness of approximately 0.0005". Functional assembly 25 or 45 can be configured to expand to a diameter between 27.5 mm and 37.5 mm, such as a diameter of approximately 32.5 mm. Functional assembly 25 or 45 can be configured to be expanded via control 24 or 44, respectively, and/or via user interface 205 of console 200 (e.g. inflated and deflated by delivery and extraction, respectively, of air, water and/or other fluids by console 200).

Functional assembly 25 or 45 comprises one or more fluid delivery elements 28 or 48, respectively. The one or more fluid delivery elements 28 or 48 can each comprise an element selected from the group consisting of needle such as a straight needle or a curved needle; nozzle; fluid jet; iontophoretic fluid delivery element; and combinations of two or more of these. The one or more fluid delivery elements 28 or 48 are configured to deliver injectate 221 and/or another fluid to tissue when functional assembly 25 or 45, respectively, is expanded (e.g. at least partially expanded with inflation fluid provided by console 200), positioning the fluid delivery elements 28 or 48 proximate (e.g. in contact with or close to) tissue to be expanded, such as luminal wall tissue of the GI tract.

The one or more fluid delivery elements 28 or 48 can be configured to be advanced (e.g. advanced into tissue) and retracted via control 24 of device 20 or control 44 of device 40, respectively. The one or more fluid delivery elements 28 or 48 can be positioned in one or more ports 27 or 47, respectively, as shown in FIG. 1. In some embodiments, a vacuum provided by console 200 causes tissue to tend toward and/or enter each port 27 or 47, such that each fluid delivery element 28 or 48, respectively, can inject fluid (e.g. injectate 221) into the engaged and/or captured tissue without having to extend significantly beyond the associated port 27 or 47 (e.g. each fluid delivery element can be configured to remain within the associated port during delivery of fluid into tissue captured within the port). By limiting excursion of fluid delivery element 28 or 48 out of port 27 or 47, respectively, risk of the fluid delivery element and/or injectate 221 penetrating through the outer surface of the GI tract is prevented or at least significantly reduced. In some embodiments, fluid can be delivered into tissue by fluid delivery element 28 or 48 with or without advancement of the fluid delivery element into the captured tissue (e.g. tissue is drawn into a port via an applied vacuum such that fluid delivery element penetrates or otherwise engages the tissue for fluid delivery without advancement of the fluid delivery element). In some embodiments, fluid delivery elements 28 or 48, ports 27 or 47, and/or other portions of tissue expansion device 20 or multi-function device 40, are of similar construction and arrangement as a tissue expansion device described in applicant's co-pending U.S. patent application Ser. No. 16/900,563, entitled "Injectate Delivery Devices, Systems and Methods", filed Jun. 12, 2020.

In some embodiments, functional assembly 25 or 45 comprises three or more fluid delivery elements 28 or 48, respectively, which can be arranged in a circumferential pattern, such as three fluid delivery elements 28 or 48 arranged along a circumference and separated by approximately 120°. The multiple fluid delivery elements 28 or 48 can be configured to be advanced individually (e.g. via multiple controls 24 or 44 respectively), or simultaneously (e.g. via a single control 24 or 44). In some embodiments, two fluid delivery elements 28 or 48 are separated by approximately 180°. In some embodiments, four fluid delivery elements 28 or 48 are separated by approximately 90°.

In some embodiments, system 10 includes injectate 221 which can be provided by console 200 to device 20, and injectate 221 can be delivered into tissue by the one or more fluid delivery elements 28 or 48. Injectate 221 can comprise a material selected from the group consisting of: water; saline; a fluid with a dye such as a visible dye such as indigo carmine; methylene blue; India ink; SPOT™ dye; a gel; a hydrogel; a protein hydrogel; a fluid containing a visualizable media such as a media visualizable under X-ray such as a radiopaque powder (e.g. tantalum powder), ultrasound imaging and/or magnetic resonance imaging; and combinations of these.

In some embodiments, device 20 and/or console 200 are configured to reduce the fluid (e.g. liquid or gas) in balloon 26 as injectate 221 is delivered into tissue such as submucosal tissue, such as to prevent excessive force being applied to tissue proximate the expanding tissue (i.e. due to the decreasing luminal diameter proximate the expanding tissue in contact with balloon 26). In some embodiments, system 10 is constructed and arranged to inflate balloon 26 to a first target pressure, such as a pressure of approximately 0.7 psi. Injectate 221 is delivered via fluid delivery elements 28 to submucosal tissue (e.g. simultaneously or sequentially). Fluid contained within balloon 26 can be removed or added to maintain the pressure at or below a second target pressure, for example a pressure higher than the first target pressure such as a pressure between 0.8 psi and 0.9 psi. Fluid of up to 10 ml can be injected while maintaining the second target pressure (e.g. no more than the second target pressure) in the balloon (e.g. by decreasing the amount of fluid in the balloon to cause approximately 1 mm steps of diameter decrease of balloon 26).

In some embodiments, tissue expansion device 20 is further constructed and arranged to provide geometric information (e.g. diameter information) of one or more axial segments of a luminal structure such as the duodenum. In these embodiments, device 20 and expandable assembly 25 can be constructed and arranged similar to lumen diameter sizing device 30 and expandable assembly 35, respectively, described herebelow.

In some embodiments, system 10 comprises one or more separate devices for estimating or otherwise measuring (e.g. "sizing") the diameter of luminal tissue, such as lumen diameter sizing device 30. Sizing device 30 is constructed and arranged to be placed into one or more locations of the GI tract or other internal location of the patient and measure the diameter or other geometric parameter of tissue. In some embodiments, sizing device 30 is constructed and arranged similar to device 30 or device 100 described herebelow in reference to FIG. 9. Sizing device 30 can be configured to measure the diameter of multiple locations of GI tract tissue, such as multiple diameters along the length of one or more axial segments of the duodenum or other intestinal location.

Device 30 comprises handle 32 which attaches to a proximal end of shaft 31 and includes connector 33 for operable attachment to console 200. Positioned on the distal end of shaft 31 or on a distal portion of device 30 is functional assembly 35. Functional assembly 35 can comprise an expandable cage, balloon 36, or other expandable element as described herein, constructed and arranged to measure the inner surface diameter of tubular tissue (e.g. average diameter, equivalent diameter, minimum diameter, cross sectional area and/or other geometric measure of the inner surface of tubular tissue), such as a diameter of the duodenum or jejunum.

Balloon 36 or 46 can comprise a compliant balloon, a non-compliant balloon, a pressure-thresholded balloon and/or otherwise be constructed and arranged as described in detail herein. Functional assembly 35 or 45 can be configured to be expanded via control 34 or 44, respectively, and/or via user interface 205 of console 200 (e.g. inflated and deflated by delivery and extraction, respectively, of fluids by console 200).

Fluids delivered by console 200 to functional assembly 35 or 45 (e.g. fluids supplied by reservoir 220) can be provided at one or more predetermined pressures, or pressure profiles. Diameter measurements can be accomplished by performing a visualization procedure (manual or automated) that assesses functional assembly 35 or 45 diameter. Alternatively or additionally, functional assembly 35 or 45 can be controllably filled with a fluid, and controller 250 can include an algorithm (e.g. algorithm 251 described herein in reference to FIG. 9) that correlates the fluid volume and/or fluid pressure to the diameter of tubular tissue in contact with functional assembly 35 or 45. In some embodiments, subsequent selection (e.g. device model or size selection) and/or expansion diameter (e.g. inflated diameter chosen for sufficient apposition) of functional assemblies 130, 25 and/or 45 of devices 100, 20 and/or 40, respectively, can be determined using the information provided by sizing device 30 and/or console 200. In some embodiments, device 30 or 40 performs one or more sizing procedures as described herein.

In some embodiments, functional assembly 35 or 45 comprises a balloon, expandable cage and/or other expandable element that includes two or more electrodes configured to provide a tissue impedance measurement whose value can be correlated to a level of apposition of functional assembly 35 or 45, respectively, and whose expanded diameter (e.g. visually or otherwise measured) correlates to a diameter of tubular tissue in contact with the expandable element. Alternatively or additionally, functional assembly 130 of device 100, functional assembly 25 of device 20 and/or functional assembly 45 of device 40 can be used to measure a diameter of the inner surface of tubular tissue, such as has been described herein in reference to functional assembly 35 and device 30.

In some embodiments, system 10 comprises one or more devices, such as multi-function device 40 shown, that are constructed and arranged to perform two or more functions selected from the group consisting of: treat target tissue such as to deliver energy or otherwise ablate target tissue; expand tissue such as to expand one or more layers of submucosal tissue (e.g. proximate to and/or including target tissue); and determine or estimate a diameter (e.g. an average diameter, equivalent diameter, minimum diameter, cross sectional area and/or other geometric measure) of a lumen of tubular tissue; and combinations of two or more of these. Multi-function device 40 is constructed and arranged to be placed into one or more locations of the GI tract or other internal location of the patient and perform two or more of the functions listed above. In some embodiments, multi-function device 40 is of similar construction and arrangement as device 100 described herein in reference to FIGS. 6 and/or 9. Multi-function device 40 can be configured to perform the multiple functions at multiple segments of GI tract, such as multiple relatively contiguous axial segments of the duodenum or other intestinal location as is described herein.

Device 40 comprises handle 42 which attaches to a proximal end of shaft 41 and includes connector 43 for operable attachment to console 200. Positioned on the distal end of shaft 41 or on a distal portion of device 40 is functional assembly 45. Functional assembly 45 can comprise an expandable cage, a balloon (e.g. balloon 46 shown), and/or other expandable element constructed and arranged to be positioned in apposition with and/or in close proximity to the inner wall of tubular tissue, such as tissue of the duodenum, jejunum and/or other intestinal location. Balloon 46 can comprise a compliant balloon, a non-compliant balloon, a pressure-thresholded balloon and/or otherwise be constructed and arranged as described in detail herein. Functional assembly 45 can be configured to be expanded via control 44 and/or via user interface 205 of console 200 (e.g. inflated and deflated by delivery and extraction, respectively, of fluids by console 200).

Functional assembly 45 can comprise treatment element 135', which can comprise a fluid at an ablative temperature delivered into functional assembly 45 by console 200 and/or an energy delivery element permanently positioned on, in and/or within functional assembly 45 (e.g. an energy delivery element configured to deliver thermal energy, electrical energy, light energy, sound energy and/or chemical energy as described herein). In some embodiments, treatment element 135' comprises a mechanical abrader configured to treat tissue through abrasion. In some embodiments, treatment element 135' is of similar construction and arrangement as functional element 139a of device 100 of FIG. 9 and/or treatment element 135 of device 100 of FIG. 1. Functional assembly 45 can be configured to both ablate (e.g. via a hot or cold ablative fluid) and neutralize (e.g. via a cooling or warming fluid, respectively), prior to and/or after the ablation, as described herein.

Alternatively or additionally, functional assembly 45 can comprise one or more elements configured to expand tissue, such as fluid delivery elements 48. Fluid delivery elements 48 can each be positioned within one or more ports 47 as shown. Fluid delivery elements 48 and ports 47 can be constructed and arranged as described herein in reference to fluid delivery element 139c and ports 137, respectively, of device 100 of FIG. 1.

Devices 100, 20, 30 and/or 40 can comprise one or more functional elements, such as functional elements 139, 29, 39 and/or 49, respectively, shown positioned in, on and/or within functional assemblies 130, 25, 35 and 45, respectively. Alternatively or additionally, one or more functional elements 139, 29, 39 and/or 49 can be located at a different location of the associated device, such as in, on and/or within the associated shaft and/or handle of the device. In some embodiments, one or more functional elements 139, 29, 39 and/or 49 comprise a sensor, such as a sensor selected from the group consisting of: physiologic sensor; blood glucose sensor; blood gas sensor; blood sensor; respiration sensor; EKG sensor; EEG sensor; neuronal activity sensor; blood pressure sensor; flow sensor such as a flow rate sensor; volume sensor; pressure sensor; force sensor; sound sensor such as an ultrasound sensor; electromagnetic sensor such as an electromagnetic field sensor or an electrode; gas bubble detector such as an ultrasonic gas bubble detector; strain gauge; magnetic sensor; ultrasonic sensor; optical sensor such as a light sensor; chemical sensor; visual sensor such as a camera; temperature sensor such as a thermocouple, thermistor, resistance temperature detector or optical temperature sensor; impedance sensor such as a tissue impedance sensor; and combinations of two or more of these. Alternatively or additionally, one or more functional elements 139, 29, 39 and/or 49 comprise a transducer, such as a transducer selected from the group consisting of: an energy converting transducer; a heating element; a cooling element such as a Peltier cooling element; a drug delivery element such as an iontophoretic drug delivery element; a magnetic transducer; a magnetic field generator; an ultrasound wave generator such as a piezo crystal; a light producing element such as a visible and/or infrared light emitting diode; a motor; a pressure transducer; a vibrational transducer; a solenoid; a fluid agitating element; and combinations of two or more of these. Functional elements 139, 29, 39 and/or 49 can be electrically connected to EDU 260 (e.g. to receive power, send signals and/or receive signals), such as via an electrical connection provided by connector 203. Functional elements 139, 29, 39 and/or 49 can send or receive signals from controller 250 of console 200, such as one or more sensor signals used to control ablation energy provided by console 200. Functional elements 139, 29, 39 and/or 49 can be activated and/or otherwise controlled via controls 104, 24, 34 and/or 44, respectively. Alternatively or additionally, user interface 205 of console 200 can be configured to allow operator control of functional elements 139, 29, 39 and/or 49.

In some embodiments, console 200 comprises one or more functional elements 209, comprising a sensor or transducer as described herein. Functional element 209 can comprise one or more pressure sensors, such as one or more pressure sensors configured to provide a signal used to regulate fluid delivery provided to one or more of devices 100, 20, 30 and/or 40. Functional element 209 can comprise one or more temperature sensors, such as one or more temperature sensors that provide a signal used to regulate temperature of one or more fluids of console 200. Functional element 209 can be positioned to measure a parameter (e.g. temperature or pressure) of fluid within reservoir 220, within pumping assembly 225 and/or within a fluid conduit of console 200.

In some embodiments, system 10 comprises one or more agents configured to be delivered to the patient, such as agent 420 described herein. Agent 420 can be delivered by one or more of devices 100, 20, 30, 40 and/or 50, or by a separate device such as a syringe or other medication delivery device. In some embodiments, injectate 221 comprises agent 420, such as when agent 420 is delivered by one or more fluid delivery elements 139c as described herein. In some embodiments, agent 420 comprises an anti-peristaltic agent, such as L-menthol (i.e. oil of peppermint). Alternatively or additionally, agent 420 can comprise glucagon, buscopan, hyoscine, somatostatin, an opioid agent, and/or any anti-peristaltic agent. Agent 420 can be delivered into the GI tract, such as via endoscope 50a, sheath 80 and/or devices 100, 20, 30 and/or 40. Agent 420 can be delivered systemically, such as via an intravenous or intra-arterial access line, or injected directly into tissue. Agent 420 can comprise a drug or other agent as described herein in reference to agent 420 of FIGS. 7 and/or 9.

As described above, user interface 205 can comprise safety-switch 206 such as a foot-activated switch. Safety-switch 206 can be configured to allow a clinician to activate, modify and/or maintain (e.g. maintain in an "on" state) one or more processes of system 10 without having to use his or her hands (e.g. without having to use a digit of the hand). In some embodiments, system 10 is constructed and arranged to perform a function selected from the group consisting of: automatic contraction (e.g. deflation) of expandable assembly 130 if safety-switch 206 is not activated (e.g. depressed); automatic replacement of ablative fluid (e.g. hot fluid) with neutralizing fluid (e.g. cold fluid) if safety-switch 206 is not activated; initiate introduction of ablative fluid (e.g. hot fluid) into expandable assembly 130 by activation of safety-switch 206 (e.g. after expandable assembly has been pre-expanded with cold fluid and user has confirmed proper position for treatment); allow hands-free activation (e.g. initiation) of a treatment step such that one or more operators can maintain their hands one or more of endoscope 50 and/or devices 100, 20, 30 and/or 40; allow hands-free activation (e.g. initiation) of a treatment step such that the required number of operators is reduced; cause a function to cease if safety-switch 206 is not activated (e.g. depressed); and combinations of these.

Each of devices 100, 20, 30 and/or 40 can be provided in one or more sizes, such as one or more lengths of the associated shaft 110, 21, 31 and/or 41, respectively, and/or one or more diameters (e.g. expanded diameter) of the associated expandable assembly 130, 25, 35 and/or 45, respectively. Luminal sizing as described herein or other anatomical information can be used to select the appropriately sized device to treat the patient. In some embodiments, system 10 of FIG. 1 is configured to perform a medical procedure on a patient as described herein in reference to FIG. 14.

In some embodiments, the systems, devices and methods of the present inventive concepts can reduce the need for insulin therapy in a larger proportion of patients, such as to provide durable glycemic control with or without the therapies administered to the patient prior to the treatment of the present inventive concepts, or with a decrease in dosage of one or more previously administered medications.

The systems, devices and methods of the present inventive concepts can be configured to treat patients with microvascular disease or patients with a high risk of microvascular disease, such as to improve patient health and/or eliminate or otherwise reduce the need for one or more medications (e.g. one or more insulin medications). The treatment can be configured to reduce diabetic retinopathy (e.g. as shown in a reduction in diabetic retinopathy score), proteinuria and/or peripheral neuropathy severity. Additionally or alternatively, the treatment can be configured to reduce the effects of macrovascular disease such as myocardial infarction, stroke, peripheral vascular disease, CV death, and combinations of two or more of these.

Figure 2:
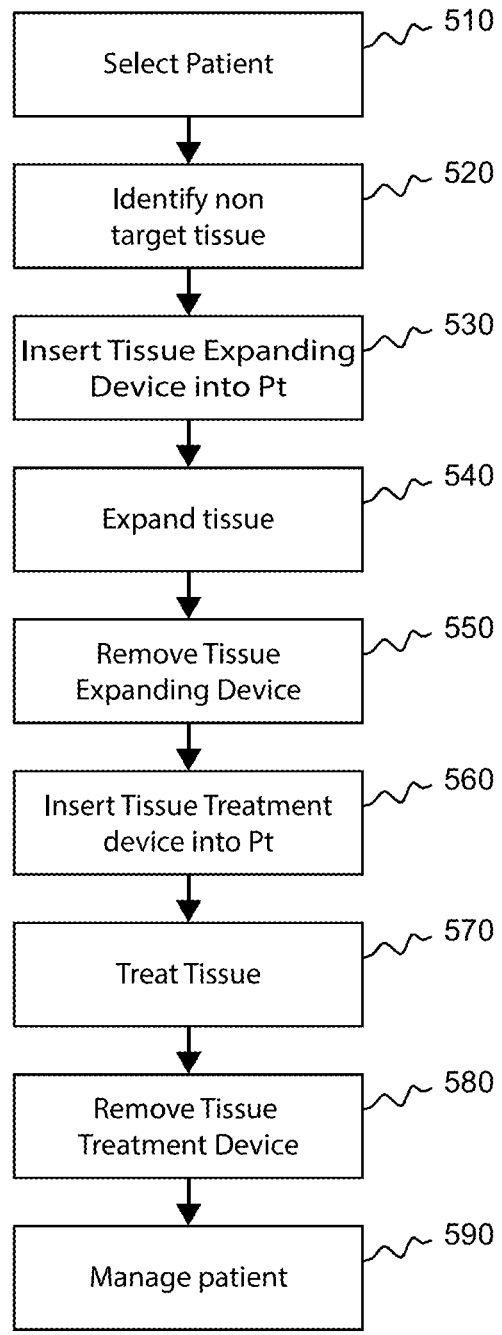
FIG. 2 illustrates a flow chart of a method for treating target tissue of a patient, consistent with the present inventive concepts.

Referring now to FIG. 2, a flow chart of a method of treating target tissue of a patient is illustrated, consistent with the present inventive concepts. In some embodiments, the method of FIG. 2 is accomplished using system 10 of FIG. 1 described hereabove, or system 10 of FIG. 6 described herebelow. In Step 510, a patient is selected for treatment. The patient can be selected to treat a patient disease or disorder selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease (e.g. as a secondary prevention); stroke/TIA; cognitive decline or dementia (e.g. Alzheimer's); diabetic nephropathy; neuropathy; retinopathy; diabetic heart disease and/or heart failure; and combinations of these. In some embodiments, the patient is selected to treat two or more of the above diseases or disorders, such as a patient selected to treat both a form of diabetes and hypercholesterolemia.

The patient selected can be taking one or more medicines to treat their diabetes. The patient selected can have an HbA1c level between 7.5% and 12.0%, between 7.5% and 10%, or between 7.5% and 9.0%. In some embodiments, the patient selected can have an HbA1c level between 6.0% and 12.0%. Patients with higher HbA1c levels and/or other higher disease burden can receive more aggressive treatments (e.g. more tissue treated and/or higher number of repeated treatments over time) as described herebelow in reference to Step 570.

Patient selection can be based on the current level of one or more parameters representing one or more various biomarkers or other representative values of physiologic conditions (e.g. as compared to an average among diabetic and/or non-diabetic patients), such as a level of a parameter selected from the group consisting of: body mass index (BMI) level; waist circumference; HbA1c level; fasting glucose; insulin resistance; liver fibrosis; cholesterol or triglyceride level; duration of years exhibiting type 2 diabetes; fasting C-peptide or C-Peptide stimulation in response to a meal; age; and combinations of these.

Prior to placing any device in the patient, or at any time thereafter (e.g. during or after the procedure), one or more agents can be introduced into the patient, such as an agent introduced into the GI tract directly, such as agent 420 described hereabove in reference to FIG. 1. In some embodiments, agent 420 comprises L-menthol (i.e. oil of peppermint) or other agent configured to provide an anti-peristalsis effect. In these embodiments, a few drops of agent 420 can be placed in an irrigation lumen of an endoscope or other body inserted device with a fluid delivery channel. In some embodiments, approximately 8 mL of L-menthol is mixed with approximately 0.2 nL of Tween 80 (polysorbate 80) in approximately 500 mL of distilled water (i.e. to create an approximately 1.6% solution). Approximately 20 mL of this mixture can be sprayed through a working channel of endoscope 50a, or more as required to dampen peristalsis. In some embodiments, the solution can vary between approximately 1.6% and 3.2%. Tween and/or sorbitan monostearate can be used as an emulsifier.

One or more agents can be delivered once the endoscope or other agent delivery device enters the duodenum. In other embodiments, agent 420 is delivered intravenously, and can comprise glucagon and/or buscopan.

In some embodiments, an endoscope is inserted into the patient (e.g. endoscope 50a of FIG. 1). In these embodiments, subsequently inserted devices can be placed through a working channel of the endoscope and/or alongside the endoscope. In some embodiments, an endoscope and an attachable sheath (e.g. scope attachable sheath 80 of FIG. 1) are both inserted into the patient, and subsequently inserted devices can be placed through a working channel of the endoscope, through the attachable sheath and/or alongside the endoscope and the attached sheath. Each patient inserted device can be inserted over a guidewire. In some embodiments, an endoscope stiffening device is used, such as an endoscope stiffening system provided by Zutron Medical of Lenexa, Kans., USA.

In Step 520, non-target tissue can be identified. Non-target tissue can be identified with a visualization device, such as endoscope 50a of system 10 of FIG. 1. The non-target tissue can comprise the ampulla of Vater, also known as the papilla, the pancreas, or other tissue to which treatment may adversely affect the patient. Step 520 and/or another step of the method of FIG. 2 can include marking the non-target tissue (or tissue proximate the non-target tissue), such as with a tattoo, ink or other visualizable substance, such as a visual agent placed in the mucosa and/or submucosa in or proximate the ampulla of Vater. In some embodiments, one or more markers similar to marker 195 described herebelow in reference to FIG. 3 or 5A-E are deployed in the patient to provide a reference location relative to non-target tissue. Tissue expansion and/or tissue treatment performed in subsequent steps can avoid the non-target tissue identified and potentially marked (e.g. with one or more markers 195) in step 520.

In Step 530, a tissue expansion device is inserted into the patient. Step 530 can include selecting a particular model of tissue expansion device, such as a particular size or other configuration of a tissue expansion device. In some embodiments, the tissue expansion device is constructed and arranged similar to device 20 and/or device 40 of FIG. 1 described hereabove, or device 100 or device 20 described herebelow in reference to FIG. 6. The tissue expansion device can be inserted over a guidewire, such as a Savary-Gilliard® guidewire or other relatively stiff guidewire. The guidewire can be advanced such that its distal end is in the jejunum. During advancement of the tissue expansion device, the guidewire can be held taut in order to prevent the tissue expansion device from forming a loop in the stomach. In some embodiments, the tissue expansion device is inserted through a working channel of an endoscope, such as endoscope 50a of FIG. 1. In other embodiments, the tissue expansion device is inserted alongside an endoscope.

The tissue expansion device is advanced into the duodenum (e.g. over a guidewire). One or more fluid delivery elements of the tissue expansion device can be positioned at least 1cm, but not more than 5 cm or 10 cm from the ampulla of Vater, to perform a first tissue expansion or otherwise a most-proximal tissue expansion (i.e. closest to the ampulla of Vater). In some embodiments, one or more fluid delivery elements of the tissue expansion device are positioned based on the location of a previously placed marker, such as marker 195 described hereabove in STEP 520. Prior to and/or during insertion, a stiffening wire can be inserted within the tissue expansion device. An endoscope can be positioned adjacent the tissue expansion device, such that both distal ends are beyond the ampulla of Vater (e.g. beyond a tattoo or other marker or marking identifying the ampulla of Vater, as described herein).

In some embodiments, prior to insertion of the tissue expansion device, a lumen diameter sizing device is inserted to the patient, such as device 30 of FIG. 1. Luminal diameter or other information provided by the sizing device can be used to select and/or control the tissue expansion device. The sizing device can be placed over a guidewire as described hereabove or it may be delivered through the working channel of an endoscope. Prior to and/or during insertion, a stiffening wire can be inserted within the sizing device.

The sizing device expandable element (e.g. balloon) is positioned in the post-papillary duodenum and inflated at a particular location within the duodenum with a fluid (such as air or saline) and the pressure of the fluid within the balloon is determined by a pressure sensor attached to the proximal end of the device. The volume of delivered fluid can be detected by the system. The fluid can be delivered slowly, such as until a stable pressure reading of approximately 0.7 psi (or approximately 0.9 psi or 2.0 psi) is determined by the pressure sensor (i.e. a threshold pressure is achieved). The volume of fluid within the balloon at a given pressure is used to ascertain the lumen diameter by reference-checking against a calibration step performed before the sizing procedure (e.g. via one or more algorithms of system 10 of FIG. 1 or 6). Measurements can be taken in at least two locations within the duodenum. An algorithm selects an appropriate ablation balloon size for the individual patient.

In Step 540, tissue is expanded. In some embodiments, saline or other fluid is injected by multiple fluid delivery elements of the tissue expansion device, such as three needles or other fluid delivery elements, positioned in a tissue port and spaced approximately 1200 apart along a circumference that deliver injectate (e.g. injectate 221 of FIG. 1) into tissue. Each injection can comprise at least 1 ml, such as at least 2 ml, at least 5 ml or at least 8 ml per fluid delivery element. Volumes injected by the multiple fluid delivery elements can be selected to achieve near full circumferential expansion of submucosal tissue (e.g. without gaps, full 360° expansion).

Subsequent injections of fluid into tissue can be delivered, such as at an axial separation distance of between 1 cm and 2 cm apart from a previous injection (e.g. 1 cm to 2 cm distally in the duodenum). In some embodiments, multiple injections are positioned at least 0.5 cm apart along the axis of the duodenum, such as between 1.0 cm and 5.0 cm apart, such as approximately 1.0 cm, 2.0 cm, 3.0 cm, 4.0 cm and/or 5.0 cm apart from one another along the axis of the duodenum. In some embodiments, axial separation of injection sites (i.e. translation distance of the tissue expansion device between injections) can approximate half the length of a balloon onto which the fluid delivery elements are mounted, such as half the length of balloon 26 of FIG. 1. In some embodiments, a series of 5-15 sets (e.g. 8-12 sets) of injections (e.g. each set comprising injections from 2, 3 or more fluid delivery elements) can be performed by delivering injectate (e.g. a fluid containing a visualizable dye) to the tissue to be expanding and subsequently translating the tissue expansion device to a new axial location (e.g. after proper expansion of tissue is confirmed visually or otherwise). Each advancement and/or retraction of the tissue expansion device can be made in unison with advancement and/or retraction of an endoscope positioned alongside the tissue expansion device.

Tissue expansion can begin at a location proximate but distal to the ampulla of Vater, such as at a location at least 1 cm distal to but not more than 5 cm or 10 cm from the ampulla of Vater. A series of relatively contiguous, full circumferential submucosal tissue expansions can be performed (e.g. moving distally), for example up to the Ligament of Treitz. In alternate embodiments, multiple full circumferential tissue expansions are performed by moving the tissue expansion device from distal to proximal locations, or in a discontinuous manner.

Volumes of injections and/or axial separation of injection can be chosen to avoid axial gaps. After injections, gaps identified circumferentially and/or axially (e.g. via endoscope camera, fluoroscope or ultrasound imaging device), can be filled in as deemed necessary via additional injection (e.g. with or without rotation and/or translation of the tissue expansion device)

In some embodiments, the amount of fluid (e.g. liquid such as water or gas such as air) in an expandable assembly supporting the fluid delivery elements is reduced as the injectate is delivered into tissue, such as to prevent excessive force being applied to tissue proximate the expanding tissue (i.e. due to the decreasing lumen proximate the expanding tissue in contact with expandable assembly), such as is described in detail hereabove in reference to FIG. 1.

In some embodiments, a first volume of fluid (e.g. air) is determined that causes a balloon of the tissue expansion device to get sufficient apposition with a lumen of the GI tract (e.g. a lumen of the duodenum), such as by measuring pressure achieved within the balloon. The balloon is subsequently compacted (i.e. fluid removed), and filled with a second volume that is less than the first volume, and a confirmation of a lower pressure can be performed. Vacuum is applied within the GI lumen (e.g. via an insufflation port of an endoscope or other inserted device), causing the lumen to collapse onto the balloon without compressing the luminal wall. A second vacuum is applied to one or more tissue ports on the balloon (e.g. tissue ports 27 of FIG. 1), causing tissue to be drawn into the tissue ports. One or more needles (e.g. fluid delivery elements 28 of FIG. 1) can be advanced into the tissue contained in the tissue ports, while avoiding the potential of the needles penetrating an outer layer and/or outside of the GI wall tissue, as has been described in detail hereabove. In some embodiments, tissue is penetrated by the fluid delivery elements at the time of the application of the vacuum, without the advancement of the fluid delivery element, also as described hereabove.

Multiple injections (e.g. three injections from three equally separated fluid delivery elements) can be performed simultaneously or sequentially. A vacuum can be applied prior to delivery of fluid, such as to draw tissue toward the fluid delivery element (e.g. into three associated ports as described in reference to FIG. 1). After fluid delivery, the vacuum can be removed and the tissue expansion device advanced (or retracted).

The injectate delivered can include an agent that is directly visualizable by an operator (e.g. via an endoscope camera or other camera), radiographically visualizable (e.g. via a fluoroscope or other X-ray imaging device) and/or ultrasonically reflectable or otherwise visualizable (e.g. via an ultrasound imaging device), such as an injectate 221 comprising visualizable material, as described hereabove in reference to FIG. 1. Visualization of the expanded tissue can be used to determine proper volume of injectate delivered as well as sufficient tissue expansion (e.g. sufficient thickness, axial length and/or circumferentiality of tissue expansion). The pressure of the expandable assembly (e.g. balloon) or the volume of fluid within the expandable assembly can also be monitored to determine if a proper volume of injectate has been delivered to achieve adequate tissue expansion.

In Step 550, the tissue expansion device is removed, for example using an over-the wire exchange leaving the guidewire in place. An endoscope and/or sheath can also be removed during this step. In some embodiments, the tissue expansion device is also configured to ablate or otherwise treat tissue (e.g. in addition to tissue expansion), and the tissue expansion device remains in place to perform Step 570.

In Step 560, a tissue treatment device is inserted into the patient (e.g. if not already in place to perform the tissue expansion step described above, such as when the tissue treatment device is of similar construction and arrangement to multi-function device 40 described hereabove in reference to FIG. 1). Step 560 can include selecting a particular model of a tissue treatment device, such as a particular size or other configuration of a tissue treatment device. In some embodiments, the tissue treatment device is constructed and arranged similar to device 100 and/or device 40 of FIG. 1 described hereabove, and/or device 100 of FIG. 6 described herebelow. In some embodiments, prior to selection of the tissue treatment device, a lumen diameter sizing device, such as device 30 of FIG. 1, is inserted and used to determine the size of a tissue treatment device to be used (e.g. to select a particular diameter of an expandable treatment assembly of the treatment device).

The tissue treatment device can be placed through an endoscope, such as endoscope 50a of FIG. 1, or through a scope attached sheath, such as sheath 80 of FIG. 1. Alternatively or additionally, the tissue treatment device can be placed over a guidewire, such as guidewire 60 of FIG. 1. In some embodiments, the tissue treatment device is placed over the same guidewire used to introduce the tissue expansion device of Steps 530-550. The tissue treatment device can be advanced to the duodenum. In some embodiments, the tissue treatment device can be advanced to the duodenum over a guidewire without an endoscope in place, subsequent to which an endoscope can be advanced to a similar location in the duodenum. In some embodiments, prior to and/or during insertion, a stiffening wire can be inserted within the tissue treatment device.

In Step 570, target tissue is treated (e.g. ablated) by one or more treatment elements of the tissue treatment device, such as treatment element 135 positioned on expandable assembly 130 of device 100 of FIG. 1. The target tissue can comprise one or more portions of the mucosal layer of the duodenum. Treated tissue can further comprise at least an inner layer of neighboring submucosal tissue. One or more circumferential ablations or other treatments can be performed along a length of the GI tract (e.g. along one or more axial segments of the GI tract), such as along a length of the duodenum at least 1 cm distal to the ampulla of Vater, such as at a location at least 1 cm distal to but within 3 cm, 5 cm or 10 cm of the ampulla of Vater. In some embodiments, all ablations are performed at least 2 cm or at least 3 cm distal to the ampulla of Vater (e.g. tissue within 1 cm, 2 cm or 3 cm of the ampulla of Vater is not ablated). In some embodiments, one or more circumferential ablations (e.g. a most-proximal duodenal axial segment ablated) is performed based on the position of a previously placed marker, such as marker 195 described hereabove in STEP 520. In some embodiments, tissue treatments are only performed at locations that have had submucosal tissue expansion performed and/or confirmed (e.g. visually). In other embodiments, tissue treatments are performed without any tissue expansion, avoiding the need for Steps 530-550.

In some embodiments, a thermal treatment is provided by sufficiently hot or cold fluid introduced into a balloon of the tissue treatment device to ablate tissue. In other embodiments, different forms of energy delivery or other tissue treatments are performed, as described in detail in reference to system 10 of FIG. 1 or system 10 of FIG. 6.

The tissue treatment device can treat a series of axial segments of GI tract tissue comprising lengths between 1 cm and 5 cm each, such as approximately 3 cm in length each. The tissue treatment device can treat a cumulative axial length of GI tract tissue (e.g. an axial length of duodenal mucosa tissue) of less than or equal to 3 cm, 6 cm, 9 cm, 15 cm, or 20 cm. The tissue treatment device can be constructed and arranged to treat more than 3 cm of axial length of duodenal mucosa, such as more than 3.4 cm, more than 6 cm, more than 7 cm, more than 8 cm or more than 9 cm (e.g. approximately 9.3 cm), such as to achieve a clinical benefit for a diabetes or other patient as described herebelow in reference to applicant's clinical study (including the results presented in—FIGS. 21-44). In some embodiments, at least 10%, 15%, 25%, 30% and/or 50% of the duodenal mucosa distal to the ampulla of Vater is treated. The axial length and/or overall volume of tissue treated can correspond to a patient parameter, such as the longevity of the disease or other disease parameter as described in detail herebelow (e.g. higher disease burden correlating to larger volumes of tissue treated).

In some embodiments, at least 3 axial segments of duodenal mucosal tissue are treated (e.g. sequentially treated), such as with a treatment element configured to deliver energy to a delivery zone with a length between 1.0 cm and 4.0 cm (e.g. tissue contacting length of a balloon filled with ablative fluid), such as a delivery zone length between 1.9 cm and 3.3 cm, or approximately 3 cm in length. In some embodiments, at least 4 axial segments of duodenal mucosal tissue are treated, such as at least 6 axial segments of duodenal mucosal tissue are treated. In these embodiments, the treatment element can be configured to deliver energy to a delivery zone with a length between 0.7 cm and 2.0 cm (e.g. tissue contacting length of a balloon filled with ablative fluid). In some embodiments, the treatment element comprises ablative fluid delivered into a balloon, such as the balloon 136 described herein. Multiple tissue treatments are performed by repositioning the treatment element (e.g. treatment element 135 of FIG. 1), which can further include expanding an expandable assembly (e.g. expandable assembly 130 of FIG. 1) onto and/or into which the treatment element treating the tissue can be positioned. Contact between the target tissue and the treatment element can be accomplished using desufflation techniques to bring the tissue toward the treatment element, as described in detail hereabove. Tissue treatment is performed, such as by filling the expandable assembly with ablative temperature fluid and/or delivering any form of energy to the target tissue such as is described herein. In embodiments where the tissue treatment device is delivered over a guidewire, the guidewire can be retracted (e.g. at least retracted to a location proximal to the treatment element) prior to any tissue treatments.

Multiple treatments can be performed by advancing or retracting the tissue treatment element and/or tissue treatment device. In some embodiments, the tissue treatment element is positioned at a distal location and a series of tissue treatments are performed, such as at least 3 tissue treatments performed in which the tissue treatment device is retracted approximately the length of the tissue contacting portion of the treatment element such as to treat relatively contiguous, non-overlapping, full circumferential axial segments of the duodenum. After each tissue treatment, confirmation of being away from (e.g. distal to) any non-target tissue marked and/or otherwise identified (e.g. in Step 520) can be performed (e.g. be visualizing a previously placed marker 195). In some embodiments, a marker 195 is placed to avoid any damage to the ampulla of Vater. In some embodiments, after three axial segments of duodenal mucosa are treated (e.g. treated distally to proximally), an assessment of the linear distance between the most proximal treatment segment and the ampulla of Vater is performed (e.g. one or more components of system 10 is used to determine the distance). If sufficient length is determined (e.g. the determined distance is above a threshold), additional (more proximal) axial tissue segments can be treated. During translation of the tissue treatment device over a guidewire, undesired movement of the guidewire is prevented or otherwise reduced by the operator.

In some embodiments, the system of the present inventive concepts (e.g. system 10 of FIG. 1 or 6) is configured to allow only one ablation per (pre-determined) time period, such as to prevent two ablations within the time period such as to prevent repetitive ablation in the same or at least similar (e.g. overlapping) portions of the GI tract (e.g. rapid treatment of similar treatment zones).

In some embodiments, the tissue treatment of Step 570 should be completed within approximately 120 minutes or within approximately 60 minutes of the initiation of tissue expansion performed in Step 540, such as within approximately 45 minutes, 30 minutes and/or 20 minutes. Performance of tissue treatment within this time window prevents an unacceptable amount of injectate dissipation from the expanded tissue (e.g. submucosal tissue) space. In some embodiments, the system of the present inventive concepts (e.g. system 10 of FIG. 1 or 6) is configured to prevent a tissue treatment (e.g. ablation) until a submucosal expansion step has been performed.

The amount of target tissue treated and/or the number of treatments performed can correlate to (e.g. be proportional to) one or more patient conditions (e.g. more severe correlates to more tissue treated and/or more treatments performed over time). This increased treatment can comprise an increased axial length of tissue treated (e.g. an increased cumulative axial length of duodenum ablated or otherwise treated), a deeper depth of treatment and/or a larger number of treatments performed over time in order to achieve a sustained treatment response. Increased treatments can correlate to a higher burden of the patient's disease (e.g. relatively long duration since diagnosis, higher HbA1c level than a standard diabetic patient and/or more mucosal hypertrophy than a standard diabetic patient). In some embodiments, the volume of target tissue treated and/or the number of treatments performed is proportional to the patient's HbA1c level.

In some embodiments, the tissue treatment is modified to avoid creation of a duodenal stenosis or stricture, such as to limit one or more of: amount of energy delivered; peak energy delivered; duration of energy delivered; length of tissue treated; depth of tissue treated; and combinations of these. In some embodiments, a duodenal stenosis or stricture is treated with balloon dilatation.

In some embodiments, tissue expansion is not performed prior to tissue treatment. In some embodiments, lumen diameter sizing is not performed, or is performed with a tissue expansion device and/or a tissue treatment device. In some embodiments, a single device is inserted into the patient to perform two or more of: lumen diameter sizing; tissue expansion; and tissue treatment; such as a device similar to device 40 of FIG. 1.

In Step 580, the tissue treatment device is removed. In addition, any guidewires, endoscopes, scope attached sheaths, or other inserted devices are removed.

In Step 590, a step of managing the patient post-procedurally can be performed. Post-procedure patient management can comprise one or more of: a liquid diet for at least 1 day, 4 days, 5 days, 7 days or 14 days; a soft diet for at least 1 day, 4 days, 5 days, 7 days, or 14 days; a low sugar and/or low fat diet for at least 1 week, 1 month or 1 year; a standardized diabetic (e.g. ADA) diet for at least 1 week, 1 month or 1 year; and nutritional counseling for at least 1 week, 1 month or 1 year.

The therapy provided by the systems, methods and devices of the present invention can lead to numerous therapeutic benefit outcomes to the patient receiving the treatment. In some embodiments, the patient has an outcome selected from the group consisting of: improvement in HbA1c, fasting glucose and/or post-prandial glucose; at least a 1% improvement in HbA1c; a resultant HbA1c of less than 7.5%, less than 7%, less than 6.5%, or less than 6% (e.g. at a time period after a tissue treatment procedure of at least 1 month, 3 months, 6 months or 12 months); improvement in one or more triglyceride levels; improvement in AST, ALT, liver fibrosis panel, liver fibrosis score, NAFLD assessment and/or or NASH assessment; improvement in risk of myocardial infarction, stroke, TIA and/or peripheral vascular disease or diabetic cardiomyopathy; improvement in microvascular disease risk such as nephropathy, retinopathy and/or neuropathy; reduced development of end-stage renal disease, blindness and/or amputation; reduced insulin requirement (e.g. in patients with insulin-dependent diabetes) or other injectable therapy requirement; reduced medication requirement (e.g. in patients with diabetes) either in number of medicines or dosage of medicines; improved fetal birth outcomes (e.g. in patients with gestational diabetes); improved fertility in patients with polycystic ovarian syndrome and/or reduced hirsutism; weight loss of at least 5% of excess body weight, or at least 10%, 20%, 30% or 40% of excess body weight; reduced blood pressure; reduced cardiovascular risk; improved diabetes control and/or reduced diabetic complications; reduced obesity and/or reduced weight; reduced cognitive decline or prevention of dementia; and combinations of these.

The therapy provided by the systems, methods and devices of the present invention can have a clinically significant durability that lasts for at least 3 months, at least 6 months, at least 1 year or at least 2 years. The durability of the treatment can be enhanced by treating more volumes of tissue, such as by treating deeper and/or longer lengths of duodenal mucosa, or by treating the patient multiple times in the same or different regions of the duodenum, small intestine and/or stomach. The durability can be improved by selecting patients with a prior history of dietary compliance and medication compliance and/or a duration of the disease within a particular time window such as less than 2 year or 5 years, or less than 7 years or 10 years.

The systems, methods and devices of the present invention can be constructed and arranged to avoid or reduce the likelihood of one or more adverse events. In some embodiments, pancreatitis is avoided by excluding the ampulla of Vater while performing tissue expansion (e.g. submucosal tissue expansion) and/or tissue treatment (e.g. hot fluid and/or other tissue ablation). In some embodiments, duodenal stenosis and/or stricture can be avoided by performing one or more of the following: ablating only mucosal tissue proximate expanded submucosal tissue layers; ablating only mucosal tissue proximate submucosal tissue layers expanded within 15 minutes, 30 minutes or 45 minutes of ablation; avoiding a second ablation to a tissue segment ablated within 24 hours; and treating tissue (e.g. ablating) only when the operator has direct visualization (e.g. endoscopic visualization) and/or other visualization (e.g. via X-ray or ultrasonic visualization devices) of the tissue treatment element and the tissue being treated.

Applicant has conducted human studies with the systems, methods and devices of the present inventive concepts.

Included below are results of early studies and associated data collected through Jul. 18, 2014.

Some patients received treatment of approximately 9 cm of relatively full-circumferential axial length of duodenal mucosa (via three approximately 3 cm hot fluid balloon-based ablations), and some patients received treatment of less than or equal to 6 cm of relatively full-circumferential axial length of duodenal mucosa (via two or less approximately 3 cm hot fluid balloon-based ablations).

Early results showed: baseline HbA1c was 9.2% and FPG was 187 mg/dl. 1 month post-procedure, HbA1c was reduced by 1.1% in LS-DMR patients (patients receiving duodenal mucosa treatments of approximately 9 cm (e.g. 9.3 cm) of duodenal tissue) but only 0.1% in SS-DMR patients (patients receiving duodenal mucosa treatment of approximately 3 cm (e.g. 3.4 cm) of duodenal tissue, the data representing 12 LS-DMR patients vs 7 SS-DMR patients, each group at 1 month (p=0.058). By 3 months, HbA1c was reduced by approximately 2% in LS-DMR patients but was unchanged in SS-DMR patients (N=5 in each group at 3 months). FPG reductions in LS-DMR patients were −64 mg/dl and −67 mg/dl at 1 and 3 months.

Figure 21:
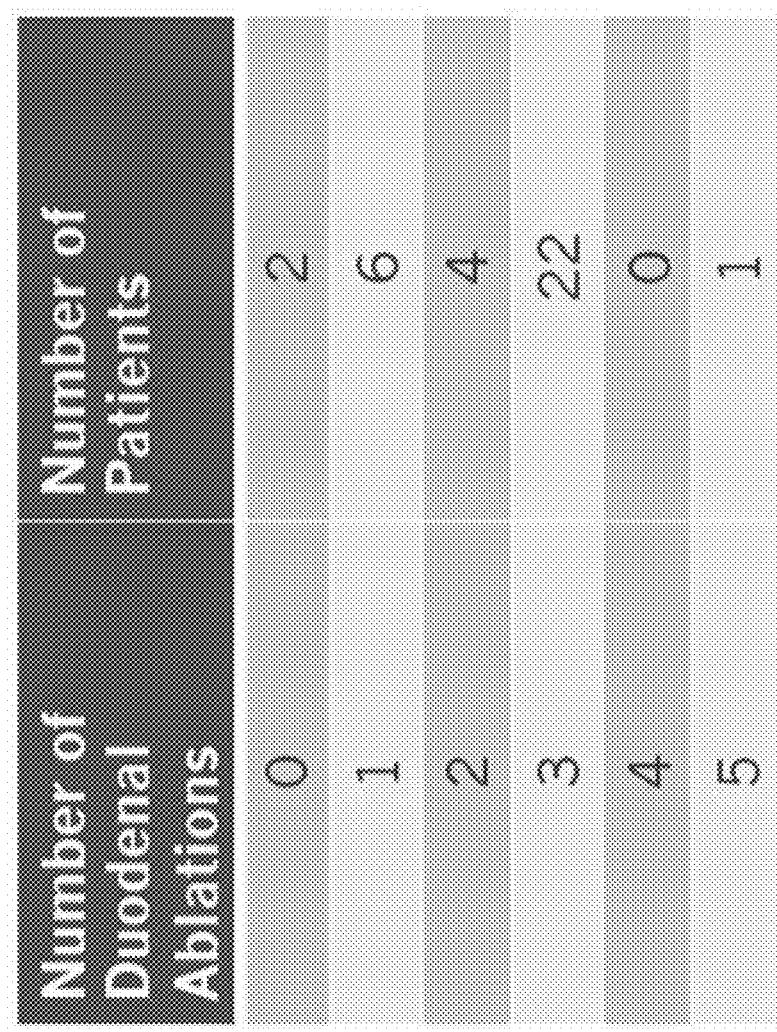
FIG. 21 is a chart showing the number of patients receiving numbers of treatments, consistent with the present inventive concepts.

Referring to FIG. 21, a breakdown of a number of patients who received various quantities of duodenal axial segment treatments comprising delivery of heat from an ablative fluid delivered to a balloon-based treatment assembly is illustrated. Thirty five patients were treated in a dosimetric evaluation of the systems, methods and devices described herein. In the study, an ablation is defined as an axial length of circumferentially ablated tissue, ablated with a single positioning of the balloon and subsequent hot fluid delivery to the balloon. Ablation dose is defined as the total length of circumferentially ablated tissue on a single procedural day. A single patient received 5 ablations (the highest dose administered), and duodenal stenosis presented as food intolerance and epigastric discomfort. After endoscopic balloon dilation, the patient recovered without further issue.

This patient with the duodenal stenosis lost a substantial amount of weight in the 2 weeks after the development of stenosis (nearly 10 kilograms). Controlled duodenal stenosis may be an effective means of achieving substantial weight loss with its attendant benefits on metabolic or obesity-related ailments. Creation of a therapeutic restriction can be performed as described in applicant's co-pending U.S. patent application Ser. No. 17/095,108, titled "Systems, Devices and Methods for the Creation of a Therapeutic Restriction in the Gastrointestinal Tract", filed Nov. 11, 2020, the content of which is incorporated herein by reference in its entirety.

In some embodiments, the systems, devices and methods of the present inventive concepts can be configured to deliver at least two ablations to target tissue (e.g. at least two sequential deliveries of energy or other treatments to different axial segments of GI mucosa), such as to deliver at least three ablations to target tissue. In some embodiments, a minimum and/or maximum amount of duodenal mucosa is treated, such as has been described hereabove.

Referring to FIG. 22, a table of cumulative demographic information for the first 21 patients of the applicant's studies is illustrated. These baseline characteristics are generalizable and relevant to the Type 2 diabetes population.

In some embodiments, the systems, devices and methods of the present inventive concepts can be configured to treat patients with a characteristic selected from the group consisting of: duration of diabetes less than 10 years; age between 18 yrs and 75 yrs; BMI between 20 and 60, such as a BMI between 24 and 40; and combinations thereof.

Referring to FIG. 23, a table of results of applicant's studies, detailing recorded dose dependent improvements in glycemic control is illustrated. Applicant measured three validated measures of glycemic control, Hemoglobin A1c (HbA1c), fasting plasma glucose (FPG), and two hour post-prandial glucose (2hPG).

In some embodiments, the systems, devices and methods of the present inventive concepts can be configured to provide a therapeutic benefit selected from the group consisting of: a reduction in HbA1c of at least 0.7%, 1.0% or 1.5% at three months, such as a reduction of approximately 2.18 at three months; an FPG of no more than 150 mg/dl, 126 mg/dl or 100 mg/dl, such as an FPG that can result with a reduction of approximately 63.5 mg/dl; a 2hPG of no more than 250, 200 or 175, such as an 2hPG that can result with a reduction of approximately 103.7; and combinations thereof.

In some embodiments, an absolute change of at least 0.7%, 1.0%, 1.5% and/or 2.0% in HbA1c is expected. In some embodiments, a relative change above an HbA1c target is expected, such as a relative change of at least 50%, 75% or 100%, such as when the target HbA1c is an HbA1c of approximately 6.5%, 7.0% or 7.5%. It has been reported that a 1% absolute change in HbA1c correlates to a 40% reduction in risk of microvascular complication due to diabetes.

Figure 24:
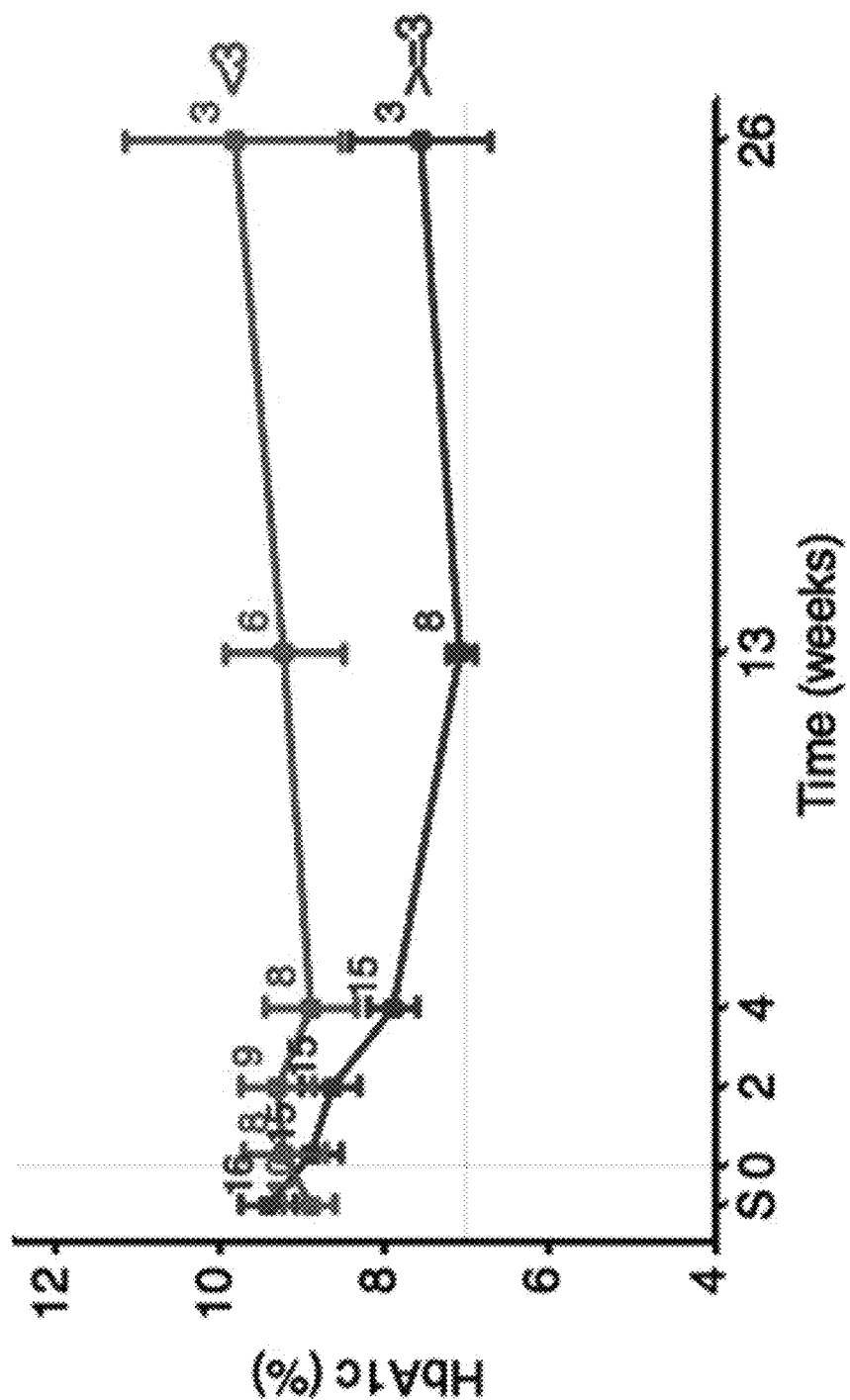
FIG. 24 illustrates a graph illustrating HbA1c reductions in patients receiving three or more ablations, consistent with the present inventive concepts.

Referring to FIG. 24, a graph illustrating an approximately 2% HbA1c reduction in patients receiving three or more ablations compared with no change in those receiving fewer than 3 ablations is illustrated.

In some embodiments, the systems, devices and methods of the present inventive concepts can be configured to achieve an HbA1c level at or below 7.5%, or 7.0% or 6.5%, such as at a time period of 3 months or more, such as by ablating a cumulative length of duodenal mucosa greater than 6 cm, greater than 7 cm, greater than 8 cm or greater than 9 cm (e.g. via 2, 3 or more ablations as described herein).

Figure 25:
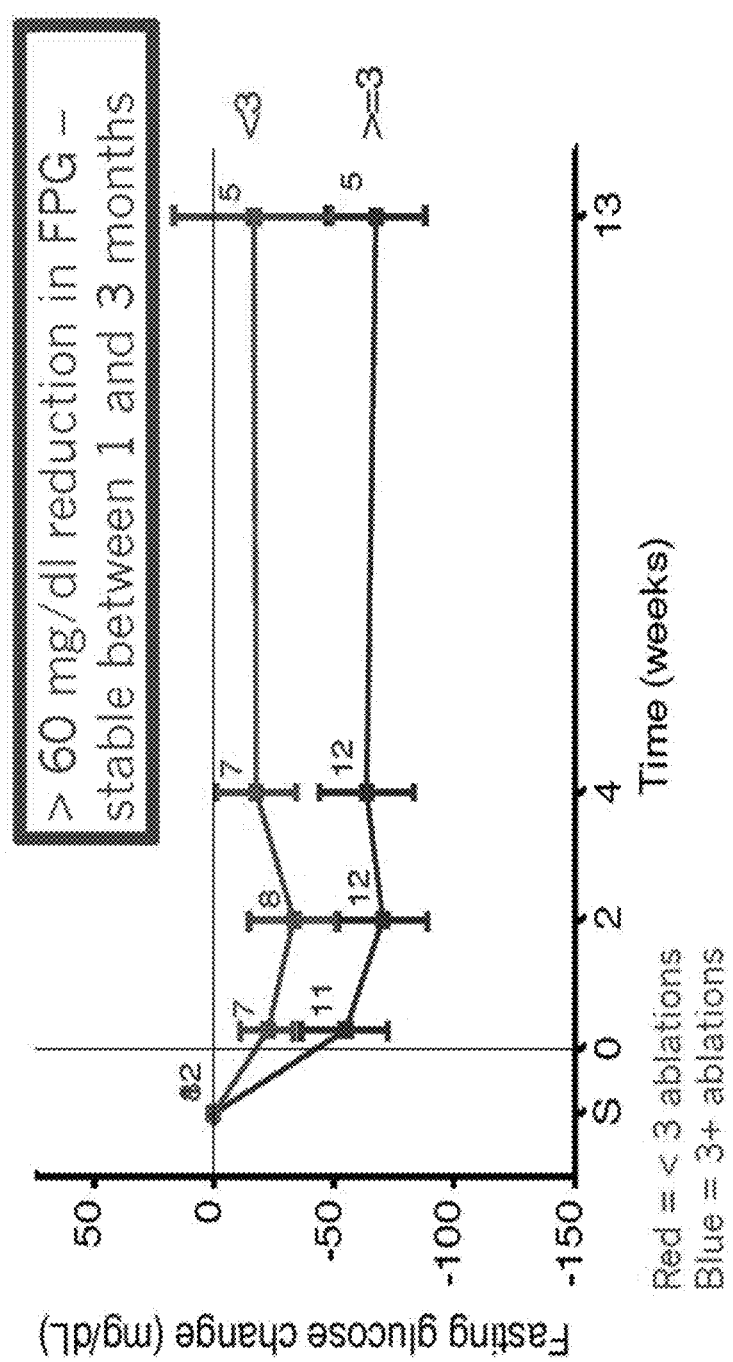
FIG. 25 illustrates a graph illustrating reduction in FPG levels, consistent with the present inventive concepts.

Referring to FIG. 25, a graph illustrating a similar reduction in FPG levels, which remain stable between one and three month post procedure is illustrated.

Figure 26:
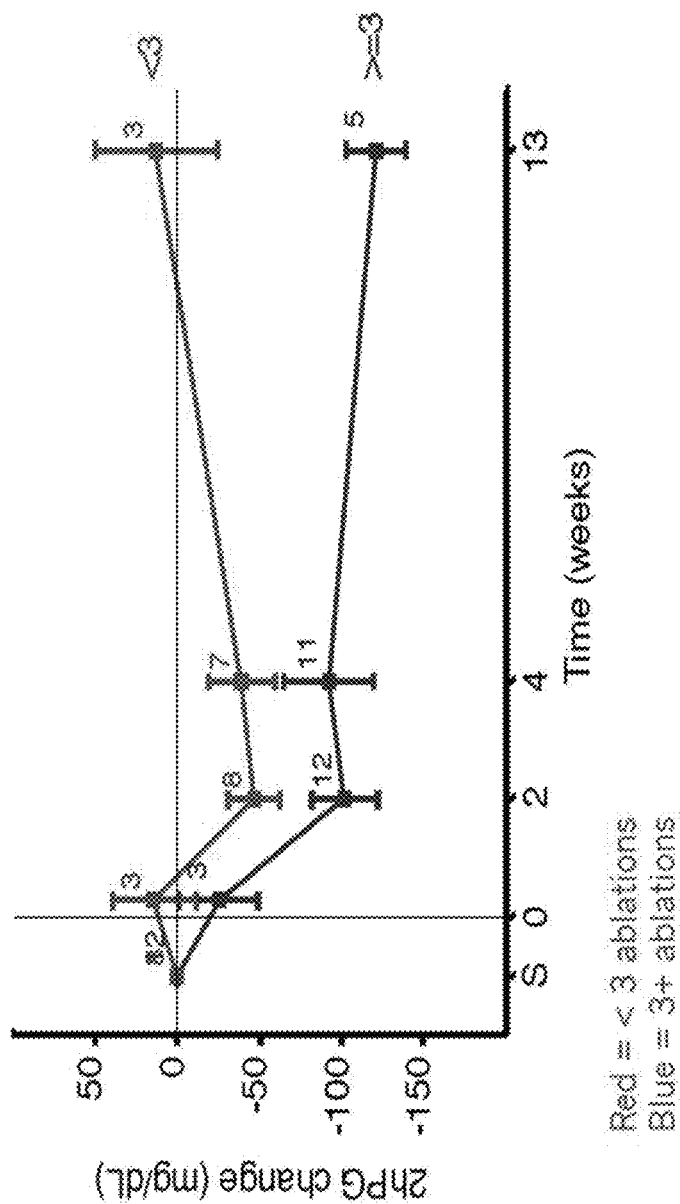
FIG. 26 illustrates a graph illustrating improvement in 2hPG measurements, consistent with the present inventive concepts.

Referring to FIG. 26, a graph illustrating similar improvement in 2hPG measurements is illustrated.

Figure 27:
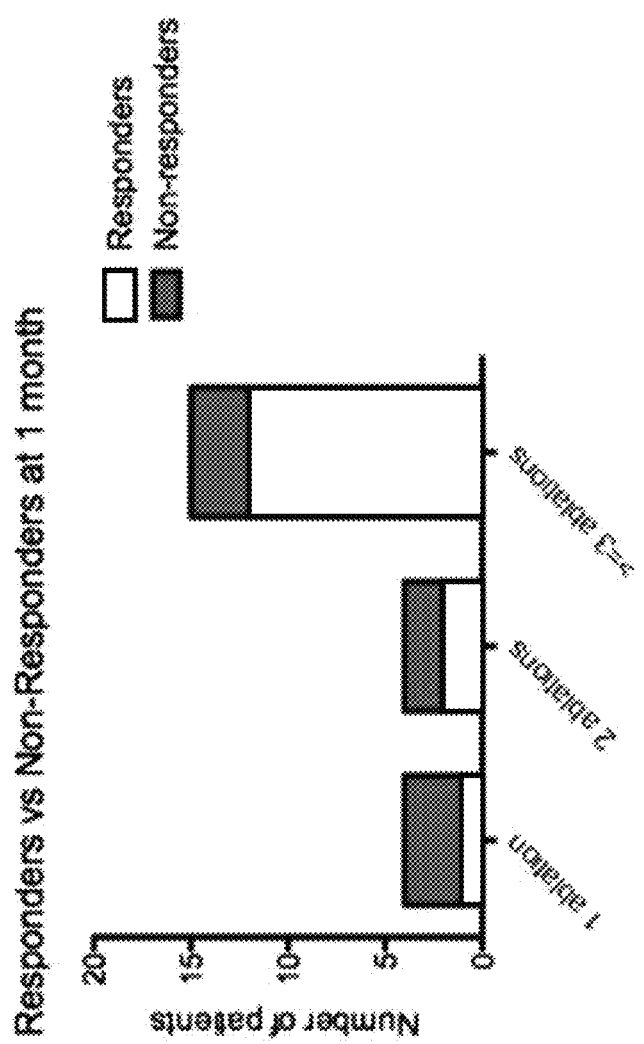
FIG. 27 illustrates a graph showing treatment response rates, consistent with the present inventive concepts.

Referring to FIG. 27, a graph of treatment response rates, showing that more ablations correlate to a higher percentage of positive patient outcomes is illustrated. Responders, or patients with positive clinical results, are defined as having an HbA1c reduction of at least 0.7% at 1 month.

Figure 28:
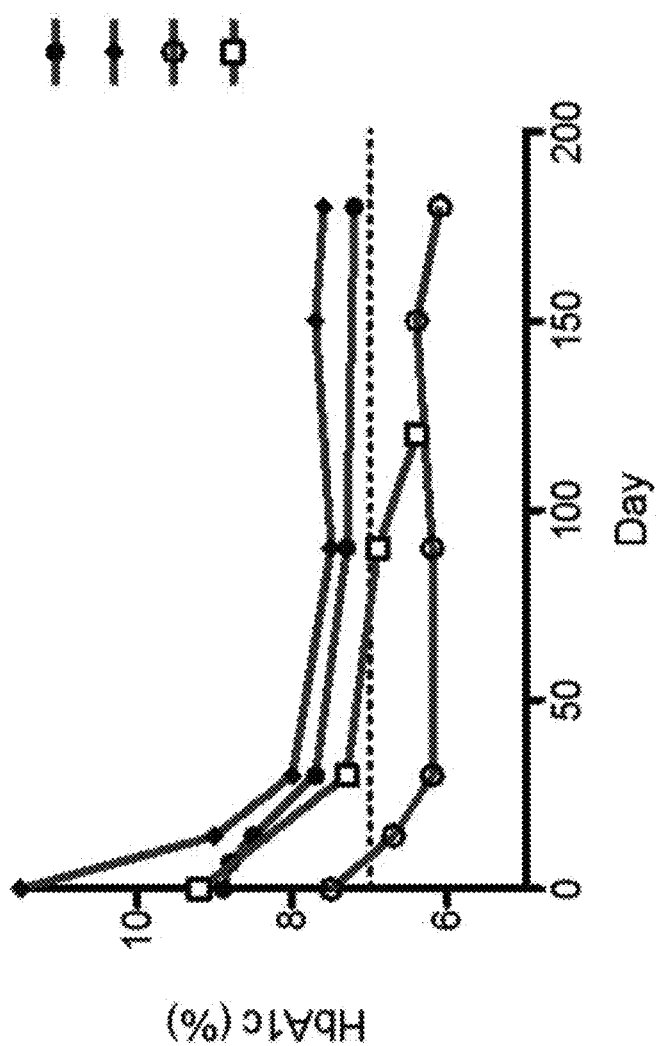
FIG. 28 illustrates a graph of HbA1c percentages measured for at least 120 days post treatment, consistent with the present inventive concepts.

Referring to FIG. 28, a graph of HbA1c percentages, measured for at least 120 days post treatment, showing a durable treatment effect in four out of five patients is illustrated.

In some embodiments, the systems, devices and methods of the present inventive concepts can be configured to maintain HbA1c below 7.5% at 150 days. Note that 3 out of 4 patients are also on lower levels of medications than were being administered prior to the tissue treatment procedure.

Figure 29:
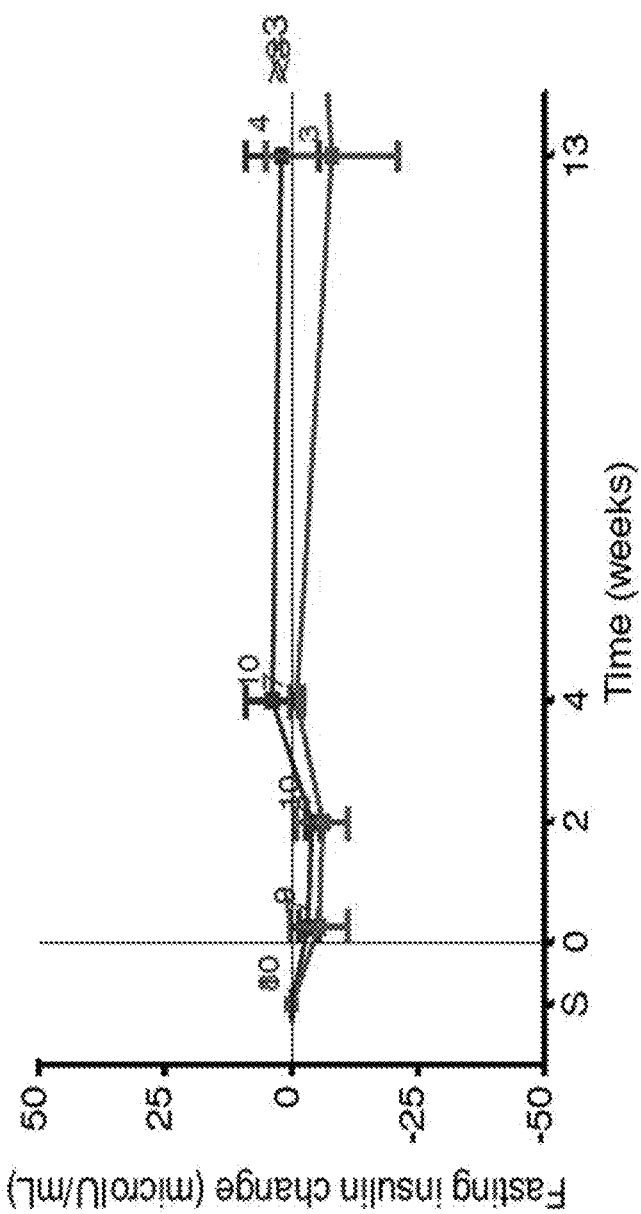
FIG. 29 illustrates a graph of fasting insulin change data over a 3 month period, consistent with the present inventive concepts.

Referring to FIG. 29, a graph of fasting insulin change data, over 3 months, showing an improvement in the health of the beta cell is illustrated.

Figure 30:
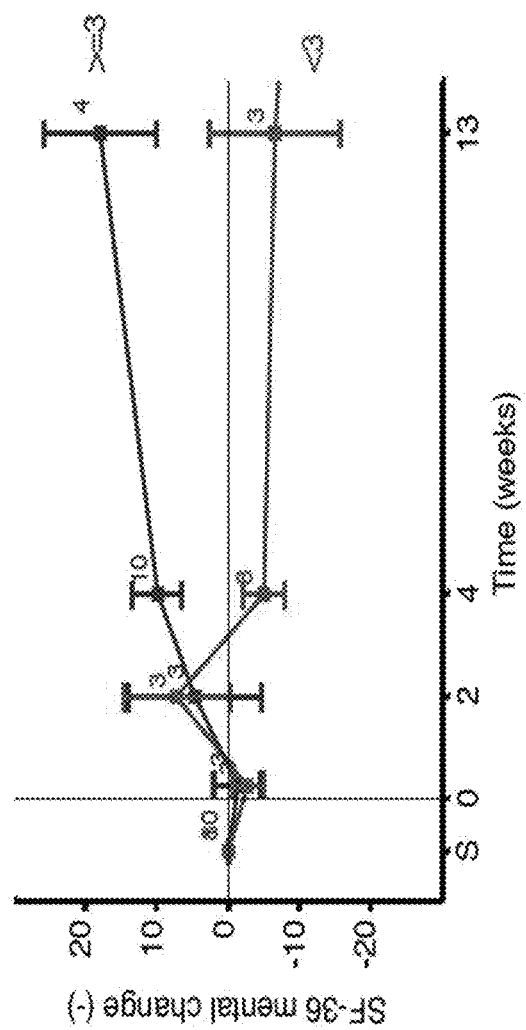
FIG. 30 illustrates a graph of SF-36 mental value changes, consistent with the present inventive concepts.

Referring to FIG. 30, a graph of SF-36 Mental value changes, showing improved patient satisfaction through better glycemic control is illustrated.

In some embodiments, the systems, devices and methods of the present inventive concepts can be configured to cause an improvement in a patient condition as measured by the clinical standard SF-36 Health Survey, such as an improvement in the SF-36 Mental Change score of at least 3 points, at least 5 points or at least 10 points.

Figure 31:
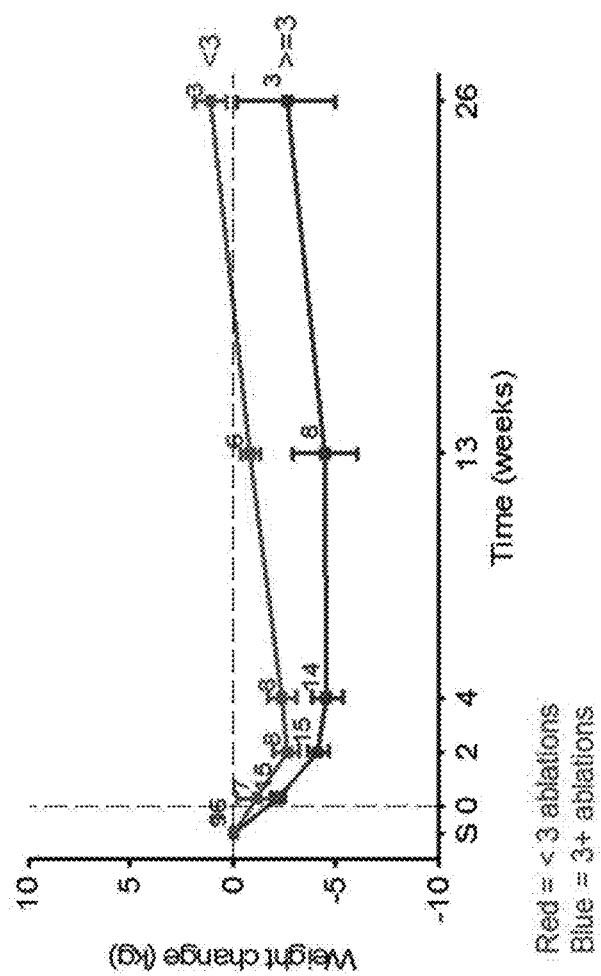
FIG. 31 illustrates a graph of weight change in study patients, consistent with the present inventive concepts.

Referring to FIG. 31, a graph of weight change in study patients, showing that weight loss was also noticed in a dose dependent manner is illustrated.

In some embodiments, the systems, devices and methods of the present inventive concepts can be configured to achieve at least 3 kg or at least 4 kg of weight loss.

Figure 32:
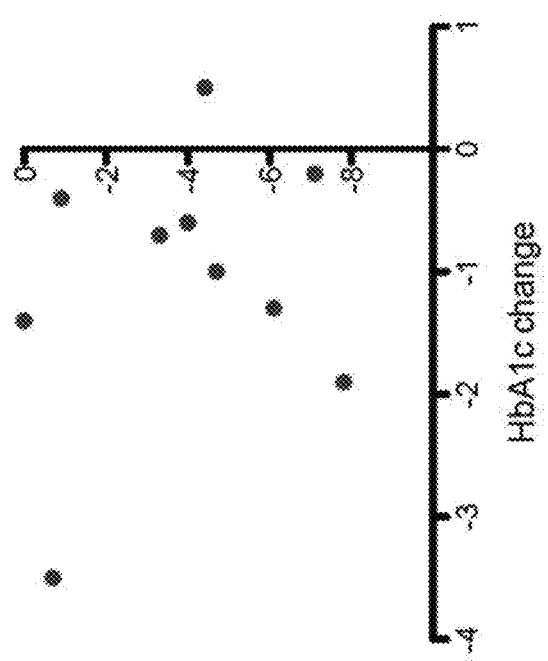
FIG. 32 illustrates a graph regarding weight loss and HbA1c, consistent with the present inventive concepts.

Referring to FIG. 32, a graph suggesting that weight loss and HbA1c are not well correlated based on 30 day post treatment data is illustrated.

Figure 33:
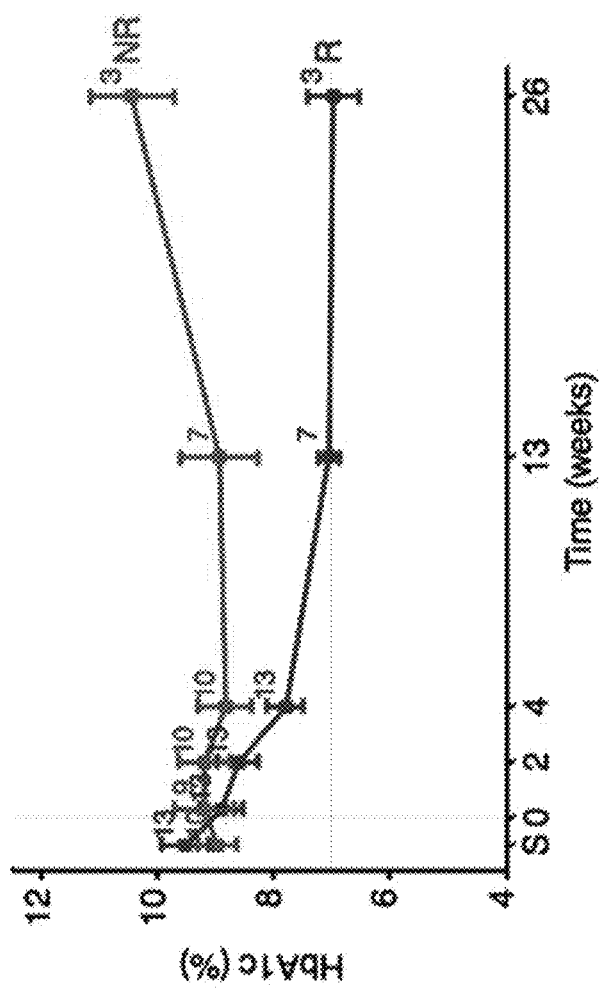
FIG. 33 illustrates a graph of HbA1c percentages over a six week period comparing responders and non-responders, consistent with the present inventive concepts.

Referring to FIG. 33, a graph of HbA1c percentage over a twenty six week period, comparing responders R and non-responders NR is illustrated.

Figure 34:
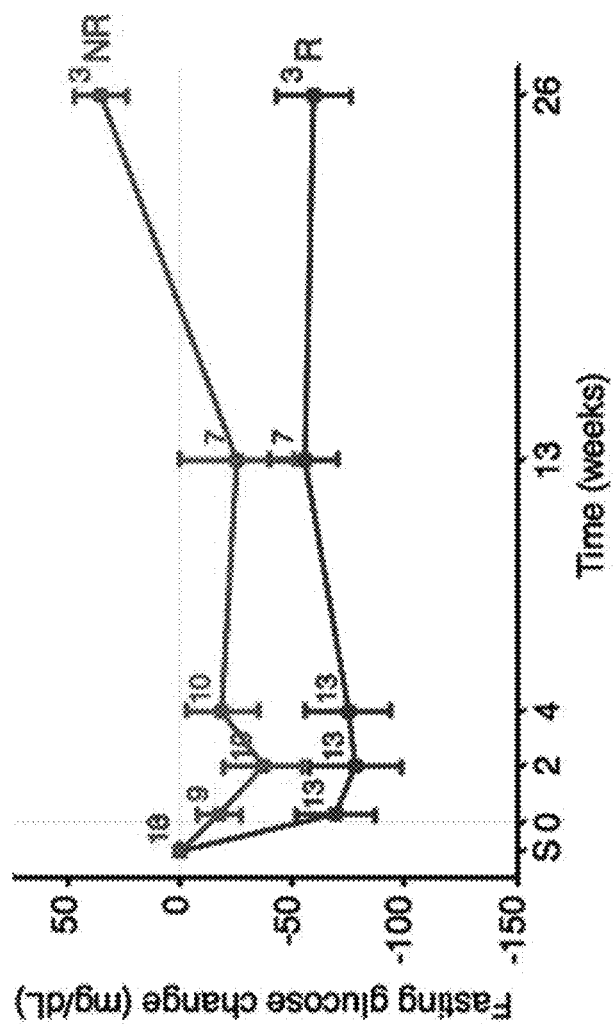
FIG. 34 illustrates a graph of fasting glucose change over a twenty-six week period comparing responders and non-responders, consistent with the present inventive concepts.

Referring to FIG. 34, a graph of Fasting glucose change (mg/dL) over a twenty six week period, comparing responders R and non-responders NR is illustrated.

Figure 35:
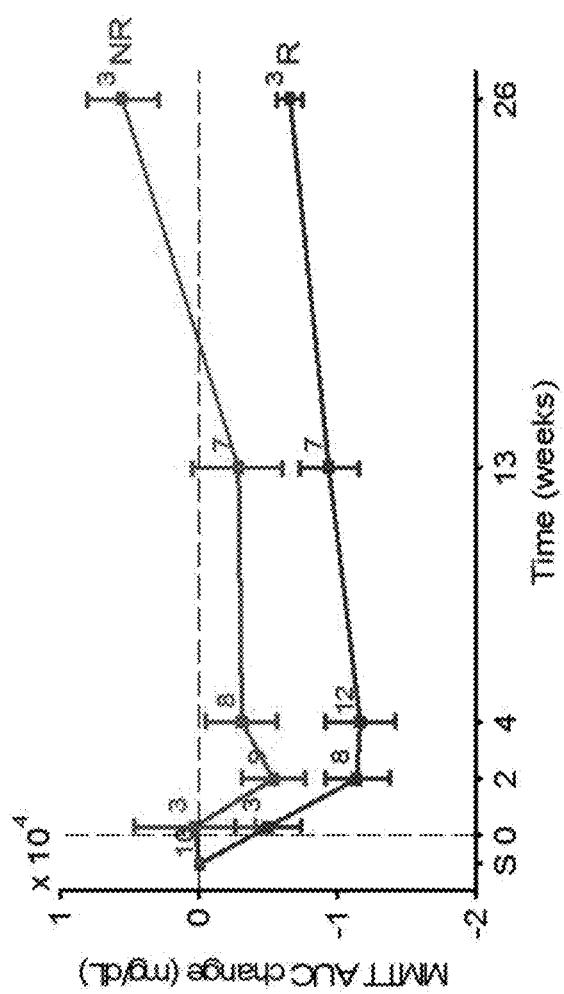
FIG. 35 illustrates a graph of change under the curve of a mixed meal tolerance test, consistent with the present inventive concepts.

Referring to FIG. 35, a graph of the change in the area under the curve of a mixed meal tolerance test is illustrated.

Figure 36:
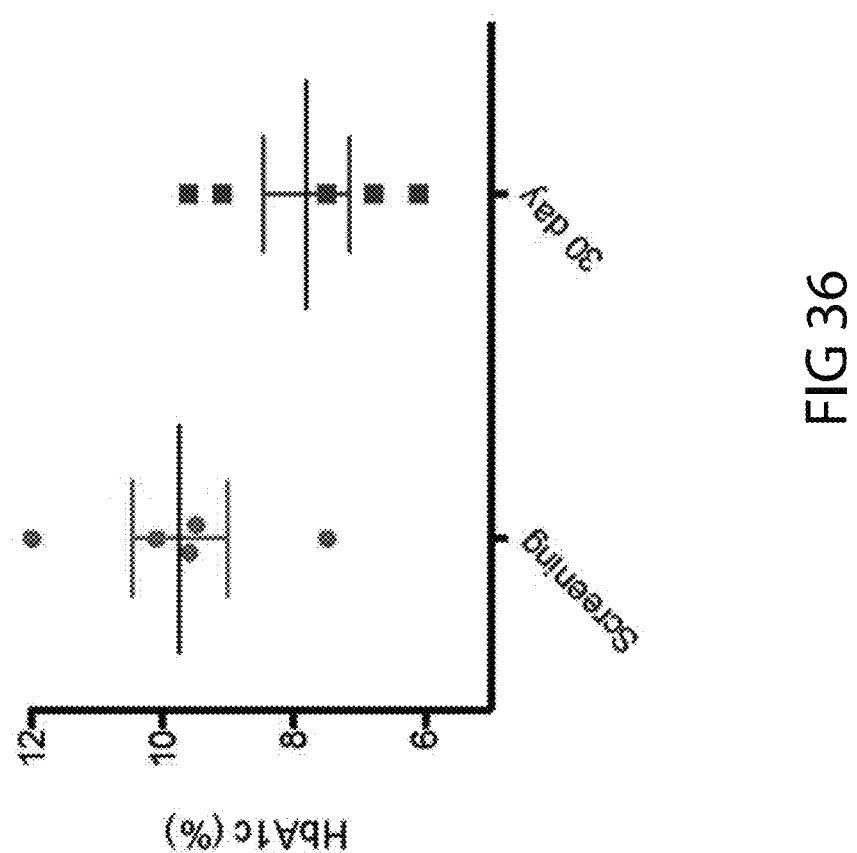
FIG. 36 illustrates a graph of three patients exhibiting a large treatment effect, consistent with the present inventive concepts.

Referring to FIG. 36, a graph of three patients exhibiting a large treatment effect, a 1.9% HbA1c improvement at 30 days is illustrated.

Referring to FIG. 37, tables presenting the large effect size of high dose cohort being statistically significantly better than low dose cohort are illustrated.

Human studies using the systems, devices and methods of the present inventive concepts have demonstrated significant effectiveness, such as at least a 2% HbA1c reduction in numerous patients at 3 months, a strong indication of clinical value for patients with poorly controlled glucose levels. The studies demonstrated excellent concordance between HbA1c and other surrogate markers such as fasting glucose and post-prandial glucose. The studies also demonstrated clinically meaningful weight loss. In some embodiments, the systems, devices and methods of the present inventive concepts can be used to treat naïve patients with an HbA1c of more than 6%, 6.5%, or 7%. The treatment could further include the administration of metformin. The treatment of the present inventive concepts (with or without the administration of metformin or other single drug) could provide a therapeutic benefit to the patient better than a treatment comprising drug therapy alone (e.g. metformin and/or another single drug therapy). In some embodiments, metformin and a second-line drug can be included in the treatment of the present inventive concepts. Treatment outcomes would include improvement in HbA1c, such as patients who achieve an improvement (i.e. reduction) of at least 1% in HbA1c and/or patients who achieve a target HbA1c of less than or equal to 6.0%, 6.5%, 7.0%, or 7.5%. Treatment can also include reduction in hypoglycemic events, improved quality of life, weight loss, and combinations of the above.

Described below are results of continued studies and associated data collected through Jul. 8, 2015.

Applicant's continued studies included the recording of various patient parameters affected by the treatment of the present inventive concepts, these parameters including but not limited to: HbA1c, fasting blood glucose and post prandial glucose. Patients received between one and five ablations (e.g. two to five sequential ablations performed along two to five axial segments of the duodenum distal to the ampulla of Vater) on a single procedural day. The ablations were delivered by an expandable balloon filled with hot fluid at an ablative temperature, as described in detail herein.

Referring to FIG. 38, a table presenting the patient demographics of the 39 patients from which the data were collected is illustrated.

Procedures were completed using general anesthesia. All patients were discharged on either the day of procedure (19/39) or after an overnight stay (20/39). The number of patients available (included) for each follow up study described in FIGS. 39-44, has the following distribution:

| Elapsed Time since Procedure | 2 Day | 14 Day | 1 Month | 3 Months | 6 Months | 9 Months | 12 Months |
|---|---|---|---|---|---|---|---|
| # of Pts at Followup | 39 | 39 | 39 | 38 | 34 | 21 | 21 |

The average baseline HbA1c was 9.5% (SD 1.3%) in 39 patients treated between August 2013 and December 2014. HbA1c was 8.1% (SD 1.3%) 1 month post-procedure, 7.3% (SD 1.2%) 3 months post-procedure, and 8.1% (SD 1.6%) 6 months post-procedure. These HbA1c improvements in the entire cohort are seen despite substantial masking of treatment effect due to medication reductions in highly responsive patients in the months immediately after the procedure. The average HbA1c improvement in 21 patients at a 1 year followup is a reduction 0.5% (e.g. a reduced HbA1c level as compared with the patient's HbA1c level that was present level prior to the performing of the tissue treatment procedure, such as a reduction from 8.5% to 8.0%, or from 7.5% to 7.0%), despite the fact that 9 out of these 21 patients were on reduced glycemic medicines compared to before their procedure.

Figure 39:
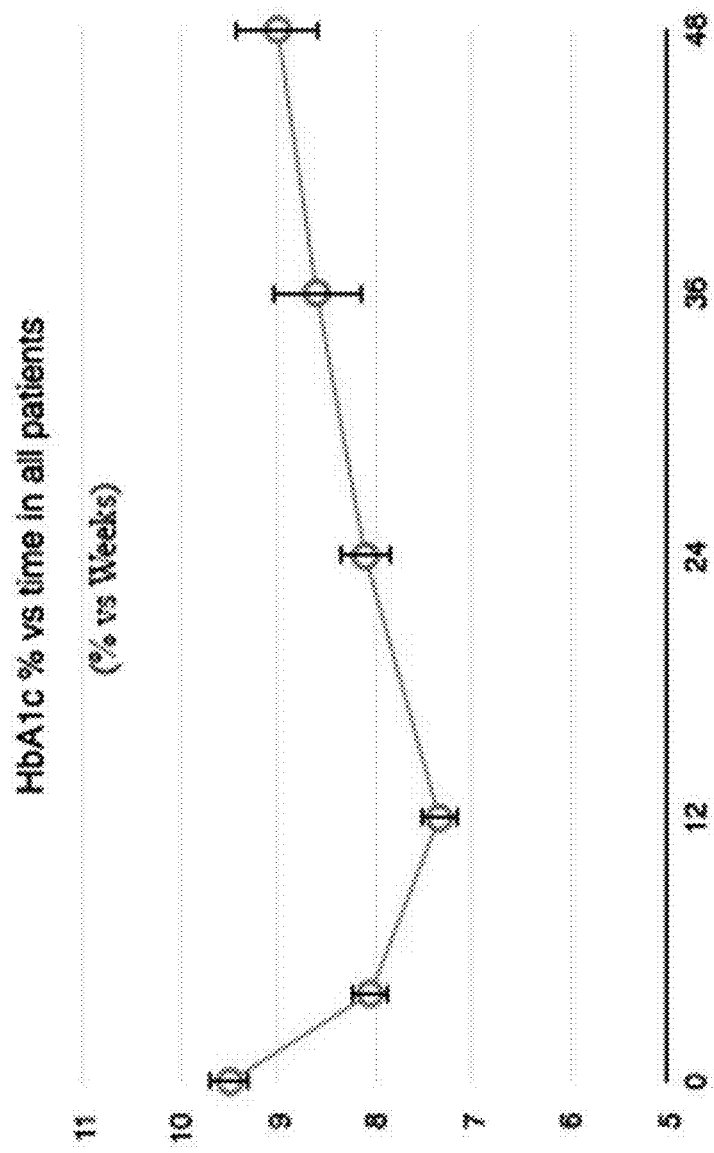
FIG. 39 illustrates a graph showing the average HbA1c in all available subjects treated by the systems, devices, and methods of the present inventive concepts.

Referring to FIG. 39, the average HbA1c (%) in all available (at the time of followup) subjects treated by the systems, devices and methods of the present inventive concepts is illustrated.

The magnitude of the treatment effect was analyzed as a function of treated dose (i.e. a dosimetric analysis was performed). Patients who had approximately 9 cm (e.g. 9.3 cm) of duodenal tissue treated (e.g. in at least three applications of thermal energy to duodenal tissue) were labeled to have received a "Long Segment DMR" ("LS-DMR"). Patients who had approximately 3 cm (e.g. 3.4 cm) of duodenal tissue treated (e.g. in two or less applications of thermal energy to duodenal tissue) were labeled as "Short Segment DMR" ("SS-DMR"). At 1 month follow up, HbA1c was reduced by an average of 1.7% (SD 1.0%) in LS-DMR and by 0.7% (SD 1.2%) in the SS-DMR (n=28 vs 11 at 1 months). At 3 months follow up, HbA1c was reduced by an average of 2.5% (SD 1.3%) in LS-DMR and by 1.2% (SD 1.8%) in SS-DMR (n=28 vs 10 at 3 months, p<0.05 for LS vs SS).

Figure 40:
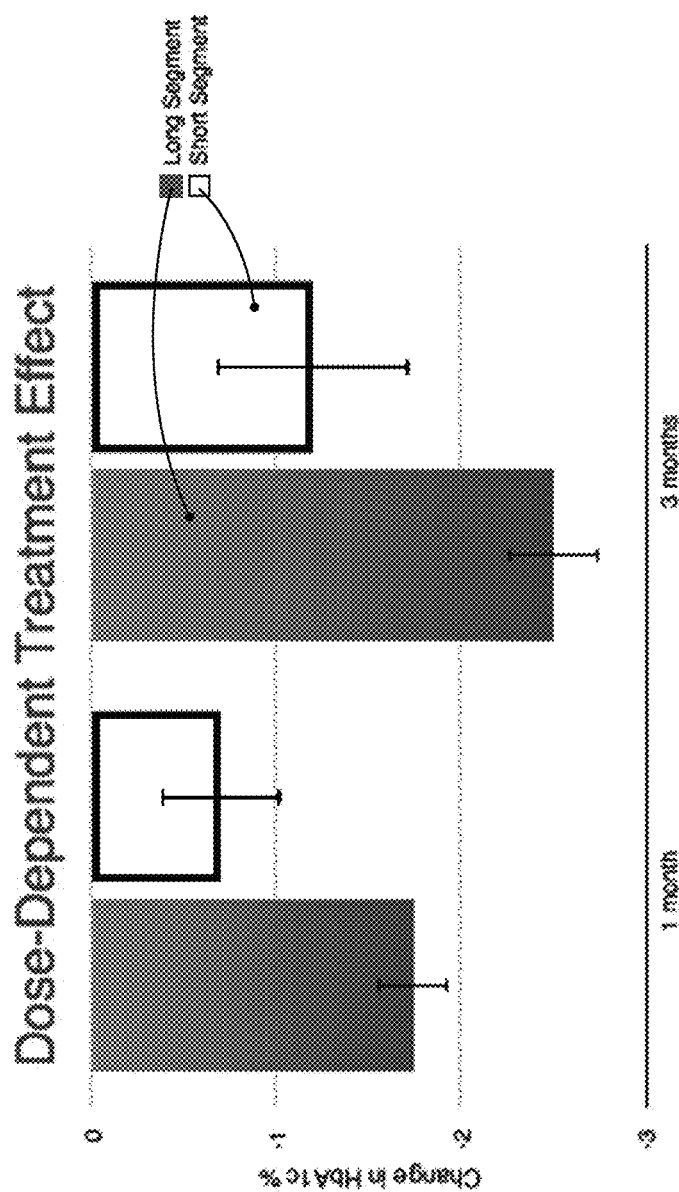
FIG. 40 illustrates a graph showing the average change in HbA1C from baseline in patients with LS-DMR and SS-DMR, consistent with the present inventive concepts.

Referring to FIG. 40, the average change in HbA1c (%) from baseline in patients with LS-DMR and SS-DMR (p<0.05 for the difference at 3 months) is illustrated.

These clinical studies did not specify a medication treatment algorithm for the treating diabetologist to prescribe. Note that the treating diabetologist was not made aware of the patients' treatment allocation when determining the appropriate post-procedure management strategy. As such, clinical decisions with respect to medication adjustments in individual patients were made but these adjustments were not well controlled with respect to a rigorous efficacy evaluation. By the time of the six month post-procedure follow up visit, several patients experienced changes to their glycemic medications that would be expected to confound efficacy analysis at later time points (see FIG. 42). In particular, 13 out of 26 LS-DMR patients experienced reductions in medications and 1 patient experienced an increase in medication prescription, compared to 4 with reductions and 3 with increases among the SS-DMR patients.

Referring to FIG. 41, the number of patients in each treatment arm with medication changes preceding the six month post-procedure follow up visit is illustrated.

At 6 months, LS-DMR patients experienced a decline in HbA1c of 1.6% (SD 1.6%) on average (n=26) despite the fact that 13 of 26 patients had reductions in glycemic medicines that would be expected to mask the magnitude of the procedure's treatment effect. The impact of medication reductions is evident in the analysis of fasting plasma glucose (FPG) in LS-DMR patients whose baseline HbA1c was between 7.5% and 10%. Patients whose meds were unchanged after the procedure ("stable meds" group in left side graph) retain stable FPG between week 12 and week 24. Patients, whose medicines were reduced, however, experienced a decay in treatment effect, the timing of which is coincident with the timing of prescribed medication reductions.

Figure 42:
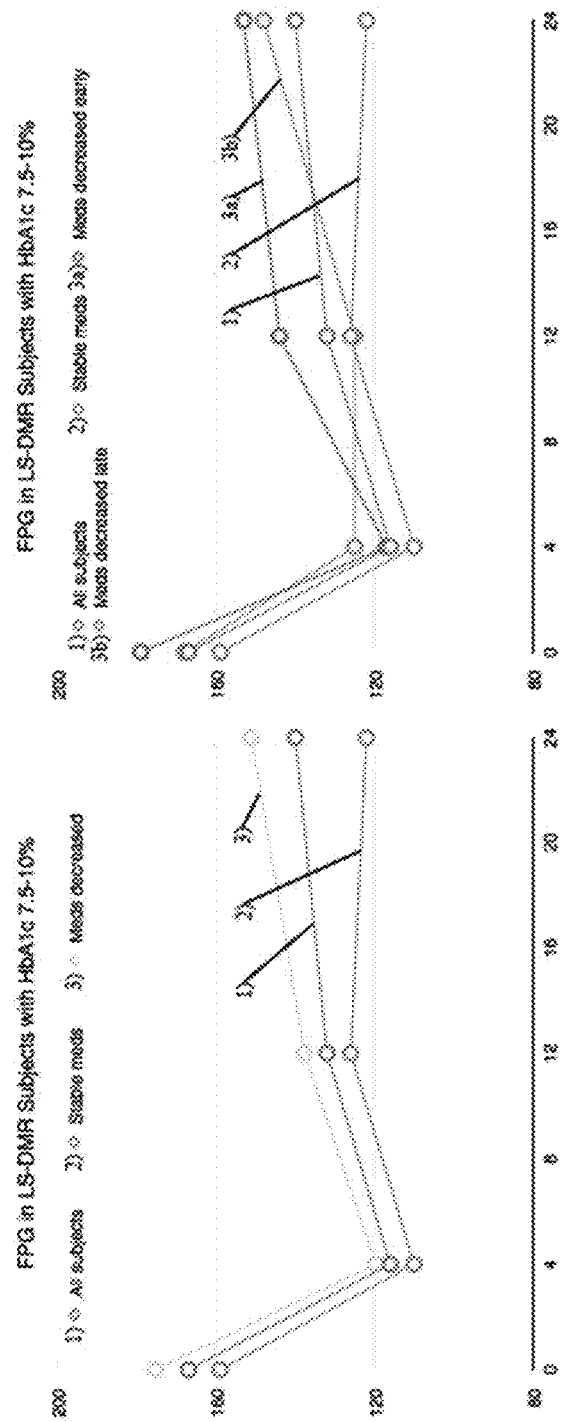
FIG. 42 illustrates graphs showing the average fasting plasma glucose in LS-DMR patients with a baseline HbA1C between 7.5% and 10%, consistent with the present inventive concepts.

Referring to FIG. 42, the average fasting plasma glucose in LS-DMR patients with baseline HbA1c between 7.5% and 10% is illustrated. The graph on the left shows FPG in all patients ("all patients"), the subset who experienced medication reductions ("meds decreased") and those whose medications were held constant through 24 week follow up ("stable meds"). The graph on the right shows the effect of medication reductions within the first 12 weeks ("meds decreased early") compared to those with medication reductions between week 12 and week 24 ("meds decreased late"). The timing of medication reductions corresponds to the timing of worsening FPG measurements.

Analysis of patients on consistent medications with a baseline HbA1c of between 7.5% and 10% revealed a mean HbA1c of 8.6 (SD 0.9; n=7) at baseline, 6.6 (SD 0.8; n=7) at 3 months, 7.2 (SD 0.6; n=6) at 6 months, and 7.3 (SD 0.3; n=4) at 12 months post procedure. These patients also experienced a reduction of fasting plasma glucose of 32 mg/dl (SD 21) at 3 months, 36 mg/dl (SD 24) at 6 months, and 20 mg/dl (SD 15) at 12 months.

Figure 43:
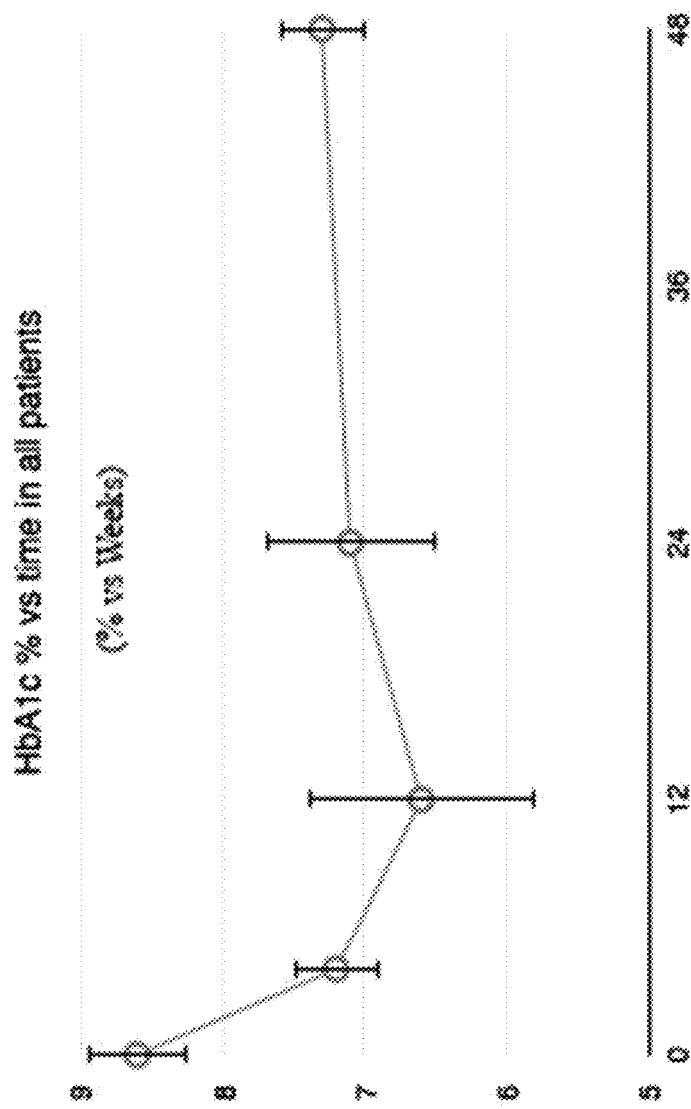
FIG. 43 illustrates a graph showing mean HbA1C in LS-DMR patients with baseline HbA1c between 7.5% and 10% and consistent antidiabetic medications, consistent with the present inventive concepts.

Referring to FIG. 43, the mean HbA1c in LS-DMR patients with baseline HbA1c between 7.5% and 10% and consistent antidiabetic medications is illustrated. Taken together, HbA1c measurements and fasting plasma glucose levels in LS-DMR patients with a baseline HbA1c level between 7.5% and 10% suggest durability of treatment response through 12 months of follow up.

Patient quality of life was assessed using the SF-36 standardized questionnaire. At screening, LS-DMR patients had a physical composite score (PCS) of 47 (SD 9) and a mental composite score of 46 (SD 11). At 6 months, patients in the LS-DMR group saw an increase in PCS of 3.1 points (SD 10; n=22) and MCS of 3.4 points (SD 14; n=22; p<0.05). The data suggest an improvement in the mental quality of life for poorly controlled diabetic patients who received LS-DMR.

Patients received a follow-up endoscopy at 1 month and/or 3 months post-procedure per protocol. Of the 19 patients who have received a follow-up endoscopy at 1 month, 4 patients had a reduction in height and/or width of plicae in the duodenum near the treatment area but otherwise the mucosa appeared to be healing normally with no scarring. No luminal narrowing indicative of stenosis was present in any of the 1 month endoscopies. Of the 37 patients who have received a follow-up endoscopy at 3 months, two patients had an endoscopically apparent reduction in height and/or width of plicae in the duodenum near the treatment area. All other patients had normal endoscopies with the mucosa fully healed and no evidence of scarring. No luminal narrowing was observed in any of the 3 month endoscopies. These results indicate that the treatment can effectively ablate the mucosa without damage to the duodenal structure and that the mucosa regrows quickly within the ablated region. The reduction in height and width of the plicae may be indicative of a reduction in the mucosal redundancy as part of the normal healing process.

A second procedure of the present inventive concepts was performed in 3 previously treated patients. There were no particular procedural challenges or significant adverse events associated with the second procedure in these three patients. Two patients had been non-responders to initial procedure, and their second procedure did not successfully improve glycemic control. A third patient had an improvement in glycemic control through 3 months after the first procedure, but this benefit was not fully sustained through the 6 month follow up visit. A repeat procedure was performed in month 8, and the patient has since been followed for six months after the second procedure. 14 months after the first procedure, therefore, the patient has an HbA1c of 7.3% (reduction of at least 2%) and a FPG of 100 mg/dl.

Figure 44:
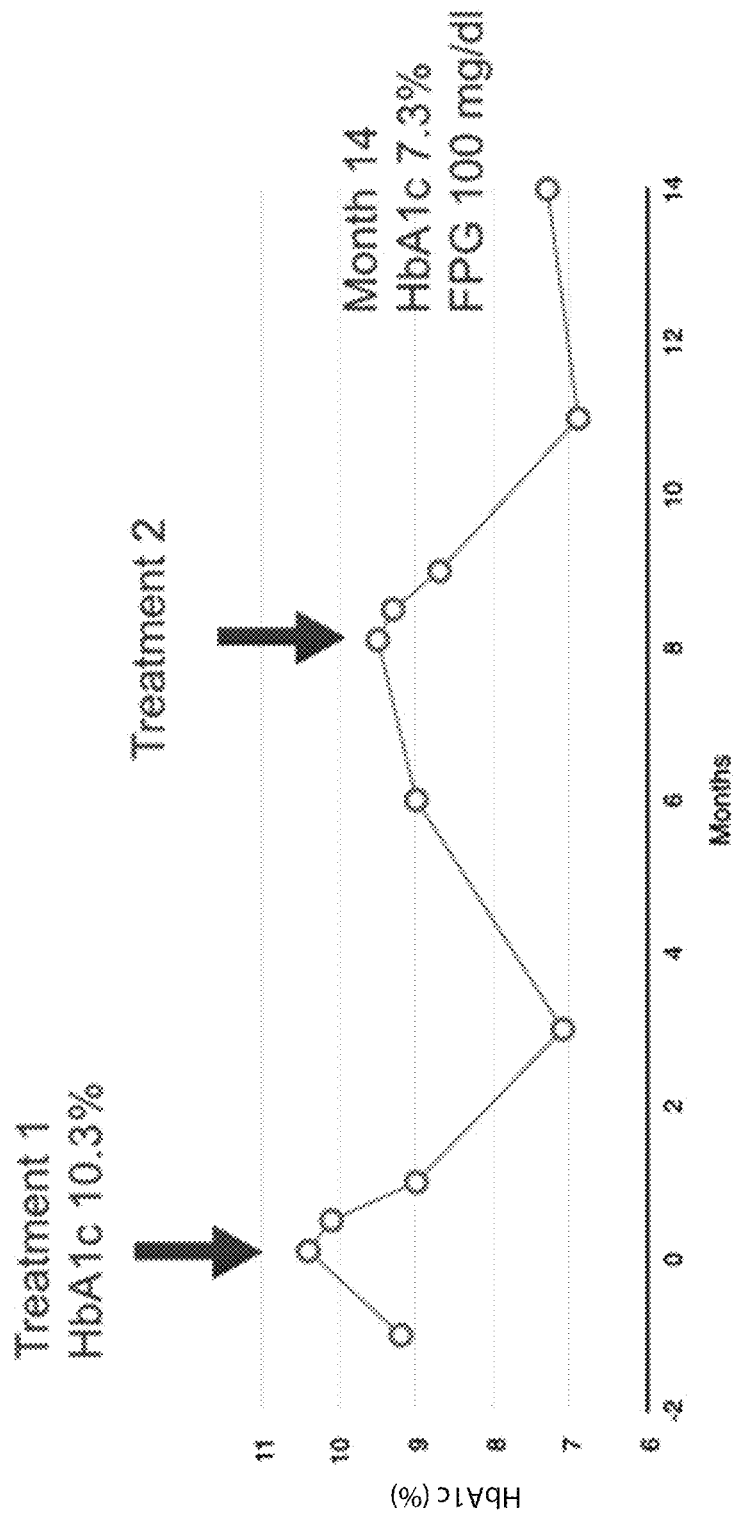
FIG. 44 illustrates a graph showing HbA1c over time in a single patient receiving two treatments at different intervals, consistent with the present inventive concepts.

Referring to FIG. 44, HbA1c over time in a single patient receiving two treatments (at month 0 and month 8, respectively) is illustrated.

The above summary provides clinical data on 39 patients enrolled and treated in an initial study focused on procedural and patient safety and clinical effectiveness. The results demonstrate that the procedure can be safely completed with devices performing as intended, that the procedure can be well tolerated by patients, and that there exists a strong suggestion of significant clinical effectiveness. The limited number and transient nature of adverse events suggest that the safety profile of the technology and procedure is favorable. Although there were three adverse events of duodenal stenosis formation, all were endoscopically treated with non-emergent endoscopic balloon dilation using techniques familiar to operators and resolved with no long-term sequelae. Other significant potential risks, including pancreatitis, perforation, bleeding, infection, or ulcer, have not been observed. No evidence for malabsorption, severe hypoglycemia, or late complications was found. The experience thus far indicates a safe procedure that can be well tolerated by patients. Mean HbA1c is reduced in treated patients despite net medication reductions in the patient cohort. In addition, a statistically significant dosimetric treatment response is also observed, with LS-DMR patients responding more effectively than SS-DMR patients. In addition, LS-DMR patients experienced more medication reductions (to prophylactically avoid hypoglycemia) than SS-DMR patients. This observation was made despite the fact that neither patients nor the treating endocrinologist was aware of the length of treated tissue in individual patients. Furthermore, 23/27 LS-DMR patients experienced an HbA1c reduction of at least 1% at 3 months of follow up, compared to 6/10 SS-DMR patients. Patients on consistent medications with a baseline HbA1c of between 7.5% and 10% showed evidence of a durable response to treatment, with persistent reductions in HbA1c and fasting glucose through 12 months of treatment follow up. This durable treatment response is observed even without aggressive diabetes management on the part of the treating physician, such as may be achieved through education, lifestyle recommendations, or aggressive pharmacotherapy. The treatment of the present inventive concepts may offer an even more significant and durable clinical effect when coupled with intensive medical management. The treatment effect does not appear to be weight dependent. Patients did not report any food intolerance or change in food preference that might explain this HbA1c reduction. While patients lost a small amount of weight, the magnitude of weight loss is likely not enough to explain the degree of HbA1c improvement. Furthermore, there did not appear to be any correlation between the magnitude of HbA1c reduction and weight loss.

In some embodiments, the systems, device and methods of the present inventive concepts can reduce the need for insulin therapy in a larger proportion of patients, such as to provide durable glycemic control with or without the therapies administered to the patient prior to the treatment of the present inventive concepts, or with a decrease in dosage of one or more previously administered medications.

The systems, devices and methods of the present inventive concepts can be configured to treat patients with microvascular disease or patients with a high risk of microvascular disease, such as to improve patient health and/or eliminate or otherwise reduce the need for one or more medications (e.g. one or more insulin medications). The treatment can be configured to reduce diabetic retinopathy (e.g. as shown in a reduction in diabetic retinopathy score), proteinuria and/or peripheral neuropathy severity. Additionally or alternatively, the treatment can be configured to reduce the effects of macrovascular disease such as myocardial infarction, stroke, peripheral vascular disease, CV death, and combinations of these.

Figure 3:
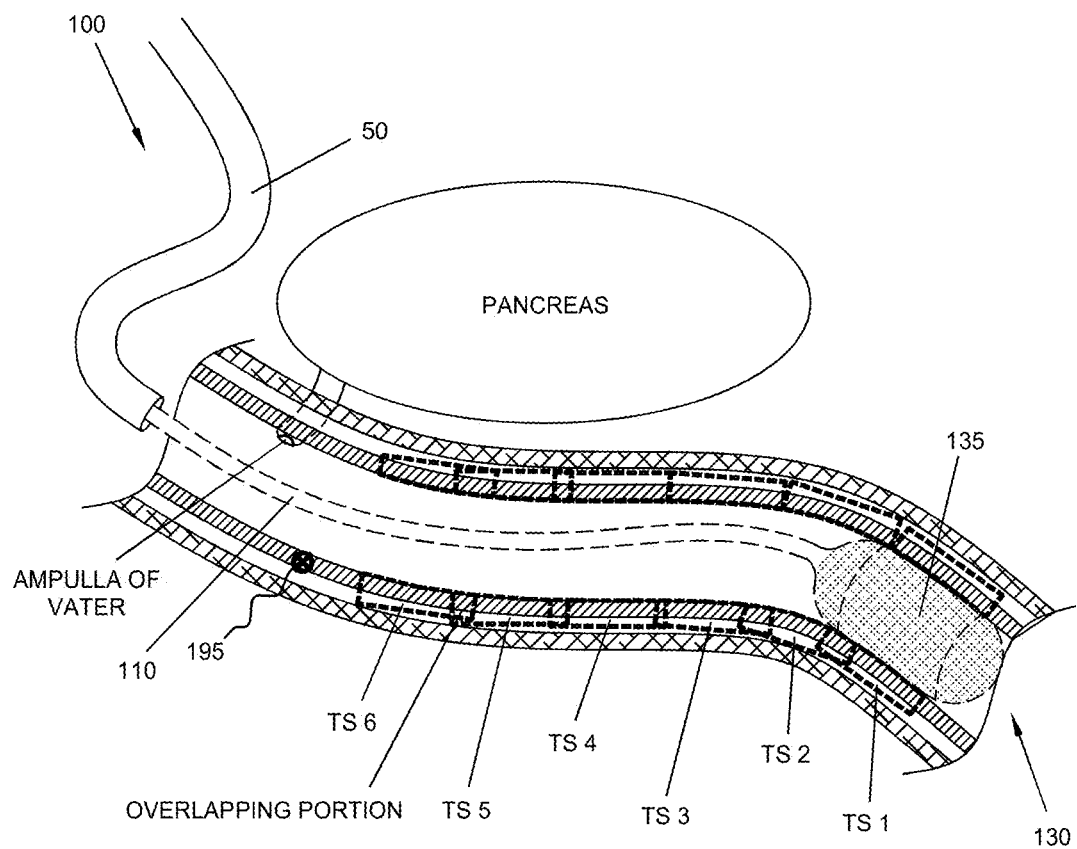
FIG. 3 illustrates a side sectional view of the distal portion of a tissue treatment device inserted into a curvilinear section of duodenum, consistent with the present inventive concepts.

Referring now to FIG. 3, a side sectional view of the distal portion of a tissue treatment device inserted into a curvilinear section of duodenum is illustrated, consistent with the present inventive concepts. Tissue treatment device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control device 100, such as is described hereabove in reference to device 100 of FIG. 1. Tissue treatment device 100 can be configured for delivery over a guidewire, via a lumen from a proximal portion of shaft 110 to a distal portion of shaft 110, or via a rapid exchange sidecar or other lumen in the distal portion of shaft 110 (guidewire lumen and sidecar not shown but known to those of skill in the art). Shaft 110 is shown inserted through introducer 50 which can comprise an endoscope, sheath, vascular introducer, laparoscopic port, or other body introduction device.

Tissue treatment device 100 further comprises a treatment assembly, expandable assembly 130, which can include a balloon and/or be of similar construction and arrangement as expandable assembly 130 of FIG. 1. Fluid at an ablative temperature (i.e. a sufficiently high or low temperature to ablate tissue), treatment element 135, has been delivered to expandable assembly 130, as described hereabove, to deliver energy to one or more portions of a delivery zone and to treat one or more portions of target tissue.

A marker 195 has been positioned on the wall of the GI tract to be used as a reference to identify non-target tissue (e.g. a marker placed on tissue in relation to the ampulla of Vater, such as at a location distal to but proximate the ampulla of Vater). Marker 195 can comprise an element selected from the group consisting of: a visible marker (e.g. visible via camera 52 of endoscope 50a); a radiographic marker; an ultrasonically visualizable marker; a magnetic marker; ink; dye; and combinations of these. Marker 195 can comprise multiple markers positioned in various locations (e.g. various locations used as a reference to identify multiple different or similar segments of non-target tissue.

Expandable assembly 130 has been positioned in a distal portion of duodenal tissue, such as a section that includes a previously expanded segment of submucosal tissue (submucosal tissue expansion not shown). Expandable assembly 130 has been radially expanded such as to contact the mucosal surface of the duodenum at a discrete tissue segment of target tissue, tissue segment TS1 as shown. Tissue segment TS1 is located distal to a series of sequential tissue segments of target tissue, tissue segments TS2 through TS6 as shown. Expandable assembly 130 and treatment element 135 (ablative fluid) are shown in FIG. 3 positioned to ablate or otherwise treat tissue segment TS1. Each of tissue segments TS1 through TS6 has a corresponding delivery zone (not shown) to which energy is delivered from expandable assembly 130 to cause the appropriate treatment of target tissue. In some embodiments, a series of adjoining segments are treated sequentially (i.e. from distal segment TS1 to each correspondingly more proximal segment TS2 through TS6 or from proximal segment TS6 to each correspondingly more distal segment TS5 through TS1). In some embodiments, a complete treatment comprises treatment of at least three adjacent segments (e.g. TS1 through at least TS3, TS2 through at least TS4, TS3 through at least TS5 or TS4 through at least TS6). Alternatively, anon-continuous pattern can be treated (e.g. TS1 followed by TS3 followed by TS2, and the like). In some embodiments, marker 195 is positioned in reference to the ampulla of Vater (e.g. proximate the ampulla of Vater), and all segments to be treated are positioned distal to the ampulla of Vater, such as can be determined by visualizing marker 195.

Expandable assembly 130 can be sized to allow positioning in curved segments of the GI tract with a minimum radius of curvature, such as a curved segment of the duodenum and/or jejunum with an average radius of curvature less than 5 cm over a 75 arc, or less than 3 cm over a 75° arc. In these curved segments (and straighter segments as well), expandable assembly 130 can be expanded without exerting undesired force onto tissue (e.g. expanded to contact the tissue wall). In some embodiments, expandable assembly 130 is constructed and arranged to treat curved segments of the GI tract and comprises a length less than or equal to 30 mm, such as less than or equal to 25 mm, less than or equal to 20 mm, or less than or equal to 15 mm.

After treatment of tissue segment TS1, expandable assembly 130 can be repositioned to tissue segment TS2, just proximal to tissue segment TS1, with or without contracting expandable assembly 130 prior to the repositioning. Subsequently, a second tissue treatment (e.g. a second energy delivery) can be performed. The steps of repositioning and treating portions of target tissue are repeated until one or more of tissue segments TS3, TS4, TS5, and TS6 have been treated. In some embodiments, an ablation reducing step is performed after each tissue segment treatment, such as by delivering a treatment neutralizing cooling fluid after a hot fluid ablation or delivery of a treatment neutralizing warming fluid after a cool (e.g. cryogenic) ablation, each as described herein. Alternatively or additionally, a cooling or warming fluid can be delivered, prior to a heat or cryogenic ablation, respectively, as described herein.

In a single clinical procedure, the combined length of target tissue segments TS1 through TS6 can represent between 10% and 100% of the length of the duodenal mucosa length distal to the ampulla of Vater, such as when between 2 and 50 axial segments of tissue receive between 2 and 50 energy deliveries from expandable assembly 130 (e.g. ablative fluid 335 is introduced into expandable assembly 130 2 to 50 sequential times). In some embodiments, each of tissue segments TS1 through TS6 have a maximum axial length of less than 20 cm, less than 15 cm, less than 10 cm, less than 5 cm, less than 3 cm or less than 2 cm. In some embodiments, the cumulative axial length of tissue segments treated, (e.g. two or more of tissue segments TS1 through TS6) is less than 100 cm, less than 50 cm, less than 25 cm, or less than 10 cm. In some embodiments, at least 6 cm or at least 9 cm of the duodenum is treated. Alternatively or additionally, other tissue (e.g. other tissue of the GI tract) can be treated, such as has been described hereabove.

Target tissue segments TS1 through TS6 typically include common border or overlapping tissue segments, such as is shown in FIG. 3. While the embodiment of FIG. 3 shows six target tissue segments being treated, more or fewer segments can be treated. In some embodiments, three axial tissue segments are treated (e.g. TS1, TS2 and TS3). In some embodiments, four axial tissue segments are treated (e.g. TS1, TS2, TS3 and TS4). In some embodiments, five axial tissue segments are treated (e.g. TS1, TS2, TS3, TS4 and TS5). In some embodiments, all GI tract tissue treated is distal to the ampulla of Vater.

Tissue treatments can be performed in a contiguous manner (e.g. a 1st portion, followed by a 2nd portion whose distal end is proximate the proximal end of the 1st portion, followed by 3rd portion whose distal end is proximate the proximal end of the 2nd portion, etc); however any order can be performed. In some embodiments, multiple contiguous or discontiguous tissue segments are treated simultaneously. In some embodiments, contiguous tissue segments are treated by device 100 continuously, as expandable assembly 130 is relatively continuously translated proximally and/or distally, such as via a manual or automated retraction and/or advancement, respectively, as is described in reference to FIG. 6 herebelow. In some embodiments, treatment of target tissue is performed as expandable assembly 130 translates at a rate of at least 1 cm per minute, at least 2 cm per minute, at least 5 cm per minute, or at least 10 cm per minute. In some embodiments, a segment of non-treated GI tissue is positioned between two segments of treated GI tissue, such as a non-treated segment of GI tissue in a sharp bend.

Referring now to FIGS. 4A, 4B and 4C, perspective, side and end views, respectively, of an expandable element comprising a balloon is illustrated, consistent with the present inventive concepts. Balloon 136 comprises an expandable element of the present inventive concepts, which can be configured receive a treatment element comprising fluid at an ablative temperature for treating target tissue, such as balloon 136 of FIG. 1 described hereabove. Balloon 136 can be constructed and arranged of one or more biocompatible materials, such as a material selected from the group consisting of polyethylene terephthalate (PET); nylon; latex; polyurethane; and combinations of these. In some embodiments, balloon 136 comprises a wall thickness, Dim G, such as a wall thickness between 0.0002" and 0.0010", such as a wall thickness of approximately 0.0005".

In some embodiments, balloon 136 comprises a tissue contacting portion with a diameter of Dim A as shown. Dim A can comprise a diameter of approximately between 16.0 mm and 35.0 mm, such as a diameter between 19.0 mm and 32.0 mm. In some embodiments, balloon 136 comprises a tissue contacting portion, with a length defined by Dim D as shown. Dim D can comprise a length between 16.0 mm and 35.0 mm, such as a length between 19.5 mm and 32.9 mm. In some embodiments, balloon 136 comprises a tapered distal end, distal taper DT, which transitions from the tissue contacting portion with a curved segment, Dim B, with a radius between 7 mm and 9 mm, such as a radius of approximately 8 mm. Distal taper DT can comprise a taper, Dim F as shown, such as a taper between 27° and 33°, such as a taper of approximately 30°. In some embodiments, balloon 136 comprises a tapered proximal end, proximal taper PT, which transitions from the tissue contacting portion with a curved segment, Dim C, with a radius between 0.4 mm and 0.6 mm, such as a radius of approximately 0.5 mm. Proximal taper PT can comprise a taper, Dim E as shown, such as a taper between 42° and 48°, such as a taper of approximately 45°.

In some embodiments, the tissue contacting portion of balloon 136 comprises a surface area of between 1750 $mm^2$ and 2150 $mm^2$, such as a surface area of approximately 1950 $mm^2$. In some embodiments, a system of the present inventive concepts (e.g. system 10 of FIG. 1) comprises multiple tissue treatment devices (e.g. device 100 of FIG. 1), each comprising a balloon 136 with different tissue contacting portion lengths and/or diameters. In these embodiments, the surface area of the tissue contacting portion can comprise a relatively equivalent area for each device, such as when each tissue contacting portion surface area comprises an of between 1750 $mm^2$ and 2150 $mm^2$, such as a surface area of approximately 1950 $mm^2$. Similar surface areas for the different tissue treatment device's tissue contacting portions provide the advantage of: similar ablative fluid delivery settings; similar change in balloon temperature with fluid replacement (i.e. between cold and hot water or hot and cold water) to allow a steep "shoulder" of thermal profile within the balloon; similar uniformity of thermal profile along the balloon surface such as during the replacement of cold/hot water with one another within the balloon; similar tissue contact along the surface of the balloon including in bends of the GI tract.

Balloon 136 can be constructed and arranged to be filled with a particular volume of fluid (e.g. ablative fluid), such as a volume of between 10 ml and 35 ml, such as a volume between 12.5 ml and 30.0 ml. Balloon 136 can comprise a tubular stem extending from each of distal taper DT and/or proximal taper PT, such as to facilitate fluid attachment of balloon 136 to a shaft, such as shaft 110 of FIG. 1.

In some embodiments, the systems of the present inventive concepts can comprise two or more balloons 136, such as a first balloon 136 used in a first tissue treatment device (e.g. device 100 of FIG. 1 or FIG. 6) and a second balloon 136 used in a second tissue treatment device (e.g. device 100' of FIG. 6). The first balloon 136 and the second balloon 136 can comprise similar or dissimilar properties, such as similar or dissimilar tissue contacting lengths and/or diameters, such as to treat different segments of the GI tract.

Figure 5:
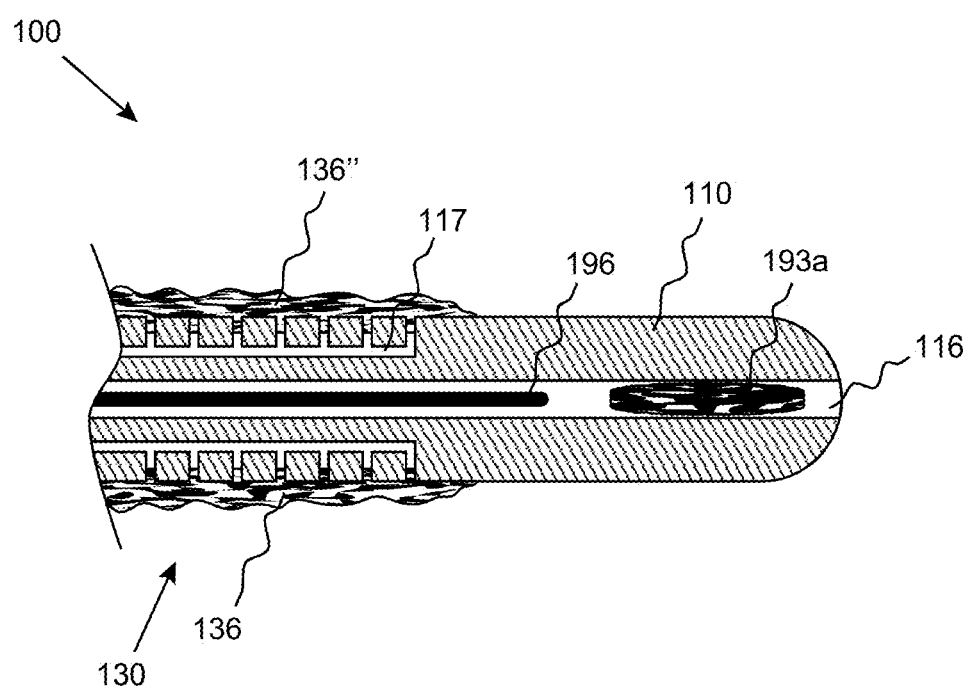
FIG. 5 illustrates a side sectional view of the distal portion of a tissue treatment device including an agent dispensing element, consistent with the present inventive concepts.

Referring now to FIG. 5, a side sectional view of the distal portion of a tissue treatment device including an agent dispensing element is illustrated, consistent with the present inventive concepts. Tissue treatment device 100 comprises shaft 110 which includes lumen 116 exiting the distal end of shaft 110. Positioned on a distal portion of shaft 110 is an expandable treatment assembly, expandable assembly 130 which includes a tissue treatment element, agent dispensing element 136". Shaft 110 and expandable assembly 130 are constructed and arranged such that shaft 110 can be inserted within and/or alongside an endoscope, such as endoscope 50a of FIG. 1. Lumen 116 and/or another lumen of shaft 110 can be constructed and arranged to allow over-the-wire delivery of shaft 110. Shaft 110 can comprise a length (e.g. at least 100 cm) such that expandable assembly 130 can be positioned proximate the distal end of the duodenum of a patient.

Agent dispensing element 136" is constructed and arranged to coat or otherwise apply one or more agents to target tissue. Tissue treatment device 100 and/or an associated system 10 can comprise one or more agents to be delivered by agent dispensing element 136", such as tissue modifying agent 135"; described herebelow in reference to FIGS. 5A-5E. Agent dispensing element 136" can comprise a material configured to expand, such as an expansion that occurs when agent dispensing element 136" comes into contact with a fluid (e.g. tissue modifying agent 135" or another fluid). Agent dispensing element 136" can be constructed and arranged to apply one or more tissue modifying agents 135" to target tissue. Tissue modifying agent 135" can comprise a chemical or other agent configured to cause target tissue necrosis or otherwise treat target tissue. Tissue modifying agent 135" can comprise an agent selected from the group consisting of a chemical peeling agent; a mild acid such as glycolic acid; trichloroacetic acid; a mild base; phenol; retinoic acid; and combinations of these.

In some embodiments, agent dispensing element 136" comprises a material selected from the group consisting of: a sponge material (e.g. a natural or synthetic sponge material); a foamed polyurethane; a polyvinyl alcohol (PVA) sponge; a hydrogel; a super-absorbent polymer; and combinations thereof. Shaft 110 further includes lumen 117 which travels to a proximal portion of shaft 110 and is constructed and arranged to provide one or more fluids to agent dispensing element 136".

Device 100 can comprise one or more deployable occluding elements, such as occluder 193a, shown positioned within lumen 116 of shaft 110. Device 100 can further include translatable push rod 196 configured to be advanced to deploy occluder 193a from the distal end of lumen 116. Occluder 193a can be configured to radially expand to at least partially occlude a segment of the gastrointestinal tract, as described herebelow in reference to FIGS. 5A-5E, such as to prevent undesired migration of tissue modifying agent 135" to non-target tissue. Occluder 193 can comprise one or more expandable materials or elements such as an expandable balloon and/or an expandable sponge (e.g. similar to agent dispensing element 136"). Occluder 193 can include digestible and/or biodegradable materials. Occluder 193 can be configured to evacuate the body via the body's natural digestive system and/or to be removed such as via a grasping element deployed through an endoscope. In some embodiments, additional occluders 193 can be deployed via rod 196 and lumen 116, such as two occluders 193 positioned at opposite ends of a segment of GI tract to be treated by agent dispensing element 136", also as described herebelow in reference to FIGS. 5A-5E.

Device 100 of FIG. 5 can be included as part of a system, such as system 10 of FIG. 1 or FIG. 6. The system can include an agent delivery unit, such as a console 200, configured to deliver one or more agents to agent dispensing element 136", and the system can include the agent to be applied onto target tissue, tissue modifying agent 135". In some embodiments, agent 420 of FIG. 1 comprises tissue modifying agent 135".

Referring now to FIGS. 5A-5E, side sectional views of a series of steps for treating a surface of GI tissue with the tissue treatment device of FIG. 5 are illustrated, consistent with the present inventive concepts. In FIG. 5A, endoscope 50a has been inserted into a segment of GI tract as shown (e.g. the duodenum). Endoscope 50a includes multiple working channels, lumens 51 and 54, and a visualization device, camera 52. A marker 195 has been positioned on the wall of the GI tract to be used as a reference to identify non-target tissue (e.g. tissue of the ampulla of Vater that should not be treated). Marker 195 can comprise one or more markers of similar construction and arrangement and/or placement to marker 195 of FIG. 3 described hereabove. Marker 195 can be positioned on and/or in tissue using device 100 of FIG. 5 and/or another device such as endoscope 50a.

Device 100 of FIG. 5 has been inserted through lumen 51 of endoscope 50a and advanced to a location distal to the position of marker 195 as shown. Occluder 193a is partially deployed from the distal end of shaft 110, such as via advancement of rod 196 described hereabove in reference to FIG. 5. Agent dispensing element 136" is in its radially compact state (e.g. prior to introduction of tissue modifying agent 135"). Device 100 can be of similar construction and arrangement to device 100 of FIG. 1 or device 100 of FIG. 6. In alternative embodiments, device 100 is inserted over a guidewire (e.g. not through endoscope 50a) and/or through a sheath.

Referring now to FIG. 5B, occluder 193a has been deployed, and tissue modifying agent 135" is being introduced into agent dispensing element 136" such as to partially expand agent dispensing element 136". Tissue modifying agent 135" can be provided via a fluid delivery device (e.g. a fluid pump) fluidly attached to lumen 117 shown in FIG. 5. In some embodiments, the fluid delivery device is constructed and arranged as is described herein in reference to console 200 of system 10 of FIG. 1 or to energy delivery unit 250 and/or console 200 of system 10 of FIG. 6.

Referring now to FIG. 5C, agent dispensing element 136" has been fully expanded to contact the wall of the GI segment, and device 100 has been partially retracted such that tissue modifying agent 135" coats the full-circumferential wall, or at least a partial-circumferential portion, of the GI segment distal to agent dispensing element 136". During the retraction of device 100, tissue modifying agent 135" is provided (e.g. continuously provided) to agent dispensing element 136".

Referring now to FIG. 5D, device 100 has been further retracted to a proximal end of the GI segment to be treated. Additionally, flow of tissue modifying agent 135" to agent dispensing element 136" has been stopped, agent dispensing element 136" has been withdrawn into lumen 51 of endoscope 50*a* (leaving the distal end of shaft 110 extending out of endoscope 50*a*), device 100 has subsequently been even further retracted, and a second occluding element, occluder 193*b* has subsequently been partially deployed from the distal end of shaft 110 (e.g. via control rod 196 in a similar fashion to the deployment of occluder 193*a*).

In some embodiments, agent dispensing element 136" is radially compressed prior to capture into lumen 51 (e.g. via application of a dehydrating agent, application of a vacuum capture via an advanceable sleeve, and the like). In some embodiments, a second agent (e.g. a neutralizing agent configured to stop and/or reverse the effects of tissue modifying agent 135") is delivered by agent dispensing element 136" prior to capture of agent dispensing element 136" into lumen 51. Alternatively or additionally, the neutralizing or other agent can be delivered via lumen 54. Delivery of a neutralizing agent can be performed to prevent adverse effect to non-target tissue.

Referring now to FIG. 5E, occluder 193*b* has been fully deployed, and endoscope 50*a* and device 100 have been removed from the patient. Tissue modifying agent 135" is present on the inner layer (i.e. mucosal layer) of the GI segment between occluders 193*a* and 193*b*, such that this full circumferential segment can be treated. In some embodiments, the segment between occluders 193*a* and 193*b* defines the entire segment of tissue to be treated in that clinical procedure. In other embodiments, multiple segments (e.g. defined by additional occluders 193), can be treated in a single clinical procedure. In these single segment and multi-segment embodiments, the amount of target tissue treated with tissue modifying agent 135" (e.g. the inner tissue layer between occluders 193*a* and 193*b* as described in reference to FIGS. 5A-5E) can be selected as described herein (e.g. at least 10%, at least 15%, at least 20%, at least 25%, at least 30% or at least 50% of the length of the duodenum distal to the ampulla of Vater). In some embodiments, the amount of target tissue treated with device 100 of FIGS. 5 and 5A-5E is selected to cause the treatment achieved as described hereabove in reference to FIG. 2 and—FIGS. 21-44. In some embodiments, the cumulative axial length treated is at least 4 cm, 5 cm, 6 cm, 7 cm, 8 cm or 9 cm of the duodenum.

Referring now to FIG. 6, a schematic view of a system for treating target tissue of a patient is illustrated, consistent with the present inventive concepts. System 10 includes tissue treatment device 100, which includes shaft 110 mounted on its proximal end to handle 102. Shaft 110 can comprise one or more shafts, such as outer shaft 110*a* and inner shaft 110*b*, slidingly received by outer shaft 110*a*. The distal portion of tissue treatment device 100 has been positioned in a segment of the GI tract. System 10 can further include tissue expansion device 20 and/or console 200, each of which can be of similar construction and arrangement to tissue expansion device 20 and/or console 200, respectively, of FIG. 1. Console 200 can be operably (e.g. fluidly, mechanically and/or electrically) attach to tissue treatment device 100, tissue expansion device 20 and/or another device or component of system 10, such as via connector 203. System 10 is configured to treat target tissue TT, which can include duodenal mucosa or other tissue as described herein to provide therapeutic benefit to the patient, such as the therapeutic benefits and other results presented in FIGS. 21-32. System 10 can be further configured to deliver an injectate into target tissue TT to expand tissue proximate target tissue TT (including target tissue TT itself), such as to expand one or more layers of tissue proximate target tissue TT.

System 10 can be configured to treat one or more patient diseases or disorders selected from the group consisting of: diabetes; pre-diabetes; impaired glucose tolerance; insulin resistance; obesity or otherwise being overweight; a metabolic disorder and/or disease; and combinations of these. In some embodiments, system 10 can be configured to treat one or more patient diseases or disorders selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome; hypertriglyceridemia; hypercholesterolemia; psoriasis; GERD; coronary artery disease; stroke; TIA; cognitive decline; dementia; diabetic nephropathy; neuropathy; retinopathy; diabetic heart disease; diabetic heart failure; and combinations of these.

Treatment of target tissue TT can be performed after expanding target tissue TT and/or after expanding tissue proximate target tissue TT (e.g. expanding a submucosal layer of tissue and subsequently treating the neighboring mucosal layer of tissue). Tissue expansion by device 20 can greatly alleviate the need for precision of treatment, such as precision of delivery of energy, precision of debriding or other removal of tissue and/or precision of delivery of an ablative fluid, due to the increased size (e.g. increased depth) of the target tissue TT including an associated safety-margin of tissue to which treatment causes no significant adverse event (e.g. a submucosal layer expanded prior to neighboring mucosal layer ablation). In the embodiment of FIG. 6, target tissue TT includes one or more tubular tissue segments, such as one or more axial tissue segments within a body lumen of a mammalian patient. In some embodiments, target tissue TT expanded and/or treated comprises a continuous segment (e.g. a continuous, full-circumferentially treated segment) and/or multiple discontinuous segments (e.g. multiple full-circumferentially treated segments) of a duodenum, such as a volume of tissue comprising at least 15% of the duodenal mucosa distal to the ampulla of Vater, at least 20% of the duodenal mucosa distal to the ampulla of Vater, at least 25% of the duodenal mucosa distal to the ampulla of Vater, at least 30% of the duodenal mucosa distal to the ampulla of Vater, at least 50% of the duodenal mucosa distal to the ampulla of Vater, or at least 67% of the duodenal mucosa distal to the ampulla of Vater. The entirety of tissue treated can comprise tissue distal to the ampulla of Vater, such as in a procedure in which at least 50% of post-ampullary duodenal mucosa is treated.

In some embodiments, the target tissue TT comprises a treatment portion including duodenal mucosal tissue and a safety-margin portion comprising at least an innermost layer of the duodenal submucosa (e.g. an innermost layer of duodenal submucosa expanded by a device of the present inventive concepts). System 10 can be configured to treat the duodenal mucosa while avoiding damage to duodenal adventitial tissue (e.g. non-target tissue), such as by avoiding damage to: tissue beyond the mucosa; tissue beyond the superficial submucosa; and/or tissue beyond the deep submucosa. In some embodiments, system 10 comprises marker 195, such as marker 195 shown deployed in segment of the GI tract of FIG. 6 and described hereabove in reference to FIGS. 1 and 3. Marker 195 can be positioned or otherwise deployed via endoscope 50a, device 100, and/or another device (e.g. a catheter device) of system 10.

System 10 can include one or more tissue treatment devices such as first tissue treatment device 100 and second tissue treatment device 100' (singly or collectively, device 100). First device 100 and/or second device 100' can be further constructed and arranged to expand tissue, as described in detail herein. Alternatively or additionally, system 10 can include separate tissue expansion device 20. First device 100 can be used in a first clinical procedure comprising expansion and/or treatment of target tissue TT, and second device 100' can be used in a second clinical procedure comprising expansion and/or treatment of target tissue TT. In some embodiments, the second clinical procedure is performed at least twenty-four hours after the first clinical procedure. Tissue expansions and/or treatments performed in the second clinical procedure can be constructed and arranged based on one or more outcomes of the first clinical procedure. Additional tissue expansion and/or tissue treatment devices can be included in system 10, such as to perform a third or other subsequent clinical procedures including tissue expansions and/or treatments.

First device 100 and second device 100' can be similar or dissimilar devices, and can be constructed and arranged to perform similar or dissimilar treatments to similar or dissimilar volumes of tissue. Differences between first device 100 and second device 100' can include but are not limited to: type of ablative treatment provided such as type of energy delivered; type of non-ablative treatment provided; type of tissue treatment assembly; type of tissue treatment element; length of the device; diameter of a portion of the device; and combinations of these. In some embodiments, first device 100 comprises a first tissue treatment element constructed and arranged to deliver a different form of energy than a second tissue treatment element of second device 100'. Alternatively or additionally, first device 100 can comprise a first tissue treatment element with a different geometry (e.g. different diameter, length and/or tissue contact surface area or shape), than a second tissue treatment element of second device 100'.

System 10 can include one or more body introduction devices, such as endoscope 50a. Endoscope 50a can comprise a standard GI endoscope such as an endoscope with one or more working channels configured to slidingly receive first device 100 (as shown), second device 100' and/or another elongate device of system 10. Additionally or alternatively, system 10 can include other body introduction devices, such as a laparoscopic port, vascular introducer, sheath (e.g. a scope attached sheath such as sheath 80 of FIG. 1) and/or other introducer.

System 10 includes console 200, which includes user interface 205, controller 250, reservoir 220, vacuum source 230 and inflation source 240. Console 200, via connector 203, is operably connected to handle 102 of device 100 via tubes 204a and/or cable 204b. User interface 205, controller 250, reservoir 220, vacuum source 230, inflation source 240, controller 203 can be of similar construction and arrangement to similar components of device 100 of FIG. 1.

System 10 can include injectate 221, which is delivered to device 100 or device 20 by reservoir 220. Injectate 221 can comprise a fluid selected from the group consisting of water; saline; a fluid with a dye such as a visible dye such as indigo carmine; methylene blue; India ink; SPOT™ dye; a gel; a hydrogel; a protein hydrogel; a fluid containing a visualizable media such as a media visualizable under X-ray, ultrasound imaging and/or magnetic resonance imaging; ethylene vinyl alcohol (EVOH); and combinations of these. In some embodiments, injectate 221 can comprise a material constructed and arranged to cause a narrowing or other restriction that results in a therapeutic benefit to the patient, such as is described in applicant's co-pending U.S. patent application Ser. No. 17/095,108, titled "Systems, Devices and Methods for the Creation of a Therapeutic Restriction in the Gastrointestinal Tract", filed Nov. 11, 2020, the entire content of which is incorporated herein by reference in its entirety. In these embodiments, injectate 221 can comprise a material configured to remain in place (e.g. within one or more tissue layers of the GI tract) for an extended period of time, such as at least 1 day, 1 week, 1 month, 3 months or 6 months. Injectate 221 can comprise a biopolymer (e.g. EVOH) and/or an adhesive (e.g. cyanoacrylate)

In some embodiments, console 200 comprises an energy delivery unit, EDU 250. EDU 250 can be constructed and arranged to deliver ablative fluids or other ablative energy to one or more components of device 100, such as an expandable tissue treatment assembly, expandable assembly 130 described herebelow, or to a separate tissue treatment device, such as device 100'. In some embodiments, console 200 comprises a motion control mechanism, motion transfer assembly 270. Motion transfer assembly 270 can be constructed and arranged to rotate, translate, vibrate and/or otherwise move one or more components of device 100, such as expandable assembly 130 and/or expandable assembly 160, each described in detail herebelow. In some embodiments, motion transfer assembly 270 is constructed and arranged to rotate another device or component of system 10, such as a tissue treatment element or other component of treatment device 100. In some embodiments, motion transfer assembly 270 is constructed and arranged to steer a shaft of one or more components of system 10, such as one or more shafts 110 of device 100.

Tissue treatment device 100 can comprise one or more shafts 110 (e.g. a single shaft or multiple columnal shafts) which attach on their proximal end to handle 102. A distal portion of one or more shafts 110 can include a radially expandable assembly 160 comprising one or more fluid delivery elements 168, each attached to a fluid delivery tube 162. Fluid delivery tubes 162 can travel proximally through one or more shafts 110 and into handle 102. Handle 102 can fluidly attach (e.g. via one or more ports and/or via tubes 204a) to console 200 such that injectate 221 and/or another fluid can be provided to fluid delivery element 168 via reservoir 220. In some embodiments, two fluid delivery elements 168 are included (e.g. mounted 180° apart on expandable element 166). In some embodiments, three fluid delivery elements 168 are included (e.g. mounted 120° apart on expandable element 166). In some embodiments, four or more fluid delivery elements 168 are included (e.g. four elements mounted 90° apart on expandable element 166). In some embodiments, three or more fluid delivery tubes 162 are attached to expandable element 166 with spacing to accommodate advancement of endoscope 50a proximate to expandable element 166. A distal portion of one or more shafts 110 further include a tissue treatment assembly, expandable assembly 130 as shown. Expandable assembly 130 can be positioned distal or proximal (as shown) to expandable assembly 160 (i.e. when device 100 is configured to both treat tissue and expand tissue and includes both expandable assembly 130 for tissue treatment and expandable assembly 160 for tissue expansion).

Motion transfer assembly 270 can be configured to rotate expandable 3 assembly 130 and/or expandable assembly 160 independently or in unison. Motion transfer assembly 270 can be configured to translate expandable assembly 130 as treatment is applied to a portion of target tissue TT. In some embodiments, contiguous tissue segments are treated by device 100 continuously as motion transfer assembly 270 causes expandable assembly 130 to translate at a rate of at least 10 cm/minute, or at a rate of least 20 cm/minute. In some embodiments, expandable assembly 130 is manually translated, such as at a rate of at least 10 cm/minute, or at least 20 cm/minute. Motion transfer assembly 270 can be configured to translate expandable assembly 130 between a first tissue treatment and a second tissue treatment (e.g. between a first segment of duodenal mucosa treated in the first treatment and a second segment of duodenal mucosa treated in the second treatment). Motion transfer assembly 270 can include one or more rotational and/or linear drive assemblies, such as those including rotational motors, magnetic drives, lead screws and/or other linear actuators, and the like which are operably connected to shaft 110a and/or 110b. Shafts 110a and/or 110b are constructed with sufficient column strength and/or torque transfer properties to adequately rotate and/or translate expandable assembly 130 and/or expandable assembly 160, respectively. Motion transfer assembly 270 can be in communication with controller 250, such as to activate, adjust and/or otherwise control motion transfer assembly 270 and thus the motion of expandable assembly 130 and/or expandable assembly 160. Motion transfer assembly 270 can be manually driven and/or automatically (e.g. motor) driven. Alternatively or additionally, motion transfer assembly 270 can be used to advance and/or retract expandable assembly 130 and/or expandable assembly 160 from a first position to treat a first portion of target tissue, to a second position to treat a second portion of target tissue. In these embodiments, repositioning of expandable assembly 130 and/or expandable assembly 160 can be configured to provide overlapping treatment.

Shafts 110a and 110b can include one or more lumens passing therethrough, and can comprise wires and/or optical fibers for transfer of data and/or energy such as RF energy to a functional element. such as functional element 139 of expandable assembly 130 and/or functional element 169 of expandable assembly 160. Shafts 110a and/or 110b can comprise one or more shafts, such as one or more concentric shafts configured to deliver and/or recirculate hot and/or cold fluid through expandable assembly 130 and/or expandable assembly 160. In some embodiments, a heated fluid is used to pre-heat one or more device 100 components and/or to deliver a bolus of hot fluid energy, each as described in applicant's co-pending U.S. patent application Ser. No. 16/438,362, entitled "Heat Ablation Systems, Devices and Methods for the Treatment of Tissue, filed Jun. 11, 2019, the entire content of which is incorporated herein by reference in its entirety. Device 100 can comprise multiple tissue treatment assemblies, such as a second expandable assembly positioned proximal to the expandable assembly 130 and a third expandable assembly positioned distal to expandable assembly 130 (e.g. expandable assembly 160 as shown in FIG. 6).

The distal end of shaft 110 (e.g. the distal end of shaft 10b) can comprise a bulbous element, bulbous tip 115. In these embodiments, bulbous tip 115 can be sized to fit through a working channel of endoscope 50a, such as when bulbous tip 115 has a diameter less than 6 mm or less than 4 mm. Alternatively, bulbous tip 115 can have a larger diameter, such as a diameter or other geometry configured to assist in smoothly traversing plicae, such as a diameter of at least 8 mm. In some embodiments, bulbous tip 115 comprises a diameter between 4 mm and 9 mm, such as a diameter between 4 mm and 6 mm. In some embodiments, bulbous tip 115 comprises at least a radiopaque portion.

Shafts 110a and 110b of FIG. 6 are sized and configured such that shaft 110a slidingly receives shaft 110b, such that they can be advanced and/or retracted in unison or independently. Differential motion between shafts 110a and 110b can be used to change the distance between expandable assembly 130 and expandable assembly 160. In some embodiments, motion transfer assembly 270 is configured to rotate and/or axially translate shafts 110a and/or 110b such that expandable assembly 130 and/or expandable assembly 160, respectively, are rotated and/or translated. In some embodiments, device 100 comprises a flexible portion (e.g. a flexible portion of shafts 110a and 110b, such as a flexible distal portion of shaft 110b) with a diameter less than 6 mm. In some embodiments, the flexible portion is configured to pass through a working channel of an endoscope with a diameter of less than or equal to 6.0 mm, 4.2 mm, 3.8 mm, 3.2 mm or 2.8 mm. In some embodiments, device 100 comprises a shaft length of 100 cm or longer, or otherwise comprises a length sufficient to be orally and/or nasally inserted into a patient, and subsequently advanced to reach the esophagus, stomach, duodenum and/or jejunum; and/or rectally inserted into a patient, and subsequently advanced to reach the terminal ileum of that patient. In FIG. 6, shafts 110a and 110b have been inserted through a working channel (e.g. a 6 mm working channel), lumen 51, of endoscope 50a, typically a GI endoscope. Shafts 110a and/or 110b can be inserted over a standard interventional guidewire, such as guidewire 60 shown exiting the distal end of shaft 110b. In an alternative embodiment, shafts 110a and 110b are positioned in a side-by-side configuration, such as to be placed in two separate lumens of endoscope 50a or in two other non-coaxial locations. In some embodiments, one or both of shafts 110a or 110b passes through a body lumen or other internal body location alongside endoscope 50a (i.e. not through lumen 51, traveling relatively parallel with but external to endoscope 50a). Shaft 110a and/or 110b can include a manipulating element constructed and arranged to deflect and/or steer a distal portion of the shaft, such as via one or more handle 102 controlled and/or motion transfer assembly 270 controlled pull wires that extend and are attached to a distal portion of the shaft (pull wires not shown but well known to those of skill in the art), such as to deflect and/or steer expandable assembly 130 and/or expandable assembly 160 towards and/or away from tissue and/or assist in navigating expandable assembly 130 and/or expandable assembly 160 through tortuous anatomy.

Handle 102 can comprise one or more controls included in user interface 105. In some embodiments, user interface 105 comprises one or more controls selected from the group consisting of: electrical control; mechanical control; button; knob; switch; lever; touchscreen; and combinations of these. In some embodiments, a mechanical control is operably attached to a mechanical assembly, such as a cam or other mechanical advantage mechanism used to transmit a force (e.g. transmit force to a pull wire). In some embodiments, an electrical control is used to attach one or more components of system 10 to power and/or to activate an electrically powered mechanical mechanism such as a solenoid or an electronic valve. User interface 105 can be configured to allow an operator to initiate, regulate, modify, stop and/or otherwise control one or more functions of console 200 and/or device 100.

In some embodiments, user interface 105 comprises one or more knobs or other controls used to advance and/or retract one or more fluid delivery elements 168, positioned on expandable element 166 of expandable assembly 160, each described in detail herebelow. In some embodiments, one or more fluid delivery elements 168 are advanced and/or retracted via a force limiting assembly 140. Force limiting assembly 140 can be constructed and arranged to allow a single control (e.g. a sliding knob) to advance multiple fluid delivery elements 168 simultaneously. In some embodiments, advancement and/or retraction of one or more fluid delivery elements 168 is limited by one or more mechanical stops.

In some embodiments, user interface 105 comprises a button, touch screen display and/or other control used to initiate, regulate, modify, stop and/or otherwise control one or more parameters of console 200, such as a tissue expanding fluid parameter selected from the group consisting of: flow rate of tissue expanding fluid; duration of tissue expanding fluid flow; volume of tissue expanding fluid; temperature of tissue expanding fluid; pressure of tissue expanding fluid; a tissue expanding fluid threshold parameter level (e.g. maximum or minimum flow rate, duration, volume, temperature and/or pressure); type of tissue expanding fluid; and combinations thereof. In some embodiments, user interface 105 comprises a button, touch screen display and/or other control used to initiate, regulate, modify, stop and/or otherwise control one or more parameters of EDU 250, such as an ablation parameter selected from the group consisting of: flow rate of ablative fluid; volume of ablative fluid; pressure of ablative fluid; temperature of ablative fluid; type of energy delivered; type of RF energy delivered (e.g. monopolar, bipolar or both); amount of RF energy delivered (e.g. voltage, current and/or power delivered); and combinations of these.

Device 100 of FIG. 6 includes an outer shaft 110*a* and an inner shaft 110*b* (generally shaft 110 or shafts 110). Expandable assembly 160 is mounted to shaft 110*b*, and expandable assembly 130 is mounted proximal to expandable assembly 160, shown positioned on shaft 110*a*. In some embodiments, device 100 comprises a single shaft, and expandable assembly 130 and/or expandable assembly 160 are mounted to that single shaft. Expandable assembly 160 is constructed and arranged to deliver fluid, via one or more fluid delivery elements 168, into target tissue TT, such as to expand tissue proximate target tissue TT. In some embodiments, expandable assembly 160 can be configured in one or more various forms to treat, modify, manipulate, measure and/or diagnose target tissue TT and/or other tubular tissue. Expandable assembly 160 can comprise one or more expandable elements 166, such as one or more expandable elements selected from the group consisting of: an inflatable or otherwise expandable balloon; a radially expandable stent or cage; an array of splines; one or more radially deployable arms; a spiral or other helical structure; a furlable structure such as a furlable sheet; an unfurlable structure such as an unfurlable sheet; a foldable structure such as a foldable sheet; an unfoldable structure such as an unfoldable sheet; and combinations of these. In some embodiments, expandable assembly 160 is inflatable (e.g. an inflatable balloon), and inflation fluid can be delivered into expandable assembly 160 via an inflation tube 161. Inflation tube 161 can comprise a lumen of shaft 110*b* (or a tube within shaft 110*b*) that travels proximally through shaft 110*b* and shaft 110*a*, such as to receive inflation fluid delivered by inflation source 240. Expandable assembly 160 can be positioned distal to expandable assembly 130 as shown in FIG. 6, or alternatively, expandable assembly 160 can be positioned proximal to expandable assembly 130, such as when expandable assembly 130 is mounted to shaft 110*b* and expandable assembly 160 is mounted to shaft 110*a*.

Expandable assembly 130 can be radially expandable, similar to expandable assembly 160 and/or it can include one or more radially expandable elements, such as those described hereabove in reference to expandable assembly 160 and/or expandable element 166. System 10 can be configured to allow expansion of expandable assembly 130 to cause one or more treatment elements 135 to approach and/or contact a tissue wall such as a duodenal wall, such as when one or more treatment elements 135 comprise an ablative fluid delivered to a balloon and configured to ablate tissue, or when one or more treatment elements 135 comprise an electrode configured to deliver RF energy to ablate tissue. Expandable assembly 130 can be configured to expand to a diameter less than the diameter of the target tissue TT, such as when a vacuum is applied to cause the target tissue TT diameter to decrease sufficiently to make contact with expandable assembly 130 and/or one or more treatment elements 135. System 10 can be configured to allow expansion of treatment assembly 130 to cause one or more treatment elements 135 to be positioned at a fixed distance from the luminal wall of tubular tissue, such as a positioning at a fixed distance of at least 250 microns, at least 500 microns, or at least 1 mm from a tissue wall, such as when one or more treatment elements 135 are configured to deliver ablative fluid to the target tissue TT and/or to deliver light energy to the target tissue TT. In addition to treating target tissue TT, treatment assembly 130 and/or one or more treatment elements 135 can be configured in one or more various forms to modify, manipulate, measure and/or diagnose target tissue TT and/or other tubular or non-tubular tissue. Expansion of treatment assembly 130 can occur prior to, during and/or after treatment of target tissue TT by treatment element 135. Treatment element 135 can be mounted on, within and/or inside of an expandable assembly, such as on, within and/or inside of an expandable balloon. Treatment assembly 130 can be constructed and arranged to expand and contact luminal wall tissue without applying an undesired force to the luminal wall tissue, such as by applying a pressure of less than 2.0 psi or less than 1.2 psi. Expandable assembly 130 can be constructed and arranged to expand to a diameter between 20 mm and 35 mm, such as to a diameter between 20 mm and 27.5 mm. Expandable assembly 130 can be constructed and arranged to contact luminal wall tissue with a pressure of at least 0.6 psi.

In some embodiments, expandable element 136 of expandable assembly 130 and/or expandable element 166 of expandable assembly 160 comprise inflatable or otherwise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In some embodiments, expandable element 136 and/or expandable element 166 comprise a balloon which is fluidly attached to an inflation tube, such as inflation tube 161 which travels proximally through shaft 110*a* and/or 110*b* and is attached to one or more tubes 204*a* and/or an inflation port on handle 102.

In some embodiments, expandable assembly 160 is constructed and arranged to exert no more than a maximum threshold force on tissue, such as luminal wall tissue. The threshold force can comprise a force less than 2.0 psi, such as a force less than 1.2 psi. Expandable assembly 160 can be constructed and arranged to contact luminal wall tissue with a force of at least 0.6 psi. Expandable assembly 160 can be constructed and arranged to expand to a target diameter, such as a diameter of at least 10 mm, at least 15 mm, at least 25 mm, at least 30 mm or at least 40 mm. In some embodiments, expandable assembly 160 is constructed and arranged to expand to a diameter between 20 mm and 35 mm, such as a diameter between 20 mm and 27.5 mm. In some embodiments, expandable assembly 160 has its diameter controlled by a component of system 10 (e.g. controller 250 and/or inflation source 240), such as to control the diameter to at least 10 mm, at least 15 mm, at least 20 mm, at least 25 mm, at least 30 mm, or at least 40 mm, or to control the diameter to a diameter between 20 mm and 35 mm. In some embodiments, expandable assembly 160 is constructed and arranged to expand to its target diameter in less than 60 seconds, such as less than 30 seconds or less than 15 seconds. In some embodiments, expandable assembly 160 is expanded to a target diameter by inflating with fluid delivered at a constant pressure (e.g. approximately 0.7 psi) until the target diameter is reached. In some embodiments, expandable assembly 160 is constructed and arranged to expand to a diameter less than the diameter of the lumen of the GI tract proximate expandable assembly 160. In these embodiments, vacuum can be applied (e.g. via an endoscope 50a or device 100 insufflation port), which brings the tissue of the luminal wall toward a tissue capture port 167 and/or a fluid delivery element 168.

In some embodiments, expandable assembly 130 is constructed and arranged to exert no more than a maximum threshold force on tissue, such as luminal wall tissue. Expandable assembly 130 can be constructed and arranged to treat tissue while maintaining a pressure of at least 0.6 psi. Expandable assembly 130 can be constructed and arranged to expand to a target diameter, such as a diameter of at least 10 mm, at least 15 mm, at least 25 mm, at least 30 mm or at least 40 mm. In some embodiments, expandable assembly 130 is constructed and arranged to expand to a diameter between 20 mm and 35 mm, such as a diameter between 20 mm and 27.5 mm. In some embodiments, expandable assembly 130 has its diameter controlled by a component of system 10 (e.g. controller 250, inflation source 240 and/or EDU 250), such as to control the diameter to at least 10 mm, at least 15 mm, at least 20 mm, at least 25 mm, at least 30 mm, or at least 40 mm, or to control the diameter to a diameter between 20 mm and 35 mm. In some embodiments, expandable assembly 130 is constructed and arranged to expand to a diameter less than the diameter of the lumen of the GI tract proximate expandable assembly 130. In these embodiments, vacuum can be applied (e.g. via an endoscope 50a or device 100 insufflation port), which brings the tissue of the luminal wall toward expandable assembly 130 and/or treatment element 135.

In some embodiments, expandable assembly 130 and/or expandable assembly 160 comprise a length of at least 10 mm, such as a length between 10 mm and 40 mm, a length between 15 mm and 30 mm, or a length between 20 mm and 25 mm. In some embodiments, expandable assembly 130 and/or expandable assembly 160 comprise a length less than or equal to 15 mm, such as when configured to treat curvilinear portions of the GI tract. Multiple assemblies positioned on shafts 110a and/or 110b (e.g. between two and twenty treatments and/or expandable assemblies), such as expandable assembly 130 and expandable assembly 160, can be separated along a shaft by a distance less than or equal to 25 mm, such as a distance less than or equal to 20 mm. This separation distance can comprise the distance between a distal end of a tissue contacting portion of a first expandable element, and the neighboring proximal end of a tissue contacting portion of a second expandable element. In some embodiments, expandable assembly 130 comprises a length, and the separation distance between expandable assembly 130 and expandable assembly 160 is less than or equal to the expandable assembly 160 length. In these embodiments, expandable assembly 130 can comprise a similar length to that of expandable assembly 160, such as when both expandable assembly 130 and expandable assembly 160 comprise an ablation element as is described herebelow. Expandable assembly 130 and/or expandable assembly 160 can be sized, constructed and/or arranged to expand tissue and/or ablate tissue, or otherwise perform a function, while positioned in a curved segment of the GI tract.

Expandable assembly 130 and/or expandable assembly 160 can be resiliently biased, such as a resilient bias in a radially expanded or radially compacted state. In some embodiments, expandable assembly 130 and/or expandable assembly 160 are expanded and/or compacted by a control shaft, such as control shaft included in conduit 132 or another conduit of device 100 and manipulatable by an operator of system 10 and/or by motion transfer assembly 270. Expandable assembly 130 and/or expandable assembly 160 can be constructed and arranged to achieve a round or non-round shape (e.g. a football shape) when expanded. Expandable assembly 130 and/or expandable assembly 160 can approximate a tubular shape when expanded, such as a relatively constant diameter or varying diameter tubular shape. Expandable assembly 130 and/or expandable assembly 160 can be configured to un-fold to a radially expanded state, or to fold to a radially compacted state.

Expandable assembly 160 and at least one fluid delivery element 168 are configured to expand or otherwise modify tissue, such as to expand one or more layers of tissue. One or more fluid delivery elements 168 can comprise a needle, fluid jet and/or iontophoretic fluid delivery element configured to deliver injectate 221 into target tissue, such as to expand submucosal or other tissue of the GI tract. Console 200 can comprise a reservoir or control means for delivering a pre-determined amount of injectate 221 to tissue by device 100, such as a volume of fluid of at least 1 ml, or a volume of fluid of at least 2 ml, 5 ml, 10 ml or 25 ml. Device 100 can be configured to inject fluid into multiple injection sites (e.g. simultaneously or sequentially), such as a set of multiple injection sites selected from the group consisting of: at least 3 injection sites along a circumference of tubular tissue, a first circumferential injection site separated from a second circumferential injection site by approximately 1cm, or between 0.5 cm to 5 cm, or between 1 cm and 3 cm, or between 1 cm and 2 cm; two or more injection sites that are axially and/or radially spaced; two or more injections sites that are separated based on the diameter of the tubular tissue into which they are injected; and combinations of these. Fluid can be injected with the assistance of one or more vacuum applying elements positioned on or near fluid delivery elements 168, such as tissue capture ports 167 shown. Tissue capture ports 167 can be of similar construction and arrangement to tissue capture ports 47 of FIG. 1 described hereabove. Tissue capture ports 167 are configured to apply negative pressure proximate the injection site, such as to capture tissue within the port and avoid the fluid delivery element 168 from having to radially exit tissue capture port 167 to penetrate the tissue. Tissue capture ports 167 can comprise one or more portions that are radiopaque. Console 200 and/or tissue capture ports 167 can be configured to discharge or otherwise release tissue from tissue capture port 167, such as by applying a positive pressure to tissue capture port 167. Device 100 can comprise one or more sensors configured to monitor the vacuum level in tissue capture port 167 and/or a fluidly connecting lumen.

As described hereabove, system 10 can be constructed and arranged to both expand tissue and treat tissue. In some embodiments, one or more devices 100 can be constructed and arranged to both expand tissue and treat tissue, such as via a tissue treatment assembly, expandable assembly 130. Alternatively or additionally, system 10 can comprise a separate device for tissue treatment, tissue treatment device 100'. Device 100' can comprise one or more tissue treatment elements configured to treat target tissue TT, such as a tissue treatment assembly similar to expandable assembly 130 described herein. Console 200 can further include an energy delivery unit, EDU 250, which can be operably attached to first device 100 (as shown), tissue second tissue treatment device 100' and/or tissue expansion device 20. EDU 250 can be configured to provide numerous forms of energy to one or more treatment elements of device 100 and/or device 100', such as an energy form selected from the group consisting of: RF energy; microwave energy; laser energy; sound energy such as subsonic sound energy or ultrasound energy; chemical energy; thermal energy such as heat energy or cryogenic energy provided by an ablative fluid; and combinations of these.

In some embodiments, system 10, device 100 and/or device 100' (singly or collectively device 100) can be constructed and arranged as is described in applicant's co-pending U.S. patent application Ser. No. 13/945,138, entitled "Devices and Methods for the Treatment of Tissue", filed Jul. 18, 2013, the entire content of which is incorporated herein by reference in its entirety. In some embodiments, device 100 can be constructed and arranged to ablate tissue with an ablation treatment selected from the group consisting of: delivery of thermal energy from a balloon filled with fluid at an ablative temperature; RF energy ablation such as monopolar and/or bipolar RF energy ablation; delivery of an ablative fluid directly to tissue; cryoablation; delivery of laser energy; delivery of sound energy such as subsonic sound energy or ultrasonic sound energy; plasma energy delivery; argon plasma coagulation; microwave energy delivery; delivery of non-laser light energy; and combinations of these. In some embodiments, device 100 can be constructed and arranged to perform a non-ablative treatment of target tissue, such as with a non-ablative treatment selected from the group consisting of: mechanical removal of mucosal tissue; chemical, sclerosant or pharmaceutical injection into the submucosa; radioactive seed deposition; chemical spray such as an acid spray; pharmacologic administration such as drug delivery via an agent-eluting balloon; and combinations of these. Device 100 can be constructed and arranged to resect tissue, such as to resect tissue selected from the group consisting of: plicae tissue; mucosal tissue; submucosal tissue; and combinations of these.

One or more components of console 200 can include a pump and/or reservoir which can provide and/or remove one or more fluids to and/or from one or more devices of system 10, such as device 100, device 20 and/or endoscope 50a. Fluids can be provided (e.g. by EDU 250) to thermally prime (e.g. hot or cold priming) one or more components of system 10, as described in detail herebelow. Tissue ablating fluids can be provided, such as hot or cold ablative fluids provided by EDU 250 to expandable assembly 130 of device 100. Tissue neutralizing fluids can be provided (e.g. by EDU 250) such as cooling fluids provided after elevated temperature ablation, warming fluids provided after cryogenic ablation and/or chemically neutralizing fluids delivered to neutralize a chemical agent. Fluids can be provided (e.g. a gas) to insufflate a portion of the GI tract, such as fluids provided through a lumen of endoscope 50a or a lumen of device 100. Console 200 can include one or more fluid reservoirs (e.g. one or more reservoirs included in reservoir 220, vacuum source 230, inflation source 240 and/or energy delivery unit 250) constructed and arranged to supply or receive fluids to and/or from device 100. In some embodiments, console 200 includes one or more reservoirs, one or more pumps, and one or more cooling or heating units such that console 200 recirculates or otherwise continuously provides one or more hot and/or cold fluids through a device of system 10, such as to recirculate fluid through one or more portions of device 100, device 20 and/or endoscope 50a.

Expandable assembly 130 can include one or more elements constructed and arranged to ablate or otherwise treat target tissue TT, such as tissue treatment element 135 shown. Treatment element 135 can comprise one or more elements selected from the group consisting of: a bolus of ablative fluid; recirculating ablative fluid; continuously replenished ablative fluid; an electrical energy delivery element such as one or more electrodes constructed and arranged to deliver RF energy; a fluid delivery element such as a nozzle or permeable surface constructed and arranged to deliver ablative fluid directly in contact with target tissue TT; a balloon such as a balloon constructed and arranged to receive a bolus of ablative fluid and deliver hot or cold thermal energy to ablate target tissue TT; a balloon such as a balloon constructed and arranged to receive a recirculating ablative fluid and deliver hot or cold thermal energy to ablate target tissue TT; a laser energy delivery element such as an optical fiber, a focusing lens and/or other optical component; a sound energy delivery element such as a piezo-based element configured to deliver ultrasonic and/or subsonic energy; a tissue abrading element; and combinations of these. Treatment element 135 can be positioned on, in, within and/or passing through one or more components of expandable assembly 130, such as a balloon, cage, spline or other component as are described herein. Expandable assembly 130 and/or treatment element 135 can comprise an energy distribution element, such as one or more optical components configured to rotate, translate and/or otherwise distribute laser or other light energy to target tissue. In some embodiments, expandable assembly 130 and/or treatment element 135 comprise an energy distribution element including a rotating element such a rotating mirror; a rotating prism and/or a rotating diffractive optic. In some embodiments, device 100 comprises one or more fibers that deliver laser or other light energy to a treatment element 135 when expandable assembly 130 comprises a balloon filled with light-scattering material.

In some embodiments, device 100 delivers thermal (e.g. heat or cryogenic) energy to tissue, such as when expandable assembly 130 and/or treatment element 135 comprises an ablative fluid delivered to a balloon, and the ablative fluid comprises a hot or cold volume of fluid at a temperature sufficient to ablate tissue when the balloon contacts the tissue. The hot or cold volume of fluid can be provided to expandable assembly 130 via EDU 250. System 10 can be configured to deliver thermal energy to tissue as is described in applicant's co-pending U.S. patent application Ser. No. 16/438,362, entitled "Heat Ablation Systems, Devices and Methods for the Treatment of Tissue", filed Jun. 11, 2019, or as is described in applicant's co-pending U.S. patent application Ser. No. 14/917,243, entitled "Systems, Methods and Devices for Treatment of Target Tissue", filed Mar. 7, 2016, the entire contents of each of which is incorporated herein by reference in their entirety.

In some embodiments, device 100 delivers RF energy to tissue, such as when treatment element 135 comprises one or more electrodes constructed and arranged to receive RF energy provided by EDU 250. In these embodiments, the one or more electrodes can comprise one or more conductive dots or other conductive elements positioned on an expandable element such as a balloon. In some embodiments, EDU 250 is configured to deliver RF energy to one or more electrodes of device 100, such as in a monopolar mode through a grounding pad such as ground pad 70 and/or in a bipolar mode between two or more electrodes of device 100. System 10 can be configured to deliver RF energy to tissue as is described in applicant's co-pending U.S. patent application Ser. No. 16/711,236, entitled "Electrical Energy Ablation Systems, Devices and Methods for the Treatment of Tissue", filed Dec. 11, 2019, the entire content of which is incorporated herein by reference in its entirety.

In some embodiments, device 100 delivers ablative fluid directly to tissue, such as when treatment element 135 comprises one or more nozzles or other ablative fluid delivery elements. In these embodiments, treatment element 135 can be constructed and arranged to ablate target tissue TT by delivering ablative fluid provided by EDU 250. Treatment element 135 can include one or more fluid delivery elements selected from the group consisting of: nozzle such as a nozzle configured to deliver a cone or other shaped spray of fluid; needle; opening; hole; slit; permeable membrane; misting element; vaporizer; and combinations of these. Treatment element 135 can comprise the fluid delivery element and/or the ablative fluid. Ablative fluid can comprise one or more liquids or gases that are delivered to target tissue TT at a temperature above or below a threshold that would ablate tissue. In some embodiments, the ablative fluid delivered by treatment element 135 comprises steam, such as steam at a temperature of 100° C. or above. In some embodiments, the ablative fluid delivered by treatment element 135 comprises a vaporized fluid at a temperature below 100° C., such as a vaporized fluid at a temperature between 70° C. and 90° C. In some embodiments, the ablative fluid delivered by treatment element 135 comprises a gas, such as a gas between 60° C. and 99° C., such as a gas delivered to tissue at a temperature between 70° C. and 90° C. In some embodiments, the ablative fluid delivered by treatment element 135 comprises a vaporized liquid, such as a vaporized liquid delivered to tissue at a temperature below 100° C., such as at a temperature between 70° C. and 90° C. Alternatively or additionally, an ablative fluid delivered by treatment element 135 can comprise one or more liquids or gases that cause tissue necrosis or otherwise treat target tissue TT using one or more chemically active agents (e.g. ablation not primarily caused by delivery or removal of heat from tissue). In these embodiments, the agent can comprise an agent selected from the group consisting of: sclerotic agent; acid; base; saline; alcohol; carbon dioxide; nitrous oxide; nitrogen; acetic acid; glycerol; and combinations of these. In these embodiments, a counter-acting neutralizing agent can be included, such as a neutralizing agent delivered by device 100 or another device or component of system 10 that is used to neutralize, impede, reduce and/or limit tissue ablation caused by the delivery of a necrotic agent-based ablative fluid. The counter-acting agent can be delivered by treatment element 135 and/or another component of device 100 or system 10. The neutralizing agent can comprise an agent selected from the group consisting of: anti-sclerotic agent; base; acid; buffer solution; saline; water; and combinations of these. System 10 can be configured to deliver ablative fluid directly to tissue as is described in applicant's co-pending U.S. patent application Ser. No. 14/609,334, entitled "Ablation Systems, Devices and Methods for the Treatment of Tissue", filed Jan. 29, 2015, the entire content of which is incorporated herein by reference in its entirety.

Expandable assembly 130 can be positioned on shaft 110*a* as shown. Treatment element 135 is electrically, fluidly, mechanically and/or otherwise operably connected to conduit 132. Conduit 132 can comprise one or more elongate filaments selected from the group consisting of: a wire such as one or more wires configured to deliver electrical or other power and/or transmit electrical or other data signals; an optical fiber such as one or more optical fibers configured to deliver power and/or transmit data signals; a tube such as a fluid delivery or a vacuum supplying tube; a lumen such as a fluid delivery lumen or a vacuum supplying lumen; a control rod such as an advanceable and/or retractable control rod; and combinations of these. Conduit 132 travels proximally through shaft 110*a* and operably attaches to console 200 (e.g. via connector 203), such as to operably attach to one or more of: reservoir 220; vacuum source 230; inflation source 240; EDU 250; motion transfer assembly 270; and/or combinations of these, and/or to attach to another component, assembly or device of system 10. In some embodiments, one or more portions (e.g. one or more filaments) of conduit 132 extend to expandable assembly, such as one or more filaments selected from the group consisting of: a control rod; an inflation tube; an inflation lumen; a fluid delivery tube; a wire; an optical fiber; and combinations of these.

In some embodiments, conduit 132 comprises one or more fluid delivery tubes and/or lumens constructed and arranged to deliver and/or recirculate heated or chilled fluid into expandable assembly 130, such as heated or chilled fluid received from EDU 250 and delivered into treatment element 135, such as when treatment element 135 comprises ablative fluid and/or a balloon or other fluid reservoir receiving the ablative fluid, where the ablative fluid is at a temperature sufficient to ablate tissue when expandable assembly 130 contacts the tissue. Alternatively or additionally, conduit 132 can comprise one or more fluid delivery tubes constructed and arranged to deliver an ablative fluid to expandable assembly 130, such as ablative fluid provided by EDU 250 and delivered directly to target tissue TT by one or more treatment elements 135, such as when treatment element 135 comprises a fluid delivery element such as a nozzle. Conduit 132 can further comprise one or more insulating layers configured to prevent transfer of heat into and/or out of conduit 132. Conduit 132 can include a surrounding lumen which receives a circulating fluid configured to provide an insulating, warming and/or cooling effect on conduit 132 and/or any fluid contained within conduit 132. Conduit 132 and/or another fluid delivery tube of system 10 can comprise one or more elongate hollow tubes, such as a hollow tube positioned within shaft 110*a*. Alternatively, conduit 132 and/or another fluid delivery tube of system 10 can comprise a lumen within a shaft, such as a lumen within shaft 110*a*. In some embodiments, conduit 132 and/or another fluid delivery tube of system 10 comprises both a lumen and a hollow tube, such as when the lumen and hollow tube are fluidly connected in an end-to-end configuration. Conduit 132 typically attaches to console 200 with one or more operator attachable fluid connection ports (e.g. attaching to tubes 204a), such as a fluid connection port included in handle 102 positioned on the proximal end of shaft 110a. Conduit 132 can comprise one or more fluid delivery tubes including one or more valves, not shown but such as a duck-bill or other valve used to regulate flow within conduit 132, such as to regulate flow pressure and/or direction.

In some embodiments, conduit 132 comprises one or more elongate filaments constructed and arranged to transmit energy and/or data. Conduit 132 can comprise one or more wires constructed and arranged to deliver RF energy to one or more electrode-type treatment elements 135, such as when the treatment elements 135 are configured to ablate target tissue TT in monopolar and/or bipolar modes as described herein. Conduit 132 can comprise one or more filaments constructed and arranged to deliver laser energy, such as one or more optical fibers constructed and arranged to deliver laser energy to one or more lenses or other optical component-type treatment elements 135, such as to ablate target tissue TT with laser or other light energy. Conduit 132 can comprise one or more wires or other energy transfer filaments constructed and arranged to allow a sound producing-type treatment element to ablate target tissue TT with sound energy such as ultrasonic or subsonic sound energy. Conduit 132 can comprise one or more wires or optical fibers configured to transmit information, such as information received from a sensor of system 10 as described herebelow.

In some embodiments, conduit 132 and/or shaft 110 comprises one or more control rods constructed and arranged to cause one or more treatment elements 135 and/or fluid delivery elements 168 to rotate and/or translate, such as when conduit 132 is operably attached to motion transfer assembly 270, such as prior to, during and/or after expansion of a tissue layer and/or delivery of energy to target tissue. In some embodiments, one or more treatment elements 135 comprise a surface configured to abrade or otherwise disrupt tissue as it is rotated and/or translated by movement of conduit 132. Alternatively or additionally, one or more fluid delivery elements 168 and/or treatment elements 135 can deliver energy and/or fluid to tissue, and movement of one or more control rod of conduit 132 and/or shaft 110 changes the location of the tissue segment receiving the energy and/or fluid. Motion of one or more fluid delivery elements 168 and/or treatment elements 135 can be configured to expand and/or treat a full circumferential (i.e. 360°) segment of tubular tissue, or a partial circumferential (e.g. 45°-350°) segment of tubular tissue. Motion of one or more treatment elements 135 and/or fluid delivery elements 168 can be configured to expand and/or treat a particular axial length of tubular tissue, such as an axial length comprising at least 15% of the axial length of the duodenum distal to the ampulla of Vater, or at least 20% of the axial length of the duodenum distal to the ampulla of Vater, or at least 25% of the axial length of the duodenum distal to the ampulla of Vater, or at least 30% of the axial length of the duodenum distal to the ampulla of Vater; or at least 50% of the axial length of the duodenum distal to the ampulla of Vater. In some embodiments, only tissue distal to the ampulla of Vater is expanded and/or treated, as has been described in detail hereabove.

EDU 250 can comprise multiple heat or cold sources used to modify the temperature of one or more fluids provided by and/or passing through EDU 250, console 200, device 100 and/or device 20. The heat or cold sources can be at a fixed temperature or they can be variable. In some embodiments, a first heat or cold source is at a fixed temperature and a second heat or cold source is at a variable temperature.

In some embodiments, a cooling fluid is delivered, prior to, during and/or after a heat ablation treatment of target tissue TT, such as to precisely control target tissue ablation and avoid ablation of non-target tissue. The cooling fluid can be provided by EDU 250 or another component of console 200, and it can be delivered to tissue, such as target or non-target tissue, and/or it can be delivered to a component of system 10 such as to reduce the temperature of a component of treatment assembly 160 or a component of device 500. Expandable assembly 130, expandable assembly 160, treatment element 135, fluid delivery element 168 and/or another component of system 10 can be constructed and arranged to deliver the cooling fluid to one or more tissue surfaces, such as a cooling fluid delivered to expandable assembly 130 via conduit 132 and/or a separate inflation tube or lumen (e.g. inflation tube 131 shown) and configured to reduce the temperature of one or more volumes of tissue (e.g. a cooling step performed prior to a hot fluid ablation step and/or a cooling step performed subsequent to a hot fluid ablation step). In some embodiments, system 10 is configured to deliver fluid at a sufficiently high temperature to ablate target tissue TT, after which a cooling fluid is automatically and/or semi-automatically delivered to remove thermal energy from target tissue TT and/or other tissue, such as cooling fluid delivered for a time period of at least 2 seconds, at least 5 seconds, at least 10 seconds or at least 20 seconds. In these embodiments, a cooling step can be performed prior to the heat ablation step, such as is described hereabove in reference to FIG. 2.

Ablation provided by system 10 can comprise a non-desiccating or a desiccating ablation. In some embodiments, a non-desiccating ablation is performed for a first portion of target tissue TT such as in a first tissue treatment, and a desiccating ablation is performed for a second portion of target tissue TT such as in a second tissue treatment. Non-desiccating ablations can be performed to treat overlapping portions of target tissue TT, and/or to avoid creation of tissue debris if desired. Desiccating ablations can be performed to achieve a higher thermal gradient, to remove excess tissue, and/or to ablate rapidly if desired. Console 200, treatment element 135 and/or other components of system 10 can be configured to treat target tissue TT with a non-desiccating ablation, such as by avoiding tissue temperatures above 100° C., avoiding the creation of steam, or otherwise avoiding deleterious desiccation of tissue. System 10 can be configured to minimize heat production in the outermost 50% of a mucosal layer, such as to ablate the outermost 50% of the mucosal layer via thermal conduction. System 10 can be configured to minimize heat production in the outermost 80% of a mucosal layer, such as to ablate the outermost 80% of the mucosal layer via thermal conduction. System 10 can be configured to maximize the flow of electrical current, such as through the innermost 50% of a mucosal layer, or through the innermost 20% of a mucosal layer. In some embodiments, system 10 can be configured to avoid detachment of tissue particles.

EDU 250 can be configured to deliver a hot or cold fluid to thermally prime (i.e. pre-heat or pre-chill, respectively) one or more components of system 10. In some embodiments, the one or more components include: conduit 132; a fluid delivery tube such as a tube within shaft 110a (e.g. inflation tube 131); a fluid delivery lumen such as a lumen within shaft 110*a* and/or shaft 110*b*; shaft 110*a*; shaft 110*b*; fluid delivery element 168; treatment element 135; and combinations of these. System 10 can be configured to thermally prime one or more components by circulating or recirculating hot fluid (pre-heat) or cold fluid (pre-chill), such as a hot or cold liquid or gas. In some embodiments, expandable assembly 130 contains and/or treatment element 135 delivers a hot fluid, and one or more components of system 10 are pre-treated with a hot gas. Alternatively or additionally, system 10 can comprise one or more insulators surrounding one or more conduits, lumens and/or shafts of device 100 and/or system 10, such as an insulator surrounding conduit 132 and/or tube 131 and configured to prevent transfer of heat across (e.g. into or out of) conduit 132 and/or tube 131.

Console 200, treatment element 135 and/or other components of system 10 can be configured to treat target tissue TT such that the temperature of at least a portion of the target tissue TT rises rapidly, such as at a rate of greater than or equal to 17.5° C. per second. Treatment can be delivered to cause the temperature of at least a portion of the target tissue TT to reach a setpoint temperature between 60° C. and 90° C., such as a setpoint temperature between 65° C. and 85° C. System 10 can be configured to cause the target tissue TT to elevate to a setpoint temperature and maintain that setpoint temperature, such as by maintaining the setpoint temperature for a time period between 2 and 40 seconds. In these embodiments, the setpoint temperature can be between 60° C. and 90° C., such as a setpoint temperature between 65° C. and 85° C. that is maintained for between 5 and 15 seconds. In some embodiments, after a setpoint temperature is achieved and/or maintained, the treatment can be adjusted (e.g. by adjusting energy delivery from EDU 250) such that tissue temperature decreases over time, such as to match a tissue response of the target tissue TT.

System 10 can be configured to maintain target tissue TT or other tissue under a threshold (e.g. below a maximum temperature of a heat ablation or above a minimum temperature of a cryogenic ablation) and/or within a temperature range, such as in a closed-loop configuration through the use of one or more sensors such as functional element 139 of expandable assembly 130 or functional element 169 of expandable assembly 160, each described in detail herebelow. In some embodiments, tissue temperature is maintained below 100° C., such as between 60° C. and 90° C., such as between 65° C. and 85° C. In some embodiments, system 10 is configured to maintain the temperature of target tissue TT at a setpoint temperature. The setpoint temperature can vary over time. System 10 can be configured to deliver energy at a level that increases and/or decreases over time. In some embodiments, treatment element 135 is constructed and arranged to cause the temperature of at least a portion of target tissue TT to rapidly rise to a setpoint (e.g. a setpoint between 60° C. and 75° C.). After the target tissue TT reaches the setpoint temperature, system 10 can deliver energy or otherwise treat the target tissue TT to maintain the setpoint temperature for an extended time period.

In some embodiments, EDU 250 is configured to heat or chill one or more fluids, such as one or more ablative fluids provided by EDU 250, or other fluids. In some embodiments, expandable assembly 130 is configured to heat or chill one or more fluids, such as when functional element 139 comprises a heating and/or cooling element. Applicable heating and cooling elements include but are not limited to heat exchangers, heating coils, peltier components, refrigeration assemblies, gas expansion coolers, and the like. Heating and cooling can be applied to a source of fluid (e.g. a reservoir of console 200), or to fluid that is withdrawn from device 100 (e.g. a recirculating fluid and/or a body extracted fluid such as recovered, previously delivered, ablative or insufflating fluid). EDU 250 can include one or more pumps configured to deliver and/or extract fluid at a particular flow rate, pressure, or other fluid delivery parameter.

Expandable assembly 130 and/or expandable assembly 160 can be configured to seal a body lumen location, such as to create a full or partial occlusive barrier at a location within the duodenum or other location in the GI tract. System 10 can be configured to cause a fluid or other seal comprising an occlusive barrier selected from the group consisting of a pressure seal; a cryogenically applied seal such as an ice ball seal; a vacuum seal; a full circumferential seal; a partial circumferential seal; and combinations of these. In some embodiments, treatment element 135 treats a portion of target tissue TT located proximal or distal to the occlusive barrier. System 10 can include multiple expandable assemblies configured to seal a body lumen location, such as first expandable assembly which provides a seal at a proximal end of a segment of tubular tissue, and a second expandable assembly which provides a seal at a distal end of the tubular tissue segment. In some embodiments, treatment element 135 treats a portion of target tissue TT located between the two sealed locations, such as between two locations of the duodenum, each duodenal location sealed by an expandable component or assembly of device 100. One or more expandable assemblies can be configured to occlude a first location of a body lumen, followed by subsequent occlusions of one or more different locations within the body lumen. System 10 can be configured to apply a vacuum between two occlusive elements, such as a vacuum applied by one or more treatment elements 135, via one or more functional elements 139 of expandable assembly 130 and/or functional element 169 of expandable assembly 160, and/or by another device or component of system 10. Applied vacuum can be used to modify (e.g. change the shape of) the tubular tissue between the two occlusive elements and/or to increase the sealing force and/or the circumferentiality of the seal. In some embodiments, system 10 is configured to deploy a detached-balloon configured to occlude a body lumen, where the detached-balloon can later be punctured or otherwise deflated for physiologic removal by the GI tract (e.g. similar to occlusive element 193 of FIGS. 5 and 5A-5E). Deployed balloons or other occlusive elements of system 10 can be positioned to protect tissue, such as to protect the ampulla of Vater and/or the pylorus from adverse effects that can be caused by treatment of target tissue TT by treatment element 135.

Expandable assembly 130 can comprise at least one functional element 139, and expandable assembly 160 can comprise at least one functional element 169, each as shown. Functional elements 139 and/or 169 can be elements selected from the group consisting of: a sensor; a transducer; an ablation element such as one or more electrodes configured to deliver electrical energy such as radiofrequency (RF) energy; a fluid delivery element such as a needle, a fluid jet, a permeable membrane and/or an exit port; a heating element; a cooling element; and combinations of these.

In some embodiments, expandable assembly 160 is configured to ablate tissue, such as via functional element 169. Functional element 169 of expandable assembly 160 can comprise one or more ablation elements, such as those described herein. In some embodiments, functional element 169 comprises an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these. In these embodiments, either or both expandable assembly 130 and expandable assembly 160 can be used to ablate target tissue TT. EDU 250 or another component of system 10 can be configured to deliver RF or other energy to any functional element 139 and/or 169. System 10 can include ground pad 70, such as a standard RF energy delivery ground pad typically placed on the patient's back, such that EDU 250 can supply RF energy to a functional element 139 and/or 169 and/or any other electrodes of system 10 in monopolar, bipolar and/or combined monopolar-bipolar energy delivery modes.

In some embodiments, functional element 139 of expandable assembly 130 and/or functional element 169 of expandable assembly 160 comprises an abrasive element configured for abrading target tissue, such as an abrasive element attached to a balloon or expandable cage.

In some embodiments, expandable assembly 160 is further configured to perform at least one non-tissue expanding function. In some embodiments, expandable assembly 160 is configured to ablate tissue, as described hereabove. Alternatively or additionally, expandable assembly 160 and/or expandable assembly 130 can be configured to occlude or partially occlude a lumen surrounded by tissue (as described hereabove), such as a lumen of the GI tract to be occluded during an insufflation procedure, also as described hereabove. Expandable assembly 130 and/or expandable assembly 160 can be configured to manipulate tissue, such as to linearize and/or distend GI tissue by frictionally engaging (e.g. when expanded) and applying forces to the tissue (e.g. by advancing and/or retracting shaft 110a and/or 110b). In some embodiments, one or more expandable assemblies 130 and/or expandable assemblies 160 can perform a function selected from the group consisting of: linearizing curvilinear tissue; distending tissue; expanding tissue; occluding a body lumen; and combinations of these. Expandable assembly 130 and/or expandable assembly 160 can be configured to test and/or diagnose tissue, such as when expandable assembly 130 and/or expandable assembly 160 is used to measure a diameter of tubular tissue into which it has been inserted. Diameter measurements can be performed in various ways, including but not limited to: injection of a radiopaque fluid into expandable assembly 130 and/or expandable assembly 160 and fluoroscopic measurement of the injected fluid; controlled inflation of expandable assembly 130 and/or expandable assembly 160 to a pressure whose level corresponds to a luminal diameter; and combinations of these. In some embodiments, device 100 includes an expandable assembly that can be expanded with one or more control rods (e.g. one or more control rods of conduit 132), such as to perform a diametric measurement of tubular tissue by precision measurement of control rod advancement (e.g. when control rod position correlates to expandable assembly diameter). Alternatively or additionally, tubular tissue diameter can be determined by measuring the diameter of an expandable assembly when it initially, circumferentially contacts the wall of tubular tissue (e.g. when a specific radial force is achieved and/or when contact is observed such as using fluoroscopy or ultrasound visualization devices). In some embodiments, system 10 includes a separate device used to perform a diameter measurement, such as sizing device 30 shown. Sizing device 30 can be of similar construction and arrangement to device 30 described hereabove in reference to FIG. 1. One or more energy delivery or other ablation parameters can be adjusted based on the measured diameter of target tissue TT and/or a target tissue segment.

Treatment element 135 can be configured to treat various thicknesses of GI tissue, such as at least the innermost 500 microns of duodenal tissue, or at least the innermost 1 mm of duodenal tissue. In some embodiments, treatment element 135 can be configured to ablate or otherwise treat a thickness of at least 600 microns, at least 1 mm or at least 1.25 mm, such as when treating the mucosa of the stomach. Treatment element 135 can be configured to treat a volume of tissue comprising a surface area and a depth, where the ratio of magnitude of the depth to the magnitude of the surface area is less than or equal to 1 to 100 (e.g. less than 1%), or less than or equal to 1 to 1000 (e.g. less than 0.1%). In some embodiments, expandable assembly 130 and/or expandable assembly 160 are configured to be in a relatively rigid state, such as during treatment of target tissue TT.

Treatment element 135 and/or other treatment elements of the present inventive concepts can be arranged in an array of elements, such as a circumferential or linear array of elements. The circumferential array can comprise a partial circumferential array of treatment elements 135, such as an array covering approximately 45 to 3000 of circumferential area. Partial circumferential arrays of treatment elements 135 can treat a first target tissue segment and a second target tissue segment in two sequential steps, where the array is rotated between treatments (e.g. energy deliveries). The circumferential array can comprise a full 360 array of treatment elements 135, such that a full circumferential volume of target tissue TT can be treated in single or multiple treatments (e.g. energy deliveries) that do not require repositioning of expandable assembly 130. In some embodiments, less than 3600 of tubular tissue is treated, such as by treating a circumferential portion of tissue comprising less than or equal to a 350°, or between 3000 and 350°, such as to prevent a full circumferential scar from being created.

Two or more treatment elements 135 can be arranged in a helical array. In some embodiments, at least three, four or five treatment elements 135 independently treat target tissue, in similar or dissimilar treatments (e.g. similar or dissimilar amounts of energy, provided simultaneously and/or sequentially by EDU 250).

In some embodiments, console 200, EDU 250 and/or another device or component of system 10 provides electrical or other energy to a component of device 100, such as electrical energy provided to a heating coil in a distal portion of device 100, now shown but typically connected to one or more wires of conduit 132 that travel proximally through shaft 110a to handle 102. Console 200, EDU 250 and/or another device or component of system 10 can provide energy such as electrical energy to one or more functional elements 139 and/or 169 such as when a functional element 139 and/or 169 comprises a transducer or other powered component.

In some embodiments, treatment element 135 comprises one or more treatment elements that are constructed and arranged to treat the entire amount of tissue to be treated ("desired treatment area") with a single energy delivery and/or at least without having to reposition device 100. In these embodiments, treatment element 135 can comprise an array of treatment elements positioned along substantially the entire desired treatment area of the target tissue, or treatment element 135 can comprise one or more treatment elements configured to rotate and/or translate along substantially the entire desired treatment area of tissue. Treatment element 135 and/or other tissue treatment elements of the present inventive concepts can be configured to treat at least 25% of the desired treatment area of the duodenum simultaneously and/or without having to reposition device 100. Alternatively, treatment element 135 and/or other ablation elements of the present inventive concepts can be configured to treat a first portion of the desired treatment area followed by a second portion of the desired treatment area. The first and second treated tissue segments can be overlapping and they can have non-parallel central axes (e.g. tissue segments in a curved portion of the duodenum). Three or more target tissue segments can be treated, such as to cumulatively ablate at least 10% or at least 25% of the duodenal mucosa (e.g. at least 10% or 25% of the duodenal mucosa distal to the ampulla of Vater).

System 10 can be configured to ablate or otherwise treat target tissue TT, such as duodenal mucosal tissue, while avoiding damaging non-target tissue, such as the GI adventitia. Target tissue TT can include at least a portion of safety-margin tissue comprising tissue whose ablation causes minimal or no adverse effect to the patient, such as sub-mucosal tissue of the GI tract. Target tissue TT can comprise one or more portions of tissue that are treated simultaneously or sequentially. In some embodiments, the target tissue TT comprises at least 10% or at least 25% of the duodenal mucosa distal to the ampulla of Vater. In some embodiments, the target tissue TT includes the full mucosal thickness of at least a portion of duodenal tissue, as well as at least the innermost 100 microns of submucosal duodenal tissue, or at least the innermost 200 microns of submucosal duodenal tissue. The target tissue TT can include at least one of ileal mucosal tissue or gastric mucosal tissue.

Endoscope 50a can be a standard endoscope, such as a standard GI endoscope, or a customized endoscope, such as an endoscope including sensor 59 configured to provide information related to the tissue expansion and/or tissue treatment of the present inventive concepts. Endoscope 50a can include camera 52, such as a visible light, ultrasound and/or other visualization device used by the operator of system 10 prior to, during and/or after the expansion and/or treatment of target tissue TT, such as during insertion and/or removal of endoscope 50a and/or shafts 110a and 110b of device 100. Camera 52 can provide direct visualization of internal body spaces and tissue, such as the internal organs of the GI tract. Endoscope 50a can be coupled with or otherwise include a guidewire, e.g. guidewire 60, such as to allow insertion of endoscope 50a into the jejunum and/or advancement of device 100. Device 100 can be constructed and arranged such that endoscope 50a can be advanced within 5 cm of expandable assembly 130 and/or expandable assembly 160.

System 10 can be constructed and arranged to perform insufflation of a body lumen, such as insufflation of a segment of the GI tract. The body lumen can be pressurized, such as by using one or more standard insufflation techniques. Insufflation fluid can be introduced through second lumen 54 of endoscope 50a. Second lumen 54 travels proximally and connects to a source of insufflation liquid and/or gas, such as console 200, and typically a source of air, carbon dioxide, water and/or saline. Alternatively or additionally, insufflation fluid can be delivered by device 100, such as through shaft 110a and/or 110b, and/or through a port in expandable assembly 130 and/or expandable assembly 160, such as when an associated functional element 139 and/or 169, respectively comprises a fluid delivery port attached to a source of insufflation liquid and/or gas (e.g. provided by console 200). Alternatively or additionally, a separate device configured to be inserted through endoscope 50a and/or to be positioned alongside endoscope 50a, can have one or more lumens configured to deliver the insufflation fluid. System 10 can include one or more occlusive elements and/or devices, such as expandable assembly 130, expandable assembly 160, occlusive element 193 of FIG. 5 and/or another expandable device configured to radially expand such as to fully or partially occlude a body lumen, such that insufflation pressure can be achieved and/or maintained over time (e.g. reduce or prevent undesired migration of insufflation fluid). The one or more occlusive elements and/or devices can be positioned proximal to and/or distal to the luminal segment to be insufflated.

Console 200 can be configured to remove fluid from a body lumen such as a segment of the GI tract. Removed fluids include but are not limited to: tissue expansion fluid; ablative fluid; condensate of delivered ablative fluid; insufflation fluids; excess bodily fluids; chyme; digestive fluids; gas; and combinations of these. Fluids can be removed prior to, during and/or after expansion of target tissue TT by one or more fluid delivery elements 168 and/or treatment of target tissue TT by treatment element 135. Treatment element 135, fluid delivery element 168, a functional element 139 and/or a functional element 169 can be constructed and arranged to remove fluid from a body lumen. Console 200 can be configured to apply a vacuum (e.g. suction), such as to remove fluid via at least one treatment element 135, fluid delivery element 168, an outflow drain, or other fluid extraction port of system 10. In some embodiments, extracted fluids are recycled, such as for subsequent delivery by at least one treatment element 135 and/or fluid delivery element 168 to tissue.

Console 200 can be configured to deliver one or more gases (e.g. carbon dioxide, nitrogen, nitrous oxide and/or air) to at least one treatment element 135, fluid delivery element 168 and/or another gas delivering component of system 10. In some embodiments, at least one treatment element 135 and/or fluid delivery element 168 comprises a gas jet nozzle configured to deliver gas to target tissue, such as a gas than has been processed to remove moisture or otherwise is relatively dry (e.g. less than the dew point of air, or at a relative humidity less than 20% or less than 10%). In some embodiments, system 10 is configured to deliver gas to cause agitation of an ablative fluid previously delivered within a body lumen. System 10 can be configured to deliver relatively dry or other gas to move ablative fluid in a body lumen. The delivered gas can comprise a cooling gas, such as a gas below 37° C., a gas between 0° C. and 7° C. such as a gas between 2° C. and 7° C., and/or a gas at approximately 4° C. System 10 can deliver cooling gas for a time period of at least 10 seconds, at least 20 seconds or at least 30 seconds. In some embodiments, system 10 delivers cooling gas at a temperature less than 0° C. for a time period less than or equal to 20 seconds, less than or equal to 10 seconds, or less than or equal to 5 seconds. In some embodiments, system 10 is configured to deliver gas at a temperature at or above 42° C., such as to remove moisture or otherwise dry a tissue wall of the GI tract. System 10 can be configured to deliver carbon dioxide gas.

Functional elements 139 and/or 169 can comprise a sensor. In some embodiments, functional element 139 and/or 169, sensor 59 and/or another sensor of system 10 can comprise a sensor selected from the group consisting of: temperature sensor such as a thermocouple, thermistor, resistance temperature detector or an optical temperature sensor; strain gauge; impedance sensor such as a tissue impedance sensor; pressure sensor; blood sensor; optical sensor such as a light sensor; sound sensor such as an ultrasound sensor; electromagnetic sensor such as an electromagnetic field sensor; visual sensor; and combinations of these. The sensors can be configured to provide information to one or more components of system 10, such as to controller 250 and/or console 200, such as to monitor the expansion and/or treatment of target tissue TT and/or to expand and/or treat target tissue TT in a closed loop configuration. Fluid delivery by reservoir 220 and/or energy delivery from EDU 250 can be initiated, regulated, modified, stopped and/or otherwise controlled based on one or more sensor readings.

Controller 250 can comprise one or more algorithms 251, which can be constructed and arranged to automatically and/or manually control and/or monitor one or more devices, assemblies and/or components of system 10. Algorithm 251 of controller 250 can be configured to determine one or more tissue expansion and/or tissue treatment parameters. In some embodiments, algorithm 251 processes one or more functional element 139 and/or 169 sensor signals to modify one or more of: volume of tissue expansion fluid delivered; rate of tissue expansion fluid delivery; temperature of tissue expansion fluid delivery; amount of ablative fluid delivered; rate of ablative fluid delivery; energy delivered; power of energy delivered; voltage of energy delivered; current of energy delivered; and/or temperature of ablative fluid or energy delivered. Expandable assembly 130 can deliver energy to a surface of tissue, an "delivery zone", which is a subset of the target tissue TT treated by that energy delivery (i.e. due to the conduction of heat or other energy to neighboring tissue). Algorithm 251 can comprise an algorithm configured to determine a delivery zone parameter such as a delivery zone parameter selected from the group consisting of: anatomical location of a delivery zone; size of delivery zone; percentage of delivery zone to receive energy; type of energy to be delivered to a delivery zone; amount of energy to be delivered to a delivery zone; and combinations of these. Information regarding the delivery zone parameter can be provided to an operator of system 10. This information can be employed to set a delivery zone parameter, assist the operator in determining the completion status of the procedure (e.g. determining when the procedure is sufficiently complete) and/or to advise the operator to continue to complete a pre-specified area or volume of target tissue. The total area of treatment or number of delivery zones or number of treatments during a particular procedure (any of which can be employed in algorithm 251) can be defined by patient clinical or demographic data.

Functional elements 139 and/or 169 can comprise a gravimetric sensor. In some embodiments, functional element 139 comprises an accelerometer or other sensor configured to provide a signal representing the orientation of expandable assembly 130 and/or treatment element 135 as it relates to the force of earth's gravity. In embodiments in which treatment element 135 delivers ablative fluid to target tissue TT, the signal provided by functional element 139 can provide information for manual and/or automated control of ablative fluid delivery direction. In some embodiments, gravimetric orientation of device 100 is provided to an operator, such as via a screen on user interface 205 of console 200 and/or user interface 105 of handle 102. In some embodiments, the signal from functional element 139 is recorded by controller 250, such as to adjust a spray pattern delivered by expandable assembly 130 and/or treatment element 135, such as via algorithm 251. Based on a signal from functional element 139, treatment element 135 and/or shaft 110a can be positioned to deliver ablative fluid in upward and/or side-ways (i.e. horizontal) directions, such as to allow delivered fluid to flow across the walls of a lumen in a downward direction. Controller 250 and/or algorithm 251 can be configured to adjust the flow pattern of ablative fluid delivery by adjusting the rotation and/or translation of expandable assembly 130 (e.g. by creating an asymmetric movement). Controller 250 can be configured to adjust the flow pattern of ablative fluid delivery by adjusting which of multiple treatment elements 135 deliver ablative fluid (e.g. by turning on one or more electronic fluid valves) or by adjusting a nozzle direction or nozzle flow path geometry of treatment element 135 (e.g. when treatment element 135 comprises a rotatable nozzle and/or a nozzle with an adjustable orifice). In some embodiments, controller 250 utilizes a signal from functional element 139 to manipulate one or more treatment elements 135 to deliver fluid in a relatively upward direction. In some embodiments, system 10 includes a fluid removal element as described hereinabove, such as a treatment element 135 configured to remove fluid by an outflow drain, and the fluid removal element is gravimetrically oriented by a signal provided by functional element 139.

Functional elements 139 and/or 169 can comprise a chemical detection sensor, such as a chemical detection sensor to confirm proper apposition of expandable assembly 130 and/or expandable assembly 160. In this configuration, a chemical sensor such as a carbon dioxide sensor can be placed distal to expandable assembly 130 and/or expandable assembly 160, and a fluid such as carbon dioxide gas can be introduced proximal to the expandable assembly 130 and/or expandable assembly 160. Detection of the introduced fluid by a functional element 139 and/or 169 can indicate inadequate apposition of expandable assembly 130 and/or expandable assembly 160, respectively. Readjustment to achieve sufficient apposition can prevent inadequate expansion and/or treatment of target tissue TT (e.g. inadequate delivery of fluid and/or inadequate transfer of energy) and/or prevent inadequate measurement, modification, manipulation and/or diagnosis of target tissue TT.

Functional element 139, functional element 169, sensor 59 and/or another sensor of system 10 can be a sensor configured to provide information related to the tissue treatment and/or expansion performed by expandable assembly 130 and/or expandable assembly 160, respectively, such as a visual sensor mounted to expandable assembly 130 and/or expandable assembly 160 that is configured to differentiate tissue types that are proximate expandable assembly 130 and/or expandable assembly 160. In some embodiments, system 10 is constructed and arranged to differentiate mucosal and submucosal tissue, such as to adjust one or more treatment parameters (e.g. to stop treatment and/or modify the temperature of treatment) based on the differentiation. Applicable visible sensors include but are not limited to: visible light camera; infrared camera; CT Scanner; MRI; and combinations of these. In some embodiments, energy provided by EDU 250 is based on one or more signals from the visible sensor, such as a sensor providing a signal correlating to tissue color wherein the energy delivered is modified based on a tissue color change and/or tissue expansion injectate 221 comprise a visible dye or other visualizable marker used to assess tissue expansion.

One or more functional elements 139 and/or 169 can comprise a temperature sensor configured to monitor the temperature of treatment provided by expandable assembly 130 and/or expandable assembly 160 and/or tissue proximate expandable assembly 130 and/or expandable assembly 160. Functional elements 139 and/or 169 can each comprise multiple temperature sensors, such as multiple temperature sensors positioned on expandable assembly 130 and/or expandable assembly 160, respectively, with a spacing of at least one sensor per square centimeter. Energy delivered by EDU 250 can be based on signals recorded by the multiple temperature sensors.

Fluid delivered by reservoir 220 (e.g. injectate 221) can be based on signals recorded by one or functional elements 139 and/or 169. One or more functional elements 139 and/or 169 can comprise one or more sensors, such as one or more of a visual sensor such as a camera; a temperature sensor; a pH sensor; an ultrasound transducer; and combinations of these. In some embodiments, injectate 221 comprises one or more dyes (e.g. visible dye, ultrasonically visualizable material and/or radiopaque dye), and functional element 139 and/or 169 comprises one or more cameras (e.g. visible light camera, ultrasound imager and/or x-ray camera) that image the tissue being expanded and produce a signal correlating to the amount of tissue expansion based on the amount of dye present in the expanded tissue. In some embodiments, injectate 221 is delivered at a temperature different than the temperature of the tissue being expanded (e.g. above or below body temperature), and functional element 139 and/or 169 comprises a sensor that measures the temperature proximate the tissue being expanded and produces a signal correlating to the amount of tissue expansion based on the measured temperature (e.g. based on the difference between the measured temperature and body temperature). In some embodiments, injectate 221 comprises a pH different than the pH of the tissue being expanded, and functional element 139 and/or 169 comprises a sensor that measures the pH proximate the tissue being expanded and produces a signal correlating to the amount of tissue expansion based on the measured pH (e.g. based on a change in the measured pH that occurs during tissue expansion). In some embodiments, functional element 139 and/or 169 comprises an ultrasound transducer directed at the tissue being expanded and produces a signal correlating to the amount of tissue expansion based on an analysis of an image of the expanding tissue produced by the ultrasound transducer.

A functional element 139 and/or 169 can comprise a transducer. In these and other embodiments, functional element 139, functional element 169 and/or another transducer of system 10 can be a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; a motor; a vibrational transducer; a fluid agitating element; and combinations of these.

In some embodiments, console 200 and/or another device of component of system 10 is configured to deliver a visualizable material, such as when injectate 221 and/or another fluid of system 10 includes a visualizable material delivered to one or more fluid delivery elements 168 and/or one or more treatment elements 135. In some embodiments, visualizable material is delivered by fluid delivery element 168 onto and/or beneath the surface of tissue, to assist in the tissue expansion of target tissue TT, such as to assess the status of tissue expansion as described hereabove. In some embodiments, visualizable material is delivered by treatment element 135 onto and/or beneath the surface of tissue, to assist in the treatment of target tissue TT, such as to assess the status of tissue ablation, such as via a camera-based functional element 139. In some embodiments, the visualizable material is selected from the group consisting of: colored dye; radiopaque agent; ultrasonically visible material; magnetically visible material; and combinations of these. An imaging device of system 10, such as a camera based functional element 139 and/or 169 and/or imaging device 410 described herebelow, can be used to create an image of the visualizable material during and/or after delivery of the visualizable material.

In some embodiments, console 200 or another device of component of system 10 is configured to deliver abrasive particles, such as abrasive particles delivered to one or more treatment elements 135 and/or fluid delivery elements 168. In some embodiments, visualizable material is also delivered by console 200 to assist in the treatment of tissue, such as to improve cellular disruption caused by a mechanical abrasion treatment by visualizing the treatment in real time.

In some embodiments, EDU 250 is configured to deliver at least RF energy, and system 10 includes ground pad 70 configured to be attached to the patient (e.g. on the back of the patient), such that RF energy can be delivered in monopolar delivery mode to one or more electrode-based treatment elements 135 of device 100 or to one or more electrodes of another device of system 10 (e.g. second device 100'). Alternatively or additionally, EDU 250 can be configured to deliver energy in a bipolar RF mode, such as bipolar energy delivered between any two electrode-based treatment elements 135 of device 100 or between any other two electrodes of another treatment device of system 10. Alternatively or additionally, EDU 250 can be configured to deliver energy in a combined monopolar-bipolar mode.

EDU 250 can be configured to deliver RF and/or other forms of energy to one or more treatment elements 135 of expandable assembly 130 and/or a treatment element of expandable assembly 160. In some embodiments, EDU 250 delivers energy selected from the group consisting of: RF energy; microwave energy; plasma energy; ultrasound energy; light energy; and combinations of these. Energy can be continuous and/or pulsed, and can be delivered in a closed-loop fashion as described hereabove. Energy delivery parameters such as power, voltage, current and frequency can be held relatively constant or they can be varied by EDU 250, such as in a closed loop fashion based on one or more signals provided by a sensor-based functional element 139 and/or 169. Energy delivery can be varied from a first tissue location (e.g. a first portion of target tissue TT) to a second location (e.g. a second portion of target tissue TT), such as a decrease in energy from a first treated location to a second treated location when the second treated location is thinner than the first treated location. Alternatively or additionally, energy delivery can be varied during a single application of energy to a single tissue location, such as by adjusting one or more energy delivery parameters during a continuous energy delivery. Alternatively or additionally, one or more energy delivery parameters can be varied between a first treatment of target tissue and a second treatment of target tissue, for example a first treatment performed during a first clinical procedure and a second treatment performed during a second clinical procedure, such as when the second treatment is performed at least twenty-four hours after the first treatment.

As described hereabove, console 200 typically includes one or more fluid pumps, such as one or more peristaltic, displacement and/or other fluid pumps; as well as one or more heat exchangers and/or other fluid heating elements internal and/or external to device 100. EDU 250 and/or another component of console 200 or system 10 can be configured to rapidly deliver and/or withdraw fluid to and/or from expandable assembly 130 and/or expandable assembly 160 via one or more fluid transport means. Fluid transport means can include a pump configured to deliver fluid at a flow rate of at least 50 ml/min and/or a pump and/or vacuum source configured to remove fluid at a flow rate of at least 50 ml/min. In some embodiments, console 200 is configured to deliver fluid, such as a liquid, at a flow rate of at least 500 ml/min, or at least 750 ml/min. A pump and/or vacuum source can be configured to continuously exchange hot fluid and/or to perform a negative pressure priming event to remove fluid from one or more fluid pathways of device 100. Console 200, device 100 and/or device 20 can include one or more valves in the fluid delivery and/or fluid withdrawal pathways or one or more other valves in the fluid pathway within expandable assembly 130 and/or expandable assembly 160. Valves can be configured to control entry of fluid into an area and/or to maintain pressure of fluid within an area. Valves can be used to transition from a heating fluid, such as a fluid of 90° C. maintained in a treatment assembly for approximately 12 seconds, to a cooling fluid, such as a fluid between 4° C. and 10° C. maintained in the assembly element for approximately 30 to 60 seconds. Typical valves include but are not limited to: duck-bill valves; slit valves; electronically activated valves; pressure relief valves; and combinations of these. Console 200 can be configured to rapidly inflate and/or deflate expandable assembly 130 and/or expandable assembly 160. Console 200 can be configured to purge the fluid pathways of device 100 and/or device 20 with a gas such as air, such as to remove cold and/or hot fluid from the devices and/or to remove gas bubbles from the devices.

User interface 205 of console 200 and/or user interface 105 of handle 102 can include a graphical user interface configured to allow one or more operators of system 10 to perform one or more functions such as entering of one or more system input parameters and visualizing and/or recording of one or more system output parameters. User interface 205 and/or user interface 105 can include one or more user input components (e.g. touch screens, keyboards, joysticks, electronic mice and the like), and one or more user output components (e.g. video displays; liquid crystal displays; alphanumeric displays; audio devices such as speakers; lights such as light emitting diodes; tactile alerts such as assemblies including a vibrating mechanism; and the like). Examples of system input parameters include but are not limited to: volume of tissue expanding fluid to be delivered; flow rate of tissue expanding fluid; temperature of tissue expanding fluid; type of tissue expanding fluid to be delivered; temperature of ablative fluid to be delivered such as temperature of fluid to be delivered to a nozzle or to an expandable reservoir such as a balloon; type of ablative fluid to be delivered; rate of ablative fluid to be delivered; volume of ablative fluid to be delivered; type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a cooling fluid to be delivered; temperature of a priming fluid to be delivered; flow rate of a fluid to be delivered; volume of a fluid to be delivered; number of reciprocating motions for an energy delivery element to transverse; temperature for a treatment assembly such as target temperature and/or maximum temperature; insufflation pressure; insufflation duration; and combinations of these. System input parameters can include information based on patient anatomy and/or conditions such as pre-procedural and/or peri-procedural parameters selected from the group consisting of: mucosal density and/or thickness; mucosal "lift" off of submucosa after a submucosal injection; longitudinal location of target tissue within the GI tract; and combinations of these. Examples of system output parameters include but are not limited to: temperature information such as tissue and/or treatment assembly temperature information; pressure information such as balloon pressure information and/or insufflation pressure information; force information such as level of force applied to tissue information; patient information such as patient physiologic information recorded by one or more sensors; and combinations of these.

Console 200, device 100 and/or one or more other components of system 10 can include an electronics module, such as an electronics module including a processor, memory, software, and the like. User interface 205 and/or user interface 105 are typically configured to allow an operator to initiate, regulate, modify, stop and/or otherwise control expansion and/or treatment of target tissue TT by the various components of system 10, such as by controlling reservoir 220 and/or EDU 250. User interface 205 and/or user interface 105 can be configured to modify one or more tissue treatment parameters, such as a parameter selected from the group consisting of: volume of tissue expanding fluid to be delivered; flow rate of tissue expanding fluid; temperature of tissue expanding fluid; type of tissue expanding fluid to be delivered; temperature of an ablative fluid to be delivered directly to tissue or to an expandable reservoir such as a balloon; type of ablative fluid to be delivered; rate of ablative fluid to be delivered; volume of ablative fluid to be delivered; pulse width modulation on-time and/or off-time; a time division multiplexing parameter; and combinations of these. System 10 can be configured for manual control, so that the operator first initiates the tissue treatment, then allows the treatment element 135 and/or another associated treatment element to treat the target tissue TT for some time period, after which the operator terminates the treatment.

System 10 can be configured to treat target tissue TT in constant, varied, continuous and discontinuous energy delivery or other treatment delivery profiles. Pulse width modulation and/or time division multiplexing (TDM) can be incorporated to achieve precision of an ablative treatment, such as to ensure ablation of target tissue TT while leaving non-target tissue intact.

In some embodiments, where system 10 is configured to perform hot fluid ablation, controller 250 can be configured to adjust the temperature, flow rate and/or pressure of fluid delivered to an expandable reservoir, such as when expandable assembly 130 and/or expandable assembly 160 comprise a balloon. Controller 250 can be configured to receive commands from user interface 205 or user interface 105 of device 100. In some embodiments, controller 250 receives wireless (e.g. Bluetooth) commands from user device 100 via user interface 105. Controller 250 can be configured to initiate insufflation and/or to adjust insufflation pressure. Controller 250 can be configured to deliver energy or otherwise treat target tissue in a closed-loop fashion, such as by modifying one or more tissue treatment parameters based on signals from one or more sensors of system 10, such as those described hereabove. Controller 250 can be programmable such as to allow an operator to store predetermined system settings for future use. Controller 250 can comprise memory configured to store one or more system or patient parameters.

Controller 250 can comprise an impedance monitoring assembly, such as an impedance monitoring assembly that receives impedance information from one or both of functional element 139 of expandable assembly 130 and/or functional element 169 of expandable assembly 160. EDU 250 can deliver RF energy to one or more electrode-based treatment elements of system 10 based on the impedance determined by the impedance monitoring assembly.

Numerous embodiments of the systems, methods and devices for treating target tissue TT described hereabove include controlling and/or monitoring the change in target tissue temperature to cause its ablation, such as a temperature increase above 43° C., typically above 60° C., 70° C. or 80° C., to ablate at least a portion of the target tissue TT. One or more cooling fluids can be delivered to limit or otherwise control ablation, such as to prevent damage to non-target tissue, such as the duodenal adventitia. Console 200 can be configured to deliver a fluid to tissue and/or a component and/or assembly of system 10, such as to warm and/or cool the tissue, component and/or assembly. Console 200 can be configured to deliver a cooling fluid to a luminal wall such as the duodenal wall, such as prior to a delivery of energy, during a delivery of energy and/or after a delivery of energy. In some embodiments, a chilled fluid is used to cool tissue prior to, during and/or after a high temperature ablation of tissue. System 10 can be configured to deliver a fluid at a temperature below 37° C. or below 20° C. The chilled fluid can be delivered at a temperature between 0° C. and 7° C., and in some embodiments, the chilled fluid is delivered at a temperature less than 0° C. System 10 to can be configured to deliver chilled fluid at multiple temperatures to target tissue TT and/or other tissue. System 10 can be configured to deliver a first chilled fluid at a first temperature for a first time period, followed by a second chilled fluid delivered at a second temperature for a second time period. The first and second chilled fluids can be similar or dissimilar fluids, such as similar or dissimilar liquids and/or gases. In some embodiments, the first chilled fluid is colder than the second chilled fluid, such as a first chilled fluid delivered at approximately 4° C. for a time period of approximately 5 seconds, followed by fluid delivered at a higher temperature (e.g. a temperature between 10° C. and 37° C.) for a time period of at least 5 seconds. The chilled fluid can be delivered between treatment of a first portion of target tissue and a second portion of target tissue (e.g. to the same or different tissue), such as to remove residual heat remaining after the first treatment. The cooling fluid can be delivered through functional element 139 of expandable assembly 130 and/or functional element 169 of expandable assembly 160, such as when functional elements 139 and/or 169 comprise a fluid delivery element such as a nozzle, an exit hole, a slit, or a permeable membrane. The cooling fluid can be supplied to a location within expandable assembly 130 and/or expandable assembly 160, such as when expandable assembly 130 and/or expandable assembly 160 comprises a balloon or other expandable reservoir configured to contact tissue. Alternatively or additionally, console 200 can be fluidly attached to another component of device 100 and/or system 10, the attached component not shown but configured to deliver fluid to tissue and/or a component of system 10 such as to add and/or absorb heat. Console 200 can comprise a cryogenic source used to deliver fluids at low temperatures, such as temperatures below 0° C. Typical fluids delivered include but are not limited to: liquids such as water and/or saline; gases such as carbon dioxide, nitrogen, nitrous oxide and/or air; and combinations of these.

In some embodiments, console 200 includes a desiccant and/or drying assembly configured to dehydrate or otherwise remove moisture from one or more delivered gases prior to their delivery by device 100, device 20 and/or another device of system 10.

In some embodiments, system 10 and/or device 100 are constructed and arranged to perform a fractional treatment of tissue. Device 100 can be constructed and arranged to treat target tissue with a fractional delivery of RF energy, such as monopolar and/or bipolar RF energy delivered from an array of electrodes positioned on an expandable element. In some embodiments, device 100 is configured as a laser or other light energy delivery device constructed and arranged to provide a fractional energy delivery to target tissue. In some embodiments, device 100 is configured to vaporize at least a portion of target tissue.

As described hereabove, system 10 can include one or more additional tissue expanding and/or tissue treating devices, such as treatment device 100'. Device 100' and/or other treatment devices of the present inventive concepts can be configured to treat and/or expand target tissue TT in the same clinical procedure, or in a clinical procedure performed at least twenty-four hours after the first clinical procedure. Second device 100' can be of similar or dissimilar construction to device 100. In some embodiments, second device 100' comprises an expandable assembly with a different diameter than expandable assembly 130 of device 100. In some embodiments, second device 100' comprises a treatment element with a different construction and arrangement than treatment element 135 of device 100. In some embodiments, second device 100' comprises a device selected from the group consisting of: injectate delivery device; tissue expansion device; hot fluid filled balloon device; RF energy delivery device; vapor ablation device; cryoablation device; laser ablation device; ultrasound ablation device; mechanical abrasion device; and combinations of these. Second device 100' can comprise at least one fluid delivery element selected from the group consisting of: needle; fluid jet; iontophoretic element; and combinations of these. Second device 100' can comprise at least one ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

System 10 can further include one or more imaging devices, such as imaging device 410. Imaging device 410 can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to shaft 110a and/or 110b. Imaging device 410 can be inserted through a separate working channel of endoscope 50a, such as lumen 51. In one embodiment, imaging device 410 is an ultrasound transducer connected to a shaft, not shown but surrounded by shaft 110a and typically rotated and/or translated to create a multi-dimensional image of the area surrounding imaging device 410. Alternatively or additionally, imaging device 410 can be external to the patient, such as an imaging device selected from the group consisting of: an X-ray; a fluoroscope; an ultrasound image; an MRI; a PET Scanner; a near-infrared imaging camera; a fluorescence imaging camera; and combinations of these. Image and other information provided by imaging device 410 can be provided to an operator of system 10 and/or used by a component of system 10, such as controller 250, to automatically or semi-automatically adjust one or more system parameters such as one or more energy delivery parameters.

System 10 can further include protective element 191, configured to be positioned proximate tissue to prevent damage to certain tissue during tissue ablative fluid delivery, other energy delivery, tissue expansion and/or other tissue treatment event. Protective element 191 can comprise an element selected from the group consisting of: a deployable and/or recoverable cap and/or covering; an advanceable and/or retractable protective sheath; and combinations of these. Protective element 191 can be delivered with endoscope 50a and/or another elongate device such that protective element 191 can be placed over or otherwise positioned to protect non-target tissue, such as tissue selected from the group consisting of: ampulla of Vater; bile duct; pancreas; pylorus; muscularis externae; serosa; and combinations of these. In some embodiments, protective element 191 is placed prior to treatment of at least a portion of target tissue TT, and removed in the same clinical procedure. In other embodiments, protective element 191 is implanted in a first clinical procedure, and removed in a second clinical procedure, such as a second clinical procedure as described herein. In some embodiments, protective element 191 is evacuated from the body by the patient's digestive system. System 10 can be configured to identify non-target tissue, such as via a camera used to identify the ampulla of Vater.

System 10 can be configured to prevent excessive or otherwise undesired distension of the duodenum such as distension that could cause tearing of the serosa. In some embodiments, system 10 is configured such that all tissue contacting components and/or fluids delivered by system 10 maintain forces applied on a GI wall below 2.0 psi, such as less than 1.2 psi. System 10 can be configured to avoid or otherwise minimize damage to the muscularis layer of the GI tract, such as by controlling pressure of target tissue treatment (e.g. via controlling expansion force of expandable assembly 130 and or expandable assembly 160) and/or by otherwise minimizing trauma imparted on any tissue by one or more components of system 10.

System 10 can further include one or more pharmaceutical and/or other agents 420, such as an agent configured for systemic and/or local delivery to a patient. Agents 420 can be delivered pre-procedurally, peri-procedurally and/or post-procedurally. Agents 420 can comprise one or more imaging agents, such an imaging agent used with imaging device 410. Agents 420 can be one or more pharmaceutical or agents configured to improve healing, such as agents selected from the group consisting of: antibiotics; steroids; mucosal cytoprotective agents such as sucralfate, proton pump inhibitors and/or other acid blocking drugs; and combinations of these. Alternative or in addition to agents 420, pre-procedural and/or post-procedural diets can be employed. For example, pre-procedural diets can include food intake that is low in carbohydrates and/or low in calories, and post-procedural diets can include food intake that comprise a total liquid diet and/or a diet that is low in calories and/or low in carbohydrates.

In some embodiments, system 10 does not include a chronically implanted component and/or device, only body inserted devices that are removed at the end of the clinical procedure or shortly thereafter, such as devices removed within 8 hours of insertion, within 24 hours of insertion and/or within one week of insertion. In an alternative embodiment, implant 192 can be included. Implant 192 can comprise at least one of a stent; a sleeve; and/or a drug delivery device such as a coated stent, a coated sleeve and/or an implanted pump. Implant 192 can be inserted into the patient and remain implanted for a period of at least one month, at least 6 months or at least 1 year. In some embodiments, a first clinical procedure is performed treating target tissue, and a subsequent second clinical procedure is performed, as is described herein. In these two clinical procedure embodiments, a device can be implanted in the first clinical procedure, and removed in the second clinical procedure.

System 10 can include sizing device 30 which can be constructed and arranged to be placed into one or more locations of the gastrointestinal tract or other internal location of the patient and measure the size or other geometric parameter of tissue. In some embodiments, sizing device 30 has a similar construction and arrangement to sizing device 30 of FIG. 1. In some embodiments, sizing device 30 comprises a balloon, expandable cage or other sizing element constructed and arranged to measure the inner surface diameter of a tubular tissue such as duodenal and/or jejunal tissue. A diameter measurement can be performed by inflating a balloon of sizing device 30 to one or more predetermined pressures, or pressure profiles, and performing a visualization procedure or other procedure to determine balloon diameter. Alternatively or additionally, a balloon can be filled with a fluid and one or more of fluid volume or fluid pressure is measured to determine balloon diameter and subsequently diameter of tubular tissue proximate the balloon. In some embodiments, subsequent selection (e.g. size selection) and/or expansion diameter (e.g. sized for apposition) of expandable assembly 130, expandable assembly 160 and/or a treatment assembly of treatment device 100' can be determined using these tissue geometry measurements. Alternatively or additionally, an expandable element such as a balloon or cage can comprise two or more electrodes configured to provide a tissue impedance measurement whose value can be correlated to a level of apposition of the expandable element, and whose expanded diameter (e.g. visually measured) subsequently correlated to a diameter of tubular tissue proximate the expandable element. In some embodiments, expandable assembly 130 and/or expandable assembly 160 comprise sizing device 30, such as when expandable assembly 130 and/or expandable assembly 160 comprise a balloon or other sizing element used to measure a diameter of the inner surface of tubular tissue.

System 10 can be constructed and arranged to control one or more system parameters, such as controlling one or more system parameters prior to, during or after the delivery of a thermal dose of energy, during a priming procedure, during a sizing procedure and/or during a tissue expansion procedure. System 10 can be constructed and arranged to control a system parameter selected from the group consisting of: a priming procedure parameter such as priming temperature or priming duration; a target tissue treatment parameter such as target tissue temperature or target tissue treatment duration; fluid flow rate such as treatment fluid flow rate; a pressure parameter such as a treatment element pressure maintained during treatment of target tissue; a treatment element diameter such as a treatment element diameter maintained during treatment of target tissue; and combinations thereof. System 10 can be constructed and arranged to control the size of an expandable reservoir, such as by controlling the diameter of expandable assembly 130, expandable assembly 160 and/or another expandable reservoir or assembly as described herein. In some embodiments, a user of system 10 selects a size of an expandable reservoir, such as by selecting the size from a range of available sizes of expandable assembly 130 and/or expandable assembly 160 provided to the user in a kit.

Any of the components of system 10 can include a coating, such as a lubricious coating. In some embodiments, expandable assembly 130, expandable assembly 160 and/or other radially expandable elements such as balloons include a lubricious or other material property modifying coating. In some embodiments, a radially expandable and radially compactable expandable assembly 130 and/or expandable assembly 160 comprise a hydrophilic coating, for example configured to disperse or otherwise move an ablative fluid.

Each of the components and/or devices of system 10 can be removably attached to another component, particularly device 100, device 20, console 200, EDU 250, motion transfer assembly 270, ground pad 70, endoscope 50a and/or second device 100'. Typical attachment means include but are not limited to mechanical or electromechanical connectors providing an electrical, optical and/or fluidic connection between the attached components.

Figure 7:
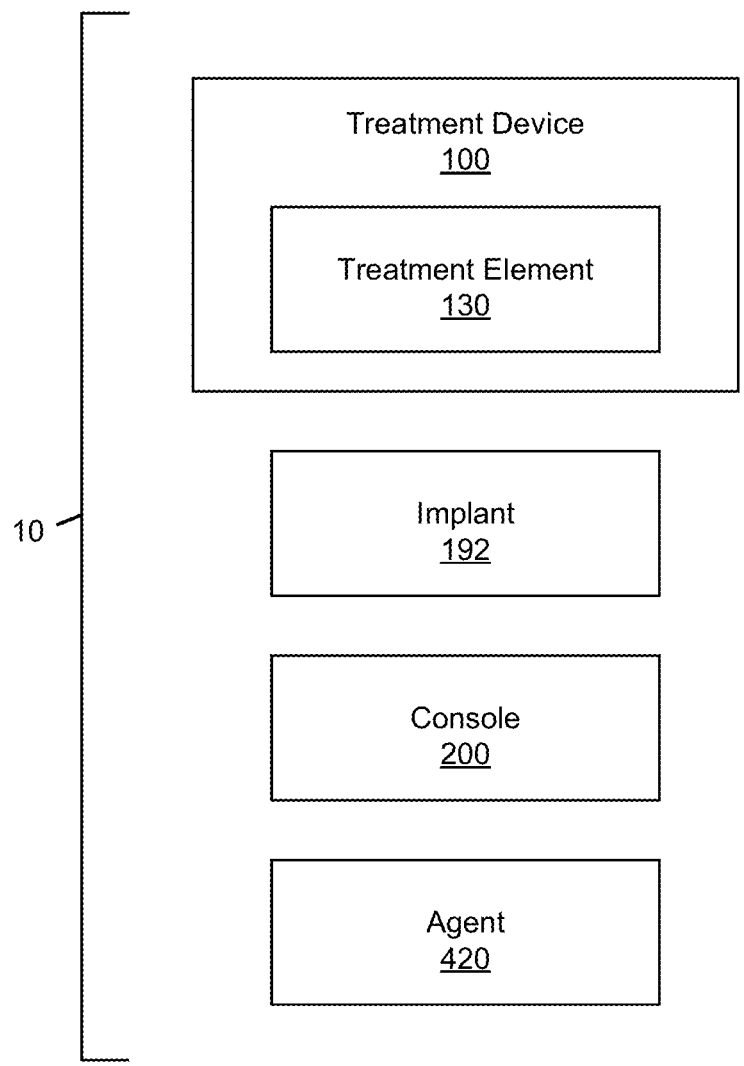
FIG. 7 illustrates a schematic view of a system for performing a medical procedure in the intestine of a patient, consistent with the present inventive concepts.

Referring now to FIG. 7, a schematic view of a system for performing a medical procedure on a patient is illustrated, consistent with the present inventive concepts. The medical procedure can comprise a diagnostic procedure (e.g. a diagnostic and/or prognostic procedure), a therapeutic procedure, or a combined diagnostic and therapeutic procedure. System 10 includes one or more tissue treatment devices, device 100. Device 100 can be configured as a tissue-modifying device, such as a device that modifies "target tissue", such as targeted mucosal tissue and/or other tissue of the intestine or other GI location whose treatment provided a therapeutic benefit to the patient. Alternatively or additionally, device 100 can be configured to deliver one or more implants, implant 192 shown and described herein. In some embodiments, device 100 is of similar construction and arrangement as device 100 described in reference to FIG. 9 or otherwise herein. Device 100 is configured to avoid adversely affecting non-target tissue, such as tissue selected from the group consisting of: gastrointestinal adventitia; duodenal adventitia; the tunica serosa; the tunica muscularis; the outermost partial layer of the submucosa; ampulla of Vater (also known as the papilla); pancreas; bile duct; pylorus; and combinations of these.

In some embodiments, system 10 further includes one or more devices that operably attach to device 100, console 200 shown and described herein. Console 200 can comprise one or more consoles and/or other devices that provide a function selected from the group consisting of: provide energy to device 100; provide an agent to device 100; manipulate and/or otherwise control device 100; and combinations of these. In some embodiments, console 200 is of similar construction and arrangement as console 200 described in reference to FIG. 9 or otherwise herein.

In some embodiments, device 100 comprises one or more catheters or other elongate devices, such as those described herein in reference to FIGS. 1 and/or 9. In some embodiments, device 100 comprises one or more robotically manipulated devices, such as is described in applicant's co-pending International PCT Patent Application Serial Number PCT/US2021/013600, entitled "Automated Tissue Treatment Devices, Systems, and Methods", filed Jan. 15, 2021.

As described herein, device 100 can comprise a tissue-modifying device, such as a device configured to deliver energy to tissue, and/or perform any other tissue-modifying procedure from one or more functional elements and/or functional assemblies, treatment element 130 shown and as described herein. Treatment element 130, also referred to as functional assembly 130 herein, can be configured to deliver energy (e.g. as provided by console 200) to target tissue such as the mucosa or other intestinal tissue (such as the submucosa of the intestine) to provide a therapeutic benefit to the patient. Alternatively or additionally, treatment element 130 can be configured to expand tissue, such as to expand submucosal tissue proximate mucosal tissue to be subsequently ablated, as described herein. Device 100 can deliver energy at a configuration sufficient to ablate the target tissue (e.g. such that the target tissue is subsequently replaced with new tissue) and/or device 100 can deliver energy at a configuration sufficient and/or directed to treat submucosal nerves. Device 100 can deliver one, two, or more forms of energy selected from the group consisting of: thermal coagulation energy; desiccation energy; non-desiccating tissue ablating energy; heat energy; cryogenic energy; radiofrequency (RF) energy; microwave energy; electroporation energy; ultrasound and/or other sound-based energy; sonoporation energy; laser and/or other light-based energy; mechanical energy (e.g. to cause abrasion); chemical energy (e.g. to abrade and/or ablate); and combinations thereof. In some embodiments, device 100 is configured to deliver energy to tissue at a level that prevents causing the target tissue from exceeding 100° C., such as to prevent the tissue temperature from exceeding 95° C., or from exceeding 90° C. In some embodiments, treatment element 130 comprises a balloon, such as a balloon configured to expand to a diameter between 19 mm and 27.5 mm when positioned in the small intestine. The balloon can comprise a non-compliant balloon such that expansion is limited to a predetermined diameter between 19 mm and 27.5 mm, and/or a diameter between 21 mm and 27 mm. In these embodiments, the balloon can receive a recirculating supply of fluid at an ablative temperature such as to ablate the mucosal layer of the segment of the small intestine in which treatment element 130 is positioned, such as to achieve a therapeutic benefit as described herein.

Device 100 can comprise a tissue-modifying device that modifies tissue by delivering one or more drugs, cellular material, and/or other agents to tissue, agent 420 shown and as described herein. In some embodiments, treatment element 130 is configured to deliver agent 420 (e.g. as provided by console 200), such as delivery to target tissue via one or more agent delivery elements of treatment element 130 selected from the group consisting of: needles; fluid jets; openings; porous membranes; iontophoretic elements; and combinations of these. Agent 420 can comprise one or more agents configured to ablate target tissue and/or otherwise cause tissue necrosis (e.g. such that the target tissue is replaced with new tissue). Alternatively or additionally, agent 420 can comprise one or more agents configured to modify the cellular function of the target tissue (e.g. with or without the target tissue being replaced with new tissue). Alternatively or additionally, agent 420 can comprise one or more agents configured to coat target tissue, such as to alter how the target tissue absorbs materials (e.g. food) passing through that particular segment of the GI tract.

In some embodiments, device 100 comprises a "pill" that surrounds or otherwise is co-formulated (e.g. as a carrier) with agent 420. In these embodiments, device 100 can be ingested (e.g. taken orally, such as when taken one or more times per day) by the patient such that agent 420 is delivered into the GI tract via this delivery method. In some embodiments, device 100 provides protection to agent 420 as it passes through the stomach (e.g. an acidic, high-motion environment). In some embodiments, device 100 comprises a material that breaks apart and/or dissolves ("dissolves" herein) if the pH of its environment is above a threshold, such as a pH threshold of 5.5 or 6.0, delivering the included agent 420 to the patient. In some embodiments, device 100 comprises a material that dissolves when exposed to intestinal enzymes, delivering the included agent 420 to the patient. In some embodiments, device 100 comprises a time-release material, such as a material that delivers agent 420 to the patient over a prolonged period of time.

In some embodiments, device 100 is configured to deliver one or more implants, implant 192. In some embodiments, treatment element 130 is configured to deliver implant 192. Implant 192 can comprise one or more tissue barrier devices, such as a device that functions as a barrier between target tissue of the GI tract (e.g. mucosal tissue and/or other tissue of the intestine or other GI location) and material (e.g. food) that passes through that particular segment of the GI tract. Implant 192 can comprise a sleeve, a stent, and/or a coating (e.g. a luminal wall coating). In some embodiments, implant 192 comprises a sleeve and/or a stent that includes one or more agents (e.g. one or more agents that elude from implant 192 over time), such as agent 420 described herein.

In some embodiments, agent 420 comprises a pharmaceutical or other agent that is provided to the patient as an adjunctive therapy (e.g. in addition to a tissue treatment performed using device 100). In these embodiments, agent 420 can comprise insulin, such as insulin that is delivered to the patient at a level that is less than the level of insulin delivered to the patient prior to a treatment performed using device 100 (e.g. an ablation or other treatment of mucosal tissue of the patient's duodenum). In some embodiments, no insulin is delivered to the patient after the treatment performed using device 100 (e.g. a previous insulin therapy is discontinued after the device 100 treatment). In some embodiments (e.g. with or without adjunctive insulin therapy), agent 420 comprises an anti-diabetic medication, such as is described in reference to FIG. 8 herein, that is provided to the patient after treatment of mucosal tissue (e.g. duodenal mucosal tissue) by system 10.

In some embodiments, system 10 is configured to perform a duodenal mucosal treatment on a patient without requiring surgery and/or without implanting a chronic implant in the patient (e.g. a sleeve, a suture, and/or other implant left within the patient for at least one week).

Figure 8:
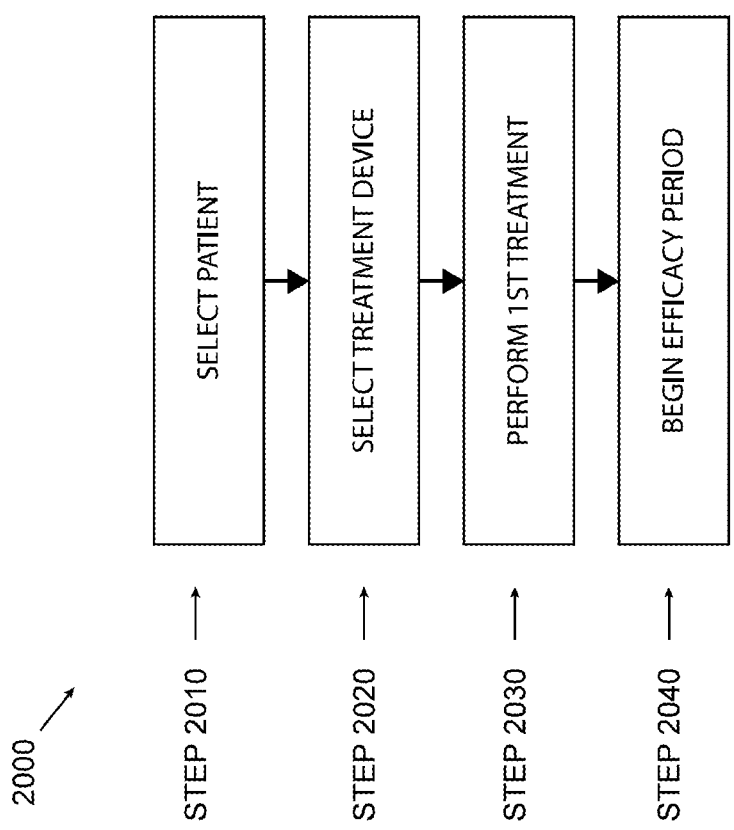
FIG. 8 illustrates a flow chart of a method for performing a medical procedure in the intestine of a patient, consistent with the present inventive concepts.

Referring now to FIG. 8, a flow chart of a method for performing a medical procedure on a patient is illustrated, consistent with the present inventive concepts. Method 2000 of FIG. 8 is described using system 10 of the present inventive concepts.

In STEP 2010, a patient is selected for treatment. The patient can comprise a diabetic patient, such as a type 2 diabetic patient that is currently taking insulin at a first dosage level, such as a dosage level of at least 10 units/day, or at least 20 units/day. In some embodiments, the patient selected for treatment is receiving insulin therapy at a dosage level of no more than 50 units/day, no more than 60 units/day, and/or no more than 0.5 units/kg/day (i.e. 0.5 units per kg of body weight of the patient per day). In some embodiments, the patient has a c-peptide level of at least 0.5 ng/mL, 0.6 ng/mL, and/or 1.0 ng/mL. In some embodiments, the patient has a fasting plasma glucose (FPG) level of at least 140 mg/dL, 160 mg/dL, and/or at least 180 mg/dL (e.g. when measured after ceasing insulin intake for at least 12 or 24 hours prior to the measurement). In some embodiments, the patient has an HbA1C level of no more than 9.5% and/or 10.0%. In some embodiments, the patient has an HbA1C level of at least 6.5%, 7%, 7.5%, 8%, 9.5%, or at least 10.0%. In some embodiments, the patient is currently taking (e.g. prior to STEP 2020) a non-insulin medication, such as a medication selected from the group consisting of: an insulin sensitizing medication such as a biguanide (e.g. metformin) and/or a thiazolidinedione (e.g. pioglitazone); an insulin secretagogue such as a sulfonylurea or a meglitinide; an alpha-glucosidase inhibitor (e.g. acarbose); a DPP-4 inhibitor; a peptide analog such as an incretin mimetic (e.g. a GLP-1 analog, GIP analog, and/or GIP antagonists); an amylin analogue (e.g. pramlintide); a glycosuric medication (e.g. empagliflozin or other SGLT2 inhibitor); and combinations of these. In some embodiments, the patient is currently taking (e.g. prior to STEP 2020) a non-insulin anti-diabetic medication.

In STEP 2020, a treatment device 100 of system 10 is selected for treating the patient. The treatment device 100 selected in STEP 2020 can comprise one or more tissue-modifying devices, such as an energy delivery device configured to deliver tissue-ablating energy. The tissue-modifying device can be configured to deliver to tissue (e.g. target tissue) one or more forms of energy selected from the group consisting of: thermal coagulation energy; desiccation energy; non-desiccating tissue ablating energy; heat energy; cryogenic energy; radiofrequency (RF) energy; microwave energy; electroporation energy; ultrasound and/or other sound-based energy; sonoporation energy; laser and/or other light-based energy; mechanical energy (e.g. to cause abrasion); chemical energy (e.g. to abrade and/or ablate); and combinations thereof. In some embodiments, a tissue-modifying device 100 selected in STEP 2020 can be further configured as an agent delivery device (e.g. to deliver agent 420 as described herein) and/or an implant delivery device (e.g. to deliver implant 192 as described herein).

The treatment device 100 selected in STEP 2020 can comprise one or more agent delivery devices, such as a device 100 configured to deliver an agent 420 comprising one or more tissue-modifying agents and/or tissue coating agents. For example, the treatment device 100 selected in STEP 2020 can deliver a tissue-modifying agent 420 selected from the group consisting of a tissue ablating agent; a tissue-sclerosing agent; a tissue cell-function-modifying agent; and combinations of these. Alternatively or additionally, the treatment device 100 selected in STEP 2020 can deliver a tissue-coating agent, such as a tissue-coating agent that is delivered by one, two, three, or more fluid delivery elements of device 100 (e.g. delivery elements 139*c* described herein), In some embodiments, an agent delivery device 100 selected in STEP 2020 can be further configured as a tissue-modifying device (e.g. an energy delivery device or other tissue-modifying device as described herein) and/or an implant delivery device (e.g. to deliver implant 192 as described herein).

The treatment device 100 selected in STEP 2020 can comprise one or more implant delivery devices, such as a device 100 configured to deliver an implant 192. For example, the treatment device 100 selected in STEP 2020 can deliver an implant 192 comprising a tissue barrier device, such as a sleeve and/or a coating. The tissue barrier device can include a tissue-modifying agent (e.g. an agent 420 as described herein). In some embodiments, an implant delivery device 100 selected in STEP 2020 can be further configured as a tissue-modifying device (e.g. an energy delivery device or other tissue-modifying device as described herein) and/or an agent delivery device (e.g. a device configured to deliver agent 420).

The treatment device 100 selected in STEP 2020 can comprise a tissue barrier device, such as a sleeve and/or a coating.

In STEP 2030, a first treatment is performed in which the patient is treated using the treatment device 100 selected in STEP 2020. For example, device 100 can be used to treat target tissue, such as mucosal and/or submucosal tissue of the duodenum and/or other small intestine location. The treatment can be used to damage, remove, and/or otherwise cause the replacement of cells of target tissue (e.g. duodenal or other mucosal tissue of the intestine). The treatment can comprise delivery of energy and/or other tissue treatment that causes an effect on tissue selected from the group consisting of: thermal coagulation; desiccation; non-desiccating tissue ablation; heat ablation; cryoablation; radiofrequency (RF) ablation; electroporation; ultrasound and/or other sound-based ablation; sonoporation; laser and/or other light-based ablation; mechanical abrasion; chemical abrasion and/or chemical ablation; and combinations thereof.

In some embodiments, STEP 2030 includes the delivery of an implant, such as a tissue barrier device as described herein.

In some embodiments, STEP 2030 includes the patient taking (e.g. ingesting) a device 100 configured as a carrier for delivering agent 420 (e.g. an agent 420 comprising a tissue coating and/or tissue-modifying agent as described herein).

In some embodiments, the most-proximal tissue treated in STEP 2030 comprises tissue that is in the post-papillary duodenum, or locations distal to the ampulla of Vater (e.g. at least 0.1 cm, 0.5 cm, and/or 1.0 cm from the ampulla of Vater). In these embodiments, the most-proximal tissue treated can be tissue located within 3 cm of the ampulla of Vater, such as within 2 cm, or within 1 cm of the ampulla of Vater.

In some embodiments, the treated tissue (e.g. duodenal mucosal tissue) in STEP 2030 comprises a cumulative axial length (e.g. cumulative length of two or more treated segments) of at least 3.0 cm, at least 5.0 cm, at least 7.5 cm, or at least 10.0 cm. In these embodiments, at least 50%, 60%, and/or 70% of the mucosal tissue within the cumulative axial length can be ablated and/or otherwise affected such as to cause necrosis ("ablated" herein). In these embodiments, no more than 20%, 10%, and/or 5% of the muscularis propria within the cumulative axial length can be adversely affected (e.g. caused to necrose). Alternatively or additionally, at least 30%, 40%, 50%, and/or 60% of the crypts of the cumulative axial length is caused to necrose. Also in these embodiments, no more than 20%, 10%, and/or 5% of the muscularis propria of the cumulative axial length can be ablated, necrosed, nor otherwise adversely affected by the treatment performed in STEP 2030. In some embodiments, the tissue treated in STEP 2030 comprises ablating and/or otherwise treating at least 10 cm$^2$, 15 cm$^2$, 20 cm$^2$, 30 cm$^2$, 40 cm$^2$, or 50 cm$^2$ of surface area of duodenal mucosal tissue. For example, in some embodiments, the treatment comprises delivering energy (e.g. thermal, electromagnetic, light, and/or sound energy) and/or a tissue-modifying agent (e.g. a necrotic agent) to a mucosal tissue surface (e.g. a continuous surface or multiple tissue surface segments) that comprises a first quantity of tissue surface area. This treatment causes a minimum surface area (e.g. at least 10 cm$^2$ of a mucosal tissue surface) to be ablated (e.g. to necrose and/or to be removed). This first quantity of tissue surface area receiving the treatment can be less than or equal to the minimum surface area that is ablated (e.g. additional tissue is ablated due to conduction of heat, chemical energy, and the like, to tissue neighboring the tissue surface receiving the treatment). In these embodiments, the sub-surface tissue (e.g. sub-surface mucosal and/or submucosal tissue layers) beneath the ablated surface can also be ablated, such as when all or a portion of the full thickness of mucosal tissue beneath the ablated surfaces are also ablated (e.g. tissue including the crypts is also fully or partially ablated).

In STEP 2040, an efficacy period begins as a result of the treatment performed in STEP 2030. In some embodiments, STEP 2040 includes the patient undergoing an adjunctive therapy, such as an adjunctive therapy comprising: the taking of one or more medications; the patient undergoing a particular diet plan (e.g. a particular diet plan with a duration of at least one week, or at least two weeks); and/or the patient participating in a particular exercise regimen. For example, in STEP 2040, the patient can take insulin (e.g. "daily insulin") at a second dosage level, such as a second dosage that is less than the first dosage, such as a dosage that is at least 15 units/day less than the first dosage, or such as a dosage that is no more than 50% of the first dosage. In some embodiments, in STEP 2040 the patient discontinues the taking of insulin (i.e. the patient is no longer on insulin therapy), such as a second dosage of zero units/day of insulin.

In some embodiments, STEP 2040 includes the patient taking a pharmaceutical and/or other agent, such as agent 420 described herein. In some embodiments, STEP 2040 includes the patient taking one, two, or more medications selected from the group consisting of: an insulin sensitizing medication such as a biguanide (e.g. metformin) and/or a thiazolidinedione (e.g. pioglitazone); an insulin secretagogue such as a sulfonylurea or a meglitinide; an alpha-glucosidase inhibitor (e.g. acarbose); a DPP-4 inhibitor; a peptide analog such as an incretin mimetic (e.g. a GLP-1 analog, GIP analog, and/or GIP antagonists); an amylin analogue (e.g. pramlintide); a glycosuric medication (e.g. empagliflozin or other SGLT2 inhibitor); and combinations of these. For example, in some embodiments STEP 2040 includes the patient taking at least one anti-diabetic medication, such as: a non-insulin anti-diabetic medication; an agonist of GLP-1 and/or a GLP-1 analog; and/or an antagonist of SGLT2 and/or an SGLT2 analog.

The treatment provided by method 2000 can result in an efficacy period that that provides one or more therapeutic benefits to the patient for an extended period of time (e.g. at least one month). In some embodiments, the efficacy period of STEP 2040 includes the patient achieving a satisfactory level of glycemic control (e.g. HbA1c maintained at a desirable level or other measure of glycemic control). The glycemic control or other therapeutic benefit can last for an extended efficacy period, such as an efficacy period of at least 3 months, at least 6 months, or at least 12 months (e.g. accompanied by avoidance of insulin therapy and/or at least a reduced level of insulin therapy compared to pre-treatment of STEP 2030). In some embodiments, during the efficacy period, STEP 2040 includes the patient taking at least one anti-diabetic medication, as described herein. Glycemic control achieved in STEP 2040 can comprise an HbA1C level of no more than 8.5%, 8.0%, 7.5%, and/or 7.0% points. Glycemic control achieved in STEP 2040 can comprise a fasting plasma glucose level of no more than 140 mg/dL, 130 mg/dL, or 120 mg/dL. Alternatively or additionally, glycemic control achieved in STEP 2040 can comprise an HbA1C level that is no more than 0.4, or 0.3, or 0.2% points over a "baseline level", in other words the level present prior (e.g. just prior) to the performance of the treatment of STEP 2030.

In some embodiments, the treatment provided by method 2000 and achieved in STEP 2040 can result in a therapeutic benefit comprising a weight loss of the patient, such as a weight loss of at least 5% compared to a baseline level. In these embodiments, the weight loss can be maintained for an efficacy period of at least 3 months. In some embodiments, the treatment provided by method 2000 and achieved in STEP 2040 can result in a therapeutic benefit comprising improvements in liver transaminases (e.g. ALT levels) and/ or liver fat levels (e.g. as measured by MRI-PDFF). Improvement in liver function by method 2000 and achieved in STEP 2040 can comprise a relative reduction of liver fat (e.g. as measured by MRI-PDFF and/or other means) of at least 20%, 25%, or 30%. Alternatively or additionally, improvement in liver function by method 2000 and achieved in STEP 2040 can comprise an absolute reduction of liver fat content of at least 3% or 5% or achieve an absolute liver fat content of no more than 10% or 5%. As described herein, in some embodiments, method 2000 is configured to reduce insulin therapy (e.g. eliminate or at least reduce insulin intake by at least 15 units/day) without worsening glycemic control (e.g. without causing an HbA1c increase of at least 0.2%).

In some embodiments, the treatment provided by method 2000 and achieved in STEP 2040 can result in a therapeutic benefit comprising a reduction in the risk of hypoglycemia, such as a reduction in the risk of a serious hypoglycemic event (e.g. as compared to baseline and/or as compared to increasing insulin use). In some embodiments, the risk of a hypoglycemic event occurring after performance of the tissue treatment procedure of the present inventive concepts is no more than 0.1% per patient per year (e.g. for patients that take no insulin during STEP 2040). In some embodiments, the risk of a hypoglycemic event occurring is no more than 0.5% per patient per year, or no more than 0.4% per patient per year (e.g. for patients that are on insulin therapy of no more than 60 units/day, such as no more than 50 units/day, and/or for patients that achieve an HbA1C level of no more than 7.5%).

In some embodiments, the treatment provided by method 2000 and achieved in STEP 2040 can result in a therapeutic benefit comprising an increased level in patient satisfaction (e.g. as compared to baseline). For example, an increased level in patient satisfaction can be demonstrated through use of a diabetes treatment and/or a patient-reported survey questionnaire (e.g. an SF-36 survey).

In some embodiments, STEP 2040 further includes the patient undergoing one or more diagnostic procedures. For example, routine blood glucose readings can be made (e.g. by the patient, such as to include and/or modify the taking of insulin). STEP 2040 can include a diagnostic procedure selected from the group consisting of: blood glucose test; blood pressure test; weight assessment; blood test; urine test; and combinations of these.

The systems and methods of the present inventive concepts can be used to treat type 2 diabetic patients that are taking insulin (receiving insulin as part of a therapeutic regime) at a first dosage level, such as to discontinue or at least reduce the insulin taken to a lower, second dosage level, while providing a therapeutic benefit such as glycemic control for an efficacy period (e.g. at least 3 months). The patients selected for treatment may meet a criteria selected from the group consisting of: age of at least 21 years, and/or at least 28 years; HbA1c less than or equal to 9.5%, or 10.0%; a c-peptide level of at least 0.5, 0.6, and/or 1.0; a fasting plasma glucose (FPG) of at least 160 mg/dL and/or at least 180 mg/dL, a body mass index (BMI) of at least 24 kg/m² or at least 30 kg/m²; a BMI of no more than 35 kg/m², no more than 40 kg/m², and/or no that 45 kg/m²; insulin therapy at a dosage level of at least 10 units/day and/or at least 20 units/day; and combinations of these. In some embodiments, the patient selected for treatment is receiving insulin therapy at a dosage level of no more than 50 units/day, no more than 60 units/day, and/or no more than 0.5 units/kg/day (i.e. 0.5 units of insulin per kg of patient body weight per day). In some embodiments, the patient selected for treatment is receiving insulin therapy and has an HbA1c of at least 7.0% and/or 7.5%. Treatment of the patients of the present inventive concepts can include treatment of one or more segments of duodenal tissue (e.g. distal to the ampulla of Vater as described herein) with a cumulative axial length of at least 6 cm, 8 cm, and/or 10 cm. The treated tissue can comprise tissue that is within 3 cm of the papilla, such as within 2 cm, 1 cm, and/or 0.5 cm of the papilla. In some embodiments, and the duodenal tissue treatment has been performed, insulin therapy may be increased (e.g. reintroduced to a level above zero) if the FPG level of the patient exceeded a threshold, such as by using a common clinical algorithm configured to titrate insulin to achieve a target FPG level.

Applicant has conducted human clinical studies in which type 2 Diabetic patients being treated with insulin received a duodenal mucosal tissue treatment using system 10 of the present inventive concepts. After the tissue treatment, patients had the insulin intake reduced (e.g. eliminated) and various therapeutic benefits were achieved for an extended efficacy period (e.g. at least three months). In one study, the patient population treated are described in two groups, an "ITT group" comprising an intention to treat population, and a "PP group" comprising a sub-group of the ITT group, in which patients that were enrolled in the study but were not treated or not followed up were excluded. The ITT group includes 16 patients, and the PP group includes 12 patients. Values described herebelow are expressed as medians (interquartile ranges, IQRs), unless stated otherwise.

The ITT group included 10 males, and 6 females.

Referring to FIG. 45, patient data prior to performance of the tissue treatment procedure of the present inventive concepts is illustrated. The patients underwent a duodenal treatment procedure of the present inventive concepts.

Referring to FIG. 46, a listing data of the procedures performed is illustrated.

Insulin treatment of the patient was stopped the day before the procedure, prior to the procedure, and reintroduced if HbA1c rose above a time-dependent threshold. The threshold was defined as follows: at 3 months, if the patient's HbA1c is no more than 9%, liraglutide treatment is continued, if above 9%, liraglutide treatment is discontinued and insulin is re-introduced; at 6 months, if the patient's HbA1c is no more than 7.5%, liraglutide treatment is continued, if above 7.5%, liraglutide treatment is discontinued and insulin is re-introduced. For two-weeks after the procedure was performed, the patients followed a diet in which clear liquids were gradually transitioned to solid foods. A solid food dietary plan, which was re-evaluated and adjusted or expanded as determined by clinicians of the patients, followed the following regimen: Harris and Benedict equation with 0-20% extra, containing less than 50% carbohydrates, ±20% proteins, and ±30% fat. Post-procedure the patients followed a drug regimen of: GLP-1RA (Liraglutide) which was self-administered after the 2-week post-procedure, once daily 0.6 mg/day. Dose was increased to 1.2 mg/day and 1.8 mg/day in one-week intervals. Post-procedure the patients also followed an exercise program comprising exercising a minimum of 30 minutes per day (e.g. exercise comprising walking, cycling, swimming, jogging, and/or dancing).

Referring to FIGS. 47 and 48, data collected at a follow-up procedure performed on 13 patients, approximately 3 months after the duodenal treatment procedure is illustrated. At the time, all of the patients were not taking insulin (i.e. the "second dosage" of the present inventive concepts was zero units/day). FIG. 47, illustrates data collected at the 3-month follow-up, and FIG. 48 includes a comparison of 3-month follow-up data to date collected at baseline (e.g. prior to the duodenal tissue treatment). Referring to FIG. 49, data collected at a follow-up procedure performed approximately 6 months after the duodenal treatment procedure is illustrated.

As described herein, the systems, devices and methods of the present inventive concepts have been shown to safely ablate duodenal mucosa and to improve glycemic control in type 2 diabetes, such as by altering enter endocrine signaling from the duodenum which causes insulin sensitization. Patients can be treated who include insulin intake in their therapy, and their insulin therapy can be eliminated or at least reduced after the duodenal mucosal treatment is performed. In some embodiments, at least 30%, 40% or 50% of patients who are treated can eliminate their need for insulin after duodenal mucosal treatment is performed. Patients who are treated and who achieve successful elimination of insulin therapy at month 6 can also be expected to maintain the benefit of that therapy 12 months after the duodenal mucosal treatment of the present inventive concepts is performed. As an example, at least 50% or 75% or 90% of patients who achieve a successful elimination of insulin therapy at month 6 can maintain the elimination of insulin therapy through 12 months without significant worsening of glycemic control, such as glycemic control that is defined as an HbA1c level that is no more than 0.4%, or 0.3%, or 0.2% over a "baseline level", in other words the level present prior (e.g. just prior) to the performance of the treatment of STEP 2030. Therapy provided to the patient after the mucosal treatment can include glucagon like peptide-1 receptor agonism (GLP-1RA) and lifestyle counseling. In the 16 patient study described hereabove, at 12 months, 56% (9/16) of patients were still off insulin therapy with a median HbA1c of 6.7%. The median insulin dose decreased from 36 to 17 units per day in non-responders at 12 months with a median HbA1c of 7.9%.

Figure 9:
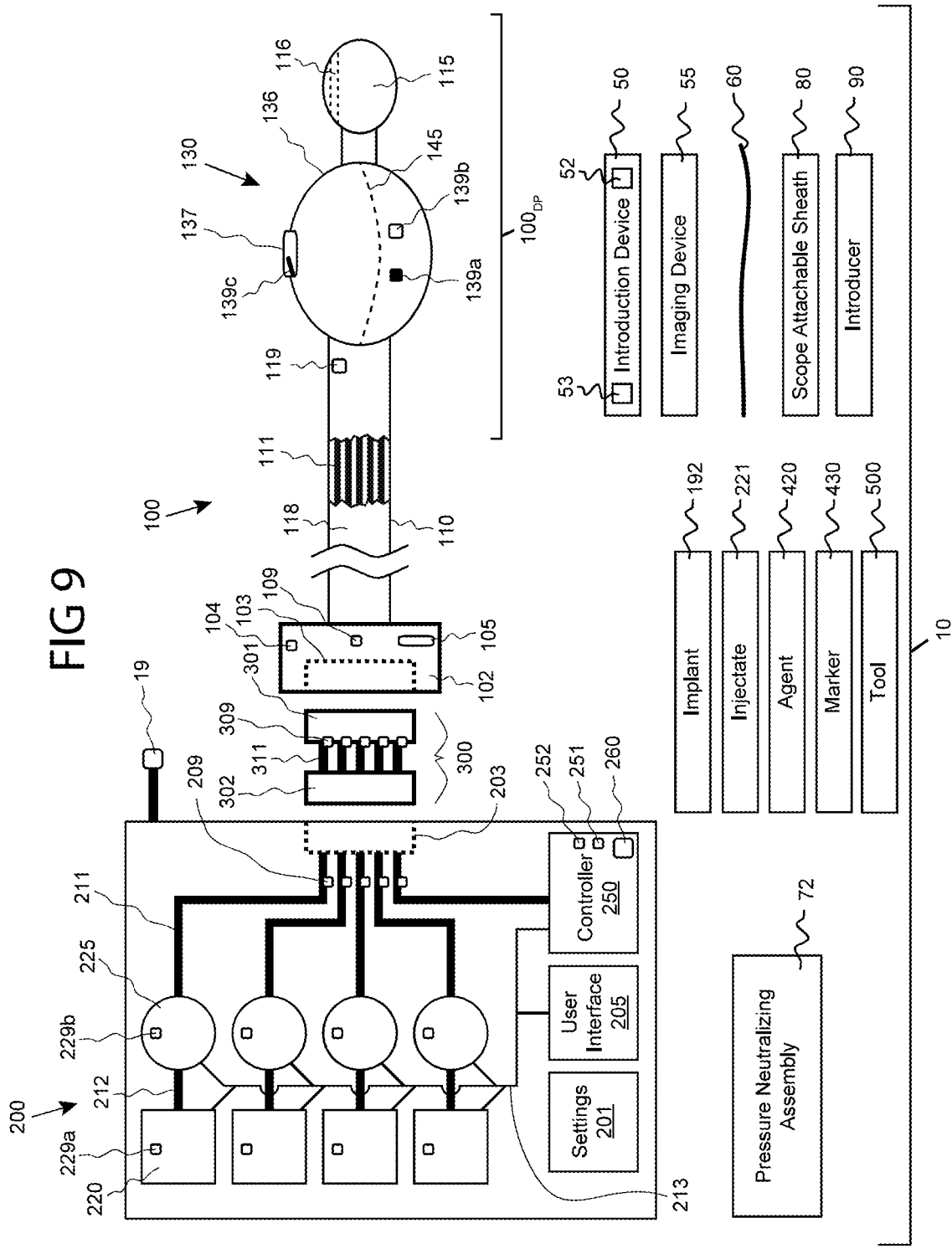
FIG. 9 illustrates a schematic view of a system for performing a medical procedure in the intestine of a patient, consistent with the present inventive concepts.

Referring now to FIG. 9, a schematic view of a system for performing a medical procedure on a patient is illustrated, consistent with the present inventive concepts. The medical procedure can comprise a diagnostic procedure (e.g. a diagnostic and/or prognostic procedure), a therapeutic procedure, or a combined diagnostic and therapeutic procedure. System 10 can be of similar construction and arrangement as system 10 described in reference to FIG. 7 and otherwise herein. System 10 comprises one or more treatment devices, device 100, (e.g. a catheter, flexible probe, and/or other elongate treatment device for insertion into a patient), and a console, console 200, which operably attaches to the one or more devices 100 (e.g. attaches to two, three or more devices 100). Device 100 comprises an elongate shaft, shaft 110, comprising one or more shafts (e.g. shafts with flexible and/or rigid segments). In some embodiments, shaft 110 comprises multiple shafts in a spiraled configuration (e.g. helical configuration).

Device 100 comprises one or more functional assemblies, assembly 130 shown (also referred to as treatment element 130 herein), which can be configured to radially expand and/or contract. Functional assembly 130 can be positioned on a distal portion of device 100 (e.g. on the distal end or a distal portion of shaft 110), distal portion $100_{DP}$. In some embodiments, functional assembly 130 comprises a non-circular cross section (e.g. to "hug" a second device such as an endoscope simultaneously inserted into the patient). Functional assembly 130 can comprise one or more tissue-contacting portions, as described herein (e.g. side walls of functional assembly 130 that contact inner wall tissue of the intestine or other GI lumen). Functional assembly 130 can comprise a tissue-contacting surface area (e.g. when expanded) of between 500 $mm^2$ to 3500 $mm^2$, such as a tissue contacting surface area of approximately between 1000 $mm^2$ and 2000 $mm^2$, or approximately between 1250 $mm^2$ and 1750 $mm^2$, or approximately 1500 $mm^2$. In some embodiments, functional assembly 130 comprises an expanded diameter of approximately 19 mm, 22 mm, 25 mm or 28 mm. In some embodiments, functional assembly 130 comprises a tissue-contacting length (e.g. when expanded) of between 10 mm and 40 mm, such as a length of approximately 15 mm, 20 mm, 25 mm or 30 mm. This tissue-contacting length represents the "treatment length" of the functional assembly 130. In some embodiments, system 10 includes a first device 100 comprising a functional assembly 130a, and a second device 100 comprising a functional assembly 130b. Functional assemblies 130a and 130b can be similar or different, such as when a functional assembly 130a and 130b have different geometries (e.g. different lengths, expanded diameters; and/or tissue contacting surface areas), deliver different treatments (e.g. deliver different forms of ablative energies and/or deliver different ablative fluids), and/or perform different neutralizing procedures.

In some embodiments, shaft 110 passes through all or a portion of functional assembly 130. In other embodiments, functional assembly 130 is positioned on a distal end of shaft 110. In some embodiments, shaft 110 comprises a non-circular cross section (e.g. to "hug" a second device such as an endoscope simultaneously inserted into the patient). In some embodiments, shaft 110 comprises one or more of: a braided portion; a tapered portion; an insertable stiffening mandrel; a variable stiffness portion; and combinations of two or more of these.

In some embodiments, functional assembly 130 comprises one or more biasing members, such as biasing member 145 shown. Biasing member 145 is constructed and arranged to apply a force to functional assembly 130, such as to place functional assembly 130 in tension along the axis of shaft 110 proximate functional assembly 130, such as when functional assembly 130 is in an unexpanded state. Biasing member 145 can be constructed and arranged to bend as functional assembly 130 expands. Biasing member 145 can comprise an element selected from the group consisting of: spring; coil spring; leaf spring; flexible filament; flexible sheet; nickel titanium alloy component; and combinations of two or more of these. In some embodiments, functional assembly 130 comprises balloon 136, and biasing member 145 is configured to avoid contacting balloon 136 when functional assembly is in its unexpanded state.

In some embodiments, functional assembly 130 comprises a shape constructed and arranged to prevent or otherwise reduce migration of functional assembly 130. In some embodiments, functional assembly 130 is constructed and arranged to perform a first procedure (e.g. one or more tissue expansion procedures, such as submucosal tissue expansion procedures performed proximate a segment of mucosal tissue to be ablated), anchor in tissue (e.g. anchoring performed prior to the first procedure, during the first procedure and/or after the first procedure) and subsequently perform a second procedure (e.g. a tissue ablation procedure), such as is described herein in reference to FIG. 13.

Device 100 can comprise one or more catheters and/or other elongate devices of similar construction and arrangement (e.g. and include similar components) as one or more of devices 100, 20, 30 and/or 40 of FIG. 1, each described in detail herein. Device 100 can be constructed and arranged to perform a medical procedure in an intestine of the patient, such as a procedure in the small intestine (e.g. in the duodenum) and/or in the large intestine. In some embodiments, system 10 further comprises a connecting assembly, assembly 300, which can be constructed and arranged to operably attach (e.g. fluidly, mechanically, electrically and/or optically connect) device 100 to console 200. In alternate embodiments, a device 100 can operably attach directly to console 200, without connecting assembly 300. Console 200 can be of similar construction and arrangement as console 200 of FIG. 1.

System 10 can further comprise body introduction device 50, guidewire 60, sheath 80 (e.g. an endoscope-attachable sheath), introducer 90 (e.g. an introducer sheath), injectate 221, and/or agent 420, each of which can be of similar construction and arrangement to the similar components described in detail herein in reference to FIGS. 1 and/or 7. In some embodiments, guidewire 60 comprises two or more guidewires. Body introduction device 50 can comprise one or more: endoscopes; laparoscopic ports; and/or vascular introducers. Body introduction device 50 can comprise a camera, such as camera 52 shown, and a display, not shown but such as a display of console 200 and/or another display used to display an image (e.g. a camera view) provided by camera 52. In some embodiments, device 50 comprises an endoscope and includes a cap, scope cap 53 shown, which is attached (or attachable) to a distal end of the endoscope, such as to limit tissue collapse that would limit visualization provided by camera 52. Scope cap 53 can extend between 2-6 mm in front of camera 52. In some embodiments, scope cap 53 is of similar construction and arrangement to the Reveal® distal attachment cap manufactured by US Endoscopy.

In some embodiments, system 10 further comprises imaging device 55, which can comprise an imaging device constructed and arranged to provide an image of the patient's anatomy (e.g. inner wall or any part of the intestine of the patient) and/or an image of all or part of device 100 or other portion of system 10, as described in detail herein. Imaging device 55 can comprise an imaging device selected from the group consisting of: endoscope camera; visible light camera; infrared camera; X-ray imager; fluoroscope; Ct Scanner; MRI; PET Scanner; ultrasound imaging device; molecular imaging device; and combinations of two or more of these. In some embodiments, a patient image is used to set, confirm and/or adjust one or more system 10 parameters, such as when imaging device 55 comprises a sensor-based functional element configured to produce a signal. In some embodiments, system 10 is configured to robotically manipulate device 100 and/or another component of system 10, such as is described in applicant's co-pending International PCT Patent Application Serial Number PCT/US2021/013600, entitled "Automated Tissue Treatment Devices, Systems, and Methods", filed Jan. 15, 2021.

In some embodiments, system 10 further comprises one or more tools, such as a tool 500 described herein.

In some embodiments, system 10 further comprises one or more functional elements, such as functional elements 19, 109, 119, 139, 229, and/or 309 shown, each of which can comprise a sensor, transducer, and/or other functional element. Functional element 19 can be operably attached to console 200 or another component of system 10. Functional element 19 can comprise a sensor configured to produce a signal, which can be used to modify a parameter of system 10, as described in detail herein. In some embodiments, one or more functional elements (e.g. functional element 19, 109, and/or 139) comprises a sensor configured to measure a patient parameter, such as a patient parameter selected from the group consisting of: a patient physiologic parameter; blood pressure; heart rate; pulse distention; glucose level; blood glucose level; blood C-peptide level; blood glucagon level; blood insulin level; blood gas level; hormone level; GLP-1 level; GIP level; EEG; LFP; respiration rate; breath distention; perspiration rate; temperature; gastric emptying rate; peristaltic frequency; peristaltic amplitude; a patient anatomical parameter such as tissue geometry information; a patient environment parameter such as room pressure or room temperature; and combinations of two or more of these.

Each of the system 10 sensors can be configured to produce a signal related to a patient parameter and/or a system 10 parameter. For purposes herein, a signal "related" to a parameter shall include signals that directly represent the parameter, as well as signals that provide information that can be correlated to or in any way relate to the parameter. For example, a sensor (e.g. a temperature or pressure sensor) placed proximate tissue or a component of system 10 can directly represent a parameter (e.g. the temperature or pressure, respectively) of locations proximate that tissue or component, respectively. Alternatively, a sensor placed at one location (e.g. one location within system 10), can provide a signal that can be analyzed to produce information representing a parameter at a different location (e.g. a different location within system 10 or a location within the patient). For example, a temperature or pressure measured at one location (e.g. within console 200, connecting assembly 300 and/or a proximal portion of device 100) can correlate to a temperature or pressure, respectively, at a different location (e.g. proximate and/or within functional assembly 130). Correlation of signals provided by a sensor of system 10 to a parameter at a location distant from the sensor can be accomplished by one or more algorithms of system 10, such as algorithm 251 described herein.

In some embodiments, a system 10 sensor is configured to produce a signal related to an anatomic and/or physiologic parameter of the patient, such as a parameter selected from the group consisting of: a parameter of the intestine; a parameter related to the anatomical geometry of a portion of the intestine; a parameter related to force and/or pressure applied to tissue (e.g. tissue of the intestine); a parameter related to a pressure within tissue (e.g. tissue within the luminal surface of the intestine); a parameter related to temperature of tissue (e.g. tissue of the intestine); and combinations of two or more of these. In some embodiments, one or more sensors of system 10 comprise a camera configured to provide an image, and the signal provided by the sensor comprises the image and/or an analysis of the image. The signal provided by the sensor can relate to a patient parameter (e.g. a patient physiologic or anatomical parameter) or a system 10 parameter (e.g. a functional assembly 130 parameter).

In some embodiments, a system 10 sensor is configured to produce a signal related to a parameter of one or more components of system 10, such as a component of console 200, connecting assembly 300 and/or device 100. For example, the signal produced by one or more sensors of system 10 can be related to a functional assembly 130 parameter, such as a parameter selected from the group consisting of: pressure within functional assembly 130; force applied to and/or by a portion of functional assembly 130; temperature of at least a portion of functional assembly 130; temperature of fluid within functional assembly 130; state of expansion of functional assembly 130; position of functional assembly 130 (e.g. position of functional assembly 130 relative to the patient's anatomy): and combinations of two or more of these.

In some embodiments, system 10 is configured to perform a therapeutic procedure selected from the group consisting of: a tissue removal procedure such as a tissue removal procedure in which mucosal intestinal tissue is removed; a tissue ablation procedure such as a tissue ablation procedure in which at least intestinal mucosal tissue is removed; a tissue expansion procedure such as a tissue expansion procedure configured to create a safety margin of tissue (e.g. a safety margin comprising expanded submucosal tissue), and/or a tissue expansion procedure configured to create a therapeutic restriction; and combinations of two or more of these. In some embodiments, system 10 is configured to treat one or more medical conditions (e.g. diseases and/or disorders), such as are described herein. For example, system 10 can be configured to treat diabetes, such as Type 2 diabetes, Type 1 diabetes, "Double diabetes" and/or gestational diabetes. System 10 can be constructed and arranged to cause functional assembly 130 to expand one or more layers of tissue (e.g. submucosal tissue), and/or to treat target tissue (e.g. target tissue comprising mucosal tissue of the duodenum or other intestinal mucosa). System 10 can be further constructed and arranged to avoid adversely affecting non-target tissue, as described herein.

In some embodiments, system 10 is constructed and arranged to alter intestinal microbiota, such as to perform a treatment that affects a patient's gut flora in a way that leads to an improvement in weight and/or metabolic status (e.g. to treat Type 2 diabetes). Device 100 and functional assembly 130 can be configured to treat target tissue including intestinal mucosa such as to destroy local bacteria and/or modify the microbiome in the treated tissue area. Target tissue can include tissue regions where the microbiota contributes to the incidence or maintenance of metabolic disease.

In some embodiments, system 10 is constructed and arranged to reduce or otherwise alter the surface area of intestinal mucosa, such as is described in applicant's co-pending U.S. patent application Ser. No. 16/379,554, entitled "Methods, Systems and Devices for Reducing the Luminal Surface Area of the Gastrointestinal Tract", filed Apr. 9, 2019. In some embodiments, system 10 is configured to reduce or otherwise alter the surface area of intestinal mucosa as a treatment for diabetes, a metabolic disease, obesity and/or hypercholesterolemia. In these embodiments, treatment of target tissue comprising mucosal folds and/or other mucosal tissue results in intestinal mucosa with reduced plicae circulares and delayed recovery or regrowth of intestinal villi. The treatment provided by system 10 can comprise a durable treatment effect that reduces the total absorptive surface area of the treated region. Alternatively or additionally, the treatment provided by system 10 can reduce enteroendocrine cell and/or absorptive cell quantities in the intestine by reducing the geometric complexity of the intestinal surface, such as by a target tissue treatment comprising ablation of intestinal tissue to a certain depth (mucosa alone; mucosa and superficial submucosa; mucosa through mid-submucosa; or mucosa through deep submucosa) that induces the healing response that leads to elimination of plicae circulares and blunting of villi for a prolonged period of time (at least two weeks, at least six weeks, at least six months or at least one year).

In some embodiments, system 10 is configured to treat sufficient duodenal mucosa to provide an improvement in a patient's diabetes, such as is described in applicant's co-pending U.S. patent application Ser. No. 17/096,855, entitled "Methods and Systems for Treating Diabetes and Related Diseases and Disorders", filed Nov. 12, 2020.

In some embodiments, system 10 is configured to treat NAFLD and/or NASH ("NAFLD/NASH" herein), such as is described in applicant's issued U.S. Pat. No. 9,757,535, entitled "Systems, Devices and Methods for Performing Medical Procedures in the Intestine", filed Sep. 23, 2016. In the embodiments, system 10 can be configured to treat patients inflicted with NAFLD/NASH, in addition to diabetes (e.g. Type 2 diabetes).

In some embodiments, system 10 is configured to create a therapeutic restriction in a patient, such as is described in applicant's co-pending U.S. patent application Ser. No. 17/095,108, entitled "Systems, Devices and Methods for the Creation of a Therapeutic Restriction in the Gastrointestinal Tract", filed Nov. 11, 2020. In some embodiments, the therapeutic restriction is created at a location selected from the group consisting of: within mucosal tissue; within submucosal tissue; between mucosal and submucosal tissue; and combinations thereof. In some embodiments, the therapeutic restriction is created at a location selected from the group consisting of: lower stomach; pylorus; proximal small intestine; duodenum; proximal jejunum; distal small intestine; distal jejunum; ileum; and combinations thereof. In some embodiments, the therapeutic restriction is created in a location selected from the group consisting of: colon; rectum; anal sphincter and combinations thereof.

System 10 can be constructed and arranged to perform one or more diagnostic procedures (e.g. one or more diagnostic and/or prognostic procedures). In some embodiments, system 10 is constructed and arranged to perform a lumen sizing procedure, such as a procedure in which one or more diameters of one or more lumen locations in the intestine are determined (e.g. estimated). In these embodiments, the relative location at which the diameter is determined can be maintained at a pressure at or near room pressure (e.g. via one or more lumens of device 100 and/or body introduction device 50). System 10 can be constructed and arranged to perform a patient imaging procedure, such as a procedure in which a patient image is collected, such as a patient image that includes functional assembly 130 positioned in a segment of the intestine. System 10 can be constructed and arranged to perform a tissue sampling procedure, such as in a biopsy procedure. In some embodiments, system 10 is constructed and arranged to perform a diagnostic and/or other procedure selected from the group consisting of: assessment of mucosal thickness and/or hypertrophy, such as while using OCT or similar imaging technologies; assessment of wall thickness, such as via endoscopic ultrasound or similar imaging technologies; visualization of enteroendocrine cell populations, such as via molecular imaging techniques or antibody labeling; assessment of the location of the ampulla of Vater, such as via bile acid labeling; and combinations of two or more of these. In some embodiments, system 10 is constructed and arranged to perform a therapeutic and/or other procedure selected from the group consisting of: an obesity treatment procedure, such as an endoluminal implant of a balloon or other volume reducing and/or restricting device in the stomach or small intestine, a suturing or anastomosing procedure to reduce and/or restrict gastrointestinal volume, and/or an intestinal bypass; a procedure including the injection of sclerosing material configured to induce scar formation; a procedure including the injection of material to create a therapeutic restriction; a procedure including the injection of drugs or other agents into the submucosal space; a microbial transplantation procedure, such as to alter gut microbial populations; and combinations of two or more of these.

In some embodiments, system 10 is constructed and arranged to perform a patient assessment, such as a patient screening to determine if an intestinal tissue ablation (e.g. a duodenal mucosa ablation) would benefit the patient. In these embodiments, system 10 and/or the methods of the present inventive concepts can be configured to compare glucagon administered orally (PO) versus glucagon administered intravenously (IV). Data gathered can include the difference in the patient's ability to suppress glucagon after a meal. Patient's whose ability to suppress glucagon falls below a threshold can be selected to receive a treatment of the present inventive concepts (e.g. an ablation or other treatment to at least the duodenal mucosa). Alternatively or additionally, analysis of fasting and/or postprandial glucagon can be compared to a threshold, and patients whose level is above the threshold can be selected to receive a treatment of the present inventive concepts (e.g. a treatment to at least the duodenal mucosa).

Device 100 of system 10 includes shaft 110, typically a flexible shaft comprising one or more lumens. In some embodiments, shaft 110 comprises varied flexibility along its length. In some embodiments, a bulbous tip is positioned on the distal end, tip 115, of device 100 as shown. Tip 115 can comprise a bulbous element with a diameter of at least 4 mm and/or a diameter less than or equal to 15 mm. In some embodiments, tip 115 comprises an inflatable bulbous tip. An operator graspable handle, handle 102 shown, is positioned on the proximal end of shaft 110. Handle 102 can comprise a user interface, such as user interface 105 shown. User interface 105 can comprise one or more user input components and/or user output components. User interface 105 can comprise one or more user input components configured to allow an operator to modify one or more operating parameters of console 200, settings 201, such as an operator-based modification based on information provided via a signal produced by a sensor of system 10. User interface 105 can comprise a control (e.g. control 104 described herein in reference to FIG. 1) or other user input component selected from the group consisting of: switch; keyboard; membrane keypad; knob; lever; touchscreen; and combinations of two or more of these. User interface 105 can comprise a user output component selected from the group consisting of: light such as an LED; display; touchscreen; audio transducer such as a buzzer or speaker; tactile transducer such as an eccentric rotational element; and combinations of two or more of these.

As described herein, functional assembly 130 can be constructed and arranged to perform a patient diagnosis and/or perform a patient treatment, such as a diagnosis and/or treatment performed on tissue of the intestine (e.g. mucosal and/or submucosal tissue of the intestine). In some embodiments, functional assembly 130 comprises an expandable assembly constructed and arranged to radially expand as determined by an operator of system 10. Functional assembly 130 can comprise an expandable element selected from the group consisting of: an inflatable balloon (e.g. balloon 136 as shown); a radially expandable cage or stent; one or more radially deployable arms; an expandable helix; an unfurlable compacted coiled structure; an unfurlable sheet; an unfoldable compacted structure; and combinations of two or more of these. Functional assembly 130 is shown in a radially expanded state in FIG. 9. Balloon 136 can comprise a compliant balloon, a non-compliant balloon and/or a balloon with compliant and non-compliant sections, as described herein. Balloon 136 can comprise a pressure-thresholded balloon, also as described herein. Balloon 136 can comprise a multi-layer construction, such as a construction with different materials positioned in different layers of balloon 136. In some embodiments, at least the distal portion of device 100, distal portion $100_{DP}$, is constructed and arranged to be: inserted through an endoscope such as body introduction device 50; inserted alongside an endoscope; inserted over a guidewire such as guidewire 60; inserted through a sheath such as scope attachable sheath 80; and/or inserted through an introducer such as introducer 90 (e.g. an introducer sheath). In some embodiments, one or more portions of device 100 are configured to be robotically manipulated.

Positioned within shaft 110 are one or more conduits (e.g. tubes) and/or lumens, conduits 111. Conduits 111 can comprise a conduit selected from the group consisting of: a fluid transport conduit (e.g. a tube or lumen configured to deliver fluids to functional assembly 130 and/or extract fluids from functional assembly 130); a tube comprising a lumen; a tube comprising a translatable rod; a hydraulic tube; a pneumatic tube; a tube configured to provide a vacuum (e.g. provide a vacuum to port 137 described herein); a lumen of shaft 110; an inflation lumen; a lumen configured to provide a vacuum (e.g. provide a vacuum to port 137); a fluid delivery lumen; a wire such as an electrically conductive wire; a linkage; a rod; a flexible filament; an optical fiber; and combinations of two or more of these. One or more conduits 111 can be configured to: transport fluid (e.g. deliver fluid and/or extract fluid); extract fluid; provide a positive pressure; provide a vacuum; and combinations of two or more of these. One or more conduits 111 can comprise a hollow tube, such as a tube comprising polyimide and/or a tube comprising a braid, such as a braided polyimide tube. One or more conduits 111 can be configured to allow the transport of: power, signals and/or materials such as fluids. A conduit 111 can be configured to slidingly receive a guidewire (e.g. guidewire 60), such as for over-the-wire delivery of device 100, such as when a conduit 111 is operably connected to a guidewire lumen, such as lumen 116 of tip 115. Alternatively, guidewire lumen 116 can both enter and exit distal portion $100_{DP}$ of device 100 (e.g. enter and exit tip 115 as shown in FIG. 9), such as for rapid-exchange manipulation of device 100 over a guidewire. In some embodiments, one or more conduits 111 can be translated within shaft 110 (e.g. advanced and/or retracted), such as to change the position of a distal end of a conduit 111 (e.g. to change the position of an outflow tube or inflow tube within functional assembly 130).

Shaft 110 can comprise one or more sensors, transducers, and/or other functional elements of system 10, such as functional element 119 shown. Functional element 119 can be positioned on (e.g. on the outer surface of), in (e.g. within the wall of) and/or within (e.g. within a lumen of) shaft 110.

Functional element 119 can be positioned proximate (e.g. nearby, on, in and/or within) one or more conduits 111, such as when functional element 119 comprises a valve, heating element, and/or cooling element configured to exert a force and/or alter the temperature of one or more fluids passing within a conduit 111.

Functional assembly 130 can comprise one or more sensors, transducers, and/or other functional elements of system 10, functional element 139, such as treatment element 139a, sensor 139b and/or fluid delivery element 139c, all shown in FIG. 9.

In some embodiments, one or more functional elements 139 are constructed and arranged as a tissue treatment element of the present inventive concepts, as described herein, such as when treatment element 139a comprises an energy delivery element configured to treat target tissue of the intestine. Treatment element 139a can be of similar construction and arrangement as treatment element 135 described herein in reference to FIG. 1. Treatment element 139a can comprise a treatment element selected from the group consisting of an ablative fluid (e.g. an ablative fluid to be maintained within balloon 136 and/or an ablative fluid to be delivered onto tissue such as via a fluid delivery element 139c); an electrode configured to deliver radiofrequency (RF) or other electrical energy to tissue; an optical element (e.g. a lens or a prism) configured to deliver laser or other light energy to tissue; a sound energy delivery element such as a piezo crystal configured to deliver ultrasound or subsonic sound energy to tissue; an agent delivery element such as a needle, nozzle or other fluid delivery element configured to deliver an ablative or other agent onto and/or into tissue; and combinations of two or more of these. In some embodiments, treatment element 139a comprises fluid at an ablative temperature. In these embodiments, treatment element 139a can comprise fluid whose temperature changes, such as when system 10 is configured to introduce a fluid both at an ablative temperature (e.g. sufficiently hot or cold to ablate) and fluid at a neutralizing temperature (e.g. a cooling fluid or a warming fluid, respectively), such as when fluid at a neutralizing temperature is delivered within functional assembly 130 before and/or after fluid at an ablative temperature is delivered within functional assembly 130, as described in detail herein.

In some embodiments, treatment element 139a comprises an energy delivery element including multiple layers of electrical conductors (e.g. conductors and/or semiconductors) configured to generate heat when electricity passes through one or more of the conductors. In these embodiments, functional element 139 can be electrically connected to one or more conduits 111 comprising one or more electrical wires. Functional assembly 130 can comprise a compliant or non-compliant balloon onto which functional element 139 is positioned. Treatment element 139a can comprise electrical conductors created by depositing one or more coatings on one or more substrates. When electricity is passed through the coating, heat is generated. The heat can be effectively transferred across the whole surface of functional element 139 mainly through conduction, but also via radiation and convection and into target tissue.

In some embodiments, one or more functional elements 139 are constructed and arranged to perform a diagnosis and/or prognosis ("diagnosis" herein), such as when sensor 139b comprises a sensor configured to sense a physiologic parameter of intestinal tissue. Sensor 139b can comprise one or more sensors, such as are described in detail herein.

In some embodiments, one or more functional elements 139 are constructed and arranged to expand tissue, such as when fluid delivery element 139c comprises one or more of: a needle, nozzle, fluid jet, iontophoretic fluid delivery element, an opening in functional assembly 130 (e.g. an opening in balloon 136) and/or other fluid delivery element configured to deliver fluid into and/or onto tissue (e.g. into submucosal tissue). In some embodiments, fluid delivery element 139c comprises an element (e.g. a needle or fluid jet) configured to deliver fluid into tissue, such as submucosal tissue, to expand the tissue receiving the injected fluid. Alternatively or additionally, fluid delivery element 139c can comprise an element (e.g. a nozzle) configured to deliver fluid onto tissue, such as ablative fluid delivered onto tissue to ablate and/or remove tissue or neutralizing fluid configured to reduce tissue trauma (e.g. limit the volume of tissue ablated). Fluid delivery element 139c can comprise a needle selected from the group consisting of: a straight needle; a curved needle; a single lumen needle; a multiple lumen needle; and combinations of two or more of these. Fluid delivery element 139c can be positioned proximate and/or within a port, such as port 137 shown. Port 137 can be placed on top of balloon 136 and/or recessed into balloon 136 (e.g. positioned within a recess of balloon 136 or other component of functional assembly 130). Port 137 can be engaged between layers of balloon 136, such as when balloon 136 comprises multiple layers including an outer layer (e.g. a layer of PET material) that surrounds at least a portion of port 137. In some embodiments, port 137 comprises an insulating element, such as an insulating element configured to prevent full circumferential ablation of an axial segment of intestine. Alternatively, port 137 can be thermally conductive, to enhance heat or cryogenic ablation proximate port 137. Port 137 can be positioned on a tissue-contacting portion of balloon 136 as shown. Port 137 can be attached to a source of vacuum, such as vacuum provided by a conduit 111, such that port 137 can engage with the tissue. Port 137 can be constructed and arranged such that tissue can be drawn into an opening of port 137, such as when tissue is drawn into port 137 prior to delivery of fluid by fluid delivery element 139c into tissue, as described herein. In some embodiments, device 100 comprises multiple ports 137 and multiple corresponding fluid delivery elements 139c, such as two, three or more pairs of ports 137 and fluid delivery elements 139c (e.g. equally spaced about a circumference of balloon 136). One or more fluid delivery elements 139c can be attached to one or more conduits 111 and can be configured to be translated (e.g. translated within a tissue-capturing opening of port 137). Translation of a fluid delivery element 139c can be limited by one or more mechanical stops constructed and arranged to limit advancement and/or retraction of the fluid delivery element 139c. One or more fluid delivery elements 139c and a fluidly attached conduit 111 can be biased by one or more springs, such as one or more springs positioned in handle 102. Fluid delivery element 139c and an associated functional assembly 130 can be of similar construction and arrangement as those described herein in reference to device 20 and/or device 40 of FIG. 1, or as described in applicant's co-pending U.S. patent application Ser. No. 16/900,563, entitled "Injectate Delivery Devices, Systems and Methods", filed Jun. 12, 2020. One or more fluid delivery element 139c can comprise a straight or a curved needle. One or more fluid delivery elements 139c can be constructed and arranged to enter tissue at an angle between 0° and 90°, such as at an angle between 30° and 60°.

In some embodiments, port 137 can be configured to engage tissue (e.g. when a vacuum is applied to port 137 via one or more conduits 111), after which target tissue can be treated by treatment element 139a. Engagement of tissue by port 137 can be used to stretch or otherwise manipulate tissue, and/or prevent migration of functional assembly 130, such that a safe and effective treatment of target tissue can be performed by treatment element 139a, such as when treatment element 139a comprises fluid at an ablative temperature or an array of electrodes configured to deliver RF energy. In these embodiments, device 100 can be configured to treat target tissue without performing an associated tissue expansion procedure (e.g. without expanding tissue in proximity to the target tissue to be treated).

Functional assembly 130 can be configured to treat target tissue, such as when functional element 139 comprises ablative fluid introduced into balloon 136 or when functional element 139 comprises one or more energy delivery elements as described herein. Functional assembly 130 can be constructed and arranged to treat a full or partial circumferential axial segment of intestinal tissue (e.g. intestinal mucosa). System 10 can be configured to treat multiple axial segments of tissue, such as multiple relatively contiguous or discontiguous segments of mucosal tissue treated simultaneously and/or sequentially. The multiple segments can comprise overlapping and/or non-overlapping borders.

Device 100 is configured to operably attach to console 200. In some embodiments, device 100 attaches directly to console 200. In other embodiments, attachment assembly 300 is positioned and operably attached between device 100 and console 200, such as to transfer materials (such as injectate 221, agent 420, hydraulic and/or pneumatic fluid, ablative fluids and/or other fluids), energy (such as ablative fluids and/or energy), and/or data between device 100 and console 200. Attachment assembly 300 comprises end 301 which attaches to device 100 via connector 103 of handle 102. Attachment assembly 300 further comprises end 302 which attaches to console 200 via connector 203 of console 200. Conduits 311 of attachment assembly 300 operably attach conduits 111 of device 100 to associated conduits 211 of console 200. Attachment assembly 300 can comprise a cassette configuration configured to operably attach to console 200. Attachment assembly 300 can comprise one or more flexible portions (e.g. coiled tubes and/or filaments) that allow movement of device 100 relative to console 200, such as to extend device 100 away from console 200 and toward a table onto which a patient is positioned. Attachment assembly 300 can comprise one or more functional elements, functional element 309 shown, such as an array of functional elements 309, each positioned proximate a conduit 311. Each functional element 309 can comprise a sensor, transducer and/or other functional element as described in detail herein.

Console 200 is configured to operably control and/or otherwise interface with device 100. In some embodiments, console 200 comprises one or more pumping assemblies, assembly 225 (four shown in FIG. 9), which can each be attached to a reservoir, reservoir 220 (four shown in FIG. 9) via one or more conduits 212. Each reservoir 220 can be constructed and arranged to store and supply fluids to device 100 and/or to extract fluids from device 100, such as is described herein in reference to system 10 of FIG. 1. An ablative fluid, a neutralizing fluid, agent 420 and/or injectate 221 can be placed or otherwise positioned within one or more reservoirs 220, such as to be transported by one or more pumping assemblies 225 into one or more conduits 111 of device 100 (e.g. via conduits 211 of console 200 and optionally via conduits 311 of connecting assembly 300). In some embodiments, console 200 is constructed and arranged to deliver a neutralizing fluid (e.g. a cooling fluid or warming fluid contained within a reservoir 220), then an ablative fluid (e.g. a hot fluid and/or a cryogenic fluid, respectively, contained within one or more reservoirs 220). In these embodiments, console 200 can be further constructed and arranged to subsequently deliver (i.e. after the ablation step), the same or a different neutralizing fluid (e.g. a cooling or warming fluid contained within a reservoir 200). In some embodiments, a first reservoir 220 provides an ablative fluid comprising a hot fluid at a temperature above 44° C., such as above 65° C., above 75° C., above 85° C. or above 95° C., and a second reservoir 220 provides a neutralizing fluid comprising a cooling fluid below 37° C., such as below 20° C. or below 15° C. In some embodiments, second reservoir 220 provides a neutralizing fluid comprising a fluid at room temperature. In some embodiments, a first reservoir 220 provides an ablative fluid comprising a cryogenic fluid, and a second reservoir 220 provides a neutralizing fluid comprising a warming fluid at or above 37° C.

Alternatively or additionally, console 200 can be configured to provide RF and/or light energy to functional assembly 130 to ablate or otherwise treat tissue, and a cooling step can be performed (e.g. via a neutralizing fluid provided by a reservoir 220 comprising fluid below 37° C.) prior to and/or after the delivery of the RF and/or light energy. In some embodiments, system 10 comprises two return paths, one for recovery of ablative fluid (e.g. hot fluid), and one for recovery of neutralizing fluid (e.g. cooling fluid), such as via separate conduits 111, 311 and/or 211. In these embodiments, two separate pumping assemblies 225 can be fluidly attached to the separate return paths.

Console 200 comprises one or more console settings 201 that can be varied, such as a change made manually (e.g. by a clinician or other operator of system 10), and/or automatically by system 10. Console 200 can comprise a central processing unit, microcontroller, and/or other controller, controller 250 shown. Controller 250 can comprise one or more signal processors, such as signal processor 252 shown. Signal processor 252 can be configured to analyze one or more sensor signals, such as to modify one or more settings 201 of console 200. Controller 250 and/or signal processor 252 can comprise one or more algorithms, algorithm 251, which can be configured to perform one or more mathematical or other functions, such as to compare one or more sensor signals (e.g. compare the signal itself or a mathematical derivation of the signal) to a threshold. Console settings 201 can comprise one or more parameters (e.g. system parameters as also referred to herein) of device 100, console 200 and/or any component of system 10. Console settings 201 can comprise one or more parameters selected from the group consisting of: delivery rate of fluid into functional assembly 130; withdrawal rate of fluid from functional assembly 130; delivery rate of fluid into tissue; rate of energy delivered into tissue; peak energy level delivered into tissue; average energy delivery rate delivered into tissue; amount of energy delivered into tissue during a time period; temperature of an ablative fluid (e.g. temperature of an ablative fluid in reservoir 220, console 200, functional assembly 130 and/or device 100); temperature of a neutralizing fluid (e.g. temperature of a neutralizing fluid in reservoir 220, console 200, functional assembly 130 and/or device 100); temperature of functional assembly 130; pressure of functional assembly 130; pressure of fluid delivered into functional assembly 130; pressure of fluid delivered into tissue; duration of energy delivery; time of energy delivery (e.g. time of day of or relative time compared to another step); translation rate such as translation rate of a functional assembly 130; rotation rate such as rotation rate of a functional assembly 130; a flow rate; a recirculation rate; a heating rate or temperature; a cooling rate or temperature; a sampling rate (e.g. a sampling rate of a sensor); and combinations of two or more of these. In some embodiments, one or more console settings 201 comprise a setting related to a system 10 parameter selected from the group consisting of: pressure and/or volume of a fluid delivered to shaft 110 to change the stiffness of shaft 110 (e.g. to modify pushability and/or trackability of shaft 110); pressure and/or volume of a fluid delivered to and/or extracted from functional assembly 130 for inflation and/or deflation (e.g. to obtain apposition of ports 137 and/or to anchor functional assembly 130 in the intestine); pressure and/or volume of a fluid delivered to one or more conduits 111, each configured as a fluid transport tube to provide an injectate, injectate 221, to one or more fluid delivery elements 139*c*, such as to advance and/or retract one or more fluid delivery elements 139*c* and/or to deliver injectate 221 into tissue (e.g. submucosal tissue); pressure and/or volume of a fluid within one or more conduits 111, each configured to provide a vacuum to one or more ports 137 to engage the one or more ports 137 with tissue and/or to cause a fluid delivery element 139*c* to engage (e.g. penetrate) tissue; a force used to advance and/or retract one or more conduits 111 and/or one or more fluid delivery elements 139*c*; and combinations of two or more of these. In some embodiments, one or more console settings 201 comprise a setting related to a system 10 parameter selected from the group consisting of: temperature, flow rate, pressure and/or duration of fluid delivered to device 100 and/or functional assembly 130; temperature, flow rate, pressure and/or duration of fluid contained within functional assembly 130 and/or circulating loops (e.g. conduits 111, 211, and/or 311) of system 10; and combinations of two or more of these. System 10 can be configured to adjust one or more console settings 201 based on one or more signals produced by one or more sensors of system 10. Based on the one or more sensor signals, system 10 can be configured to modify a console setting 201 to cause: stopping delivery of fluid and/or energy to and/or by functional assembly 130; delivering additional fluid into functional assembly 130 and/or into tissue (e.g. adjust fluid delivery rate); delivering neutralizing and/or other additional fluid into functional assembly 130 and/or into tissue; adjusting the pressure of functional assembly 130; adjusting the volume of functional assembly 130; and combinations of two or more of these. In some embodiments, algorithm 251 is configured to determine an injectate delivery parameter, such as the amount (e.g. volume and/or mass) of injectate 221 to be delivered by device 100.

In some embodiments, system 10 adjusts, via algorithm 251, a functional assembly 130 parameter based on a signal of a sensor of system 10. In these embodiments, a functional assembly 130 parameter can be adjusted during performance of a procedural step, such as an ablation step and/or a tissue expansion step. The functional assembly 130 parameter adjusted can comprise a parameter selected from the group consisting of: volume of functional assembly 130; diameter of functional assembly 130; pressure of functional assembly 130; force applied to tissue by functional assembly 130; and combinations of two or more of these. The functional assembly 130 parameter can be adjusted to prevent excessive force being applied to the intestinal wall or to maintain a minimum apposition level of functional assembly 130 with tissue of the intestine.

In some embodiments, algorithm 251 is configured to determine an expanded size for functional assembly 130, such as when system 10 comprises multiple devices 100 with different expanded diameters for functional assembly 130 and/or when the expanded diameter of functional assembly 130 can be varied by system 10 (e.g. by varying pressure and/or volume of fluid within functional assembly 130). In these embodiments, algorithm 251 can comprise a bias, such as a bias which tends toward lower diameters (e.g. rounds down to the next smaller size of a functional assembly 130 available after calculating a target value). In some embodiments, algorithm 251 is configured to select one device 100 for use in a patient, by selecting one from a kit of multiple devices 100 comprising one or more different parameters (e.g. one or more functional assembly 130 parameters). In these embodiments, algorithm 251 can also include a bias, such as a bias toward choosing a smaller functional assembly 130 (e.g. smaller length or smaller expanded diameter).

In some embodiments, algorithm 251 comprises an image analysis algorithm configured to analyze one or more patient and/or system 10 images. For example, a tissue location can be analyzed prior to, during and/or after a desufflation (e.g. aspiration) step, such as to confirm adequate apposition of a functional assembly 130 with tissue of an axial segment of tubular tissue (e.g. an axial segment of the intestine). Algorithm 251 can comprise one or more image analysis algorithms configured to assess various conditions including but not limited to: apposition of functional assembly 130 with tissue (e.g. intestinal wall tissue); effectiveness of a desufflation procedure; effectiveness of an insufflation procedure; sufficiency of a tissue expansion procedure; sufficiency of a tissue ablation procedure; and combinations of two or more of these.

In some embodiments, algorithm 251 can be configured to operatively adjust one or more operating parameters (generally console settings 201) of console 200 and/or device 100, such as an algorithm 251 that analyzes data provided by one or more sensors of system 10. Algorithm 251 can be configured to correlate a signal received by one or more sensors of system 10 positioned at a first location, to a parameter of system 10 or the patient at a second location distant from the first location (e.g. a second location proximal or distal to the first location). For example, a measured temperature or pressure within console 200 (e.g. via functional element 229*a* or 229*b*), connecting assembly 300 (e.g. via functional element 309), and/or device 100 (e.g. via functional element 119), can provide a signal related to a parameter at a remote location, such as a parameter of functional assembly 130 or the patient (e.g. a physiologic parameter at a location within the patient). Algorithm 251 can be configured to analyze a signal received from a first location and produce parameter information correlating to a second location.

In some embodiments, algorithm 251 comprises a pressure algorithm configured to modify a system parameter based on a measured pressure, such as a modification made based on the pressure within a luminal segment of the intestine in which functional assembly 130 is positioned or otherwise proximate (e.g. as measured or otherwise determined by analysis of a signal provided by a sensor of device 100, body introduction device 50 or another sensor of system 10 as described herein). In these embodiments, system 10 can be configured to modify the volume of fluid within functional assembly 130 and/or modify the pressure of functional assembly 130 based on the luminal segment pressure.

In some embodiments, system 10 is constructed and arranged to produce an image (e.g. an image produced by an imaging device and/or other sensor of the present inventive concepts). Algorithm 251 can be configured to analyze one or more images of tissue that are visualized through one or more portions of functional assembly 130, such as to determine the level of tissue expansion and/or a level of tissue ablation, such as to assess completion adequacy of one or more steps of a medical procedure.

In some embodiments, console 200 comprises multiple functional elements 209 (four shown in FIG. 9), such as a first functional element 209 comprising a heating element and a second functional element 209 comprising a cooling element. In these embodiments, connecting assembly 300 can comprise a tubeset configured to be engaged with console 200 to allow the first functional element 209 to transfer heat into fluid within connecting assembly 300 and the second functional element 209 to extract heat from (i.e. cool) fluid within connecting assembly 300. In these embodiments, system 10 can avoid the need for heated and/or cooled reservoirs 220, such as when console 200 further comprises a disposable fluid supply fluidly attached to connecting assembly 300. Connecting assembly 300 can comprise a reusable tubing set. Connecting assembly 300 can comprise a tubing set comprising multiple lumens (e.g. multiple tubes each with one or more lumens, or a single tube with multiple lumens), such as at least a first lumen configured to deliver inflation fluid (e.g. deliver inflation fluid to functional assembly 130 to perform a tissue expansion procedure and/or a tissue sizing procedure), and at least two lumens configured to deliver a recirculating fluid (e.g. to recirculate ablative fluid and/or neutralizing fluid within functional assembly 130 during a tissue ablation procedure).

Console 200 can comprise a user interface, user interface 205 shown, which can deliver commands to controller 250 and receive information (e.g. to be displayed) from controller 250. In some embodiments, console 200 comprises an energy delivery unit, EDU 260, such as an energy delivery unit configured to provide one or more of: thermal energy such as heat energy or cryogenic energy; electromagnetic energy such as radiofrequency (RF) energy; light energy such as light energy provided by a laser; sound energy such as subsonic energy or ultrasonic energy; chemical energy (e.g. a chemically ablative substance); and combinations of two or more of these. EDU 260 can be of similar construction and arrangement as EDU 260 described herein in reference to FIG. 1. Console 200 can further comprise conduits 211 which can be operably connected to device 100 (e.g. operably connected to one or more conduits 111 or other components of device 100). Conduits 211 can comprise one or more fluid transport tubes fluidly attached to pumping assemblies 225 and/or any filament bundle operably attached to controller 250 and comprising one or more filaments selected from the group consisting of: a tube comprising a lumen; a tube comprising a translatable rod; a hydraulic tube; a pneumatic tube; a tube configured to provide a vacuum (e.g. provide a vacuum to port 137); a lumen of shaft 110; an inflation lumen; a fluid delivery lumen; a wire such as an electrically conductive wire; a linkage; a rod; a flexible filament; an optical fiber; and combinations of two or more of these. Controller 250 can be operably connected to one or more of reservoirs 220, pumping assemblies 225 and/or user interface 205 via a bus, bus 213 shown. Bus 213 can comprise one or more wires, optical fibers, and/or other conduits configured to provide power, transmit data and/or receive data.

In some embodiments, console 200 is configured to operably expand functional assembly 130, such as with a liquid, gas, and/or other fluid provided by a reservoir 220 and propelled by an associated pumping assembly 225. In some embodiments, console 200 is configured to deliver fluid to tissue via one or more fluid delivery elements 139c, such as with a fluid (e.g. injectate 221) provided by a reservoir 220 and propelled by an associated pumping assembly 225. In some embodiments, console 200 is configured to deliver ablative fluid to functional assembly 130, such as ablative fluid provided by a reservoir 220 and propelled by an associated pumping assembly 225. In these embodiments, ablative fluid can be recirculated to and from functional assembly 130 by console 200. In some embodiments, console 200 is configured to deliver energy, such as electromagnetic or other energy, to functional assembly 130, such as via controller 250. Each of these embodiments is described in detail herein in reference to system 10 of FIG. 1.

One or more reservoirs 220 can each comprise one more functional elements 229a and/or one or more pumping assemblies 225 can each comprise one or functional elements 229b. Each functional element 229a and/or 229b (singly or collectively functional element 229) can comprise a sensor, a transducer, and/or other functional element. In some embodiments, one or more functional elements 229 comprise a heating element or a chilling element configured to heat or chill fluid within a reservoir 220 and/or a pumping assembly 225. Alternatively or additionally, one or more functional elements 229 comprise a sensor, such as a temperature sensor, pressure sensor and/or a flow rate sensor configured to measure the temperature, pressure and/or flow rate, respectively, of fluid within, flowing into, and/or flowing out of a reservoir 220 and/or pumping assembly 225.

In some embodiments, console 200 operably attaches to and controls multiple devices 100, such as two or more devices 100 of similar construction and arrangement to devices 100, 20, 30 and/or 40 described herein in reference to FIG. 1.

As described herein, system 10 can include injectate 221. In some embodiments, injectate 221 comprises a material selected from the group consisting of: water; saline; a gel; a hydrogel; a protein hydrogel; a cross-linked hydrogel; a cross-linked polyalkyleneimine hydrogel; autologous fat; collagen; bovine collagen; human cadaveric dermis; hyaluronic acid; calcium hydroxylapatite; polylactic acid; semi-permanent PMMA; dermal filler; gelatin; mesna (sodium 2-sulfanylethanesulfonate); and combinations of two or more of these. In some embodiments, injectate 221 comprises beads (e.g. pyrolytic carbon-coated beads) suspended in a carrier (e.g. a water-based carrier gel). In some embodiments, injectate 221 comprises a solid silicone elastomer (e.g. heat-vulcanized polydimethylsiloxane) suspended in a carrier, such as a bio-excretable polyvinylpyrrolidone (PVP) carrier gel. In some embodiments, injectate 221 has an adjustable degradation rate, such as an injectate 221 comprising one or more cross linkers in combination with polyalkylene imines at specific concentrations that result in hydrogels with adjustable degradation properties. In some embodiments, injectate 221 and/or agent 420 comprises living cells, such as living cells injected into the mucosa or submucosa of the intestine to provide a therapeutic benefit.

In some embodiments, injectate 221 comprises a visualizable and/or otherwise detectable (e.g. magnetic) material (e.g. in addition to one or more materials of above) selected from the group consisting of: a dye; a visible dye; indigo carmine; methylene blue; India ink; SPOT™ dye; a visualizable media; radiopaque material; radiopaque powder; tantalum; tantalum powder; ultrasonically reflective material; magnetic material; ferrous material; and combinations of two or more of these.

In some embodiments, injectate 221 comprises a material selected from the group consisting of: a peptide polymer (e.g. a peptide polymer configured to stimulate fibroblasts to produce collagen); polylactic acid; polymethylmethacrylate (PMMA); a hydrogel; ethylene vinyl alcohol (EVOH); a material configured to polymerize EVOH; dimethyl sulfoxide (DMSO); saline; material harvested from a mammalian body; autologous material; fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; a sclerosant; an adhesive; cyanoacrylate; a pharmaceutical agent; a visualizable material; a radiopaque material; a visible dye; ultrasonically reflective material; and combinations of two or more of these. As described herein, in some embodiments a volume of injectate 221 is delivered into tissue to create a therapeutic restriction (e.g. a therapeutic restriction with an axial length between 1 mm and 20 mm), as described herein, or as is described in applicant's co-pending U.S. patent application Ser. No. 17/095,108, entitled "Systems, Devices and Methods for the Creation of a Therapeutic Restriction in the Gastrointestinal Tract", filed Nov. 11, 2020. In some embodiments, a volume of injectate 221 is delivered into tissue to create a safety margin of tissue that is created (e.g. an expanded tissue layer is created) prior to an ablation procedure, as is described herein.

In some embodiments, injectate 221 comprises a fluorescent-labeled material or other biomarker configured to identify the presence of a biological substance, such as to identify diseased tissue and/or other tissue for treatment by functional assembly 130 (e.g. to identify target tissue). For example, injectate 221 can comprise a material configured to be identified by imaging device 55 (e.g. identify a visualizable change to injectate 221 that occurs after contacting one or more biological substances). In these embodiments, imaging device 55 can comprise a molecular imaging device, such as when imaging device 55 comprises a molecular imaging probe and injectate 221 comprises an associated molecular imaging contrast agent. In these embodiments, injectate 221 can be configured to identify diseased tissue and/or to identify a particular level of one or more of pH, tissue oxygenation, blood flow, and the like. Injectate 221 can be configured to be delivered onto the surface of an intestinal lumen or other luminal surface tissue, and/or to be delivered into tissue (i.e. beneath the surface).

In some embodiments, injectate 221 comprises a material selected from the group consisting of autologous fat; collagen; bovine collagen; human cadaveric dermis; hyaluronic acid; calcium hydroxylapatite; polylactic acid; semi-permanent PMMA; dermal filler; gelatin; and combinations of two or more of these. In some embodiments, injectate 221 comprises a material whose viscosity changes (e.g. increases) after delivery into tissue, such as a fluid whose viscosity increases as it is heated to body temperature.

System 10 can be constructed and arranged to deliver injectate 221 into tissue to deliver a bolus of medication and/or to create a drug or other agent depot within tissue of the patient, such as within mucosal tissue and/or submucosal tissue of the intestine. In some embodiments, an injectate 221 positioned within tissue is activated based on one or more signals produced by a sensor, such as a bioactive glucose sensor that responds to the detection of an analyte and leads to (e.g. via one or more components of system 10) release or other activation of injectate 221. For example, injectate 221 can comprise an anti-diabetic agent, such as insulin, and a sensor (e.g. implant 192 configured as a sensor) can comprise a glucose sensor that detects a glucose change, such as the higher glucose levels that occur after a meal. Injectate 221 can comprise a drug or other agent selected from the group consisting of: a steroid; an anti-inflammatory agent; a chemotherapeutic; a proton pump inhibitor; a sclerosant agent; a differentiation factor such as trans-retinoic acid; an anti-hyperglycemic agent such as GLP-1 analogue or others; an anti-obesity agent; an anti-hypertensive agent; an anti-cholesterol agent such as a statin or others; and combinations of two or more of these. In some embodiments, injectate 221 comprises a steroid or other anti-inflammatory agent delivered to a therapeutic restriction of the present inventive concepts (e.g. delivered into an existing restriction or to create a restriction). In some embodiments, injectate 221 comprises one or more steroids and/or other anti-inflammatory agents delivered to the site of chronic inflammation, such as a site of ulcerative colitis or Crohn's disease. In some embodiments, injectate 221 comprises one or more steroids or other anti-inflammatory agents delivered at the site of celiac disease (e.g. the proximal small intestine) and/or otherwise delivered to treat celiac disease. In some embodiments, injectate 221 comprises one or more chemotherapeutic agents delivered to the site of a cancerous or pre-cancerous lesion.

Injectate 221 can be injected into tissue in a single procedure or multiple procedures. System 10 can be configured to determine an injectate 221 delivery parameter (e.g. determined by algorithm 251), such as by performing an analysis based on a patient demographic parameter and/or a patient physiologic parameter, such as age, weight, HbA1c level and cholesterol level. The injectate delivery parameter can comprise a parameter selected from the group consisting of: volume of injectate 221 delivered; length and/or area of a tissue layer receiving injectate 221; type of material included in injectate 221; viscosity of injectate 221; titration result of injectate 221; and combinations of two or more of these.

As described herein, system 10 can include agent 420, which can include one or more agents delivered to the patient (e.g. orally, transdermally, via injection, or otherwise). In some embodiments, agent 420 comprises a material selected from the group consisting of: anti-peristaltic agent, such as L-menthol (i.e. oil of peppermint); glucagon; buscopan; hycosine; somatostatin; a diabetic medication; an analgesic agent; an opioid agent; a chemotherapeutic agent; a hormone; and combinations of two or more of these.

In some embodiments, agent 420 comprises cells delivered into the intestine, such as living cells delivered into intestinal mucosa or submucosa, such as via a fluid delivery element 139*c* or otherwise.

As described herein, system 10 can comprise one or more sensors, transducers and/or other functional elements, such as functional element 109, functional element 119 and/or functional element 139 (e.g. 139*a*, 139*b* and/or 139*c*) of device 100 and/or functional element 209 and/or functional element 229 (e.g. 229*a* and/or 229*b*) of console 200. In some embodiments, system 10 comprises connecting assembly 300 which can include one or more functional elements 309.

In some embodiments, one or more functional elements 109, 119, 139, 209, 229 and/or 309 comprise a transducer selected from the group consisting of: an energy converting transducer; a heating element; a cooling element such as a Peltier cooling element; a drug delivery element such as an iontophoretic drug delivery element; a magnetic transducer; a magnetic field generator; a sound generator; an ultrasound wave generator such as a piezo crystal; a light producing element such as a visible and/or infrared light emitting diode; a motor; a pressure transducer; a vibrational transducer; a solenoid; a fluid agitating element; and combinations of two or more of these.

In some embodiments, one or more functional elements 109, 119, 139, 209, 229 and/or 309 comprise a visualizable element, such as an element selected from the group consisting of: a radiopaque marker; an ultrasonically visible marker; an infrared marker; a marker visualizable by a camera such as an endoscopic camera; a marker visualizable by an MRI; a chemical marker; and combinations of two or more of these.

In some embodiments, one or more of functional elements 109, 119, 139, 209, 229 and/or 309 comprise a sensor configured to produce a signal, the sensor selected from the group consisting of: physiologic sensor; blood glucose sensor; blood gas sensor; blood sensor; respiration sensor; EKG sensor; EEG sensor; neuronal activity sensor; blood pressure sensor; flow sensor such as a flow rate sensor; volume sensor (e.g. a volume sensor used to detect a volume of injectate 221 not delivered into tissue); pressure sensor; force sensor; sound sensor such as an ultrasound sensor; electromagnetic sensor such as an electromagnetic field sensor or an electrode; gas bubble detector such as an ultrasonic gas bubble detector; strain gauge; magnetic sensor; ultrasonic sensor; optical sensor such as a light sensor; chemical sensor; visual sensor such as a camera; temperature sensor such as a thermocouple, thermistor, resistance temperature detector or optical temperature sensor; impedance sensor such as a tissue impedance sensor; and combinations of two or more of these. Each sensor can be configured to produce a signal that directly correlates to or is otherwise related to a patient parameter or a system 10 parameter. One or more console settings 201 can be manually adjusted (e.g. by a clinician or other operator of system 10) and/or automatically (e.g. by algorithm 251 of system 10) based on the sensor signal.

In some embodiments, one or more of functional elements 109, 119, 139, 209, 229 and/or 309 comprise a pressure sensor that produces a signal related to one or more of: pressure within functional assembly 130; the level of apposition of functional assembly 130 with the intestine; the diameter of the intestine proximate functional assembly 130; muscular contraction of the intestine; pressure within a reservoir 220; pressure within connecting assembly 300; pressure within a lumen of shaft 110; and combinations of two or more of these. One or more console settings 201 can be adjusted (e.g. manually or automatically) based on the pressure sensor signal. In some embodiments, a pressure sensor produces a signal related to the pressure within functional assembly 130, console 200 delivers and/or extracts fluids to and/or from functional assembly 130 via one or more conduits 111, and console 200 adjusts the volume of functional assembly 130 to maintain pressure in functional assembly 130 below a threshold.

In some embodiments, one or more of functional elements 109, 119, 139, 209, 229 and/or 309 comprise a temperature sensor that produces a signal related to one or more of: temperature of fluid in console 200 (e.g. in one or more reservoirs 220); temperature of elongate shaft 110; temperature of fluid within elongate shaft 110; temperature of functional assembly 130; temperature of fluid within functional assembly 130; temperature of an ablative fluid; temperature of a neutralizing fluid; temperature of tissue proximate the functional assembly; temperature of target tissue; temperature of non-target tissue; and combinations of two or more of these. One or more console settings 201 can be adjusted (e.g. manually or automatically) based on the temperature sensor signal.

In some embodiments, system 10 comprises a sensor (e.g. a functional element 109, 119, 139, 209, 229 and/or 309 comprising a sensor) configured to detect a parameter related to a level of treatment of tissue, such as a parameter selected from the group consisting of: color, density and/or saturation of tissue (e.g. a color change to tissue that occurs during ablation or to an injectate 221 present in the tissue during ablation or other treatment); temperature of local tissue and/or temperature of other body tissue; texture, length and/or diameter of villi or other mucosal feature (e.g. as detected via a camera-based sensor, such as when ablation causes a blunting and/or drooping of villi or other intestinal tissue); electrical resistance, impedance and/or capacitance of tissue (e.g. as altered by ablation of tissue); pressure and/or force of peristaltic contractions (e.g. as altered by ablation of tissue); compliance of tissue and/or the entire duodenum in radial and/or axial directions (e.g. as altered by ablation of tissue); chemical composition of film adhered to mucosal tissue (e.g. as altered by ablation); types, quantities and/or locations of bacterial colonies present (e.g. as altered by ablation); and combinations of two or more of these.

In some embodiments, system 10 comprises a sensor (e.g. a functional element 109, 119, 139, 209, 229 and/or 309 comprising a sensor) configured to detect a parameter related to a level of tissue expansion, such as a parameter selected from the group consisting of: color, density and/or saturation related to injected dye or particles which alter tissue appearance (e.g. as determined via a camera-based sensor); temperature of tissue (e.g. that can be altered briefly due to delivery of injectate 221 and/or inflammation response due to injectate 221 delivery); texture, length and/or diameter of villi or mucosal features (e.g. as determined via a camera-based sensor) such as spacing between villi or other intestinal tissue features that can change (e.g. increased spacing, disappearance or reduction of plicae, blebs of injectate 221 present) due to submucosal tissue expansion; electrical resistance, impedance and/or capacitance of tissue (e.g. as altered by delivery of injectate 221); pressure and/or force of peristaltic contractions (e.g. as altered by delivery of injectate 221); compliance of tissue and/or the entire duodenum in radial and/or axial directions (e.g. as altered by injectate 221, such as to make tissue more compliant until the muscularis layer is contacted); chemical composition of film adhered to mucosa (e.g. as altered by injectate 221, such as when injectate 221 creates a biologic response that is detectable); types, quantities and/or locations of bacterial colonies present; and combinations of two or more of these.

In some embodiments, system 10 comprises a sensor (e.g. a functional element 109, 119, 139, 209, 229 and/or 309 comprising a sensor) configured to assess engagement of port 137 with tissue (e.g. to determine if adequate engagement is present during a tissue expansion or tissue ablation step in which vacuum is applied to port 137 to engage port 137 with tissue). In some embodiments, a sensor is positioned to detect injectate in a conduit 111 of device 100 in which the vacuum is applied. The detector can comprise an optical sensor, and/or a window which is visualizable by an operator (e.g. to see injectate that is recovered), such as when the injectate comprises visible material.

In some embodiments, one or more functional elements 109, 119, 139, 209, 229 and/or 309 comprises one or more temperature sensors that produces a signal related to a first temperature representing the temperature of ablative fluid delivered to functional assembly 130 and a second temperature related to the temperature of fluid extracted from functional assembly 130. In these embodiments, system 10 can be configured to assess (e.g. via algorithm 251) the effect (e.g. quantity) of tissue treated (e.g. depth of tissue ablated), such as by analyzing the first temperature and the second temperature (e.g. a comparison of the two). In some embodiments, the first and/or second temperature is measured by one or more sensors of connecting assembly 300 (e.g. two or more functional elements 309 comprising thermistors or other temperature sensors) and/or one or more sensors of device 100 (e.g. two or more functional elements 109, 119 and/or 139 comprising thermistors or other temperature sensors).

In some embodiments, one or more of functional elements 109, 119, 139, 209, 229 and/or 309 comprise a sensor configured to provide a signal related to lumen diameter information. In these embodiments, the sensor can comprise a sensor selected from the group consisting of: pressure sensor; optical sensor; sound sensor; ultrasound sensor; strain gauge; electromagnetic sensor; an imaging device such as a camera; and combinations of two or more of these. One or more console settings 201 can be adjusted (e.g. manually or automatically) based on the lumen diameter information.

In some embodiments, one or more of functional elements 109, 119, 139, 209, 229 and/or 309 comprise a sensor including an imaging device configured to provide a signal related to image information. The imaging device can comprise a device selected from the group consisting of: visible light camera; infrared camera; endoscope camera; MRI; Ct Scanner; X-ray camera; PET Scanner; ultrasound imaging device; and combinations of two or more of these. In these embodiments, controller 250 or another assembly of system 10 can comprise signal processor 252 and/or algorithm 251, each of which can be configured to analyze the image information provided by the imaging device. One or more console settings 201 can be adjusted (e.g. manually or automatically) based on the image information. Based on the image information, system 10 can be configured to modify a console setting 201 to cause an event selected from the group consisting of: stopping delivery of fluid and/or energy to functional assembly 130; delivering additional fluid into functional assembly 130 and/or into tissue; delivering neutralizing fluid into functional assembly 130 and/or into tissue; adjusting the pressure of functional assembly 130; adjusting the volume of functional assembly 130; and combinations of two or more of these.

Shaft 110 of device 100 can comprise one or more coatings, coating 118, along all or a portion of its outer and/or inner surfaces. In some embodiments, coating 118 is positioned on at least a portion of the outer surface of shaft 110, and the coating 118 is configured to prevent or otherwise reduce inadvertent translation of device 100 through the intestine (e.g. an anti-migration coating configured to reduce undesired translation and/or rotation of device 100). Alternatively or additionally (e.g. on a different portion), coating 118 can comprise a lubricous coating. In some embodiments, coating 118 is positioned on one or more lumens of shaft 110, such as a lubricous coating configured to assist in the translation of one or more filaments within the lumen. In some embodiments, coating 118 comprises a coating positioned on at least a portion of shaft 110 and selected from the group consisting of: a hydrophilic coating (e.g. to improve lubricity); a coating comprising bumps (e.g. atraumatic projections configured to roughen a surface to reduce friction); a coating comprising a surface exposed to grit blasting (e.g. to roughen a surface to reduce friction); an insulative coating: parylene; PTFE; PEEK; a coating comprising a colorant (e.g. to improve or otherwise improve visibility of shaft 110 in-vivo); and combinations of two or more of these. In some embodiments, coating 118 comprises a coating positioned on at least a portion of functional assembly 130 (e.g. on at least a portion of a balloon 136) and selected from the group consisting of: a lubricous coating; a surface roughening coating; a silicone coating; an insulative coating; and combinations of two or more of these.

In some embodiments, multiple conduits 111 are in fluid communication with functional assembly 130 (e.g. to simultaneously or sequentially inflate and/or deflate functional assembly 130) and/or port 137 (e.g. to simultaneously or sequentially provide a vacuum to port 137). In these embodiments, simultaneous and/or redundant delivery or extraction of fluids (e.g. application of a vacuum) can be initiated based on the signal provided by one or more sensors of system 10. For example, if a sensor detects a first conduit 111 is fully or partially occluded, the second conduit 111 can be used to additionally or alternatively deliver and/or extract fluids.

In some embodiments, system 10 is configured to maintain the pressure of functional assembly 130 relative to a threshold (e.g. pressure is maintained below a pressure threshold, above a pressure threshold, and/or within a threshold comprising a range of pressures), such as during treatment and/or diagnosis of target tissue of the intestine (e.g. during a tissue expansion and/or tissue ablation procedure). Functional assembly 130 can comprise a balloon 136 comprising a compliant balloon; a non-compliant balloon; a pressure-thresholded balloon; and/or a balloon comprising compliant and non-compliant portions, as described herein. Pressure can be maintained at a particular pressure or within a particular range of pressures by monitoring one or more sensors of system 10, such as sensor 139b and/or a sensor-based functional element 119, 109, 209 and/or 229. A lower pressure threshold can comprise a pressure of 0.3 psi, 0.5 psi or 0.7 psi. A lower pressure threshold can be selected to ensure sufficient contact of functional assembly 130 with tissue. An upper pressure threshold can comprise a pressure of 1.0 psi, 1.2 psi, 2.5 psi or 4.0 psi. An upper pressure threshold can be selected to avoid damage to tissue, such as damage to an outer layer of intestinal tissue (e.g. a serosal layer of the intestine). Pressure can be monitored such that console 200 can modulate or otherwise control one or more inflow and/or outflow rates of fluid delivered to and/or extracted from functional assembly 130. Pressure can be monitored to maintain flow rates to or from functional assembly 130 to a minimum rate of at least 250 ml/min, 500 ml/min, 700 ml/min or 750 ml/min. In some embodiments, pressure is determined by a sensor positioned outside of balloon 136, such as when pressure is maintained in functional assembly within a narrow range of pressures, such as at a pressure of between 1.05 psi and 0.55 psi. In these embodiments, a luminal sizing step can be avoided. In some embodiments, system 10 comprises one or more devices 100 and/or one or more functional assemblies 130, such as to provide an array of functional assemblies 130 with different lengths and/or diameters. In these embodiments, the upper and/or lower pressure thresholds can be independent of functional assembly 130 size.

In some embodiments, conduits 111 comprise an inflow tube and an outflow tube fluidly connected to functional assembly 130. Fluid can be delivered to functional assembly 130 by console 200 via one or more conduits 111 at various flow rates, such as flow rates up to 500 ml/min, 1000 ml/min, 1500 ml/min, 2000 ml/min and/or 2500 ml/min. Fluid can be extracted from functional assembly 130 by console 200 via one or more conduits 111 at various flow rates, such as flow rates up to 500 ml/min, 750 ml/min, or 1000 ml/min.

In some embodiments, treatment element 139a can comprise fluid at a sufficiently high temperature to ablate tissue (such as liquid above 60° C. or steam). Delivery of superheated fluid through a conduit 111 can be performed, such as when functional element 119 comprises an orifice configured to cause the superheated fluid to boil upon entering functional assembly 130, providing steam at 100° C. Delivery of cooled fluids through a conduit 111 can be performed. In some embodiments, a fluid (cooled or otherwise) is introduced through a conduit 111 and through a functional element 119 comprising a valve, such that expansion of the fluid into functional assembly 130 results in a cooling effect.

In some embodiments, functional assembly 130 is constructed and arranged to both expand tissue (e.g. expand submucosal tissue) and ablate target tissue (e.g. treat duodenal mucosal tissue), such as is described herein in reference to multi-function device 40 of FIG. 1. For example, functional assembly 130 can comprise fluid delivery element 139c which can be positioned to deliver fluid into tissue that has been drawn into (e.g. upon application of a vacuum) port 137, to expand one or more layers of tissue (e.g. one or more layers of submucosal tissue). Functional assembly 130 can further comprise treatment element 139a which can comprise ablative fluid which can be introduced into functional assembly 130 and/or an energy delivery element configured to deliver energy to tissue (e.g. RF energy, light energy, sound energy, chemical energy, thermal energy and/or electromagnetic energy), each configured to perform a therapeutic treatment on target tissue.

In some embodiments, system 10 and device 100 are configured to both expand tissue (e.g. expand submucosal tissue of the intestine) and treat target tissue (e.g. treat mucosal tissue of the intestine proximate the expanded submucosal tissue). Device 100 can comprise a single device 100 comprising one or more functional elements 139 configured to collectively expand tissue and treat target tissue, or a first device 100a configured to expand tissue and a second device 100b configured to treat target tissue. In these embodiments, injectate 221 can comprise a material configured to enhance or otherwise modify a target treatment step. For example, injectate 221 can comprise a conductive fluid (e.g. an electrically conductive fluid), such as saline configured to modify a subsequent target tissue treatment by treatment element 139a in which RF or other electrical energy is delivered to target tissue (e.g. when treatment element 139a comprises an array of electrodes). Similarly, injectate 221 can comprise a chromophore or other light absorbing material and/or a light scattering material configured to modify a subsequent target tissue treatment by treatment element 139a in which light energy is delivered to target tissue (e.g. when treatment element 139a comprises a lens, one or more conduits 111 comprise an optical fiber, and controller 250 comprises an energy delivery unit EDU 260 comprising a laser).

In some embodiments, system 10 includes one or more tools, tool 500 shown. Tool 500 can comprise a vacuum applying tool such as an endoscopic cap. Device 100 or a standard endoscopic needle device can inject a material into the wall of the duodenum while the endoscopic cap applies suction to the intestinal mucosa. A needle or other fluid delivery element of device 100 (e.g. fluid delivery element 139c) or a needle of a standard endoscopic needle device is delivered into intestinal tissue while the mucosa of the intestine is lifted by tool 500.

In some embodiments, tool 500 comprises an insufflation and/or desufflation tool, such as a catheter or other device comprising a port (e.g. a distal opening) for delivering and/or extracting fluids from the intestine. Tool 500 can be insertable through the working channel of an introduction device 50 (e.g. through an endoscope). Delivery of insufflation fluids can be performed to move tissue away from functional assembly 130 and/or move tissue away from one or more functional elements 139 or other parts of device 100. In some embodiments, insufflation is performed to stop or limit a transfer of energy to tissue (e.g. in an emergency or insufflation-controlled ablation step).

In some embodiments, tool 500, device 100, introduction device 50 and/or another component of system 10 comprises a pressure-neutralizing assembly constructed and arranged to modify the pressure within a luminal segment of the intestine (e.g. a luminal segment proximate functional assembly 130). In these embodiments, tool 500 and/or device 100 can comprise one or more openings or other elements configured as vents, such as to vent the luminal segment to room pressure (e.g. clinical procedure room pressure) or otherwise maintain the pressure in a segment of the intestine below a threshold. In some embodiments, introduction device 50 comprises an endoscope comprising a biopsy port configured to vent the luminal segment to room pressure. The pressure-neutralizing assembly can be configured to extract gas from the intestinal segment, and/or to maintain the pressure within the intestinal segment below a threshold. In some embodiments, venting is activated automatically, such as when a pressure (e.g. as measured by a sensor of the present inventive concepts) reaches a threshold (e.g. as determined by algorithm 251).

In some embodiments, tool 500 comprises a diagnostic tool, such as a diagnostic tool comprising a sensor. Tool 500 can be configured to perform a diagnostic test of the patient and/or a diagnostic test of all or a portion of system 10. Tool 500 can comprise a body-insertable tool. Tool 500 can be constructed and arranged to gather data (e.g. via an included sensor) related to a patient physiologic parameter selected from the group consisting of: blood pressure; heart rate; pulse distention; glucose level; blood glucose level; blood gas level; hormone level; GLP-1 level; GIP Level; EEG; LFP; respiration rate; breath distention; perspiration rate; temperature; gastric emptying rate; peristaltic frequency; peristaltic amplitude; and combinations of two or more of these.

Alternatively or additionally, tool 500 can comprise a tissue marking tool, such as a tissue marking tool configured to be deployed through introduction device 50 (e.g. an endoscope). In some embodiments, system 10 comprises marker 430, which can comprise a dye or other visualizable media configured to mark tissue (e.g. using a needle-based tool 500), and/or a visualizable temporary implant used to mark tissue, such as a small, temporary anchor configured to be attached to tissue by tool 500 and removed at the end of the procedure (e.g. by tool 500) or otherwise passed by the natural digestive process of the patient shortly after procedure completion. Tissue marker 430 can be deposited or deployed in reference to (e.g. to allow an operator to identify) non-target tissue (e.g. a marker positioned proximate the ampulla of Vater to be visualized by an operator to avoid damage to the ampulla of Vater), and/or to identify target tissue (e.g. tissue to be ablated). In some embodiments, tissue marker 430 is deposited or deployed in reference to tissue selected from the group consisting of: gastrointestinal adventitia; duodenal adventitia; the tunica serosa; the tunica muscularis; the outermost partial layer of the submucosa; ampulla of Vater; papilla; pancreas; bile duct; pylorus; and combinations of two or more of these.

In some embodiments, system 10 includes a tool 500 comprising a mucus removal assembly constructed and arranged to remove mucus from one or more intestinal wall locations (e.g. a full or partial circumferential segment of intestine), such as to remove mucus prior to a tissue treatment performed by functional assembly 130. Alternatively or additionally, functional assembly 130, one or more functional elements 139 and/or one or more other components of device 100 can be constructed and arranged to similarly remove mucus. In some embodiments, mucus is removed mechanically. Alternatively or additionally, mucus is removed by delivery (e.g. via one or more fluid delivery elements 139*c*) of agent 420 to a tissue surface (e.g. when agent 420 comprises a mucolytic agent).

In some embodiments, system 10 includes pressure neutralizing assembly 72, which can be constructed and arranged to monitor and/or adjust (e.g. automatically or semi-automatically) the pressure within a segment of the intestine, such as to allow one or more therapeutic or diagnostic procedures to be performed by functional assembly 130 at a particular pressure or within a particular range of pressures. Pressure neutralizing assembly 72 can be configured to deliver or extract fluids from a segment of the intestine, such as to perform an insufflation procedure, a desufflation procedure, or to otherwise modify the pressure within the segment of the intestine proximate functional assembly 130.

In some embodiments, system 10 comprises an implantable device, such as implant 192 shown. Implant 192 can comprise a tissue barrier device (e.g. a sleeve or other barrier positioned on the inner wall of the small intestine). Implant 192 can comprise a medical device, such as a drug delivery depot or other drug delivery device. Implant 192 can comprise a sensor or sensing device. In some embodiments, system 10 is configured to deliver implant 192 via a functional element 139, such as fluid delivery element 139*c* (e.g. when fluid delivery element 139*c* comprises a needle comprising a lumen through which a sensor-based implant 192 can be deployed into tissue such as mucosal tissue, submucosal tissue, other intestinal tissue and/or other tissue of the patient). In some embodiments, system 10 is constructed and arranged to deliver one or more implants 192 into tissue that is not proximate to a significant number of pain-sensing nerves. In some embodiments, implant 192 can comprise a sensor configured to measure a physiologic parameter selected from the group consisting of: blood pressure; heart rate; pulse distention; glucose level; blood glucose level; blood gas level; hormone level; GLP-1 level; GIP Level; EEG; LFP; respiration rate; breath distention; perspiration rate; temperature; gastric emptying rate; peristaltic frequency; peristaltic amplitude; and combinations of two or more of these.

In some embodiments, implant 192 comprises a sensor, such as a sensor configured to be implanted in the submucosal tissue of the intestine. In some embodiments, device 100 is configured to deploy implant 192 into tissue via a fluid delivery element 139*c* and/or another functional element of device 100. Implant 192 can comprise a sensor configured to produce a signal related to a physiologic parameter related to the concentration of a material selected from the group consisting of: fat; sugar (e.g. glucose or fructose); protein; one or more amino acids; and combinations of two or more of these. In some embodiments, implant 192 comprises a wireless communication element, such as an RF or infrared element configured to transmit information (e.g. to a receiving component of system 10). System 10 can be configured to analyze the received information, such as an analysis performed by algorithm 251 used to manage obesity, insulin resistance and/or Type 2 diabetes.

In some embodiments, one or more reservoirs 220 and/or one or more pumping assemblies 225 are constructed and arranged to provide a cryogenic gas or other cryogenic fluid to functional assembly 130, such as to perform a cryogenic ablation of target tissue and/or to cool target tissue that has been heated above body temperature. Cryogenic gas can be delivered through smaller diameter conduits 111 than would be required to sufficiently accommodate a liquid ablative or neutralizing fluid, which correlates to a reduced diameter of shaft 110. Balloon 136 can comprise a compliant balloon (e.g. a highly compliant balloon). Balloon 136 can be fluidly connected to multiple fluid transport conduits 111, singly or collectively providing inflow (i.e. delivery) and/or outflow (i.e. extraction) of the cryogenic gas. System 10 can be configured to control the pressure within balloon 136, such as at a pressure sufficient, but not much greater than that which would be required to simply inflate balloon 136. A highly compliant balloon 136 can be configured to reduce or avoid the need for a luminal sizing step to be performed. Temperature seen by the target tissue is driven by the temperature of the fluid in balloon 136. During treatment (i.e. cryogenic ablation) the pressure in balloon 136 can be maintained at a pressure at or below 20 inHg, such as below 18 inHg, 15 inHg or 10 inHg.

In some embodiments, pumping assembly 225 comprises at least two pumping assemblies 225 configured to propel fluid out of (i.e. extract fluid from) functional assembly 130 and/or another component of device 100, such as two pumping assemblies 225 which operate simultaneously during the performance of a functional assembly 130 drawdown procedure (e.g. an emergency radial contraction of functional assembly 130 that is initiated during an undesired situation, such as an emergency drawdown procedure initiated when a leak is detected). In some embodiments, two pumping assemblies 225 are configured to deliver fluid to functional assembly 130 (e.g. to balloon 136 and/or one or more fluid delivery elements 139*c*) or other component of device 100. In these embodiments, simultaneous fluid delivery can also be performed when a leak is detected, such as to simultaneously deliver a neutralizing fluid to tissue being undesirably exposed to ablative fluid. Alternatively or additionally, a second pumping assembly 225 can be configured to begin fluid delivery and/or fluid extraction when the failure of a first pumping assembly 225 is detected. Two or more pumping assemblies 225 can be fluidly attached to one or more fluid transport conduits 211.

In some embodiments, console 200 is constructed and arranged to maintain a minimum volume (e.g. a minimum level of fluid) of one or more reservoirs 220. In some embodiments, console 200 is constructed and arranged to disable a pump 225 if an undesired condition is detected, such as by a signal recorded by a functional element 229*a* and/or 229*b* that comprises a sensor configured to monitor one or more system parameters (e.g. temperature, pressure, flow rate, and the like).

In some embodiments, console 200 is constructed and arranged to limit a treatment time or to limit another treatment parameter. In these embodiments, the treatment parameter can be limited by software, such as software of algorithm 251 and/or controller 250. Alternatively, the treatment parameter can be limited by hardware (e.g. a hardware-based algorithm 251), such as hardware of controller 250 such as a temperature controlled functional element which turns off a pumping assembly 225 and/or otherwise prevents or reverses energy being delivered by a functional assembly 130 of device 100.

In some embodiments, system 10 is constructed and arranged (e.g. via algorithm 251) to adjust one or more treatment parameters, such as an adjustment based on the expanded size of a functional assembly 130, such as when system 10 comprises multiple devices 100, each comprising a different expanded size of its functional assembly 130. In these embodiments, system 10 can be constructed and arranged to adjust one or more treatment parameters selected from the group consisting of temperature of ablative fluid; volume of ablative fluid; pressure of ablative fluid; amount of energy delivered such as peak amount of energy delivered and/or cumulative amount of energy delivered; duration of treatment; amount of fluid delivered into tissue (e.g. during a tissue expansion procedure or a tissue ablation procedure); and combinations of two or more of these.

In some embodiments, console 200 is constructed and arranged to provide a first fluid at an ablative temperature, and a second fluid at a neutralizing temperature. For example, a first fluid can be provided by a first reservoir 220 such that the first fluid enters functional assembly 130 at a sufficiently high temperature to ablate tissue, such as at a temperature above 44° C. or above 60° C. A second fluid can be provided by a second reservoir 220 such that the second fluid enters functional assembly 130 at a neutralizing temperature below body temperature, such as a temperature between room temperature and body temperature, or a temperature below room temperature. Alternatively, an ablative fluid can comprise a fluid of sufficiently low temperature to ablate tissue (e.g. below 5° C.), and an associated neutralizing fluid can comprise a warmer fluid configured to reduce the tissue damaging effects of the ablative fluid, as described herein. In some embodiments, a neutralizing fluid is provided to functional assembly 130 prior to and/or after delivery of ablative fluid to functional assembly 130, as described in detail herein.

In some embodiments, at least a first conduit 111*a* provides ablative fluid to functional assembly 130 while at least a separate conduit 111*b* simultaneously withdraws ablative fluid from functional assembly 130, such as to recirculate ablative fluid within functional assembly 130. In these embodiments, functional assembly 130 can be radially expanded (e.g. initially or after a radial compacting step), by filling functional assembly 130 (e.g. with ablative fluid, neutralizing fluid and/or other fluid) by using both first conduit 111*a* and second conduit 111*b*.

In some embodiments, balloon 136 comprises at least a porous portion or a portion otherwise constructed and arranged to allow material contained within balloon 136 to pass through at least a portion of balloon 136. In these embodiments, injectate 221 can comprise a material configured to pass through at least a portion of balloon 136, such as a conductive gel material configured to modify energy delivery, such as when treatment element 139*a* comprises one or more electrodes configured to delivery RF energy to target tissue. In other embodiments, agent 420 comprises one or more agents configured to be delivered into balloon 136 and to pass through at least a portion of balloon 136 and into the intestine.

Functional assembly 130 can be configured to perform a medical procedure (e.g. a tissue expansion procedure and/or a tissue ablation or other tissue treatment procedure) on multiple axial segments of intestinal tissue. Two or more of the multiple axial segments can be treated sequentially and/or simultaneously. The two or more of the multiple axial segments can be relatively proximate each other, such as to share common boundaries or avoid significant gaps in untreated tissue. The multiple axial segments can comprise partial or full circumferential segments of intestinal tissue. The multiple axial segments can cumulatively comprise at least 3 cm in length or at least 6 cm in length, such as when between one and six treatments (e.g. between two and six treatments) are performed (e.g. functional assembly 130 is repositioned between one and five times). The multiple axial segments can cumulatively comprise a length of at least 9 cm, such as when between two and nine treatments are performed (e.g. functional assembly 130 is repositioned between one and eight times). In these embodiments, system 10 can be configured to treat diabetes, such as Type 2 diabetes. In some embodiments, system 10 is constructed and arranged to treat diabetes as described in applicant's co-pending U.S. patent application Ser. No. 17/096,855, entitled "Methods and Systems for Treating Diabetes and Related Diseases and Disorders", filed Nov. 12, 2020.

In some embodiments, system 10 is configured to initially expand functional assembly 130, with a fluid at a non-ablative temperature (e.g. a fluid configured to cool tissue without ablating it), after which a fluid at an ablative temperature can be introduced into functional assembly 130 (e.g. a fluid at sufficiently high temperature to ablate tissue).

In some embodiments, device 100 and/or another device of system 10 comprises an anchoring element, such as when port 137 is configured to fixedly engage tissue when a vacuum is applied to port 137 (e.g. via one or more conduits 111). Alternatively or additionally, inflation of balloon 136 can be used to anchor functional assembly 130 at a particular intestinal location. One or more functional elements 139 can comprise an anchor element, such as a high friction coating or surface treatment, or an extendable barb.

In some embodiments, system 10 is constructed and arranged to allow an operator to position functional assembly 130 within an axial segment of the intestine and perform a first procedure on intestinal tissue with functional assembly 130. System 10 is further constructed and arranged to anchor functional assembly 130 (prior to, during and/or after the first procedure). Subsequent to the performance of the first procedure and the anchoring of functional assembly 130, a second procedure is performed. The first procedure can comprise a tissue expansion procedure (e.g. one, two or more tissue expansion procedures at one, two, or more locations in relative proximity to each other). The second procedure can comprise a tissue ablation procedure, such as a tissue ablation procedure which ablates mucosal tissue within or otherwise proximate previously expanded submucosal tissue. Repeating of the three steps (i.e. the first procedure, the anchoring of functional assembly 130, and the second procedure) can be performed at additional locations within the intestine.

In some embodiments, console 200 and system 10 are constructed and arranged to maintain functional assembly 130 of device 100 at or below a target level of a functional assembly 130 parameter, such as at or below a target diameter, pressure and/or volume for functional assembly 130. In some embodiments, functional assembly 130 is maintained below a target pressure of 0.9 psi (e.g. during a tissue expansion, tissue ablation and/or other tissue treatment step).

In some embodiments, device 100 and system 10 are constructed and arranged to compensate for muscle contraction of the intestine (e.g. peristalsis within the intestine). For example, algorithm 251 can be configured to actively regulate a functional assembly 130 parameter (e.g. diameter, pressure within and/or flowrate to and/or from), such as when algorithm 251 anticipates, recognizes and/or compensates for muscular contraction of the intestine. In some embodiments, expansion of functional assembly 130 can be timed to occur during the bottom (lower range) of a muscular contraction (e.g. peristalsis) cycle.

In some embodiments, system 10 is constructed and arranged to perform a medical procedure comprising a tissue treatment procedure for treating a patient disease or disorder, and the amount of tissue treated is based on the severity of the patient's disease or disorder (e.g. amount of tissue treated is proportional to the severity). In some embodiments, the disease treated is diabetes, and the severity is determined by measuring one or more of HbA1c level; fasting glucose level; and combinations of two or more of these. In some embodiments, algorithm 251 is configured to determine the amount of tissue to be treated based on the severity of the patient's disease or disorder.

In some embodiments, system 10 is constructed and arranged to (e.g. via algorithm 251) introduce fluid into functional assembly 130 (e.g. into a balloon 136 of functional assembly 130) until sufficient apposition against an intestinal wall is achieved (e.g. as determined by a pressure measurement and/or image analysis provided by a sensor of the present inventive concepts). Subsequently, fluid is extracted from functional assembly 130 (e.g. until a second, lesser volume of fluid resides within functional assembly 130), after which the intestinal wall is contracted (e.g. via desufflation as described herein) such that the intestinal wall again contacts functional assembly 130.

In some embodiments, desufflation is accomplished by applying vacuum to a port (e.g. one or more ports configured to remove fluid from the intestine, such as port 137), one or more ports of shaft 110 proximal or distal to functional assembly 130 (e.g. port 112a and/or 112b described herein in reference to FIG. 12B) and/or a lumen of an endoscope or other introduction device 50.

In some embodiments, functional assembly 130 is expanded with fluid at a first pressure (e.g. a pressure of approximately 0.5 psi, 0.7, psi or 0.9 psi), and fluid is delivered into tissue by one or more fluid delivery elements 139c (e.g. three fluid delivery elements 139c). During fluid injection, system 10 can monitor pressure (e.g. a sensor of the present inventive concepts monitors pressure within functional assembly 130 and/or within a conduit in fluid communication with functional assembly 130), and if the pressure exceeds a second pressure (e.g. a pressure of at least 0.7 psi, 0.9 psi 1.1 psi, or other pressure greater than the first pressure), system 10 can reduce the pressure within the functional assembly 130 (e.g. reduce the pressure to the first pressure).

Figure 12:
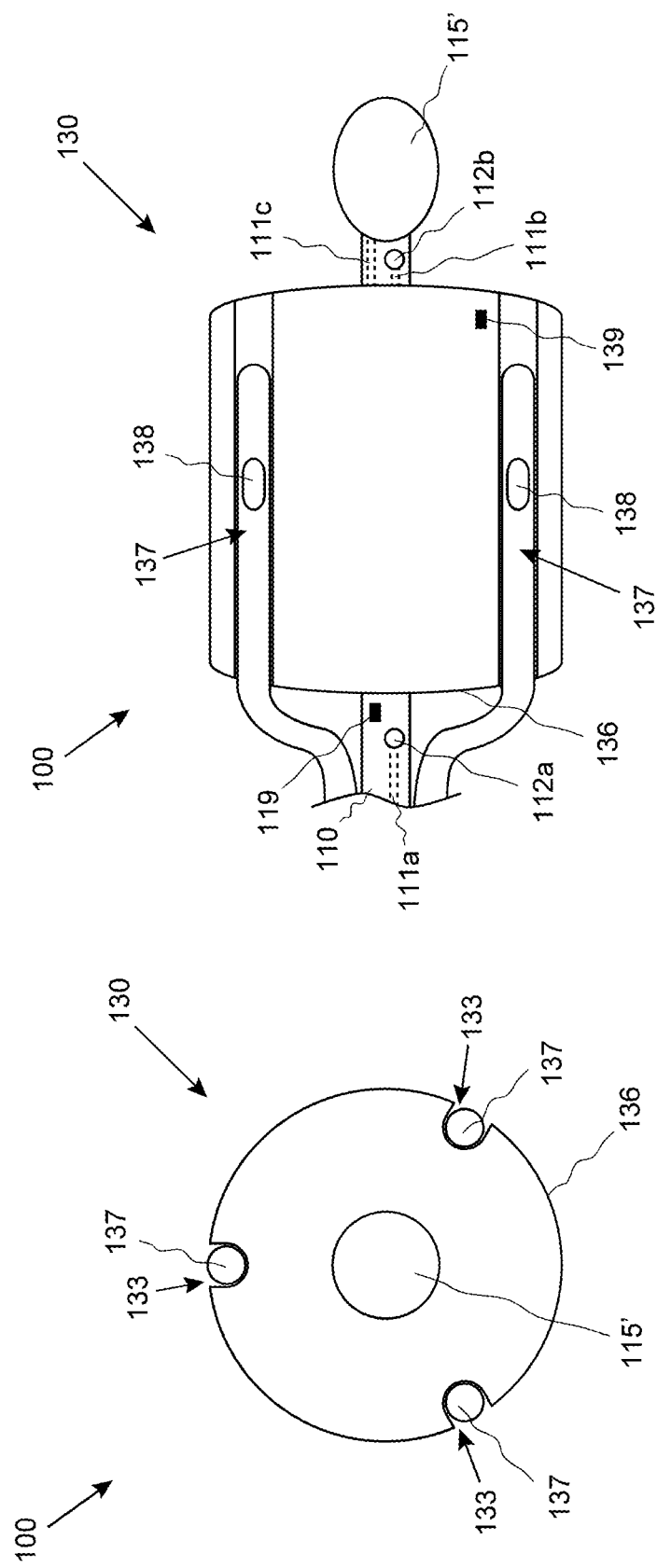
FIGS. 12A-12B illustrate end and side views of the distal portion of a catheter including recessed ports and shaft-located vacuum port, consistent with the present inventive concepts.

In some embodiments, shaft 110 or another component of device 100 comprises one or more ports configured to perform desufflation, such as ports 112a and/or 112b described herein in reference to FIG. 12B. In some embodiments, system 10 comprises a separate desufflation tool (e.g. aspiration tool), such as tool 500 constructed and arranged to extract fluid from a segment of intestine, such as a segment comprising functional assembly 130. In these embodiments, tool 500 can comprise one or more holes, slots, slits or other openings (e.g. positioned in a distal portion of tool 500) that are configured to aspirate fluids from the intestine, such as to collapse the inner wall of the intestine onto a fully expanded functional assembly 130.

In some embodiments, system 10 is configured to work in combination with a patient care practice, such as a patient diet that is maintained prior to and/or after performance of a medical device or diagnostic procedure performed using system 10. For example, a patient diet, patient exercise regimen, and/or other patient practice can be included prior to and/or after a tissue treatment procedure performed by system 10. In some embodiments, a patient diet is included to slow down healing (e.g. mucosal healing) and/or provide another enhancement to the therapy achieved. In some embodiments, mucosal healing is slowed down by a functional element 139, tool 500 and/or other component of system 10. In some embodiments, regrowth of treated mucosal tissue is enhanced by a pre-procedural and/or post-procedural patient diet. The diet can include: a liquid diet for at least one day; a low sugar diet and/or a low-fat diet for at least one week; a standardized diabetic diet for at least one week; and/or nutritional counseling for at least one week.

In some embodiments, system 10 comprises one or more materials or devices configured to modify tissue healing, such as when device 100 is constructed and arranged to treat intestinal mucosa (e.g. duodenal mucosa). For example, injectate 221, or implant 192 can be delivered in and/or proximate target tissue, such as at a time prior to, during and/or after target tissue treatment. In these embodiments, for example, injectate 221, agent 420 and/or implant 192 that is delivered (e.g. by fluid delivery element 139c or another component of device 100) can be configured to delay healing of treated tissue in the intestine, such as to provide enhanced therapeutic benefit to the patient and/or prolong the benefit (e.g. enhance or prolong HbA1c reduction). In some embodiments, injectate 221, agent 420 and/or implant 192 comprises a material selected from the group consisting of: a chemotherapeutic agent; a cytotoxic agent; 5Fluorouracil; Mitomycin-c; Tretinoin topical (Retin-A, Retin-A Micro, Renova); Bleomycin; Doxorubicin (Adriamycin); Tamoxifen; Tacrolimus; Verapamil (Isoptin, Calan, Verelan PM); Interferon alfa-2b; Interferon beta 1a (Avonex, Rebif); Interferon alfa-n3 (Alferon N); Triamcinolone (Aristospan, Kenalog-10); Imiquimod (Aldara, Zyclara); and combinations of two or more of these.

Figure 13:
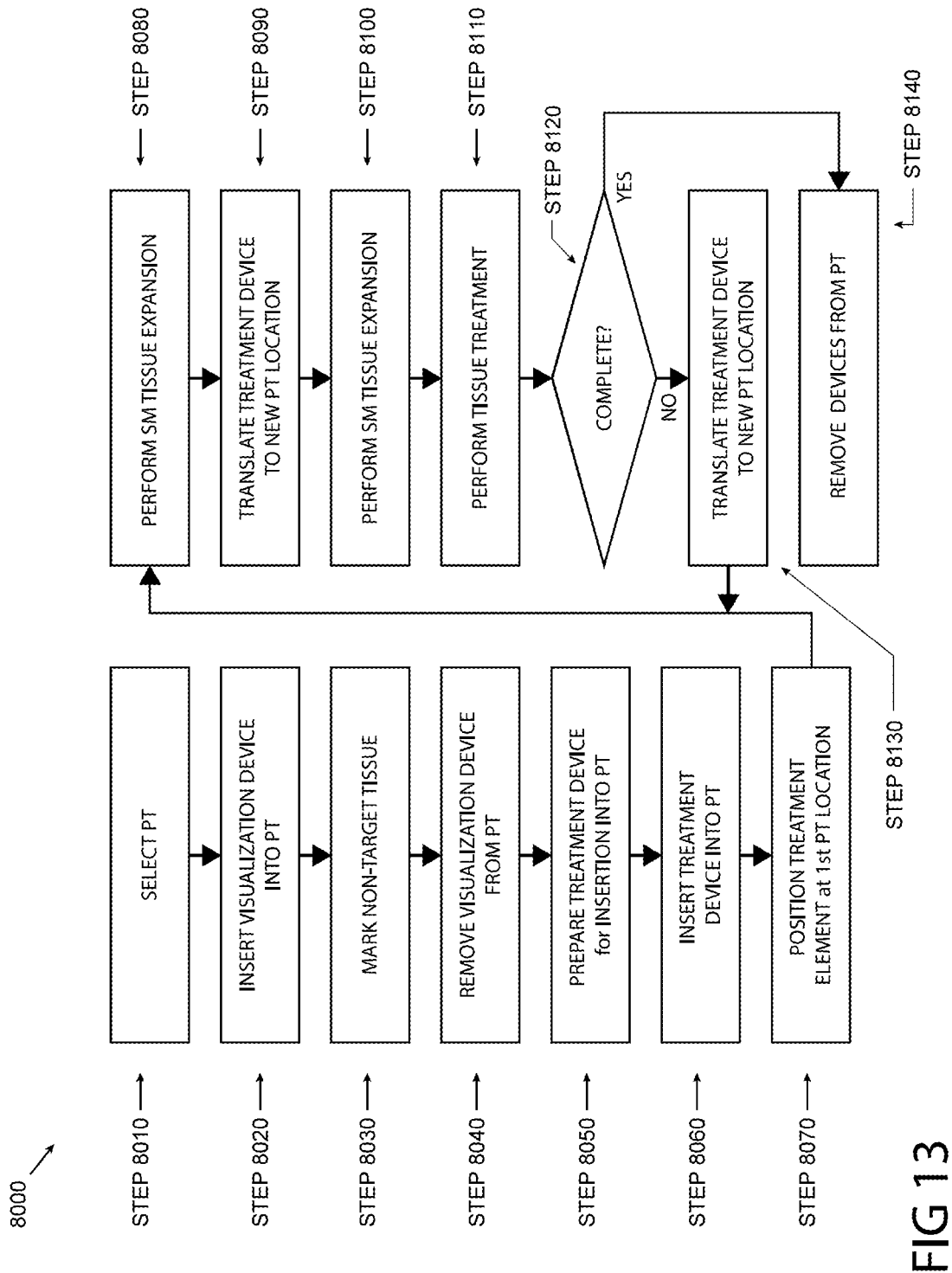
FIG. 13 illustrates a flow chart of a method of treating a patient, consistent with the present inventive concepts.

In some embodiments, system 10 of FIG. 9 is configured to perform a medical procedure on a patient as described herein in reference to FIG. 13. In some embodiments, system 10 is configured to treat a patient that is taking insulin, such as when device 100 is used to treat duodenal mucosa and agent 420 comprises a GLP-1 (or its analog) receptor agonist, and the patient stops taking insulin, as described herein. In these embodiments, the metabolic conditions of these patients can be improved or at least maintained (e.g. HbA1c level or other metabolic condition marker is not made significantly worse by the removal of insulin therapy).

Figure 10A:
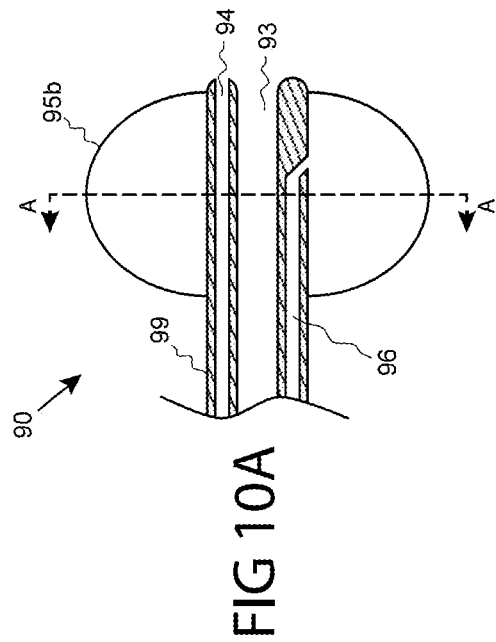
FIGS. 10 and 10A-10B illustrate an anatomic view of a system for performing a medical procedure comprising a catheter and a sheath for inserting the catheter into the intestine of the patient, consistent with the present inventive concepts.
Figure 10B:
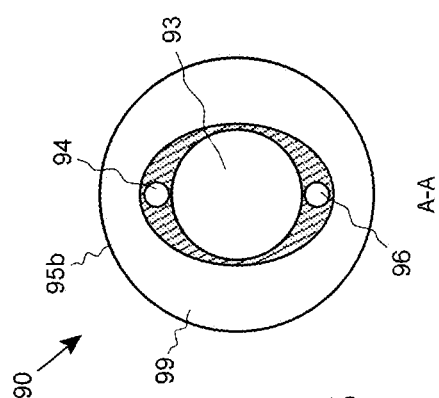
Figure 10:
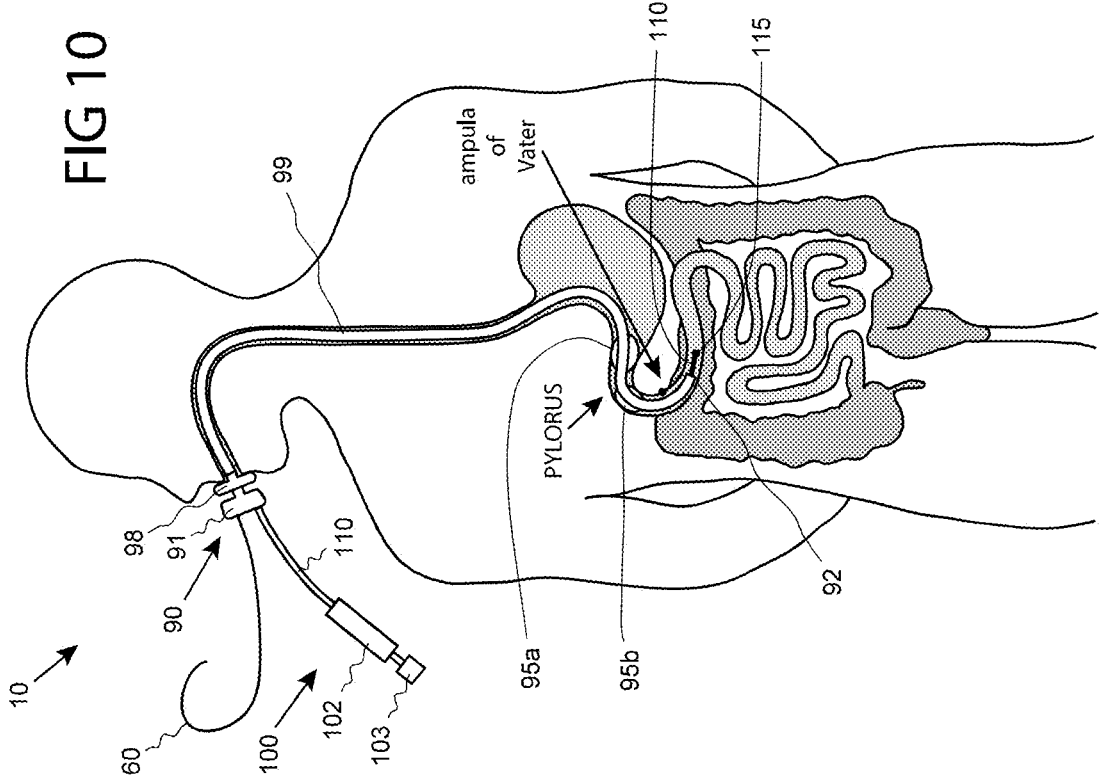

Referring now to FIG. 10, an anatomic view of a system for performing a medical procedure comprising a device (e.g. a catheter) and a sheath for inserting the device into the intestine of the patient is illustrated, consistent with the present inventive concepts. System 10 comprises device 100 which has been inserted through the mouth of the patient and advanced through the stomach to a location distal to the patient's pylorus. System 10 can further comprise introducer 90 (e.g. an introducer sheath), through which device 100 can be inserted as shown. System 10 can further comprise guidewire 60. System 10 can comprise one or more other components, such as console 200 and other components not shown, but of similar construction and arrangement to those described herein in reference to system 10 of FIGS. 1, 7, and/or 9. Device 100 comprises connector 103, handle 102, shaft 110, tip 115, and other components, such as those described herein in reference to device 100 of FIG. 9, or devices 100, 20, 30 and/or 40 of FIG. 1.

Introducer 90 comprises an elongate, flexible tube, shaft 99, and an input port 91 on the proximal end of shaft 99. Input port 91 can include a funnel-shaped or other opening configured to assist in the introduction of device 100 or other devices into a lumen of introducer 90. Input port 91, or another proximal portion of introducer 90, can be configured to attach introducer 90 to an endoscope or other body introduction device (e.g. device 50 described herein). In some embodiments, input port 91 comprises a strain relief configured to attach introducer 90 to a body introduction device. Bite block 98 can be positioned about shaft 99 at a location relatively proximate to input port 91. Positioned along a distal portion of shaft 99 are one or more anchor elements, such as anchor elements 95a and 95b shown. Anchor elements 95a and 95b can comprise a radially expandable structure, such as an expandable structure selected from the group consisting of: an inflatable balloon; a radially expandable cage or stent; one or more radially deployable arms; an expandable helix; an unfurlable compacted coiled structure; an unfurlable sheet; an unfoldable compacted structure; and combinations of two or more of these. Anchor elements 95a and 95b have been positioned at locations proximal and distal, respectively, to the pylorus, and subsequently radially expanded, such as to anchor distal end 92 of shaft 99 at a location distal to the ampulla of Vater (e.g. to avoid inadvertently treating or otherwise adversely affecting the ampulla of Vater and/or tissue proximate the ampulla of Vater). In some embodiments, anchor element 95a and/or 95b can be configured to be inflated within the duodenal bulb of the patient.

In some embodiments, shaft 99 comprises a variable stiffness along its length, such as a more flexible distal portion constructed and arranged to be positioned distal to the pylorus, than a portion that would be positioned proximal to the pylorus (e.g. to avoid a "slack" segment in the stomach when advancing device 100 through shaft 99). In some embodiments, shaft 99 comprises a shaft including a braided portion. In some embodiments, introducer 90 comprises a non-circular cross-section, such as to efficiently couple with an endoscope or other body introduction device (e.g. not shown but such as device 50 described herein), such as a non-circular cross-section selected from the group consisting of oval; kidney shape; and combinations thereof.

FIGS. 10A and 10B illustrate side sectional and end sectional views, respectively, of the distal portion of introducer 90, without an inserted device 100 nor an inserted guidewire 60. FIG. 10B is a section along line A-A of FIG. 10A. Shaft 99 includes a lumen 94, such as a lumen constructed and arranged to slidingly receive a guidewire, such as guidewire 60, to permit over-the-wire advancement and retraction of introducer 90. Shaft 99 further includes working channel 93, such as a lumen constructed and arranged to slidingly receive a treatment or diagnostic device, such as device 100 as described herein. In some embodiments, working channel 93 comprises a diameter greater than or equal to 10 mm, or 20 mm. In some embodiments, introducer 90 is advanced to a desired location (e.g. with or without device 100 residing within working channel 93), and subsequently tip 115 of device 100 is advanced out of distal end 92 of introducer 90. Shaft 99 can further comprise a lumen 96, which can be configured as an inflation lumen when one or more of anchor elements 95a or 95b comprise a balloon or other inflatable structure. Alternatively, lumen 96 can be constructed and arranged to receive a translatable rod or other filament, such as when anchor element 95a and/or 95b comprise an expandable scaffold, radially deployable arm or other structure whose expansion and contraction is controlled by the translation of the filament. Working channel 93 and/or lumen 94 can be configured as a port for delivering and/or extracting fluids from the intestine (e.g. to insufflate and/or desufflate, respectively, a segment of the intestine).

In some embodiments, system 10 of FIG. 10 comprises one or more sensors, such as one or more functional elements 109, 119, 139, 209, 229 and/or 309 described herein in reference to FIG. 9, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described herein in reference to FIG. 9, such as a functional element constructed and arranged to perform a therapeutic and/or diagnostic medical procedure, as described herein.

Figure 11:
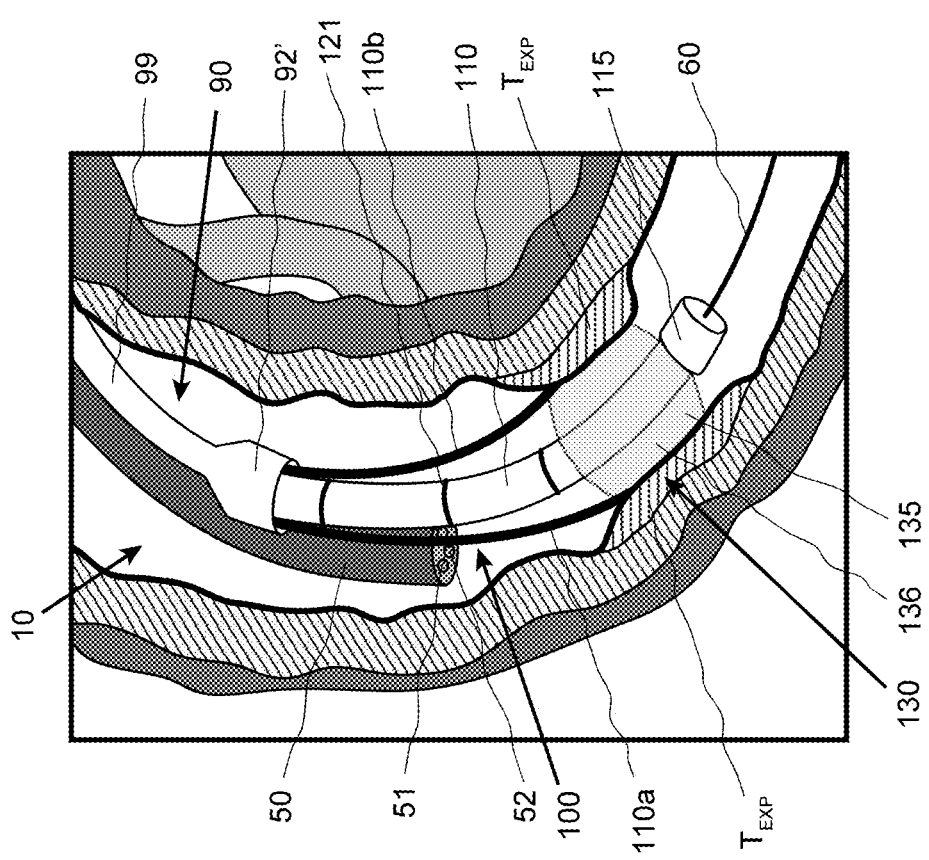
FIG. 11 illustrates a sectional view of the distal portion of a system including an endoscope and a treatment device inserted into a duodenum of a patient, consistent with the present inventive concepts.

Referring now to FIG. 11, a sectional view of the distal portion of a system including an endoscope and a treatment device inserted into a duodenum of a patient is illustrated, consistent with the present inventive concepts. System 10 includes device 100, such as a catheter or other elongate device configured to both expand tissue (e.g. circumferentially expanded tissue TEXP shown), as well as treat (e.g. ablate) target tissue. Device 100 and other components of system 10 can be of similar construction and arrangement to the similar components described herein in reference to FIGS. 1, 7, and/or 9. Device 100 is shown positioned in a side-by-side arrangement with endoscope 50, which can include one or more working channels, lumen 51 shown, and a visible light and/or infrared camera, camera 52. Device 100 has been advanced over a guidewire 60 and through introducer 90 (e.g. to a location in the small intestine of the patient). Introducer 90 includes shaft 99 with expanded distal end 92'. Distal end 92' can be sized to surround a bulbous distal end of device 100, such as tip 115 shown. In some embodiments, device 100 is advanced over guidewire 60 but not through introducer 90.

Device 100 includes a treatment assembly, functional assembly 130, which is shown in its expanded state, and positioned on a central shaft, shaft 110. Functional assembly 130 can include one or more fluid delivery elements, not shown but such as one or more (e.g. three) needles or other fluid delivery elements such as fluid delivery elements 139c described herein. The fluid delivery elements can be positioned in a circumferential arrangement (e.g. three needles positioned approximately 120° apart along functional assembly 130), each fluid delivery element fluidly attached to a fluid delivery tube, such as shafts 110a and 110b shown. The fluid delivery elements may each be positioned in a port, such as port 137, also not shown but described herein, such that a vacuum can be applied to tissue to cause the tissue to be drawn into the port 137, after which fluid can be injected into the tissue via the associated fluid delivery element. Functional assembly 130 can comprise a radially expandable assembly, such as balloon 136, into which an ablative element 135 can be positioned (e.g. an electrode configured to deliver RF or other electromagnetic energy) and/or introduced (e.g. hot or cold ablative fluid introduced into balloon 136). Device 100 can comprise one or more visualizable markers, such as radiopaque or visible marker bands, circumferential marker 121 (3 shown). In some embodiments, a neutralizing fluid (e.g. a cooling or warming fluid) is introduced into balloon 136 prior to and/or after ablation of tissue.

In the embodiment shown in FIG. 11, tissue surrounding and proximate functional assembly 130 has been expanded (circumferentially expanded tissue TEXP shown), such that ablation or other treatment can be performed by functional assembly 130 on the mucosal layer of the axial segment of the small intestine (e.g. the duodenum) proximate functional assembly 130 (e.g. proximate balloon 136), such as is described herein. After the tissue treatment is performed, functional assembly 130 can be radially compacted (e.g. balloon 136 at least partially deflated), translated (e.g. advanced or retracted to a neighboring or distant axial segment), after which similar tissue expansion (e.g. submucosal tissue expansion) and tissue treatment (e.g. mucosal tissue ablation) can be performed, such as to treat a patient medical condition (e.g. a disease and/or disorder) as described herein.

Referring now to FIGS. 12A and 12B, end and side views of the distal portion of an elongate device (e.g. a catheter) including recessed ports and shaft-located vacuum ports are illustrated, consistent with the present inventive concepts. Device 100 comprises shaft 110, functional assembly 130 (shown in its expanded state), and other components, such as one or more components of similar construction and arrangement to those described herein in reference to device 100 of FIG. 1 or FIG. 9, such as one or more conduits 111, some of which have been removed for illustrative clarity (three conduits 111 shown in FIG. 12B). In some embodiments, tip 115 comprises a bulbous tip positioned on the distal end of device 100 as shown. Functional assembly 130 is configured to radially expand and contract, and it can comprise an expandable element selected from the group consisting of an inflatable balloon such as balloon 136 shown; a radially expandable cage or stent; one or more radially deployable arms; an expandable helix; an unfurlable compacted coiled structure; an unfurlable sheet; an unfoldable compacted structure; and combinations of two or more of these as described herein. Functional assembly 130 is shown in a radially expanded state in FIGS. 12A and 12B.

In some embodiments, functional assembly 130 includes one or more recesses, such as the three recesses 133 (e.g. a recess of balloon 136) shown in FIG. 12A. Positioned within each recess 133 is a port 137, configured to capture or at least engage tissue when a vacuum is applied to each port 137, such as via one or more conduits such as conduits 111 described herein. Recesses 133 can be sized such that port 137 is relatively flush with the surface of an expanded functional assembly 130 or is otherwise constructed and arranged to limit the radial extension of each port 137 from the outer surface of an expanded functional assembly 130, such as to allow the surface of functional assembly 130 proximate each port 137 to sufficiently contact intestinal wall tissue (e.g. to avoid "tenting" of the tissue around each port 137), and/or to avoid trauma to intestinal wall tissue proximate each port 137.

In some embodiments, device 100 comprises one or more ports, port 112, configured to deliver and/or extract fluids, such as to perform an insufflation or desufflation step, such as to change the level of contact between functional assembly 130 and the intestinal wall (e.g. desufflation to achieve sufficient apposition between functional assembly 130 and the intestinal wall to ablate target tissue), as described herein. Device 100 of FIG. 12B comprises port 112a positioned on shaft 110 proximal to functional assembly 130 and port 112b positioned distal to functional assembly 130. Ports 112a and 112b are fluidly connected to conduits 111a and 111b, respectively, such that fluid can be extracted (e.g. liquids or gases extracted by console 200 described herein) from within the intestine by ports 112a and/or 112b, such as to desufflate the intestine proximal and/or distal to functional assembly 130. Alternatively or additionally, fluid can be delivered to the intestine by ports 112a and/or 112b, such as to insufflate the associated segment of the intestine. Device 100 can comprise one or more ports positioned along functional assembly 130, such as ports 137 which include openings 138 shown in FIG. 12B. Fluid can be delivered or extracted, such as to insufflate or desufflate, respectively, as described herein in reference to ports 112a and 112b. Alternatively or additionally, ports 137 including openings 138 can be configured to capture or at least frictionally engage tissue (e.g. wall tissue of the intestine), such as to complete a tissue expansion procedure and/or to anchor the distal portion of device 100, each as described herein. In some embodiments, functional assembly 130 of FIGS. 12A-B is configured to both expand one or more tissue portions and ablate one or more tissue portions. In some embodiments, ports 112a, 112b or another component of device 100 or system 10 (e.g. a working channel of introduction device 50) is configured to automatically insufflate and/or desufflate, such as an insufflation and/or desufflation triggered by a recording by a sensor of system 10 (e.g. a sensor as described herein, and whose signal is processed by algorithm 251 to automatically initiate the delivery and/or extraction of fluids from the intestine).

In some embodiments, device 100 comprises a bulbous distal tip, such as a tip configured to be inflated or otherwise expanded, such as inflatable tip 115' shown in FIGS. 12A-B, which can comprise a balloon or other expandable structure. Inflatable tip 115' can be fluidly attached to conduit 111c which can travel proximally to be attached to an inflation source, such as a pumping assembly 225 and reservoir 220 of console 200 described herein in reference to FIGS. 7 and/or 9. Inflatable tip 115' can be configured to expand to a diameter of at least 4 mm and/or a diameter of no more than 15 mm, such as an inflation that occurs after inflatable tip 115' exits a lumen (e.g. a lumen of an introduction device such as endoscope 50a or sheath 80 described herein in reference to FIGS. 1 and/or 9).

In some embodiments, device 100 comprises functional element 119 positioned in, on and/or within shaft 110. Functional element 119 can comprise a heating or cooling element configured to modify and/or control the temperature of fluid entering balloon 136.

In some embodiments, device 100 of FIGS. 12A-B comprises one or more sensors, such as one or more functional elements 109, 119 and/or 139 described herein in reference to FIG. 9, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described herein in reference to FIG. 9, such as a functional element constructed and arranged to perform a therapeutic and/or diagnostic medical procedure, as described herein.

Referring now to FIG. 13, a flow chart of a method of treating a patient is illustrated, consistent with the present inventive concepts. Method 8000 of FIG. 13 can be performed using system 10 of the present inventive concepts, such as by using devices 100, 20, 30, and/or 40 as described herein. Method 8000 will be described using system 10 of the present inventive concepts, as described herein.

Throughout method 8000, system 10 (e.g. via user interface 205 of console 200) can provide (e.g. to an operator) information related to the fluids in the various reservoirs 220, such as volume, pressure, and/or temperature information. Based on the provided information, the procedure may be aborted, modified, or proceeded as intended (e.g. manually by the operator and/or automatically by system 10). The provided information can relate to ablative fluid (e.g. hot or cold ablative fluid), neutralizing fluid (e.g. cold or warm, respectively, neutralizing fluid), injectate 221, and/or other fluid.

In STEP 8010, a patient is selected for treatment. The patient can be selected to treat one or more of the medical conditions described herein. In some embodiments, the selected patient is inflicted with Type 2 diabetes and another medical condition, such as NAFLD/NASH. One or more patient diagnostic tests can be performed such as to include or exclude a potential patient.

In STEP 8020, a visualization device is inserted into the patient by an operator of system 10 (e.g. a clinician of the patient). For example, the visualization device can comprise an endoscope (e.g. endoscope 50a described herein). Alternatively or additionally, the visualization device inserted in STEP 8020 can be a treatment device of the present inventive concepts, such as device 100 described herein, such as a treatment device that includes a camera or other visualization assembly. In these embodiments, the inserted device 100 has already been prepared for insertion via performance of STEP 8050 described herein.

In some embodiments, guidewire 60 is inserted into the patient (e.g. via a working channel of an endoscope and/or a guidewire lumen of a treatment device). Guidewire 60 can be used to introduce device 100 (in STEP 8020 or otherwise).

In some embodiments, the visualization device comprises an endoscope with a scope cap, such as cap 53 described herein in reference to FIG. 9. Scope cap 53 can prevent tissue (e.g. duodenal or other luminal wall tissue) from collapsing in front of a camera of the endoscope, such tissue collapse undesirably limiting the view provided by the visualization device.

The visualization device and other devices inserted in the various steps below, can be inserted into the patient via the mouth, such as to enter the small intestine by passing through the stomach. Alternatively, the device can be inserted via a surgical incision through the skin, and/or via minimally invasive access tools (e.g. one or more laparoscopic ports).

In STEP 8030, an optional step of marking non-target tissue is performed. Using the visualization device inserted in STEP 8020, the operator can identify the ampulla of Vater, such as to mark the ampulla of Vater to allow rapid, simplified visualization of the ampulla of Vater in later steps (e.g. to avoid adversely affecting the ampulla of Vater and its neighboring tissue). In some embodiments, the ampulla of Vater is visualized using a side-viewing visualization device (e.g. an endoscope with side-viewing capability). In some embodiments, the ampulla of Vater is marked through implantation of a marker, such as marker 430 described herein, such as a temporarily implantable marker, such as a hemostasis clip. Marker 430 can comprise a radiopaque marker (e.g. to be visualized by a fluoroscope), an ultrasonically visible marker (e.g. to be visualized by an ultrasound imaging device), and/or a magnetic marker. Marker 430 can comprise biocompatible ink.

In some embodiments, one or more patient screening procedures are performed in STEP 8030, such as to confirm that the target tissue to be treated, and/or tissue proximate the target tissue, is free of disease or other undesired conditions. If an undesired condition is identified, the procedure can be aborted (e.g. via step 8140 described herein).

In STEP 8040, the visualization device inserted in STEP 8020 can be removed from the patient, such as when the visualization device comprises endoscope 50a or other body introduction device 50. Removal of this type of visualization device can be performed leaving a guidewire (e.g. guidewire 60) in place. Alternatively, the visualization device inserted in STEP 8020 comprises a treatment device of the present inventive concepts, and the treatment device, such as a device 100 remains in the patient.

In STEP 8050, a treatment device, such as device 100, is prepared for insertion into the patient. In some embodiments, device 100 comprises the visualization device of STEP 8020, and STEP 8050 is performed prior to STEP 8020.

Device 100 is attached to console 200, such as via connecting assembly 300, and one or more procedures are performed such as to remove air from one or more lumens, balloons, and/or other spaces within device 100. In some embodiments, device 100 is prepared using method 9000 described herein in reference to FIG. 14.

Figure 14:
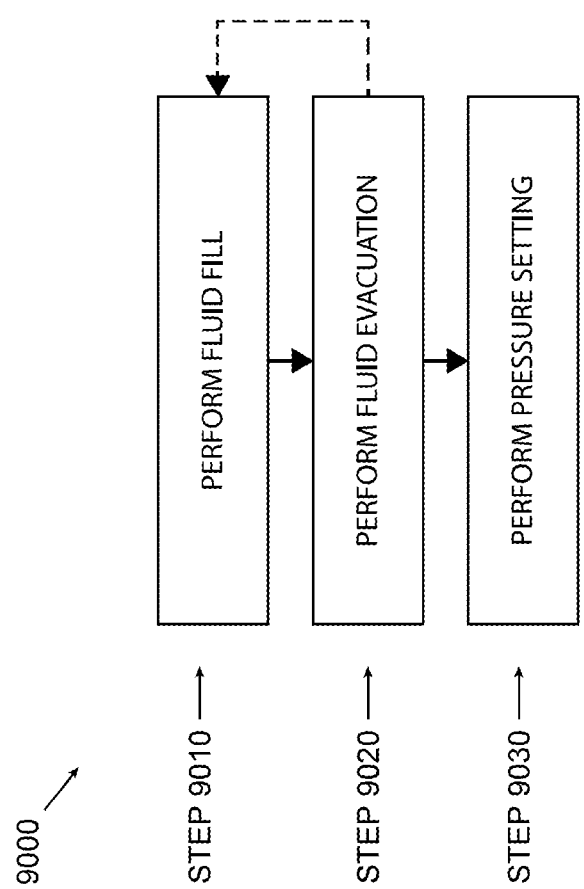
FIG. 14 illustrates a flow chart of a method of preparing a treatment device, consistent with the present inventive concepts.

In some embodiments, functional assembly 130 comprises balloon 136, and after the final procedure of STEP 8050 is performed, balloon 136 is filled with a small, but non-zero volume of fluid, at a pressure less than full vacuum, such that functional assembly 130 is in a preferred "translation state", as described herein in reference to FIG. 14. This translation state provides numerous advantages for safe and effective translation of device 100 in the duodenum and other segments of the GI tract of the patient, also as described herein in reference to FIG. 14.

In STEP 8060, device 100 is inserted into the patient (e.g. if not already inserted in STEP 8020). In some embodiments, device 100 is inserted with the corresponding functional assembly 130 in the translation state described herein in STEP 8050 and herein in reference to method 9000 of FIG. 14. In some embodiments, device 100 is inserted over a guidewire, such as guidewire 60 which can be already in place as described herein.

In some embodiments, such as when duodenal mucosal tissue is to be treated (i.e. the target tissue comprises duodenal mucosa), functional assembly 130 of device 100 is positioned proximate the duodenal bulb or segment D1 of the duodenum.

In some embodiments, device 100 is inserted after a body introduction device, such as endoscope 50a, has been recently removed (e.g. in STEP 8040).

In some embodiments, after device 100 is introduced into the patient in STEP 8060, endoscope 50a is introduced (e.g. reintroduced) into the patient as well. Subsequent translations of device 100 can be performed with simultaneous translation of endoscope 50a.

In STEP 8070, a treatment assembly configured to perform a submucosal tissue expansion, such as functional assembly 130 of device 100, is positioned at a first location in the patient's small intestine, such as a location in the duodenum distal to the pylorus and proximal to the Ligament of Treitz. Alternatively or additionally, other GI locations can be selected for tissue expansion (e.g. submucosal tissue expansion). During positioning, device 100 (e.g. functional assembly 130) can be in a translation state as described herein.

In STEP 8080, a submucosal tissue expansion is performed, such as via functional assembly 130 of device 100, the expansion performed at the location established in STEP 8070.

The tissue expansion performed in STEP 8080 can be performed using method 10000 described herein in reference to FIG. 15.

In STEP 8090, the treatment device (e.g. a catheter) is translated, such as a translation of device 100. In some embodiments, device 100 is translated such as to cause a corresponding translation of functional assembly 130 that is approximately one-half of the length of functional assembly 130 (e.g. approximately 1cm when functional assembly 130 comprises a length of approximately 2 cm). In some embodiments, functional assembly 130 is translated distally (e.g. more distal in the duodenum, further away from the ampulla of Vater toward but not passing the ligament of Treitz). Alternatively, functional assembly 130 is translated proximally. During translation, device 100 (e.g. functional assembly 130) can be in a translation state as described herein.

In STEP 8100, another submucosal tissue expansion is performed, such as via functional assembly 130 of device 100. The tissue expansion is performed at the location established in STEP 8090. Device 100 (e.g. functional assembly 130) can be in a translation state as described herein.

The tissue expansion performed in STEP 8100 can be performed using method 10000 described herein in reference to FIG. 15.

The tissue expansion performed in STEP 8100 can be performed at a duodenal or other GI location that is proximate, yet distal to the location of tissue expansion performed in step 8080. Alternatively, the tissue expansion performed in STEP 8100 can be proximal to the location of STEP 8080.

In STEP 8110, a tissue treatment procedure is performed, such as via functional assembly 130 of device 100. The tissue treatment procedure can be performed in the same location of the tissue expansion performed in STEP 8100 (e.g. without translation of functional assembly 130).

The tissue treatment performed in STEP 8110 can be performed using method 11000 described herein in reference FIG. 16. In some embodiments, prior to performing method 11000, device 100 and functional assembly 130 are established in the translation state described herein.

The tissue treatment performed in STEP 8110 can include a neutralizing procedure and an ablation procedure, such as is described herein. In some embodiments, a neutralizing procedure (e.g. a cooling or warming procedure) is performed prior to and/or after an ablation procedure (e.g. a heat or cryogenic ablation procedure, respectively) at a single axial location of the GI tract (e.g. and repeated for multiple axial locations). In some embodiments, a neutralizing procedure (e.g. a cooling or warming procedure) is performed only after (i.e. not prior to) an ablation procedure (e.g. a heat or cryogenic ablation procedure, respectively) at a single axial location of the GI tract (e.g. and repeated for multiple axial locations). In other embodiments, a neutralizing procedure (e.g. a cooling or warming procedure) is performed both prior to and after an ablation procedure (e.g. a heat or cryogenic ablation procedure, respectively) at a single axial location of the GI tract (e.g. and repeated for multiple axial locations).

In STEP 8120, a decision is made related to performing additional tissue treatments. If additional tissue treatments are desired, STEP 8130 is performed. If the procedure is complete, STEP 8140 is performed. In some embodiments, at least two, three, four, five, or six tissue treatments are performed. In some embodiments, at least 60 mm of cumulative axial length of duodenum is treated, such as to achieve a desired therapeutic benefit as described herein. The at least 60 mm of cumulative axial length can be treated via a single treatment step (e.g. a single ablation using functional assembly 130), or via multiple treatment steps (e.g. at least 3 ablations, at least 4 ablations, and/or at least 5 ablations using functional assembly 130). In these embodiments, functional assembly 130 can comprise a treatment length of at least 10 mm, such as a treatment length of no more than 100 mm.

In STEP 8130, device 100, including functional assembly 130, is translated to a new location within the GI tract, such as a location approximately 1cm distal to the current location. Alternatively, functional assembly 130 can be translated proximally (e.g. 1 cm proximally). Subsequently, STEP 8080 is repeated.

In STEP 8140, the treatment device, and any other device (e.g. endoscope 50a and/or guidewire 60) is removed from the patient, and the procedure is complete.

In some embodiments, the tissue expansion procedures (STEPS 8080 and 8100) and the tissue treatment procedures (STEP 8110) are performed with the same device, such as device 100 and/or 40 described herein. In other embodiments, the tissue expansion procedures (STEPS 8080 and 8100) are performed with a first device, such as device 20 described herein, and the tissue treatment procedures (STEP 8110) are performed with a second, different device, such as device 100 of FIG. 1.

Referring now to FIG. 14, a flow chart of a method of preparing a treatment device is illustrated, consistent with the present inventive concepts. Method 9000 of FIG. 14 can be performed using system 10 of the present inventive concepts, such as by using devices 100, 20, 30, and/or 40 as described herein. Method 9000 is described using system 10 as described herein. Method 9000 is performed using a device 100 (e.g. a catheter) that has been attached to console 200, such as via connecting assembly 300 as described herein in reference to FIGS. 1 and 9.

Throughout method 9000, system 10 (e.g. via user interface 205 of console 200) can provide (e.g. to an operator) information related to the fluids in the various reservoirs 220, such as volume, pressure, and/or temperature information. Based on the provided information, the procedure may be aborted, modified, or proceeded as intended (e.g. manually by the operator and/or automatically by system 10). The provided information can relate to ablative fluid (e.g. hot or cold ablative fluid), neutralizing fluid (e.g. cold or warm, respectively, neutralizing fluid), and/or other fluid.

In STEP 9010, a fluid fill procedure is performed, such as to fully or partially fill functional assembly 130 (e.g. balloon 136) with fluid. The fluid fill procedure can be performed: for a pre-determined period of time; until a particular volume of fluid is delivered into functional assembly 130; and/or until a pre-determined pressure is achieved within functional assembly 130. The delivery of fluid can be performed at a particular pressure or range of pressures, and/or at a particular flow rate or range of flow rates. In some embodiments, as fluid is delivered into functional assembly 130 (e.g. via one or more lumens or other conduits of device 100), fluid is simultaneously evacuated (e.g. slowly removed) from functional assembly 130 (e.g. via one or more lumens or other conduits of device 100), such that functional assembly 130 does significantly expand during the process. The fluid delivered to functional assembly 130 in STEP 9010 can be relatively cold fluid, such as fluid that is less than body temperature and/or less than room temperature. For example, the fluid provided by a reservoir 220 of console 200 can contain a fluid that is also a neutralizing fluid configured to perform a pre-cool and/or post-cool of an ablation treatment, such as is described herein in reference to method 11000 of FIG. 16.

The delivery and removal of various fluids to and/or from device 100 can be performed by one or more pumping assemblies 225 of console 200.

In STEP 9020, a fluid evacuation procedure is performed, such as to fully or partially evacuate functional assembly 130 (e.g. balloon 136) of fluid. The fluid evacuation procedure can be performed: for a pre-determined period of time (e.g. for less than 15 seconds, for less than 10 seconds, and/or for approximately 6 seconds); until a particular volume of fluid is removed from and/or remains within functional assembly 130; and/or until a pre-determined pressure is achieved within functional assembly 130. The evacuation can be performed at a particular pressure or range of pressures, and/or at a particular flow rate or range of flow rates. In some embodiments, as fluid is evacuated from functional assembly 130 (e.g. via one or more lumens or other conduits of device 100) until a particular volume remains within functional assembly 130 (e.g. within balloon 136). Removal of fluids can be performed by one or more pumping assemblies 225 of console 200. In some embodiments, the pressure within functional assembly 130 is near full vacuum at the end of STEP 9020.

In some embodiments, STEPS 9010 and 9020 are repeated one or more times, prior to performing STEP 9030, such as when device 100 is initially prepared for insertion into the patient and STEPS 9010 and 9020 are performed at least two times each.

In STEP 9030, a pressure setting procedure is performed, which establishes functional assembly 130 in a preferred "translation state" (e.g. a state in which translation of functional assembly 130 within the GI tract is safe, effective, and relatively easy). In STEP 9030, the pressure within functional assembly 130 (e.g. within balloon 136) is brought to a particular level. Alternatively or additionally, a particular volume (e.g. a minimal volume) of fluid is caused to remain within functional assembly 130.

In some embodiments, prior to performing STEP 9030, the pressure within functional assembly 130 is at or near full vacuum (e.g. as caused in STEP 9020). In STEP 9030, fluid can be delivered (and/or evacuated) such as to cause the pressure within functional assembly 130 to reach a target level related to the desired translation state. In some embodiments, the target level is below room pressure, such as at least 1 psi below room pressure (−1 psi), at least 2 psi below room pressure, or approximately −2.7 psi. Establishing a slightly negative pressure causes functional assembly 130 to be partially compacted, but not to the extent that significant rigidity occurs. In some embodiments, the translation state target level for the pressure within functional assembly 130 is no more than 5 psi below room pressure, or no more than 4 psi below room pressure. In other embodiments, the target pressure level for functional assembly 130 is less than 1 psi (i.e. 1 psi above room pressure), or less than 0.5 psi, and/or the translation state is established via a maximum volume contained within functional assembly 130, such as a volume less than 5%, or less than 10% of the "full volume" of balloon 136 (e.g. the volume to rigidly inflate a relatively non-compliant balloon 136, or the volume to inflate a compliant balloon without significantly stretching the balloon), the maximum pressure and/or volume establishing a limited (e.g. small) expansion of functional assembly 130. In some embodiments, the volume of fluid in balloon 136 during the transition state is less than 3 ml, 2 ml, or 1 ml.

Advantages of the translation state established for device 100 in STEP 9030 are that functional assembly 130 (e.g. including balloon 136 and ports 137) is established with a relatively low profile (e.g. a relatively minimal diameter surrounds shaft 110), and its components in a relatively flexible condition (e.g. not fully compacted via a complete vacuum, such that the components of functional assembly 130 are able to move with relatively low force applied). In these low profile, non-rigid states, ease of translation of functional assembly 130 is maximized or at least improved.

In some embodiments, establishing of the translation state of a treatment device (e.g. device 100) via method 9000 is performed between each tissue treatment (e.g. ablation) step and a subsequent submucosal tissue expansion step. For example, method 9000 can be performed after completion of STEP 8110 and prior to a (repeated) STEP 8080, each of method 8000 of FIG. 13 described herein.

Referring now to FIG. 15, a flow chart of a method of expanding tissue with a treatment device is illustrated, consistent with the present inventive concepts. Method 10000 of FIG. 15 can be performed using system 10 of the present inventive concepts, such as by using devices 100, 20, 30, and/or 40 as described herein. Method 10000 is described using a device 100 (e.g. a catheter) that has been attached to console 200, such as via connecting assembly 300 as described herein in reference to FIGS. 1 and 9. Delivery and removal of fluids of method 10000 can be performed by one or more pumping assemblies 225 of console 200.

Throughout method 10000, system 10 (e.g. via user interface 205 of console 200) can provide (e.g. to an operator) information related to injectate 221 in one or more reservoirs 220, such as volume, pressure, and/or temperature information. Based on the provided information, the procedure may be aborted, modified, or proceeded as intended (e.g. manually by the operator and/or automatically by system 10).

In STEP 10010, functional assembly 130 of device 100 is radially expanded, such as by the delivery of fluid into balloon 136. For example, fluid can be delivered from one or more reservoirs 220 by a pumping assembly 225. The fluid delivered in STEP 10010 can be performed: for a pre-determined period of time; until a particular volume of fluid is delivered into functional assembly 130; and/or until a pre-determined pressure is achieved within functional assembly 130. The delivery of fluid can be performed at a particular pressure or range of pressures, and/or at a particular flow rate or range of flow rates. In some embodiments, as fluid is delivered into functional assembly 130 (e.g. via one or more lumens or other conduits of device 100), fluid is simultaneously evacuated (e.g. slowly removed) from functional assembly 130 (e.g. via one or more lumens or other conduits of device 100), such that functional assembly 130 does significantly expand during the process. The fluid delivered to functional assembly 130 in STEP 10010 can be relatively cold fluid, such as fluid that is less than body temperature and/or less than room temperature (e.g. fluid provided by a reservoir 220 of console 200) that contains a neutralizing fluid configured to perform a pre-cool and/or post-cool of an ablation treatment that includes and/or generates heat (e.g. a hot fluid ablation, an RF ablation, a light ablation, and/or an ultrasound ablation). Delivery and removal of fluids can be performed by one or more pumping assemblies 225 of console 200.

In some embodiments, a fixed volume of fluid is delivered to functional assembly 130, such as a volume of at least 4 ml, at least 6 ml, or approximately 8 ml. In some embodiments, fluid is delivered until functional assembly 130 is in relatively close apposition to the wall of the GI tract within which functional assembly 130 is positioned (e.g. automatically by system 10 or manually by an operator).

In STEP 10020, vacuum is applied to one or more (e.g. all) ports 137 of functional assembly 130, such that tissue proximate each port 137 is drawn into a cavity of port 137. In some embodiments, the pressure applied to port 137 is monitored (e.g. via a location within console 200, connecting assembly 300, and/or device 100). The monitoring of the pressure can be used to confirm that the pressure maintains a minimum vacuum (e.g. at least 2 psi, at least 4 psi, or at least 6 psi below room pressure). Alternatively or additionally, the pressure can be monitored to confirm that the vacuum level is relatively stable, such as a stability correlating to a pressure that does not vary more than 0.3 psi, 0.2 psi, and/or 0.1 psi within a time window of at least 2 seconds, at least 3 seconds, and/or at least 5 seconds. If the minimum vacuum level, or stability level is not maintained, system 10 can be configured to enter an alert state (e.g. a state in which the operator is notified and/or further treatment steps are prevented until resolution is achieved).

In STEP 10030, one or more fluid delivery elements 139*c* are advanced (e.g. multiple fluid delivery elements 139*c* that are simultaneously or sequentially advanced) into the tissue captured within each corresponding port 137. In some embodiments, multiple fluid delivery elements 139*c* are advanced by a single control (e.g. a control 104 on handle 102 of device 100, as described herein). In some embodiments, two or more fluid delivery elements 139 are advanced by separate, individual controls (e.g. two or more controls 104).

In STEP 10040, injectate 221 is delivered into the submucosal tissue by one or more needles or other fluid delivery elements 139*c* (e.g. into the tissue captured within each port 137). Injectate 221 is provided via one or more reservoirs 220 and delivered by one more pumping assembly 225, such as is described herein in reference to FIGS. 1 and/or 9. In some embodiments, a fixed volume of fluid is introduced through each fluid delivery element 139*c*, such as at least 3 ml, at least 5 ml, at least 7 ml, or approximately 10 ml injected into tissue via at least two, at least three, or at least four fluid delivery elements 139*c*.

In some embodiments, pressure within the fluid pathway containing injectate 221 (e.g. within each associated reservoir 220 such as a syringe or other reservoir) is monitored during the delivery of injectate 221 to tissue. In some embodiments, injectate 221 is delivered at a flow rate than prevents the pressure within the fluid pathway from exceeding a maximum level, such as a level of no more than 150 psi, or no more than 100 psi at a fluid pathway location proximate console 200. In some embodiments, multiple fluid delivery elements 139*c* (e.g. needles) are each fluidly attached to individual, separate reservoirs 220, via separate fluid pathways, and if the associated fluid pathway pressure for a single fluid delivery element 139*c* exceeds the maximum level, the flow rate of injectate 221 delivery is reduced (e.g. reduced for all fluid delivery elements 139*c*). Pressure measurements above the maximum could relate to an occlusion or other restriction in the fluid pathway between console 200 and fluid delivery elements 139*c* and exceeding the pressure can result in system 10 entering an alert state. Configuration of system 10 to prevent exceeding the maximum pressure provides a safety measure (avoiding excessive pressure of injectate 221 delivery into the patient). In some embodiments, the pressure within each flow pathway containing injectate 221 is confirmed to be above a minimum pressure (e.g. such as a pressure of at least 20 psi). Pressure below the minimum can indicate air in the fluid pathway, or a leak, and system 10 can be configured to enter an alert state if the minimum threshold is exceeded.

In some embodiments, system 10 (via console 200) is configured to maintain a constant volume within functional assembly 130 (e.g. within balloon 136) throughout the injection of injectate 221 into tissue. For example, the volume within balloon 136 can be at a level less that the volume of balloon 136 when it is fully expanded. In some embodiments, the volume is no more than 90% of the full volume of balloon 136, such as no more than 80% of the full volume, or no more than 70% of the full volume (e.g. balloon 136 is filled with 8 ml when the full volume is 12 ml). In some embodiments, system 10 is configured to enter an alert state if the volume within functional assembly 130 is below a minimum and/or above a maximum.

In some embodiments, system 10 (via console 200) is configured to regulate the pressure (e.g. ensure the pressure is above a minimum and/or below a maximum) within functional assembly 130 (e.g. within balloon 136) during injection of injectate 221 into tissue. In some embodiments, system 10 is configured to enter an alert state if the pressure within functional assembly 130 is below a minimum and/or above a maximum.

In STEP 10050, all fluid delivery elements 139*c* are retracted, and functional assembly 130 is radially compressed. Retraction of fluid delivery elements 139*c* can be performed in a similar, typically opposite direction, to the method used to deploy them in STEP 10030 (e.g. via one or more controls 104 of handle 102 of device 100). Functional assembly 130 can be radially compressed via evacuation of the fluid within functional assembly 130, via one or more pumping assemblies 225 as described herein. In some embodiments, functional assembly 130 is radially compressed by evacuating a fixed volume of fluid (e.g. from balloon 136), such as the same or at least a similar volume to that introduced into functional assembly 130 in STEP 10010 (e.g. a volume of at least 4 ml, at least 6 ml, or approximately 8 ml).

Referring now to FIG. 16, a flow chart of a method of ablating or otherwise treating tissue with a treatment device is illustrated, consistent with the present inventive concepts. Method 110000 of FIG. 16 can be performed using system 10 of the present inventive concepts, such as by using devices 100, 20, 30, and/or 40 as described herein. Method 11000 is described using system 10 of the present inventive concepts. Method 11000 is described using a device 100 (e.g. a catheter) that has been attached to console 200, such as via connecting assembly 300 as described herein in reference to FIGS. 1 and/or 9. Delivery and removal of fluids of method 11000 can be performed by one or more pumping assemblies 225 of console 200.

Throughout method 11000, system 10 (e.g. via user interface 205 of console 200) can provide (e.g. to an operator) information related to the fluids in the various reservoirs 220, such as volume, pressure, and/or temperature information. Based on the provided information, the procedure may be aborted, modified, or proceeded as intended (e.g. manually by the operator and/or automatically by system 10). The provided information can relate to ablative fluid (e.g. hot or cold ablative fluid), and/or neutralizing fluid (e.g. cold or warm, respectively, neutralizing fluid).

In the various steps of method 11000, a reservoir 220 can be filled with an ablative fluid at an elevated temperature, such as a temperature of at least 90° C., at least 93° C., or approximately 96° C. Alternatively or additionally this elevated temperature ablative fluid can be maintained at a temperature of no more than 99° C., such as no more than 98° C., or no more than 97° C. Another reservoir 220 can be filled with a neutralizing fluid that is maintained at a temperature less than body temperature, such as a temperature of approximately room temperature. Alternatively or additionally, a reservoir 220 can be filled with a chilled fluid. The chilled fluid can be maintained at a temperature of no more than 30° C., or no more than 25° C. Alternatively or additionally, this chilled fluid can be maintained at a temperature below room temperature but above 5° C., such as above 7.5° C., or above 9° C.

In STEP 11010, an optional step of a thermal priming procedure is performed on one or more of the fluid pathways of console 200, connecting assembly 300 (if present), and device 100. In some embodiments, the fluid pathways of connecting assembly 300 are warmed, such as to a temperature of at least 60° C., 70° C., or 80° C., such as a temperature of approximately 86° C. In these embodiments, fluid pathways of device 100 can also be warmed, or not.

In STEP 11020, an optional step of performing a pre-ablation neutralizing procedure on tissue is performed (e.g. to tissue in close proximity to functional assembly 130 and/or tissue proximate and/or somewhat remote from this tissue). For example, a cooling fluid can be delivered to functional assembly 130, such as when the ablation of STEP 11030 includes and/or generates heat, such as when the ablation includes a hot fluid ablation, an electromagnetic energy ablation (e.g. an RF ablation), a light energy ablation (e.g. a laser ablation), and/or a sound energy ablation (e.g. a high intensity or other ultrasound ablation).

Upon activation by an operator via user interface 205, neutralizing fluid is introduced into functional assembly 130 (e.g. into balloon 136).

The neutralizing fluid can be delivered to functional assembly 130: for a pre-determined period of time; until a particular volume of fluid is delivered into functional assembly 130; and/or until a pre-determined pressure is achieved within functional assembly 130. The delivery of fluid can be performed at a particular pressure or range of pressures, and/or at a particular flow rate or range of flow rates. In some embodiments, as neutralizing fluid is delivered into functional assembly 130 (e.g. via one or more lumens or other conduits of device 100), fluid is simultaneously evacuated from functional assembly 130 (e.g. via one or more lumens or other conduits of device 100), at flow rates such that functional assembly 130 remains expanded (e.g. remains in contact with surrounding mucosal tissue of the duodenum or other GI mucosal tissue), but fluid within functional assembly 130 is recirculated.

Once functional assembly 130 is filled with the neutralizing fluid (e.g. for a time period of no more than 5 seconds, no more than 4 seconds, and/or no more than 3 seconds), that particular volume of neutralizing fluid can remain in place (e.g. without removal or replacement) throughout the remaining portion of STEP 11020, and/or it can be recirculated, as described herein, for the remaining portion of STEP 11020.

Tissue proximate functional assembly 130 is cooled or otherwise neutralized as long as neutralizing fluid is maintained within functional assembly 130 (e.g. in a stagnant or recirculating manner), and functional assembly 130 is in relative contact with the tissue.

In some embodiments, neutralizing fluid is delivered to functional assembly 130 in a recirculating manner, for a pre-determined time period, such as a time period of at least 5 seconds, 10 seconds, or 15 seconds. In these embodiments, for an initial period (e.g. a period of approximately 2 seconds), fluid is not evacuated from functional assembly 130, allowing functional assembly 130 to radially expand to contact tissue. Subsequently (e.g. for at least the next 3 seconds, 8 seconds, or 12 seconds), functional assembly 130 is in contact with mucosal tissue and neutralizing fluid cools the contacted mucosal tissue as well as other tissue in relative proximity to the contacted mucosal tissue (e.g. neighboring mucosal tissue, as well as deeper tissues including the neighboring submucosal tissue, gastrointestinal adventitia, the tunica serosa, and tunica muscularis).

During this tissue neutralizing procedure, one or more fluid pathway temperatures can be monitored, as described herein, such as to change temperature in a closed-loop fashion, and/or to enter an alert state if a temperature threshold is exceeded.

During this tissue neutralizing procedure, the pressure within one or more fluid pathways can be monitored, such as to adjust the pressure in a closed-loop fashion, and/or to enter an alert state if a pressure threshold is exceeded. For example, pressure below a minimum can represent a break of balloon 136 and/or other leak in the fluid pathway. Pressure above a maximum can represent an occlusion or restriction (e.g. a kink in device 100) has occurred.

Temperature and/or pressure can be monitored by one or more temperature sensor and/or pressure sensor-based functional elements of console 200, connecting assembly 300, and/or device 100, as described in detail herein in reference to FIGS. 1 and/or 9.

While STEP 11020 has primarily been described using a cooling fluid, in alternative embodiments, a warming fluid can be delivered to functional assembly 130 (e.g. to neutralize a cryogenic ablation) or an agent configured to neutralize a chemical ablation can be delivered directly to the mucosal tissue surface (e.g. a non-target tissue surface).

In STEP 11030, an ablation or other tissue treatment procedure is performed on target tissue (e.g. to tissue in close proximity to functional assembly 130 and/or tissue proximate this tissue). For example, an elevated temperature ablative fluid can be delivered to functional assembly 130, such as when the neutralizing fluid of STEP 11020 comprised fluid at a temperature below body temperature.

Ablative fluid is introduced into functional assembly 130 (e.g. into balloon 136), via manual activation by an operator or automatically by system 10 (e.g. an automatic initiation when STEP 11020 is completed).

The ablative fluid can be delivered to functional assembly 130: for a pre-determined period of time; until a particular volume of fluid is delivered into functional assembly 130; and/or until a pre-determined pressure is achieved within functional assembly 130. The delivery of fluid can be performed at a particular pressure or range of pressures, and/or at a particular flow rate or range of flow rates. In some embodiments, as neutralizing fluid is delivered into functional assembly 130 (e.g. via one or more lumens or other conduits of device 100), fluid is simultaneously evacuated from functional assembly 130 (e.g. via one or more lumens or other conduits of device 100), at flow rates such that functional assembly 130 remains expanded (e.g. remains in contact with surrounding mucosal tissue of the duodenum or other GI mucosal tissue), but fluid within functional assembly 130 is recirculated.

Once functional assembly 130 is filled with the ablative fluid (e.g. for a time period of no more than 5 seconds, no more than 4 seconds, and/or no more than 3 seconds), that particular volume of ablative fluid can remain in place (e.g. without removal or replacement) throughout the remaining portion of STEP 11030, and/or it can be recirculated, as described herein, for the remaining portion of STEP 11030.

Tissue proximate functional assembly 130 is ablated or otherwise treated as long as ablative fluid is maintained within functional assembly 130 (e.g. in a stagnant or recirculating manner), and functional assembly 130 is in relative contact with the tissue.

In some embodiments, ablative fluid is delivered to functional assembly 130 in a recirculating manner, for a predetermined time period, such as a time period of at least 5 seconds, 7 seconds, or 10 seconds.

In some embodiments, ablative fluid is introduced into functional assembly 130 immediately after completion of STEP 11020, without evacuation of the neutralizing fluid introduced in STEP 11020.

In some embodiments, ablative fluid is introduced into a tissue-contacting functional assembly 130 in a recirculating manner, for a calculated time period, the "ablation time", that is based on the temperature of cold neutralizing fluid delivered to functional assembly 130 in STEP 11020. For example, the colder the temperature of the neutralizing fluid, the longer the ablation time, and vice versa. Referring to FIG. 50, a table presenting the fluid temperatures and respective ablation times of a tissue treatment procedure is illustrated. Alternatively or additionally, the ablation time can be based on the time that the neutralizing fluid cools (e.g. extracts heat from) the tissue, the "neutralizing time". In some embodiments, the ablation time is also based on the temperature of the ablative fluid (e.g. the hotter the fluid the shorter the ablation time, and vice versa). In some embodiments, the ablation time is based on the information as shown in FIG. 50, such as when the neutralizing time is at least 5 seconds, at least 10 seconds, or approximately 15 seconds.

During this tissue ablation procedure, one or more fluid pathway temperatures can be monitored, as described herein, such as to change temperature in a closed-loop fashion, and/or to enter an alert state if a temperature threshold is exceeded.

During this tissue ablation procedure, the pressure within one or more fluid pathways can be monitored, such as to adjust the pressure in a closed-loop fashion, and/or to enter an alert state if a pressure threshold is exceeded. For example, pressure below a first minimum can represent a break of balloon 136 and/or other leak in the fluid pathway. Pressure below a second minimum (similar or dissimilar to the first), can represent that functional assembly 130 is not in adequate contact with the mucosal tissue. Pressure above a maximum can represent an occlusion or restriction (e.g. a kink in device 100) has occurred.

Temperature and/or pressure can be monitored by one or more temperature sensor and/or pressure sensor-based functional elements of console 200, connecting assembly 300, and/or device 100, as described in detail herein in reference to FIGS. 1 and/or 9.

While STEP 11020 has primarily been described using a cooling fluid, in alternative embodiments, a warming fluid can be delivered to functional assembly 130 (e.g. to neutralize a cryogenic ablation) or an agent configured to neutralize a chemical ablation can be delivered directly to the mucosal tissue surface (e.g. a non-target tissue surface).

As described in reference to a heat ablation, one or more ablation parameters of STEP 11030 can be based on one or more neutralizing parameters of STEP 11020, and vice versa. For example, a cryogenic ablation time can be based on a warming neutralizing temperature and/or neutralizing time. A chemical ablation concentration (e.g. pH), can be based on the concentration of a neutralizing procedure (e.g. a neutralizing procedure performed prior to and/or after the ablation step). An electromagnetic, light, and/or ultrasound ablation can be configured (e.g. adjustment of energy delivery and/or ablation time), based on a neutralizing procedure parameter.

In STEP 11040, an optional step of performing a post-ablation neutralizing procedure is performed (e.g. to tissue in close proximity to functional assembly 130 and/or tissue proximate and/or somewhat remote from this tissue).

The neutralizing procedure of STEP 11040 can be similar to the neutralizing step of STEP 11020. Similarly, the neutralizing step can be performed for a fixed period of time, such as a time of at least 5 seconds, at least 10 seconds, or at least 15 seconds. The neutralizing procedure of STEP 11040 can comprise one or more parameters that are determined by the parameters of the neutralizing procedure of step 11020 and/or the ablation procedure of STEP 11030. Alternatively or additionally, the neutralizing procedure of STEP 11040 can comprise one or more parameters that are used to determine one or more parameters of the procedures of STEPS 11020 and/or 11030.

After the completion of STEP 11040, or STEP 11030 (if neutralizing procedure of STEP 11040 is not performed), fluid can be withdrawn from functional assembly 130, such as for a fixed time period (e.g. no more than 10 seconds, no more than 8 seconds, and/or approximately 6 seconds), and/or until a particular volume of fluid is evacuated. After the fluid evacuation, functional assembly 130 can be transitioned to the translation state, as described herein.

In some embodiments, the functional assembly 130 of method 8000 of FIG. 13 is configured to deliver one or more different forms of energy to target tissue, such as when functional assembly 130 comprises one or more energy delivery elements configured to deliver an energy form selected from the group consisting of: electromagnetic energy; rf energy; light energy; laser light energy; sound energy; ultrasound energy; chemical energy; and combinations thereof. The functional assembly 130 can comprise a balloon (e.g. balloon 136) and/or is can include an array of energy delivery elements (e.g. an array of balloons and/or an array of electrodes). The functional assembly 130 of method 8000 can comprise a treatment length of at least 10 mm long and/or no more than 100 mm long. The functional assembly 130 can comprise an expanded diameter of at least 20 mm and/or no more than 40 mm, or no more than 30 mm.

In some embodiments, the patient identified in STEP 8010 of method 8000 of FIG. 13 has been diagnosed with a medical condition selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome (PCOS); hypertriglyceridemia; hypercholesterolemia; psoriasis; GERD; coronary artery disease (e.g. as a secondary prevention); stroke; TIA; cognitive decline; dementia; Alzheimer's disease; neuropathy; diabetic nephropathy; retinopathy; heart disease; diabetic heart disease; heart failure; diabetic heart failure; hirsutism; hyperandrogenism; fertility issues; menstrual dysfunction; cancer such as liver cancer, ovarian cancer, breast cancer, endometrial cancer, cholangiocarcinoma, adenocarcinoma, glandular tissue tumor(s), stomach cancer, large bowel cancer, and/or prostate cancer; diastolic dysfunction; hypertension; myocardial infarction; microvascular disease related to diabetes; sleep apnea; arthritis; rheumatoid arthritis; hypogonadism; insufficient total testosterone levels; insufficient free testosterone levels; and combinations of two or more of these.

In some embodiments, the results achieved immediately herein are dependent on a minimum amount of mucosal tissue (e.g. duodenal mucosal tissue) being treated (e.g. ablated, denatured, removed, and/or otherwise treated). For example, a single or cumulative (multiple treatment) axial length of at least 3 cm, at least 6 cm, at least 8 cm, and/or at least 9 cm of duodenal mucosa is treated to achieve these clinical benefits. Alternatively, at least 30% of the post-papillary duodenal mucosa is treated.

The method 8000 of FIG. 13 and other methods of the present inventive concepts can result in (e.g. cause) one or more of the following outcomes (e.g. outcomes related to the clinical benefits described herein): a reduction of surface area of mucosal tissue proximate the treated locations; an altering of hormonal signaling of the intestine proximate the treated location; replacement of the treated mucosal tissue with new tissue; a reduction in iron absorption; a reduction or increase in bile acid signaling; an altering of microbiome composition; a reduction in glucose, fat, and/or amino acid signaling and/or absorption; a reduction in GIP levels in the fasting state (e.g. by at least 5%, 10%, and/or 20%); a reduction in GIP levels in the post-prandial state (e.g. by at least 5%, 10%, and/or 20%); an increase in GLP-1 levels in the post-prandial state (e.g. by at least 5%, 10%, and/or 15%); an increase in GLP-1 levels in the post-prandial state (e.g. while not significantly altering GLP-1 levels in the fasting state); and combinations of two, three, or more of these.

Referring now to FIGS. 17-20D, results from studies conducted by applicant to investigate the safety and efficacy of duodenal mucosal resurfacing (DMR) on glycemic and hepatic parameters in patients with type 2 diabetes (T2D) are illustrated, consistent with the present inventive concepts. Referred to by the applicant as the REVITA-2 study, the study protocol comprised a double-blind, randomized trial (1:1) that employed hydrothermal DMR as an outpatient endoscopic procedure. DMR targets duodenal pathology to treat insulin-resistance related metabolic disease, including T2D. Specifically, the DMR employed in REVITA-2 utilized submucosal lift and hydrothermal ablation of the hyperplastic duodenal mucosa to promote healthy epithelial regrowth and reduce both insulin resistance and hyperinsulinemia.

REVITA-2 was conducted at nine sites in Europe, whereby participants were selected based on the following eligibility criteria: diagnosed with type 2 diabetes; a hemoglobin A1c (HbA1c) of between 7.5% and 10.0%, such as between 59 mmol/mol and 86 mmol/mol; a body mass index of between greater than or equal to 24 kg/m$^2$ and less than or equal to 40 kg/m$^2$; a fasting insulin of greater than 7.0 µU/mL, such as greater than 48.6 pmol/L; taking greater than or equal to one oral glucose lowering medications, of which at least one was metformin; and/or did not undergo a change in medication for at least 12 weeks prior to entry into the study. In some embodiments, participants were further selected to have a liver magnetic resonance imaging proton density fat fraction (MRI-PDFF) greater than or equal to 5%. In some embodiments, participants were further selected to have a fasting plasma glucose greater than or equal to 140 mg/dL. In some embodiments, participants were selected to have a fasting c-peptide greater than or equal to 0.6 ng/mL. Additional baseline characteristics and demographics of the study participants are shown in FIG. 17. A total of 75 participants were enrolled in the study.

The primary endpoints were identified as an HbA1c change at 24 weeks post-DMR and change in MRI-PDFF at 12 weeks post-DMR when fat content is greater than or equal to 5%. Additionally, the study sought to achieve no clinical or laboratory signs of adverse effects to the participants related to malabsorption, anemia, pancreatitis, biliary complications, and/or infection post-DMR.

In some embodiments, an additional endpoint was identified as a reduction in patient fasting plasma glucose (FPG) at 24 weeks post-DMR, such as a reduction in FPG of at least 26.5 mg/dL at 24 weeks.

In some embodiments, an additional endpoint was identified as a reduction in patient weight at 24 weeks post-DMR.

In some embodiments, an additional endpoint was identified as a reduction in patient hepatic insulin resistance post-DMR.

In some embodiments, an additional endpoint was identified as an improvement in patient beta cell function post-DMR.

In some embodiments, an additional endpoint was identified as the patient not changing (e.g. adjusting, discontinuing, etc.) the at least one oral glucose lowering medication post-DMR.

The participants were classified according to two populations: modified intent-to-treat (miTT) and per-protocol (PP). The miTT population included all participants who received treatment and exhibited baseline measurements for at least one of the primary endpoints. The PP population excluded all participants who experienced major protocol deviations.

REVITA-2 participants were randomly (1:1) assigned to a single DMR or sham procedure. Of the 75 participants, 39 underwent the DMR procedure and 36 underwent the sham procedure. According to the study protocol, a full DMR procedure was defined as five complete ablations or ten axial centimeters of circumferentially ablated tissue in the duodenum of the participants. In some embodiments, the procedure was performed in the post-papillary duodenum. Following discharge, participants were provided with continued nutritional counseling on the importance of diet in blood glucose regulation and prescribed a progressive diet for two weeks (e.g. liquids on days 1 through 3, pureed foods on days 4 through 6, and soft foods on days 7 through 14) prior to resuming their normal diet. Oral diabetic medications were held constant from the start of the run in period through week 24; however, if the participant experienced a hypoglycemic or hyperglycemic event, changes to their antidiabetic medication were considered.

Figures 18A, 18B:
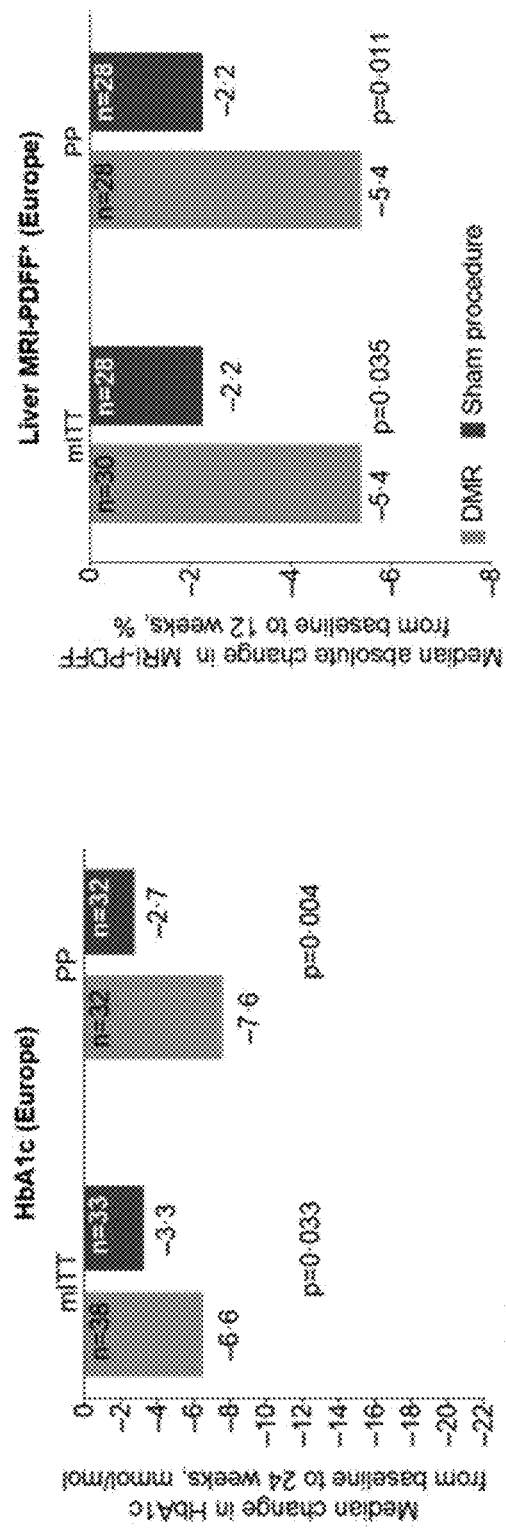

Referring specifically to FIG. 18A, participants with an HbA1c baseline of between 7.5% and 10.0% demonstrated a baseline reduction in HbA1c of greater than or equal to 6%, such as greater than or equal to 7%, at 24 weeks.

Referring specifically to FIG. 18B, participants with a BMI baseline of between greater than or equal to 24 kg/m$^2$ and less than or equal to 40 kg/m$^2$ demonstrated an absolute reduction in liver MRI-PDFF of greater than or equal to 5.4% at 12 weeks.

Figures 18C, 18D:
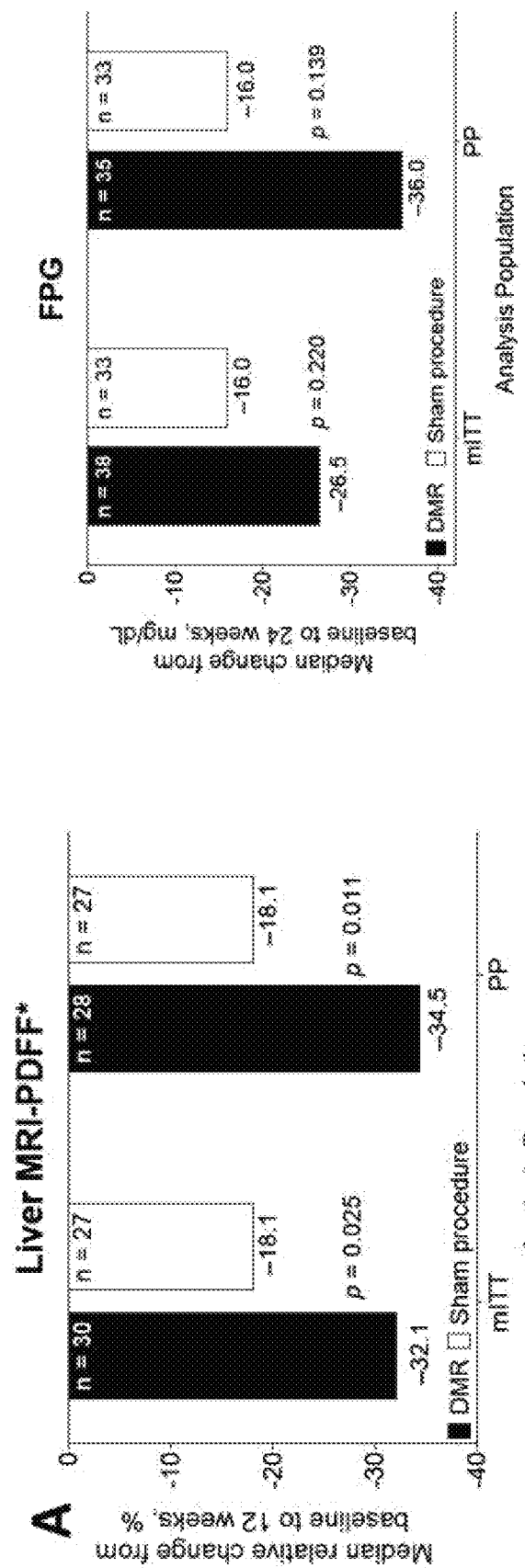

Referring specifically to FIG. 18C, participants with a fasting insulin baseline of greater than 7.0 µU/mL demonstrated a relative reduction in liver MRI-PDFF of greater than or equal to 30% at 12 weeks post-DMR, and as compared to the sham procedure relative reduction of 18%.

Referring specifically to FIG. 18D, participants with a fasting c-peptide baseline of greater than or equal to 0.6 ng/mL demonstrated a reduction in fasting plasma glucose (FPG) by greater than or equal to −25 mg/dL at 24 weeks post-DMR, such as −26.5 mg/dL, such as greater than or equal to −30 mg/dL, such as greater than or equal to −35 mg/dL, such as −36.0 mg/dL, and as compared to the sham procedure reduction of −16.0 mg/dL.

Figures 18E, 18F:
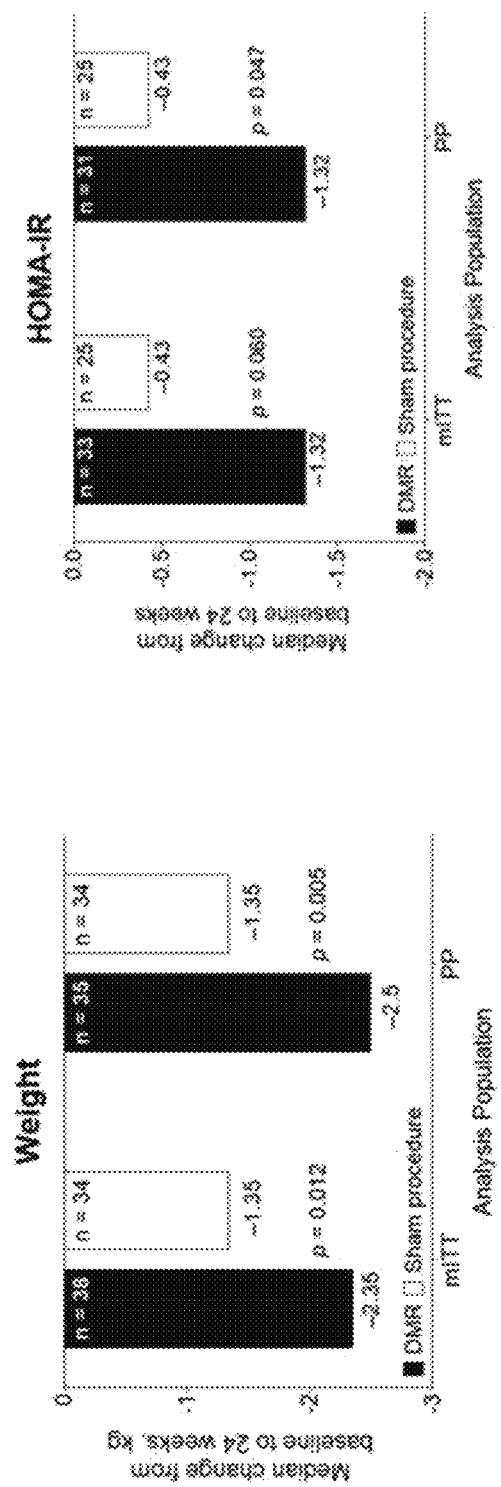

Referring specifically to FIG. 18E, participants with an MRI-PDFF baseline of greater than or equal to 5% demonstrated a reduction in weight of greater than or equal to −2.3 kg, such as greater than or equal to −2.5 kg, at 24 weeks post-DMR, and as compared to the sham procedure reduction of −1.35 kg.

Referring specifically to FIG. 18F, participants with a number of oral glucose lowering medications baseline of greater than or equal to one demonstrated a reduction in homeostatic model assessment of insulin resistance (HOMA-IR) by greater than or equal to −1.32 at 24 weeks post-DMR, and as compared to the sham procedure reduction of −0.43.

Figures 18G, 18H:
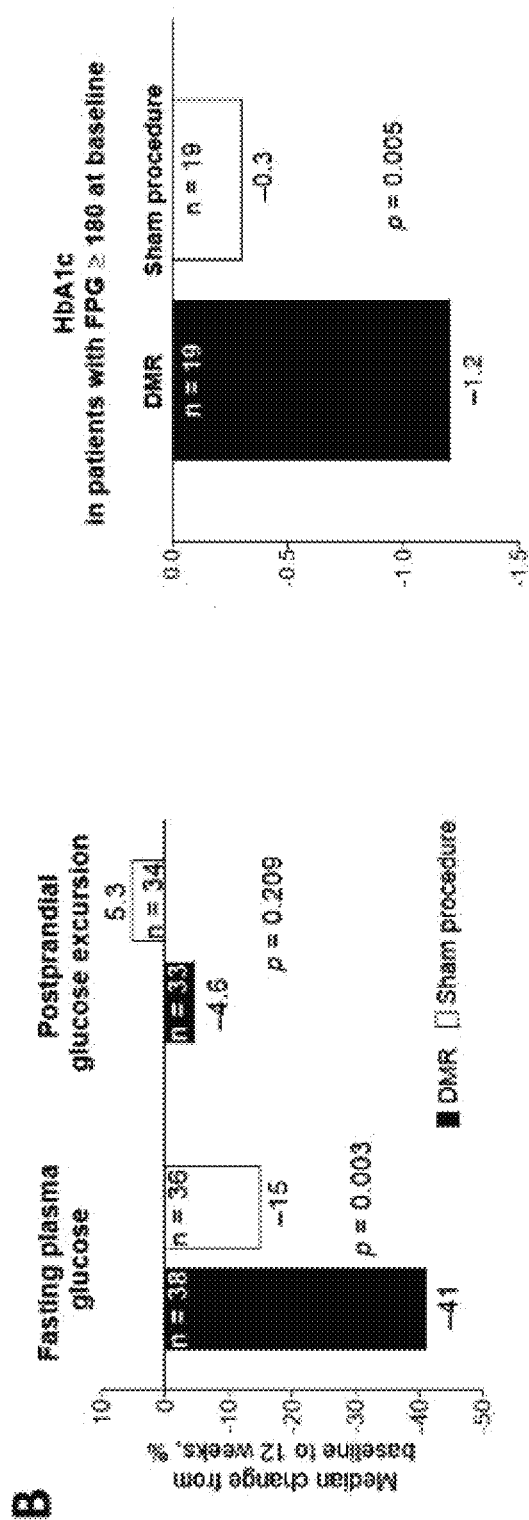

Referring specifically to FIG. 18G, participants with an FPG baseline of greater than or equal to 140 mg/dL demonstrated a reduction in FPG of greater than or equal to −41 at 12 weeks post-DMR.

Referring specifically to FIG. 18H, participants with an FPG baseline of greater than or equal to 180 mg/dL demonstrated a reduction in HbA1c of −1.2 at 24 weeks post-DMR.

Figures 18I, 18J:
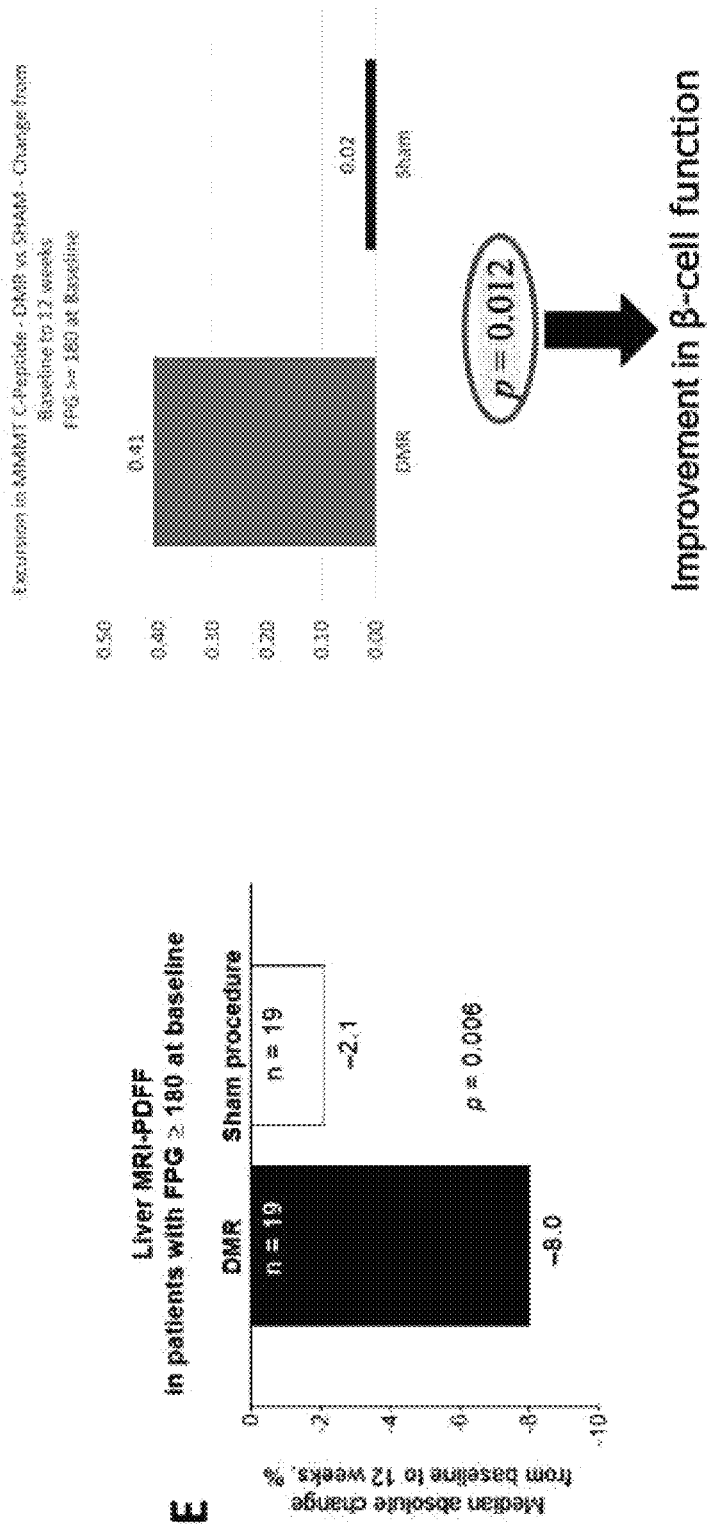

Referring specifically to FIG. 18I, participants with an FPG baseline of greater than or equal to 180 mg/dL demonstrated a reduction in liver MRI-PDFF of greater than or equal to −8% (abs %) at 12 weeks post-DMR.

Referring specifically to FIG. 18J, participants with an FPG baseline of greater than or equal to 180 mg/dL demonstrated an increase in MMTT-excursion of c-peptide by 0.41 at 12 weeks post-DMR.

Figure 18K:
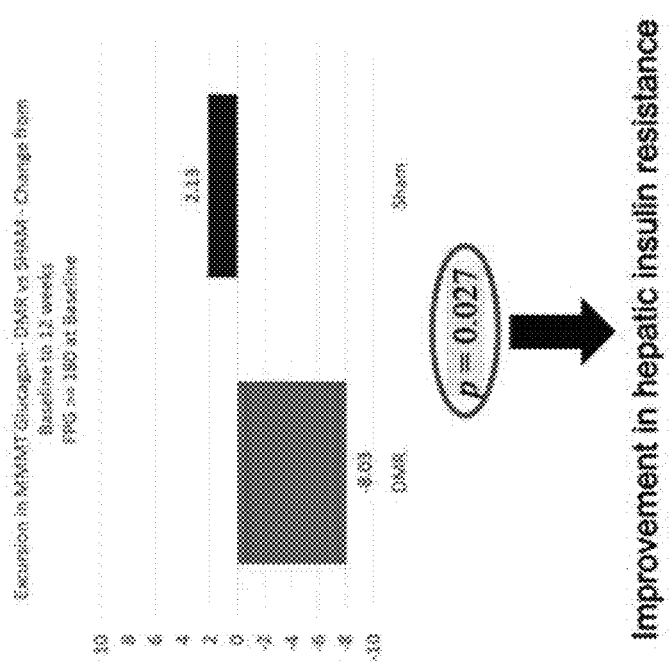

Referring specifically to FIG. 18K, participants with an FPG baseline of greater than or equal to 180 mg/dL demonstrated a reduction in MMTT-excursion of glucagon by −8 at 12 weeks post-DMR.

Applicant believes REVITA-2 represents the first randomized, sham-controlled study of a disease-modifying outpatient procedural therapy, the results of which demonstrate a single DMR is well-tolerated, safe, and elicits clinically and statistically significant improvements in HbA1c levels and liver fat content in patients with poorly controlled T2D. Within the miTT population, the results of REVITA-2 demonstrate that 24 weeks post-DMR, the median (IQR) HbA1c change was −6.6 mmol/mol as compared to −3.3 mmol/mol post-sham procedure. Additionally, the results demonstrate 12 weeks post-DMR the liver-fat change was −5.4% as compared to −2.2% post-sham procedure.

In addition to the primary endpoints described herein, secondary (e.g. exploratory) endpoints were also identified as a median change in FPG and MMTT glucose area under the curve (AUC) over 2 hours, as well as a change in MMTT C-peptide and glucagon over 2 hours from baseline to 12 weeks post-DMR. Of the 75 participants, a subset of 70 participants were included in the second endpoint analyses, of which 35 underwent the DMR procedure and 35 underwent the sham procedure. Furthermore, 39 of the 70 participants had a baseline of FPG greater than or equal to 180 mg/dL (DMR, n=20; sham, n=19).

At select study sites, participants were administered a mixed meal tolerance test (MMTT) to evaluate their hormone response to nutrients by measuring the concentration of glucose, gut and pancreatic hormones, and metabolic substrates. The baseline results were compared to results at 12 weeks post-procedure (e.g. DMR, sham). A change in MMTT can correlate to both a change in insulin secretion and/or resistance. Before beginning the assessment, the participant's blood glucose was tested with a glucometer to assess their fasting state. If the reading was above 300 mg/dL (e.g. 16.7 mmol/L), the participant was asked to confirm time and details of last oral intake. If appropriate fasting cannot be confirmed, the MMTT assessment was rescheduled. After a 10-hour overnight fast, participants were asked to ingest a liquid meal consisting of Ensure (e.g. 200 ccl) or equivalent. Meals were to be ingested within 10 min. During the test, blood samples were drawn at 0 mins (fasting) and at 15, 30, 45, 60, 90, 120 and 180 mins following the start of the meal.

Figures 19A, 19B:
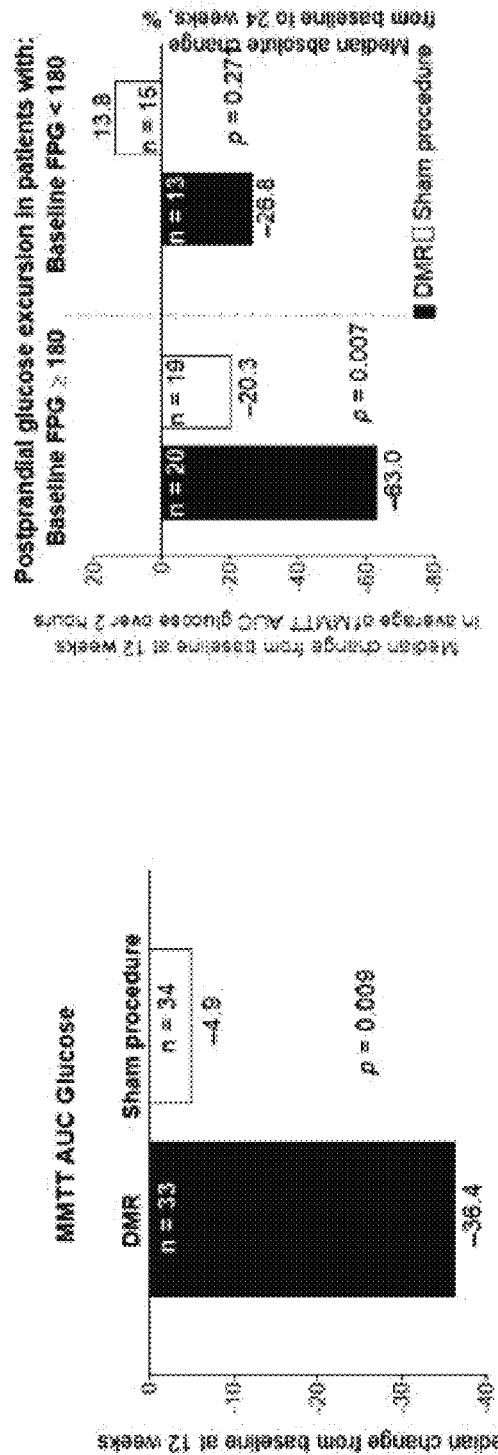

Referring specifically to FIG. 19A, participants demonstrated a reduction in median MMTT-AUC for glucose of greater than or equal to −25 mg/dl at 12 weeks post-DMR, such as greater than or equal to −30 mg/dl, such as greater than or equal to −35 mg/dl, such as −36.38 mg/dL, and as compared to the sham procedure reduction of −4.9 mg/dL. The demonstrated glucose reduction post-DMR is likely driven by a significant decrease in FPG rather than a median MMTT postprandial glucose excursion, as shown in FIG. 19B.

Referring specifically to FIG. 19B, participants with an FPG baseline of greater than or equal to 180 mg/dL demonstrated a reduction in median MMTT-AUC for glucose of greater than or equal to −50 mg/dl at 12 weeks post-DMR, such as greater than or equal to −55 mg/dl, such as greater than or equal to −60 mg/dl, such as greater than or equal to −63.03 mg/dL, and as compared to the sham procedure reduction of −20.3 mg/dL. Participants with an FPG baseline of less than 180 mg/dL demonstrated a reduction in AUC glucose of −26.81 at 12 weeks post-DMR, and as compared to the sham procedure increase of 13.8 mg/dL.

Figures 19C, 19D:
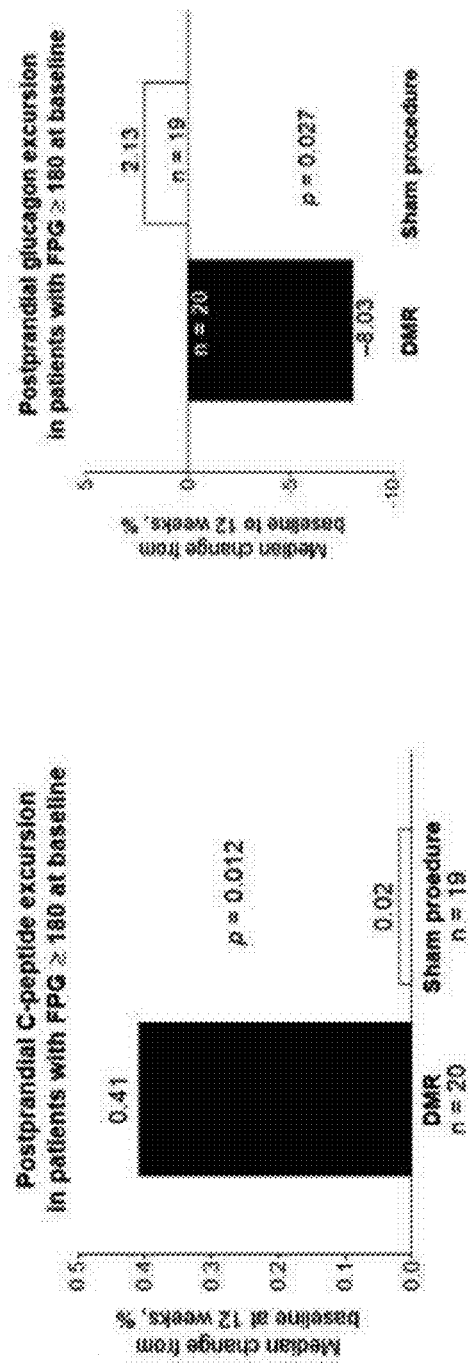

Referring specifically to FIG. 19C, participants with an FPG baseline of greater than or equal to 180 mg/dL demonstrated an increase in post-prandial c-peptide excursion of greater than or equal to 0.20 ng/mL at 12 weeks post-DMR, such as greater than or equal to 0.30 ng/mL, such as greater than or equal to 0.40 ng/mL, such as 0.41 ng/mL, and as compared to the sham procedure increase of 0.02 ng/mL.

Referring specifically at FIG. 19D, participants with an FPG baseline of greater than or equal to 180 mg/dL demonstrated a reduction in post-prandial glucagon excursion of greater than or equal to −5 pg/mL at 12 weeks post-DMR, such as greater than or equal to −6 pg/mL, such as greater than or equal to −7 pg/mL, such as greater than or equal to −8 pg/mL, such as −8.03 pg/mL, and as compared to the sham procedure increase of 2.13 pg/mL.

The results demonstrate glycemic benefit is driven by a decrease in FPG, and not by weight loss. The most pronounced benefit was demonstrated by those with a high FPG at baseline, and with which the increase in postprandial insulin and c-peptide is consistent with improvements in j-cell function in the pancreas and the decrease in postprandial glucagon is consistent with the impact of DMR on hepatic insulin resistance and hepatic glucose production. Furthermore, the observed suppression of hyperglucagonemia provides a strong mechanistic rationale for the effects of DMR on hepatic and glucose metabolism.

Applicant conducted an additional exploratory study within REVITA-2 to identify treatment-induced mechanistic differences in hepatic iron metabolism in study participants. Specifically, the applicant sought to determine the association between MRI proton density fat fraction (PDFF)-derived R2* liver ion concentration (LIC) measurements and liver fat fraction (FF), as well as the difference in the strength of association between the relative change in liver FF and LIC at 12 weeks post-DMR.

REVITA-2 participants were assigned to one of three cohorts: training case, DMR, or sham. The training case cohort included 17 non-randomized participants who received a single DMR procedure so as to allow the respective study site to familiarize itself with the procedure prior to randomization. The DMR cohort included 39 randomized participants who received a single DMR procedure. The sham cohort included 23 randomized participants who received the sham procedure.

Measurement coherence and longitudinal stability of site PDFF measurements was assessed at 6-month intervals using custom-built fat-water QA phantoms. Scans were reviewed to ensure compliance with acquisition parameters, adequate anatomical coverage, and absence of significant artefacts. A circular region of interest (ROI) measuring up to 20 mm$^2$ in diameter was placed in each of the Couinaud liver segments co-localized on PDFF maps and R2* maps for LIC, while avoiding vessels and the biliary tree. LIC was estimated from R2* data based on previously published methods. Linear regression with calculation of Pearson's correlation coefficient was used to explore the relationship between the baseline absolute liver FF and LIC measurements and the relative (e.g. % of baseline) within-participant change in liver FF and LIC for the DMR and sham cohorts.

Referring specifically to FIG. 20A, participants within the three cohorts (e.g. training, DMR, and sham) demonstrated a significant positive correlation between baseline absolute liver FF and LIC.

Referring specifically to FIG. 20B, participants within the training case cohort demonstrated a significant positive correlation between the relative change in FF and relative change in LIC at 12 weeks post-DMR.

Figures 20C, 20D:
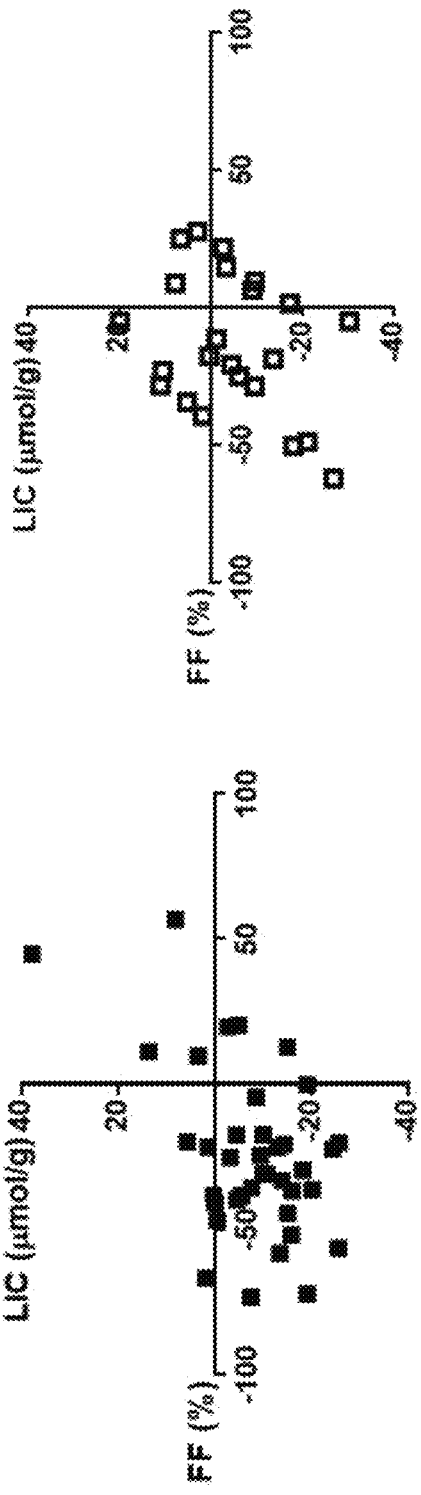

Referring specifically to FIG. 20C, participants within the DMR cohort demonstrated a significant positive correlation between the relative change in FF and relative change in LIC at 12 weeks post-DMR.

Referring specifically to FIG. 20D, participants within the sham cohort demonstrated a weaker and not significant correlation between the relative change in FF and relative change in LIC at 12 weeks post-sham procedure.

The results demonstrate a positive correlation in PDFF-derived liver FF and LIC at baseline. The relative change in liver FF and LIC at 12 weeks is more strongly correlated post-DMR as compared to the sham procedure, thus, raising the possibility of altered mechanistic effects on hepatic iron metabolism as a result of DMR. The strong positive correlation demonstrated between PDFF-derived liver FF and LIC is comparable with previously reported results, despite collating data from multiple field strengths and participants with normal range LIC levels (e.g. less than 36 µmol/g).

Previous studies conducted by applicant have demonstrated DMR reduces free fatty acid production, diacylglycerols, and ceramides. Overflow of fatty acids to the liver has been associated with increased cellular levels of toxic lipids such as diacylglycerols, ceramides, and long-chain fatty acyl-coenzyme A (CoA), which are involved in inflammatory pathways. Excess fatty free acids also promote mitochondrial dysfunction, an increase in oxidative stress, and uncouple oxidative phosphorylation. Excess fatty free acids also activate a fibrogenic response in hepatic cells that can promote the progression to (non-alcoholic steatohepatitis) NASH and cirrhosis, and the production of reactive oxygen species. These molecules can directly damage the liver, or act indirectly, by increasing oxidative stress, hepatocellular damage, liver fibrosis and tumor development.

With REVITA-2, applicant has demonstrated DMR can further reduce liver fat. Based on the known relationship between these toxic lipids (e.g. free fatty acids, diacylglycerol, ceramides), liver fat content, and the progression to NASH, the DMR procedure can likewise reduce NASH. These same factors can lead to a worsening of fibrosis and the risk of liver cancer, and thus, improvements in NASH are associated with a reduction in the rate of progression of fibrosis and a reduction in the risk of liver cancer.

The tissue treatment procedure of the present inventive concepts can be performed by a trained endoscopist in an endoscopic suite or in an operating room under general anesthesia or conscious sedation. The patient can be positioned in the preferred position as dictated by the site's requirements for endoscopic procedures. Anti-peristaltic agents may be used during the procedure. Device 100 delivery and functional assembly 130 positioning for treatment can be verified using fluoroscopic guidance. The use of fluoroscopy is limited and may be used during device 100 positioning and/or verification of functional assembly 130 location during treatment. The process of expansion, ablation, and repositioning is repeated until the needed axial length of duodenal mucosa is treated. These treatments (e.g. ablations) can be conducted without overlapping and minimizing gaps in between the areas of the mucosa that have been ablated. After all axial segment treatments have been performed, device 100 (e.g. an endoscope 50a) can be removed. The total procedure time can be approximately 60 minutes.

In some embodiments, the tissue treatment procedure of the present inventive concepts comprises placing functional assembly 130 of device 100 in the proximal duodenum distal to the papilla. Both submucosal tissue expansion and mucosal ablation of the duodenum are then performed at multiple locations of the post-papillary duodenum. Using interface 205 of console 200, functional assembly 130 is expanded (e.g. balloon 136 is inflated), and vacuum delivered (e.g. via device 100 and/or endoscope 50a) to draw the intestinal tissue into ports 137. Control 104 of handle 102 is moved to advance each fluid delivery element 139c (e.g. three needles) into the submucosal tissue captured within each of the ports 137. Console 200 delivers saline colored with an optical colorant (e.g. methylene blue or similar dye) into the submucosa through the fluid delivery elements 139c resulting in a complete circumferential lift of the mucosa. Once complete, the ablation cycle is started, and cold-hot-cold water is circulated into the functional assembly 130 (e.g. balloon 136) to complete ablation of the mucosal tissue proximate the previously expanded submucosal tissue. The functional assembly 130 is radially compressed (e.g. balloon 136 is deflated), and device 100 translated distally to position functional assembly 130 at the next axial segment of the duodenum to be treated. The process of expansion, ablation, and repositioning is repeated until the needed axial length of duodenum is treated. A full tissue treatment comprises multiple sequential ablations (usually about 5) performed from immediately beyond the ampulla of Vater to locations proximate (e.g. proximal to) the ligament of Treitz. These ablations are usually conducted without overlapping and minimizing gaps in between the areas of the mucosa that have been ablated.

For people with diabetes, any procedure that causes them to miss a meal or change their usual meal plan will require special planning to safely manage blood glucose. Patients receiving the mucosal treatment procedure of the present inventive concepts may be specifically instructed on appropriate post-procedure diet and glycemic management. Intensified glucose monitoring can be implemented during a post tissue treatment period. Patients may be instructed to maintain adequate caloric intake (e.g. with a caloric reduction of no more than 300 calories/day) and sufficient hydration during the entire post-procedure period. In some embodiments, the patient undergoes a 14-day diet plan as follows: on the day of the tissue treatment procedure, abstinence of food is maintained (water is allowed but must be sipped); on days 1-3 after the tissue treatment procedure, the patient may drink clear liquids such as tea, chicken broth and skimmed (fat-free) milk; on days 4-6 post-tissue treatment procedure, the patient should begin to eat a soft diet such as vegetarian, chicken or beef soup (broth with herbs and semolina), nonfat yogurt, tea and sugar-free gelatin; and on days 7-14 of the diet, the patient may expand their diet to include foods such as stew, fruit puree, soft vegetables, and soda crackers. After finishing the 14-day diet, the patient can resume their standard diabetes diet. Patients should consume adequate fluids (as prescribed by the clinician for SGLT2i use) to stay hydrated.

For a period of time following the mucosal treatment procedure, the patient's glycemia can be managed by assessing one or more of the following parameters: antidiabetic medication use; SMBG values; hypoglycemia and/or hyperglycemia values (e.g. as recorded in a glycemia diary); HbA1c levels; occurrence of hypoglycemia; and/or symptomatic severe hyperglycemia.

For a period of time following the mucosal treatment procedure, the patient's hyperglycemia can be managed by assessing one or more of the following parameters: blood glucose absolute value compared to rescue threshold; overall trajectory of FPG relative to run-in and baseline; isolated incidents vs a persistent elevation in blood sugar; presence or absence of hyperglycemic symptoms; and/or presence or absence of an assignable cause of high blood sugar (e.g. intercurrent infection).

As described herein, in some embodiments, system 10 includes an agent 420 that comprises a pharmaceutical or other agent that is provided to the patient as an adjunctive therapy (e.g. in addition to a tissue treatment performed using device 100). For example, agent 420 can comprise an insulin (e.g. glargine) that is taken by the patient on an "as-needed" basis, such as to reduce the risk of an undesired clinical event such as a hyperglycemic event. In some embodiments, an agent 420 comprising glargine (or equivalent) is taken by the patient when the patient's FPG exceeds 270 mg/dl (e.g. as determined by finger sticks on three consecutive days). The glargine dose can be titrated, such as can be determined by the patient's clinician.

In some embodiments, system 10 is configured to perform an intestinal mucosal treatment (e.g. a mucosal ablation) including ablation of multiple axial segments of the small intestine between the ampulla of Vater and the ligament of Treitz. Functional assembly 130 can be positioned during ablation of each axial segment to avoid treating segments that overlap (e.g. avoid multiple treatments to the same tissue). Functional assembly 130 can be positioned during ablation to minimize gap between axial segments. System 10 can be configured to treat approximately five axial segments, in other words to perform approximately five discrete tissue ablation steps (e.g. five energy deliveries). The patient can comprise an individual who is inadequately controlled on basal insulin after the failure of diabetic management that includes lifestyle modification, diet, and at least 2 oral antidiabetic agents. The therapeutic benefit to these patients provided by system 10 includes but is not limited to: elimination or at least reduction in the use of insulin; improved glycemic control; reduced insulin-associated hypoglycemia, weight gain and/or cardiovascular risks; and/or improved quality of life.

In some embodiments, system 10 is configured to record patient data, such as patient data associated with hyperglycemic events (e.g. as defined herein), and/or hypoglycemic events. A serious, clinically important hypoglycemic event can be defined as plasma glucose of less than 3.0 mmol/L (<54 mg/dL). Severe hypoglycemia can be defined as denoting severe cognitive impairment requiring external assistance for recovery. A glucose alert value can be defined as a value of less than or equal to 3.9 mmol/L (≤70 mg/dL).

In some embodiments, system 10 is configured to perform a duodenal mucosal ablation procedure, as described herein, to achieve an HbA1c level of no more than 7.0% at week 24, without the need for insulin (e.g. for patients that were taking insulin prior to the duodenal mucosal ablation procedure). Alternatively, an HbA1c level of no more than 7.0% is achieved with the amount of insulin taken at week 24 being at a lower level than was taken prior to the performance of the mucosal ablation. Alternatively, for patients that are taking insulin, system 10 is configured to perform a duodenal mucosal ablation procedure, as described herein, to reduce (e.g. eliminate), the need for insulin without worsening glycemic control in that patient (e.g. for an HbA1c level at 24 weeks following the procedure to be the same as or lower than the HbA1c level taken prior to the performance of the duodenal mucosal ablation procedure).

In some embodiments, system 10 is configured to perform a duodenal mucosal ablation procedure, as described herein, on patients with T2D that are sub-optimally controlled on two to three OADs, one of which is metformin. The mucosal procedure can be performed in these patients to lower their HbA1c.

In some embodiments, system 10 is configured to perform a duodenal mucosal ablation procedure, as described herein, on patients, where after performance of the mucosal ablation, the patient takes an agent 420 comprising liraglutide, and practices certain lifestyle modifications. In these embodiments, system 10 can be configured to achieve (e.g. in T2D patients with preserved beta-cell function) any one or more (e.g. all) of the following: a reduction in (e.g. elimination of) insulin requirements; adequate glycemic control; an improvement in a metabolic condition; an improvement in a hepatic condition such as a reduction in liver fat; and/or an improvement in one or more cardiovascular conditions.

In some embodiments, system 10 is configured to perform a duodenal mucosal ablation procedure, as described herein, on patients, where after performance of the mucosal ablation, histological changes to the duodenal mucosa are observed in the ablated segment at a time point of 24 weeks after the procedure. These histological changes can include but are not limited to: reduction in crypt density; reduction in crypt depth; reduction in villous length; reduction in total number of enteroendocrine cell numbers; and combinations of one or more of these.

System 10 can be constructed and arranged to allow a clinician to safely and effectively ablate the duodenal mucosa in T2D. Data collected by applicant has shown that a successful duodenal mucosal treatment procedure lowers HbA1c in T2D subjects on stable medications who have inadequate glycemic control. In addition, data from human clinical studies help establish the putative role of the duodenum as both an endocrine organ that is responsible for impaired metabolic signaling and a therapeutic target for patients with T2D and support the mechanism of the treatment of the present inventive concepts to positively improve the abnormal metabolic state. This improvement is mainly driven by overall reductions in fasting plasma glucose, causing a decrease in hepatic insulin resistance. This reduction in insulin resistance is believed to indirectly preserve beta-cell function, increase insulin sensitivity, decrease the need for insulin and lead to insulin withdrawal in this T2D population. Because poor adherence to medications is a significant barrier to glycemic control in the overall diabetic population, the system 10 mucosal ablation procedure that avoids daily compliance with additional medications offers an important new therapy to T2D to help reduce the morbidity and end-organ damage from this debilitating chronic illness.

Many oral antidiabetic medications act by increasing insulin secretion or improving insulin sensitivity, however, SGLT2 inhibitor drugs prevent the reuptake of glucose into the bloodstream by decreasing renal absorption of glucose and thereby increases renal excretion of glucose. Because of the SGLT2i selective action on the kidney, gastrointestinal side effects are minimized. SGLT2i's independent mechanism of action allows it to be used easily in combination with other therapies, including insulin. SGLT2i has been shown to provide a beneficial effect on weight, liver, kidneys and cardiovascular parameters. SGLT2i (e.g. empagliflozin) has been proven to be safe and tolerated well in patients, as seen in the meta-analysis done by Kohler et al (2017) and Yabe et al (2019) in T2 patients. In some embodiments, system 10 is configured to achieve euglycemia and insulin independence by combining a duodenal mucosal ablation procedure, as described herein, with administration of an agent 420 comprising at least SGLT2i (e.g. for T2D patients previously on insulin who have a preserved beta-cell function, such as beta-cell function indicated by a plasma C-peptide value of at least 0.6 ng/mL). In some embodiments, the agent 420 administered to the patient comprises SGLT2i (e.g. empagliflozin) and Metformin. In some embodiments, system 10 provides a treatment that combines duodenal mucosal ablation and agent 420 administration (e.g. where agent 420 comprises at least SGLT2i, such as when agent 420 also includes Metformin and/or does not include insulin) to improve and/or preserve beta-cell function (e.g. improve and preserve beta-cell function), such as when combined with appropriate lifestyle intervention. In some embodiments, system 10 provides a treatment that combines duodenal mucosal ablation and agent 420 administration (e.g. where agent 420 comprises at least SGLT2i, such as when agent 420 also includes Metformin and/or does not include insulin) that achieves beneficial effects on metabolic, hepatic, and/or cardiovascular states, in addition to glucose regulation (e.g. as compared to insulin treatment).

System 10 can be configured to perform a duodenal mucosal ablation procedure, as described herein, that results in a therapeutic benefit (e.g. at 24 weeks after the time of the duodenal mucosal procedure) to the patient, and can include at least a reduction (e.g. an elimination) in the amount of insulin taken by the patient as compared to the amount taken prior to the performance of the mucosal ablation. The achieved therapeutic benefits can comprise one or more benefits selected from the group consisting of HbA1c level of no more than 7.0%; improvement in ALT, AST, NAFLD-FS, FIB-4, ELF, and/or other liver parameter; improvement in Fibro Scan FS and/or with CAP score; improvement in absolute and/or relative MRI-PDFF values in subjects with baseline MRI-PDFF of greater than 5%; improvement in body weight in subjects who achieve an HbA1c of no more than 7%; improvement in body weight; improvement in fasting c-peptide; improvement in fasting plasma glucose (FPG); improvement in HOME-IR; improvement in Diabetes Treatment Satisfaction Questionnaire; improvement in RAND Short Form (36) Health Survey (SF-36); improvement in PROMIS® (Patient-Reported Outcomes Measurement Information System); improvement in cardiovascular risk score; elimination or at least reduction in insulin administered after mucosal ablation as compared to prior to mucosal ablation; change in waist circumference (e.g. reduction); improvement in TG, HDL-C, and/or LDL-C, total cholesterol, free fatty acids, and/or lipoprotein a; improvement in glucagon and/or insulin; improvement in HbA1c as compared to baseline (e.g. as stratified by three insulin dose categories, less than 20, 20-39, and 40 to 60 units/day); reduction in health care costs (e.g. diagnosis-based (IDG) costs); and combinations of these.

In some embodiments, system 10 is configured to perform a mucosal ablation procedure, as described herein, on a patient that has been screened (e.g. in a diagnostic procedure) to have an FPG of at least 180 mg/dl but less than 270 mg/dl, and an HbA1c of at least 7.5% but less than 9.5%.

In some embodiments, system 10 is configured to perform a mucosal ablation procedure, as described herein, on a patient that has been screened to having been on a stable dose of up to 2,000 mg or maximally tolerated metformin and basal insulin of 20 to 60 units/day for at least 12 weeks (e.g. with less than 10% change from baseline insulin dose allowed during the stability period).

In some embodiments, system 10 is configured to perform a mucosal ablation procedure, as described herein, on a patient that has been on insulin and another one or more anti-diabetic agents (ADAs) in addition to metformin.

In some embodiments, system 10 is configured to perform a mucosal ablation procedure, as described herein, on a patient that has undergone a screening procedure comprising an endoscopic evaluation of the esophagus, stomach, duodenum, and associated structures.

In some embodiments, system 10 is configured to perform a mucosal ablation procedure, as described herein, on a patient that has undergone a screening procedure confirming the following inclusion criteria are met: presence of T2D and currently on stable doses of metformin (maximum tolerated dose) and requiring a minimum of 20 units up to a maximum of 60 units of basal insulin; or presence of T2D and currently on basal insulin (20-60 units/day) who meet other inclusion criteria but are on other ADAs (including GLP-1a, DPP4, and the like). The successfully screened patient may further meet the following inclusion criteria: HbA1c of between 7.5% and 9.5%; FPG of between 180 mg/dl and 270 mg/dl (measured at least 24 hours after the last dose of glargine or at least 12 hours after the last dose of NPH insulin); and body mass index (BMI) of between 28 kg/m$^2$ and less than 40 kg/m$^2$.

In some embodiments, system 10 is configured to perform a mucosal ablation procedure, as described herein, on a patient that has undergone a screening procedure confirming one or more exclusion criteria are not present. For example, the exclusion criteria can comprise one, two, three, or more patient criteria selected from the group consisting of: known case of absolute insulin deficiency as indicated by clinical assessment, and a fasting plasma C-peptide of less than 0.6 ng/ml; administration of any drugs or concomitant medications (such as psychoactive drugs such as carbamazepine, phenobarbital, sympathomimetics, corticosteroids and sex hormones, etc.) that can interfere with glucose metabolism; known or documented SGLT2i intolerance; recurrent or severe urinary tract or genital mycotic infections or history of genitourinary infection; ALT level at least 2.5 times the upper limit normal values unless the findings are consistent with Gilberts disease; type 1 diabetes diagnosis or recent history of ketoacidosis; presence of ketosis-prone Type 2 diabetes; history of non-healing diabetic ulcers or amputations; history of more than 1 severe hypoglycemia episode or unawareness within past 6 months of screening; known intestinal autoimmune disease, as evidenced by a positive Anti-GAD test, including Celiac disease, or pre-existing symptoms of lupus erythematosus, scleroderma or other autoimmune connective tissue disorder, which affects the small intestine; secondary hypothyroidism or inadequately controlled primary hypothyroidism (TSH value outside the normal range at screening); known history of thyroid cancer or hyperthyroidism who have undergone treatment within past 12 months or inadequately controlled hyperthyroidism; an uncontrolled endocrine condition such as multiple endocrine neoplasia and the like (except type 2 diabetes); known history of a structural or functional disorder of the esophagus, including any swallowing disorder, esophageal chest pain disorders, or drug-refractory esophageal reflux symptoms, active and uncontrolled GERD (grade 3 esophagitis or greater); known history of a structural or functional disorder of the stomach, including gastric ulcer, chronic gastritis, gastric varices, hiatal hernia (greater than 2 cm), cancer or any other disorder of the stomach; previous GI surgery that could affect the ability to treat the duodenum such as subjects who have had a Billroth 2, Roux-en-Y gastric bypass, gastric sleeve or other similar procedures or conditions; known history of chronic pancreatitis or a recent history of acute pancreatitis within the past year; history of Hepatitis B, C or other clinically active acute liver diseases; symptomatic gallstones or symptomatic kidney stones, acute cholecystitis; clinically active systemic infection; known immunocompromised status, including but not limited to individuals who have undergone organ transplantation, chemotherapy or radiotherapy within the past 12 months, who have clinically-significant leukopenia, who are positive for the human immunodeficiency virus (HIV) or whose immune status makes the subject a poor candidate for clinical trial participation (e.g. in the opinion of the patient's clinician); history of malignancy within the past 5 years; known active coagulopathy, or current upper gastro-intestinal bleeding conditions such as ulcers, gastric varices, strictures, or congenital or acquired intestinal telangiectasia; active *Helicobacter pylori* infection; known cases of anemia, thalassemia or conditions that affect RBC turnover such as recent blood transfusion within 90 days; use of anticoagulation therapy (such as warfarin) which cannot be discontinued for 7 days before and 14 days after the procedure; use of systemic glucocorticoids (excluding topical or ophthalmic application or inhaled forms) for more than 10 consecutive days within 90 days prior to the screening; use of drugs known to affect GI motility (e.g. Metoclopramide); history of moderate to severe chronic kidney disease (CKD), with estimated glomerular filtration rate (eGFR) less than 45 ml/min/1.73 m2 (estimated by Modification of Diet in Renal Disease [MDRD]) or end stage renal failure or on dialysis; history of myocardial infarction, stroke, or major event requiring hospitalization within the last 3 months prior to screening; history of new or worsening signs or symptoms of CHD within the last 3 months; known case of severe peripheral vascular disease; known case of heart failure requiring pharmacologic therapy; clinically significant ECG findings such as new clinically significant arrythmia or conduction disturbances that increases risk and requires intervention as determined by the investigator; fasting triglyceride value of at least 600 mg/dL (increases risk of pancreatitis); participation in a weight loss program and is currently not in the maintenance phase; general contraindications to deep sedation or general anesthesia (e.g. ASA score 3 or 4) or upper GI Endoscopy; history of any illicit alcohol or substance abuse; use of weight loss medication such as Meridia, Xenical, or over the counter weight loss medications; use of dietary supplements or herbal preparations that may have unknown effects on glycemic control, risk of bleeding; and combinations of these.

In some embodiments, system 10 includes a biopsy device (e.g. device 100 or other device configured to capture tissue of the patient), such as to biopsy tissue from the pre-papillary mucosal tissue, the post-papillary mucosal tissue, or both. In these embodiments, analysis of the captured tissue can be used to modify one or more treatments performed by system 10 (e.g. mucosal ablation treatments).

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth below not be construed as being order-specific unless such order specificity is expressly stated in the claim.

What is claimed is:

1. A method of treating a medical condition of a patient, the method comprising:
   selecting a patient diagnosed with type 2 diabetes that is being treated with daily insulin at a first dosage level and having a first HbA1c level of at least 7.5%; and
   performing a tissue treatment procedure comprising treating one or more segments of the selected patient's intestinal tissue, wherein the tissue segments comprise duodenal mucosal tissue and/or duodenal submucosal tissue;
   wherein after the tissue treatment procedure is performed, the selected patient receives daily insulin at a second dosage level less than the first dosage level and maintains a second HbA1c level that is no greater than the first HbA1c level and wherein the method results in a therapeutic benefit to the selected patient comprising a reduced risk of hypoglycemia wherein the risk of hypoglycemia is reduced to a level of no more than 0.1% occurrence rate of serious hypoglycemic events per year.

2. The method according to claim 1, wherein the selected patient has a c-peptide level of at least 0.5 ng/mL prior to the performing of the tissue treatment procedure.

3. The method according to claim 1, wherein the second HbA1c level comprises an HbA1c level of the selected patient measured 24 weeks after the performance of the tissue treatment procedure.

4. The method according to claim 1, wherein the second HbA1c level is less than the first HbA1c level.

5. The method according to claim 4, wherein the second HbA1c level comprises a level of at least 0.5% less than the first HbA1c level.

6. The method according to claim 1, wherein the second HbA1c level comprises an HbA1c level less than or equal to 7.5%.

7. The method according to claim 6, wherein the second HbA1c level comprises an HbA1c level less than or equal to 7.0%.

8. The method according to claim 6, wherein the second dosage level is zero units of insulin per day.

9. The method according to claim 1, wherein the tissue treatment procedure comprises ablating the duodenal mucosal tissue and/or duodenal submucosal tissue.

10. The method according to claim 1, wherein the tissue treatment procedure comprises ablating neuronal cells of the duodenal mucosa and/or duodenal submucosa.

11. The method according to claim 1, wherein the tissue treatment procedure comprises a tissue treatment selected from the group consisting of: thermal coagulation; desiccation; non-desiccating tissue ablation; heat ablation; cryoablation; radiofrequency ablation; electroporation; ultrasound and/or other sound-based ablation; sonoporation; laser and/or other light-based ablation; mechanical abrasion; chemical abrasion and/or chemical ablation; and combinations thereof.

12. The method according to claim 1, wherein the method results in a therapeutic benefit to the selected patient comprising a decrease in total body weight.

13. The method according to claim 1, wherein the method results in a therapeutic benefit to the selected patient comprising a weight loss of at least 5% of the patient's weight prior to the performing of the tissue treatment procedure.

14. The method according to claim 1, wherein the second dosage level is zero units of insulin per day.

15. The method according to claim 1, wherein the second dosage level is no more than 50% of the first dosage level.

16. The method according to claim 1, wherein the first dosage level comprises a level of at least 10 units of insulin per day.

17. The method according to claim 16, wherein the first dosage level comprises a level of at least 20 units of insulin per day.

18. The method according to claim 16, wherein the first dosage level comprises a level of at least 50 units of insulin per day.

19. The method according to claim 16, wherein the first dosage level comprises a level of at least 60 units of insulin per day.

20. The method according to claim 1, wherein the first dosage level comprises a level of at least 0.5 units of insulin per kilogram of patient body weight per day.

21. The method according to claim 1, wherein at the time of selection, the selected patient is further taking a non-insulin anti-diabetic medication.

22. The method according to claim 1, wherein at the time of selection, the selected patient has a c-peptide level of at least 0.6 ng/mL.

23. The method according to claim 22, wherein at the time of selection, the selected patient has a c-peptide level of at least 1.0 ng/mL.

24. The method according to claim 1, wherein at the time of selection, the selected patient further comprises a patient with a fasting plasma glucose level of at least 140 mg/dL.

25. The method according to claim 24, wherein at the time of selection, the selected patient further comprises a patient with a fasting plasma glucose level of at least 160 mg/dL.

26. The method according to claim 24, wherein at the time of selection, the selected patient further comprises a patient with a fasting plasma glucose level of at least 180 mg/dL.

27. The method according to claim 1, wherein the method further comprises the selected patient taking at least one non-insulin anti-diabetic medication after the performance of the tissue treatment procedure.

* * * * *